United States Patent
Yokoyama et al.

(10) Patent No.: US 10,497,876 B2
(45) Date of Patent: Dec. 3, 2019

(54) ORGANIC ELECTROLUMINESCENT DEVICE

(71) Applicants: Hodogaya Chemical Co., Ltd., Tokyo (JP); SFC Co., Ltd., Cheongju-si (KR)

(72) Inventors: Norimasa Yokoyama, Tokyo (JP); Shuichi Hayashi, Tokyo (JP); Takeshi Yamamoto, Tokyo (JP); Naoaki Kabasawa, Tokyo (JP); Daizou Kanda, Tokyo (JP); Shunji Mochizuki, Tokyo (JP); Soon-wook Cha, Cheongju-si (KR); Sang-woo Park, Cheongju-si (KR); Ju-man Song, Cheongju-si (KR); Kyung-seok Jeon, Cheongju-si (KR)

(73) Assignees: Hodogaya Chemical Co., Ltd., Tokyo (JP); SFC Co., Ltd., Cheongju-si (KR)

( * ) Notice: Subject to any disclaimer, the term of this patent is extended or adjusted under 35 U.S.C. 154(b) by 230 days.

(21) Appl. No.: 15/535,526

(22) PCT Filed: Dec. 16, 2015

(86) PCT No.: PCT/JP2015/085232
§ 371 (c)(1),
(2) Date: Jun. 13, 2017

(87) PCT Pub. No.: WO2016/104289
PCT Pub. Date: Jun. 30, 2016

(65) Prior Publication Data
US 2017/0346009 A1 Nov. 30, 2017

(30) Foreign Application Priority Data
Dec. 24, 2014 (JP) ................................ 2014-259965

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/54* (2013.01); *C07C 211/58* (2013.01);
(Continued)

(58) Field of Classification Search
None
See application file for complete search history.

(56) References Cited

U.S. PATENT DOCUMENTS 7,846,558 B2 * 12/2010 Je ........................... C09K 11/06
428/690
8,343,637 B2 * 1/2013 Parham ................ C07D 209/80
313/504

(Continued)

FOREIGN PATENT DOCUMENTS

KR 10-2011-0084797 A 7/2011
WO 2007/043484 A1 4/2007

(Continued)

OTHER PUBLICATIONS

International Search Report dated Mar. 15, 2016, issued for PCT/JP2015/085232.

*Primary Examiner* — Robert S Loewe
(74) *Attorney, Agent, or Firm* — Locke Lord LLP; James E. Armstrong, IV; Nicholas J. DiCeglie, Jr.

(57) ABSTRACT

In the organic electroluminescent device having at least an anode, a hole injection layer, a hole transport layer, a light emitting layer, an electron transport layer and a cathode in this order, the hole injection layer includes an arylamine compound of the following general formula (1) and an electron acceptor.

(Continued)

← 8 CATHODE
← 7 ELECTRON INJECTION LAYER
← 6 ELECTRON TRANSPORT LAYER
← 5 LIGHT EMITTING LAYER
← 4 HOLE TRANSPORT LAYER
← 3 HOLE INJECTION LAYER
← 2 TRANSPARENT ANODE
← 1 GLASS SUBSTRATE

[Chemical Formula 1]

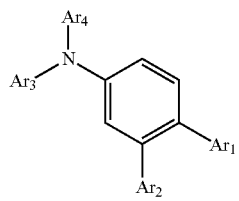

(1)

In the formula, $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group.

20 Claims, 1 Drawing Sheet

(51) Int. Cl.

| | | |
|---|---|---|
| C07C 211/54 | (2006.01) | |
| C07C 211/58 | (2006.01) | |
| C07C 211/61 | (2006.01) | |
| C07D 209/08 | (2006.01) | |
| C07D 209/86 | (2006.01) | |
| C07D 235/18 | (2006.01) | |
| C07D 239/26 | (2006.01) | |
| C07D 307/91 | (2006.01) | |
| C07D 333/76 | (2006.01) | |
| C07D 401/10 | (2006.01) | |
| C07D 401/14 | (2006.01) | |
| C07D 471/04 | (2006.01) | |
| C09B 57/00 | (2006.01) | |
| C09B 1/00 | (2006.01) | |
| H01L 51/52 | (2006.01) | |

(52) U.S. Cl.
CPC .......... *C07C 211/61* (2013.01); *C07D 209/08* (2013.01); *C07D 209/86* (2013.01); *C07D 235/18* (2013.01); *C07D 239/26* (2013.01); *C07D 307/91* (2013.01); *C07D 333/76* (2013.01); *C07D 401/10* (2013.01); *C07D 401/14* (2013.01); *C07D 471/04* (2013.01); *C09B 1/00* (2013.01); *C09B 57/00* (2013.01); *C09B 57/008* (2013.01); *H01L 51/0052* (2013.01); *H01L 51/0054* (2013.01); *H01L 51/0058* (2013.01); *H01L 51/0059* (2013.01); *H01L 51/0061* (2013.01); *H01L 51/0067* (2013.01); *H01L 51/0072* (2013.01); *H01L 51/50* (2013.01); *H01L 51/0056* (2013.01); *H01L 51/0073* (2013.01); *H01L 51/0074* (2013.01); *H01L 51/5012* (2013.01); *H01L 51/5056* (2013.01); *H01L 51/5072* (2013.01); *H01L 51/5088* (2013.01); *H01L 51/5206* (2013.01); *H01L 51/5221* (2013.01)

(56) References Cited

U.S. PATENT DOCUMENTS

| | | | |
|---|---|---|---|
| 10,014,479 B2* | 7/2018 | Kim | H01L 51/0061 |
| 2003/0165715 A1* | 9/2003 | Yoon | C07D 235/08 |
| | | | 428/690 |
| 2010/0019657 A1* | 1/2010 | Eum | C07C 211/61 |
| | | | 313/504 |
| 2010/0045170 A1* | 2/2010 | Lee | C07C 13/547 |
| | | | 313/504 |
| 2010/0102709 A1* | 4/2010 | Zeika | C07C 255/35 |
| | | | 313/504 |
| 2010/0244008 A1* | 9/2010 | Lee | C07D 409/10 |
| | | | 257/40 |
| 2010/0314615 A1* | 12/2010 | Mizuki | C07D 307/91 |
| | | | 257/40 |
| 2011/0198581 A1 | 8/2011 | Yabunouchi et al. | |
| 2012/0001154 A1* | 1/2012 | Kato | C07D 209/82 |
| | | | 257/40 |
| 2012/0181521 A1* | 7/2012 | Yabunouchi | C07D 307/91 |
| | | | 257/40 |
| 2012/0223296 A1* | 9/2012 | Werner | H01L 51/006 |
| | | | 257/40 |
| 2012/0228598 A1* | 9/2012 | Yokoyama | C07D 471/04 |
| | | | 257/40 |
| 2014/0073784 A1* | 3/2014 | Mizutani | C07D 405/14 |
| | | | 544/216 |
| 2014/0131681 A1* | 5/2014 | Ito | H01L 51/006 |
| | | | 257/40 |
| 2014/0167026 A1* | 6/2014 | Kato | C07D 457/04 |
| | | | 257/40 |
| 2014/0203257 A1* | 7/2014 | Hwang | H01L 51/0094 |
| | | | 257/40 |
| 2014/0217393 A1* | 8/2014 | Kato | C07D 403/10 |
| | | | 257/40 |
| 2014/0346482 A1* | 11/2014 | Mizuki | C07D 333/76 |
| | | | 257/40 |
| 2014/0374721 A1 | 12/2014 | Yokoyama et al. | |
| 2015/0041773 A1* | 2/2015 | Park | H01L 51/0058 |
| | | | 257/40 |
| 2015/0179940 A1 | 6/2015 | Mujica-Fernaud et al. | |
| 2015/0179953 A1 | 6/2015 | Mujica-Fernaud et al. | |
| 2015/0325794 A1* | 11/2015 | Nishimura | C07D 403/04 |
| | | | 257/40 |
| 2015/0380657 A1 | 12/2015 | Yokoyama et al. | |
| 2016/0005982 A1* | 1/2016 | Nagaoka | C07D 401/10 |
| | | | 257/40 |
| 2018/0269399 A1* | 9/2018 | Stoessel | H01L 51/0059 |

FOREIGN PATENT DOCUMENTS

| | | | |
|---|---|---|---|
| WO | 2010/044130 A1 | 4/2010 | |
| WO | 2013/054764 A | 4/2013 | |
| WO | 2014/009310 A1 | 1/2014 | |
| WO | 2014/015935 A2 | 1/2014 | |
| WO | 2014/015937 A1 | 1/2014 | |
| WO | WO-2014132871 * | 4/2014 | .......... C07D 401/10 |
| WO | 2014/129201 A1 | 8/2014 | |

* cited by examiner

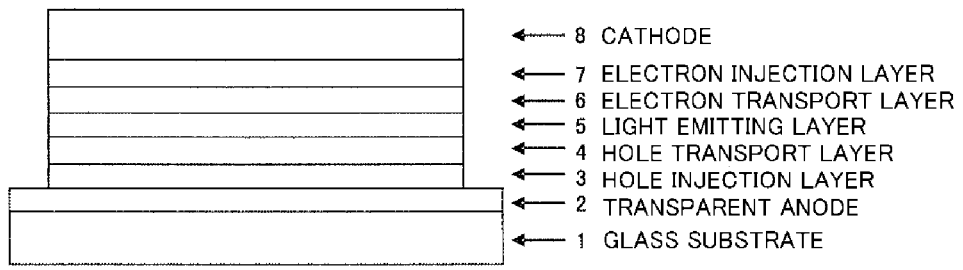

ORGANIC ELECTROLUMINESCENT DEVICE

TECHNICAL FIELD

The present invention relates to an organic electroluminescent device which is a preferred self-luminous device for various display devices. Specifically, this invention relates to organic electroluminescent devices (hereinafter referred to as organic EL devices) using specific arylamine compounds doped with an electron acceptor.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to Non-Patent Document 1, for example).

Further, there have been attempts to use triplet excitons for further improvements of luminous efficiency, and the use of a phosphorescence-emitting compound has been examined (refer to Non-Patent Document 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 3, for example).

The light emitting layer can be also fabricated by doping a charge-transporting compound generally called a host material, with a fluorescent compound, a phosphorescence-emitting compound, or a delayed fluorescent-emitting material. As described in the Non-Patent Document, the selection of organic materials in an organic EL device greatly influences various device characteristics such as efficiency and durability (refer to Non-Patent Document 2, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (NPD) and various aromatic amine derivatives are known as the hole transport materials used for the organic EL device (refer to Patent Documents 1 and 2, for example). Although NPD has desirable hole transportability, its glass transition point (Tg), which is an index of heat resistance, is as low as 96° C., which causes the degradation of device characteristics by crystallization under a high-temperature condition (refer to Non-Patent Document 4, for example). The aromatic amine derivatives described in the Patent Documents include a compound known to have an excellent hole mobility of 10$^{-3}$ cm$^2$/Vs or higher (refer to Patent Documents 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to Patent Document 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to Patent Documents 4 and 5, for example). Further, it is proposed that hole injectability can be improved by p-doping materials such as trisbromophenylamine hexachloroantimony, radialene derivatives, and F4-TCNQ into a material commonly used for the hole injection layer or the hole transport layer (refer to Patent Document 6 and Non-Patent Document 5). However, while the devices using these compounds for the hole injection layer or the hole transport layer have been improved in lower driving voltage, heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Documents

Patent Document 1: JP-A-8-048656
Patent Document 2: Japanese Patent No. 3194657
Patent Document 3: Japanese Patent No. 4943840
Patent Document 4: JP-A-2006-151979
Patent Document 5: WO2008/62636
Patent Document 6: WO2014/009310
Patent Document 7: WO2005/115970
Patent Document 8: WO2011/059000
Patent Document 9: WO2003/060956
Patent Document 10: KR-A-2013-060157
Patent Document 11: WO2013/054764

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Appl. Phys. Let., 98, 083302 (2011)
Non-Patent Document 4: Organic EL Symposium, the 3rd Regular presentation Preprints, pp. 13 to 14 (2006)
Non-Patent Document 5: Appl. Phys. Let., 89, 253506 (2006)

SUMMARY OF THE INVENTION

Problems to be Solved by the Invention

An object of the present invention is to provide an organic EL device having high efficiency, low driving voltage and a long lifetime, by combining various materials for an organic EL device, which are excellent, as materials for an organic EL device having high efficiency and high durability, in hole and electron injection/transport performances, electron blocking ability, stability in a thin-film state and durability, so as to allow the respective materials to effectively reveal their characteristics.

Physical properties of the organic compound to be provided by the present invention include (1) good hole injection characteristics, (2) large hole mobility, (3) excellent electron blocking ability, (4) stability in a thin-film state, and (5) excellent heat resistance. Physical properties of the organic EL device to be provided by the present invention include (1) high luminous efficiency and high power efficiency, (2) low turn on voltage, (3) low actual driving voltage, and (4) a long lifetime.

Means for Solving the Problems

To achieve the above object, the present inventors have noted that an arylamine material doped with an electron acceptor is excellent in hole injection and transport abilities, stability as a thin film and durability, have selected a specific arylamine compound (having a specific structure), and have produced various organic EL devices in which a material of a hole injection layer is doped with an electron acceptor such that holes can be efficiently injected and transported from an anode. Then, they have intensively conducted characteristic evaluations of the devices. Also, they have produced various organic EL devices by combining a specific arylamine compound (having a specific structure) doped with an electron acceptor and a specific arylamine compound (having a specific structure) undoped with an electron acceptor. Then, they have intensively conducted characteristic evaluations of the devices. As a result, they have completed the present invention.

Specifically, according to the present invention, the following organic EL devices are provided.

1) An organic EL device having at least an anode, a hole injection layer, a hole transport layer, a light emitting layer, an electron transport layer, and a cathode in this order, wherein the hole injection layer includes an arylamine compound represented by the following general formula (1) and an electron acceptor.

[Chemical Formula 1]

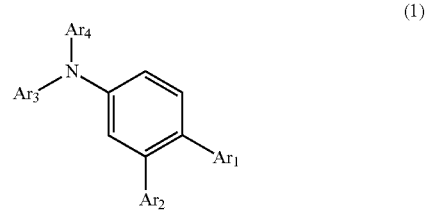

(1)

(In the formula, $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group.)

2) The organic electroluminescent device according to the above 1), wherein a layer adjacent to the light emitting layer does not contain an electron acceptor.

3) The organic EL device according to the above 1) or 2), wherein the electron acceptor is an electron acceptor selected from trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative.

4) The organic EL device according to any one of the above 1) to 3), wherein the electron acceptor is a radialene derivative represented by the following general formula (2).

[Chemical Formula 2]

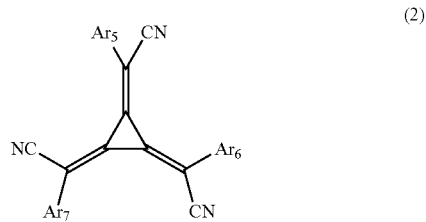

(2)

(In the formula, $Ar_5$ to $Ar_7$ may be the same or different, and represent an aromatic hydrocarbon group, an aromatic heterocyclic group, or a condensed polycyclic aromatic group, having an electron acceptor group as a substituent.)

5) The organic EL device according to any one of the above 1) to 4), wherein the hole transport layer includes only a hole transporting arylamine compound.

6) The organic EL device according to the above 5), wherein the hole transport layer includes an arylamine compound represented by the general formula (1).

7) The organic EL device according to any one of the above 1) to 6), wherein the electron transport layer includes a compound having an anthracene ring structure represented by the following general formula (3).

[Chemical Formula 3]

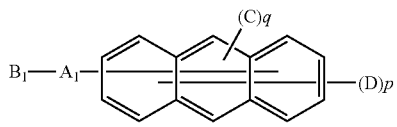

(3)

(In the formula, $A_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $B_1$ represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group; and while p and q maintain a relationship that the sum of p and q is 9, p represents 7 or 8, and q represents 1 or 2.)

8) The organic EL device according to any one of the above 1) to 6), wherein the electron transport layer includes a compound having a pyrimidine ring structure represented by the following general formula (4).

[Chemical Formula 4]

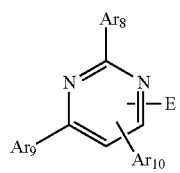

(4)

(In the formula, $Ar_8$ represents a substituted or unsubstituted aromatic hydrocarbon group or a substituted or unsubstituted condensed polycyclic aromatic group; $Ar_9$ and $Ar_{10}$ may be the same or different, and represent a hydrogen atom, a substituted or unsubstituted aromatic hydrocarbon group, or a substituted or unsubstituted condensed polycyclic aromatic group; and E represents a monovalent group represented by the following structural formula (5), provided that $Ar_9$ and $Ar_{10}$ are not simultaneously a hydrogen atom.

[Chemical Formula 5]

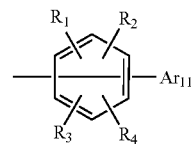

(5)

(In the formula, $Ar_{11}$ represents a substituted or unsubstituted aromatic heterocyclic group; $R_1$ to $R_4$ may be the same or different, and represent a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group.)

9) The organic EL device according to any one of the above 1) to 6), wherein the electron transport layer includes a compound having a benzotriazole ring structure represented by the following general formula (6).

[Chemical Formula 6]

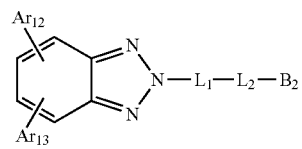

(6)

(In the formula, $Ar_{12}$ represents a substituted or unsubstituted aromatic hydrocarbon group, a substituted or unsubstituted aromatic heterocyclic group, or a substituted or unsubstituted condensed polycyclic aromatic group; $Ar_{13}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group; $L_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $L_2$ represents a divalent group of a substituted or unsubstituted condensed polycyclic aromatic or a single bond; and $B_2$ represents a substituted or unsubstituted aromatic heterocyclic group.)

10) The organic EL device according to any one of the above 1) to 9), wherein the light emitting layer includes a blue light emitting dopant.

11) The organic EL device according to the above 10), wherein the light emitting layer includes a blue light emitting dopant which is a pyrene derivative.

12) The organic EL device according to the above 10), wherein the blue light emitting dopant includes a light emitting dopant which is an amine derivative having a condensed ring structure represented by the following general formula (7).

[Chemical Formula 7]

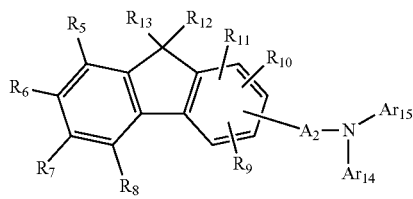

(7)

(In the formula, $A_2$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $Ar_{14}$ and $Ar_{15}$ may be the same or different, and represent a substituted or unsubstituted aromatic hydrocarbon group, a substituted or unsubstituted aromatic heterocyclic group, or a substituted or unsubstituted condensed polycyclic aromatic group, and may bind to each other via a single bond, a substituted or unsubstituted methylene group, an oxygen atom, or a sulfur atom to form a ring; $R_5$ to $R_8$ may be the same or different, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with a group selected from an aromatic hydrocarbon group, an aromatic heterocyclic group, or a condensed polycyclic aromatic group, where the respective groups may bind to each other via a single bond, a substituted or unsubstituted methylene group, an oxygen atom, or a sulfur atom to form a ring, or may bind to the benzene ring to which $R_5$ to $R_8$ bind via a substituted or unsubstituted methylene group, an oxygen atom, a sulfur atom, or a monosubstituted amino group to form a ring; $R_9$ to $R_{11}$ may be the same or different, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, where the respective groups may bind to each other via a single bond, a substituted or unsubstituted methylene group, an oxygen atom, or a sulfur atom to form a ring, or may bind to the benzene ring to which $R_9$ to $R_{11}$ bind via a substituted or unsubstituted methylene group, an oxygen atom, a sulfur atom, or a monosubstituted amino group to form a ring; and $R_{12}$ and $R_{13}$ may be the same or different, and represent a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, where the respective groups may bind to each other via a single bond, a substituted or unsubstituted methylene group, an oxygen atom, a sulfur atom, or a monosubstituted amino group to form a ring.)

13) The organic EL device according to any one of the above 1) to 12), wherein the light emitting layer includes an anthracene derivative.

14) The organic EL device according to the above 13), wherein the light emitting layer includes a host material which is an anthracene derivative.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1) include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Specific examples of the "substituent" in the "substituted aromatic hydrocarbon group", the "substituted aromatic heterocyclic group", or the "substituted condensed polycyclic aromatic group" represented by $Ar_1$ to $Ar_4$ in the general formula (1) include a deuterium atom, a cyano group, a nitro group; halogen atoms such as a fluorine atom, a chlorine atom, a bromine atom, and an iodine atom; linear or branched alkyl groups of 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group; linear or branched alkyloxy groups of 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; arylvinyl groups such as a styryl group and a naphthylvinyl group; acyl groups such as an acetyl group and a benzoyl group; and other groups, and these substituents may be further substituted with a substituent exemplified above. Further, these substituents may bind to each other via a single bond, a substituted or unsubstituted methylene group, an oxygen atom, or a sulfur atom to form a ring.

Examples of the "electron acceptor group" in the "aromatic hydrocarbon group, the aromatic heterocyclic group, or the condensed polycyclic aromatic group, having an electron acceptor group as a substituent" represented by $Ar_5$ to $Ar_7$ in the general formula (2) include a fluorine atom, a chlorine atom, a bromine atom, a cyano group, a trifluoromethyl group, and a nitro group.

Examples of the "aromatic hydrocarbon group", the "aromatic heterocyclic group", or the "condensed polycyclic aromatic group" in the "aromatic hydrocarbon group, the aromatic heterocyclic group, or the condensed polycyclic aromatic group, having an electron acceptor group as a substituent" represented by $Ar_5$ to $Ar_7$ in the general formula (2) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent other than the electron acceptor group, and specific examples of the substituent include a deuterium atom; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; and aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group, and these substituents may be further substituted with a substituent exemplified above or an electron acceptor group. Then, these substituents may bind to each other via a single bond, a substituted or unsubstituted methylene group, an oxygen atom, or a sulfur atom to form a ring.

Specific examples of the "aromatic hydrocarbon", the "aromatic heterocyclic ring", or the "condensed polycyclic aromatic" of the "substituted or unsubstituted aromatic hydrocarbon", the "substituted or unsubstituted aromatic heterocyclic ring", or the "substituted or unsubstituted condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_1$ in the general formula (3) include benzene, biphenyl, terphenyl, tetrakisphenyl, styrene, naphthalene, anthracene, acenaphthalene, fluorene, phenanthrene, indane, pyrene, triphenylene, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

Then, the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_1$ in the general formula (3) represents a divalent group that results from the removal of two hydrogen atoms from the above "aromatic hydrocarbon", "aromatic heterocyclic ring", or "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic heterocyclic group" in the "substituted or unsubstituted aromatic heterocyclic group" represented by $B_1$ in the general formula (3) include a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a carbolinyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Specific examples of the "substituent" in the "substituted aromatic heterocyclic group" represented by $B_1$ in the general formula (3) include a deuterium atom, a cyano group, a nitro group; halogen atoms such as a fluorine atom, a chlorine atom, a bromine atom, and an iodine atom; linear or branched alkyl groups of 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group; cycloalkyl groups of 5 to 10 carbon atoms such as a cyclopentyl group, a cyclohexyl group, a 1-adamantyl group, and a 2-adamantyl group; linear or branched alkyloxy groups of 1 to 6 carbon atoms such as a methyloxy group, an ethyloxy group, and a propyloxy group; cycloalkyloxy groups of 5 to 10 carbon atoms such as a cyclopentyloxy group, a cyclohexyloxy group, a 1-adamantyloxy group, and a 2-adamantyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; aryloxy groups such as a phenyloxy group, a biphenylyloxy group, a naphthyloxy group, an anthracenyloxy group, and a phenanthrenyloxy group; arylvinyl groups such as a styryl group and a naphthylvinyl group; acyl groups such as an acetyl group and a benzoyl group; and other groups, and these substituents may be further substituted with a substituent exemplified above. Further, these substituents may bind to each other via a single bond, a substituted or unsubstituted methylene group, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by C in the general formula (3) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and when a plurality of these groups bind to the same anthracene ring (when q is 2), these groups may be the same or different.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "linear or branched alkyl group of 1 to 6 carbon atoms" represented by D in the general formula (3) include a methyl group, an ethyl group, an n-propyl group, an isopropyl group, an n-butyl group, an isobutyl group, a tert-butyl group, an n-pentyl group, an isopentyl group, a neopentyl group, and an n-hexyl group.

Further, the plurality of D may be the same or different, and these groups may bind to each other via a single bond, a substituted or unsubstituted methylene group, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by D in the general formula (3) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and the plurality of D may be the same or different, and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic hydrocarbon group" or the "condensed polycyclic aromatic group" in the "substituted or unsubstituted aromatic hydrocarbon group" or the "substituted or unsubstituted condensed polycyclic aromatic group" represented by $Ar_8$, $Ar_9$, and $Ar_{10}$ in the general formula (4) include groups such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, and a triphenylenyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic heterocyclic group" in the "substituted or unsubstituted aromatic heterocyclic group" represented by $Ar_{11}$ in the structural formula (5) include groups such as a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "linear or branched alkyl group of 1 to 6 carbon atoms" represented by $R_1$ to $R_4$ in the structural formula (5) include a methyl group, an ethyl group, an n-propyl group, an i-propyl group, an n-butyl group, a 2-methylpropyl group, a tert-butyl group, an n-pentyl group, a 3-methylbutyl group, a tert-pentyl group, an n-hexyl group, an iso-hexyl group, and a tert-hexyl group.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_4$ in the structural formula (5) include groups such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{12}$ and $Ar_{13}$ in the general formula (6) include groups such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a pyridyl group, a triazinyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, and an acridinyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic hydrocarbon", the "aromatic heterocyclic ring", or the "condensed polycyclic aromatic" of the "substituted or unsubstituted aromatic hydrocarbon", the "substituted or unsubstituted aromatic heterocyclic ring", or the "substituted or unsubstituted condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $L_1$ in the general formula (6) include benzene, biphenyl, terphenyl, tetrakisphenyl, styrene, naphthalene, anthracene, acenaphthalene, fluorene, phenanthrene, indane, pyrene, triphenylene, pyridine, bipyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

Then, the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $L_1$ in the general formula (6) represents a divalent group that results from the removal of two hydrogen atoms from the above "aromatic hydrocarbon", "aromatic heterocyclic ring", or "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "condensed polycyclic aromatic" of the "substituted or unsubstituted condensed polycyclic aromatic" in the "divalent group of a substituted or unsubstituted condensed polycyclic aromatic" represented by $L_2$ in the general formula (6) include naphthalene, anthracene, acenaphthalene, fluorene, phenanthrene, indane, pyrene, and triphenylene.

Then, the "divalent group of a substituted or unsubstituted condensed polycyclic aromatic" represented by $L_2$ in the general formula (6) represents a divalent group that results from the removal of two hydrogen atoms from the above "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic heterocyclic group", in the "substituted or unsubstituted aromatic heterocyclic group" represented by $B_2$ in the general formula (6) include groups such as a pyridyl group, a bipyridyl group, a triazinyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a carbolinyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, and an acridinyl group.

Further, these groups may have a substituent, and examples of the substituent include the same substituents exemplified as the "substituent" in the "substituted aromatic heterocyclic group" represented by $B_1$ in the above general formula (3), and possible embodiments may also be the same embodiments as the exemplified embodiments.

Examples of the "aromatic hydrocarbon", the "aromatic heterocyclic ring", or the "condensed polycyclic aromatic" of the "substituted or unsubstituted aromatic hydrocarbon", the "substituted or unsubstituted aromatic heterocyclic ring", or the "substituted or unsubstituted condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_2$ in the general formula (7) include the same groups exemplified as the "aromatic hydrocarbon", the "aromatic heterocyclic ring", or the "condensed polycyclic aromatic" of the "substituted or unsubstituted aromatic hydrocarbon", the "substituted or unsubstituted aromatic heterocyclic ring", or the "substituted or unsubstituted condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_1$ in the above general formula (3).

Then, the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_2$ in the general formula (7) represents a divalent group that results from the removal of two hydrogen atoms from the above "aromatic hydrocarbon", "aromatic heterocyclic ring", or "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{14}$ and $Ar_{15}$ in the general formula (7) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and $Ar_{14}$ and $Ar_{15}$ may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_5$ to $R_{11}$ in the general formula (7) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group, and these groups may bind to each other via a single bond, a substituted or unsubstituted methylene group, an oxygen atom, or a sulfur atom to form a ring, or these groups ($R_5$ to $R_{11}$) may bind to the benzene ring to which these groups ($R_5$ to $R_{11}$) directly bind via a linking group such as a substituted or unsubstituted methylene group, an oxygen atom, a sulfur atom, or a monosubstituted amino group to form a ring.

Specific examples of the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_5$ to $R_{11}$ in the general formula (7) include a deuterium atom, a cyano group, a nitro group; halogen atoms such as a fluorine atom, a chlorine atom, a bromine atom, and an iodine atom; linear or branched alkyloxy groups of 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; disubstituted amino groups substituted with an aromatic hydrocarbon group or a condensed polycyclic aromatic group such as a diphenylamino group and a dinaphthylamino group; disubstituted amino groups substituted with an aromatic heterocyclic group such as a dipyridylamino group and a dithienylamino group; disubstituted amino groups substituted with a substituent selected from an aromatic hydrocarbon group, a condensed polycyclic aromatic group, or an aromatic heterocyclic group; and other groups, and these substituents may be further substituted with a substituent exemplified above. Further, these substituents may bind to each other via a single bond, a substituted or unsubstituted methylene group, an oxygen atom, or a sulfur atom to form a ring.

Specific examples of the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_5$ to $R_{11}$ in the general formula (7) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, and these groups may bind to each other via a single bond, a substituted or unsubstituted methylene group, an oxygen atom, or a sulfur atom to form a ring, or these groups ($R_5$ to $R_{11}$) may bind to the benzene ring to which these groups ($R_5$ to $R_{11}$) directly bind via a linking group such as a substituted or unsubstituted methylene group, an oxygen atom, a sulfur atom, or a monosubstituted amino group to form a ring.

Further, these groups may have a substituent, and examples of the substituent include the same substituents exemplified as the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_5$ to $R_{11}$ in the above general formula (7), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_5$ to $R_{11}$ in the general formula (7) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and these groups may bind to each other via a single bond, a substituted or unsubstituted methylene group, an oxygen atom, or a sulfur atom to form a ring, or these groups ($R_5$ to $R_{11}$) may bind to the benzene ring to which these groups ($R_5$ to $R_{11}$) directly bind via a linking group such as a substituted or unsubstituted methylene group, an oxygen atom, a sulfur atom, or a monosubstituted amino group to form a ring.

Specific examples of the "substituent" in the "substituted aromatic hydrocarbon group", the "substituted aromatic heterocyclic group", or the "substituted condensed polycyclic aromatic group" represented by $R_5$ to $R_{11}$ in the general formula (7) include a deuterium atom, a cyano group, a nitro group; halogen atoms such as a fluorine atom, a chlorine atom, a bromine atom, and an iodine atom; linear or branched alkyl groups of 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group; linear or branched alkyloxy groups of 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; arylvinyl groups such as a styryl group and a naphthylvinyl group; acyl groups such as an acetyl group and a benzoyl group; silyl groups such as a trimethylsilyl group and a triphenylsilyl group; disubstituted amino groups substituted with an aromatic hydrocarbon group or a condensed polycyclic aromatic group such as a diphenylamino group and a dinaphthylamino group; disubstituted amino groups substituted with an aromatic heterocyclic group such as a dipyridylamino group and a dithienylamino group; disubstituted amino groups substituted with a substituent selected from an aromatic hydrocarbon group, a condensed polycyclic aromatic group, or an aromatic heterocyclic group; and other groups, and these substituents may be further substituted with a substituent exemplified above. Further, these substituents may bind to each other via a single bond, a substituted or unsubstituted methylene group, an oxygen atom, or a sulfur atom to form a ring.

Specific examples of the "aryloxy group" in the "substituted or unsubstituted aryloxy group" represented by $R_5$ to $R_{11}$ in the general formula (7) include a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group, and these groups may bind to each other via a single bond, a substituted or unsubstituted methylene group, an oxygen atom, or a sulfur atom to form a ring, or these groups ($R_5$ to $R_{11}$) may bind to the benzene ring to which these groups ($R_5$ to $R_{11}$) directly bind via a linking group such as a substituted or unsubstituted methylene group, an oxygen atom, a sulfur atom, or a monosubstituted amino group to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_5$ to $R_{11}$ in the above general formula (7), and possible embodiments may also be the same embodiments as the exemplified embodiments.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, or a condensed polycyclic aromatic group" represented by $R_5$ to $R_8$ in the general formula (7) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_5$ to $R_8$ in the above general formula (7), and possible embodiments may also be the same embodiments as the exemplified embodiments.

In the case of the "disubstituted amino group substituted with a group selected from an aromatic hydrocarbon group, an aromatic heterocyclic group, or a condensed polycyclic aromatic group" represented by $R_5$ to $R_8$ in the general formula (7), these groups ($R_5$ to $R_8$) may bind to each other through the "aromatic hydrocarbon group", the "aromatic heterocyclic group", or the "condensed polycyclic aromatic group" included in these groups ($R_5$ to $R_8$) via a single bond, a substituted or unsubstituted methylene group, an oxygen atom, or a sulfur atom to form a ring, or these groups ($R_5$ to $R_8$) may bind to the benzene ring to which these groups ($R_5$ to $R_8$) directly bind through the "aromatic hydrocarbon group", the "aromatic heterocyclic group", or the "condensed polycyclic aromatic group" included in these groups ($R_5$ to $R_8$) via a linking group such as a substituted or unsubstituted methylene group, an oxygen atom, a sulfur atom, or a monosubstituted amino group to form a ring.

Examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_{12}$ and $R_{13}$ in the general formula (7) include the same groups exemplified as the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_5$ to $R_{11}$ in the above general formula (7), and these groups may bind to each other via a single bond, or a linking group such as a substituted or unsubstituted methylene group, an oxygen atom, a sulfur atom, or a monosubstituted amino group to form a ring.

Further, these groups may have a substituent, and examples of the substituent include the same substituents exemplified as the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_5$ to $R_{11}$ in the above general formula (7), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{12}$ and $R_{13}$ in the general formula (7) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and these groups may bind to each other via a single bond, or a linking group such as a substituted or unsubstituted methylene group, an oxygen atom, a sulfur atom, or a monosubstituted amino group to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_5$ to $R_{11}$ in the above general formula (7), and possible embodiments may also be the same embodiments as the exemplified embodiments.

Examples of the "aryloxy group" in the "substituted or unsubstituted aryloxy group" represented by $R_{12}$ and $R_{13}$ in the general formula (7) include the same groups exemplified as the "aryloxy group" in the "substituted or unsubstituted aryloxy group" represented by $R_5$ to $R_{11}$ in the above general formula (7), and these groups may bind to each other via a single bond, or a linking group such as a substituted or unsubstituted methylene group, an oxygen atom, a sulfur atom, or a monosubstituted amino group to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_5$ to $R_{11}$ in the above general formula (7), and possible embodiments may also be the same embodiments as the exemplified embodiments.

Examples of the "substituent" in the linking group "monosubstituted amino group" in the general formula (7) include the same groups exemplified as the "linear or branched alkyl group of 1 to 6 carbon atoms", the "cycloalkyl group of 5 to 10 carbon atoms", the "aromatic hydrocarbon group", the "aromatic heterocyclic group", or the "condensed polycyclic aromatic group" in the "linear or branched alkyl group of 1 to 6 carbon atoms that may have a substituent", the "cycloalkyl group of 5 to 10 carbon atoms that may have a substituent", the "substituted or unsubstituted aromatic hydrocarbon group", the "substituted or unsubstituted aromatic heterocyclic group", or the "substituted or unsubstituted condensed polycyclic aromatic group" represented by $R_5$ to $R_{11}$ in the above general formula (7).

Further, these groups may have a substituent, and examples of the substituent of the "linear or branched alkyl group of 1 to 6 carbon atoms that has a substituent" or the "cycloalkyl group of 5 to 10 carbon atoms that has a substituent" include the same substituents exemplified as the "substituent" in the "linear or branched alkyl group of 1 to 6 carbon atoms that has a substituent" or the "cycloalkyl group of 5 to 10 carbon atoms that has a substituent" represented by $R_5$ to $R_{11}$ in the above general formula (7), and examples of the substituent of the "substituted aromatic hydrocarbon group", the "substituted aromatic heterocyclic group", or the "substituted condensed polycyclic aromatic group" include the same substituents exemplified as the "substituent" in the "substituted aromatic hydrocarbon group", the "substituted aromatic heterocyclic group", or the "substituted condensed polycyclic aromatic group" represented by $R_5$ to $R_{11}$ in the above general formula (7), and possible embodiments may also be the same embodiments as the exemplified embodiments.

$Ar_1$ in the general formula (1) is preferably a "substituted or unsubstituted aromatic hydrocarbon group" or a "substituted or unsubstituted condensed polycyclic aromatic group", more preferably a phenyl group, a biphenylyl group, a terphenylyl group, a naphthyl group, a phenanthrenyl group, an anthracenyl group, a fluorenyl group, a carbazolyl group, an indolyl group, a dibenzofuranyl group, or a dibenzothienyl group.

$Ar_2$ in the general formula (1) is preferably a "substituted or unsubstituted aromatic hydrocarbon group" or a "substituted or unsubstituted condensed polycyclic aromatic group", more preferably a phenyl group, a biphenylyl group, a terphenylyl group, a naphthyl group, a phenanthrenyl group, an anthracenyl group, or a fluorenyl group, and above all, a phenyl group, particularly, an unsubstituted phenyl group is preferable.

As the arylamine compound represented by the general formula (1), an arylamine compound represented by the following general formula (1a) or general formula (1b) is more preferably used.

[Chemical Formula 8]

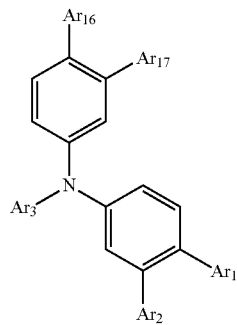

(1a)

(In the formula, $Ar_1$ to $Ar_3$ represent the same meanings as described in the above general formula (1), and $Ar_{16}$ to $Ar_{17}$ may be the same or different, and represent a substituted or unsubstituted aromatic hydrocarbon group, a substituted or unsubstituted aromatic heterocyclic group, or a substituted or unsubstituted condensed polycyclic aromatic group.)

[Chemical Formula 9]

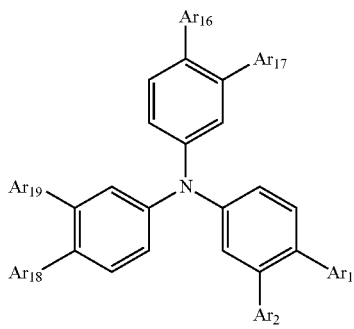

(1b)

(In the formula, $Ar_1$ to $Ar_2$ represent the same meanings as described in the above general formula (1), and $Ar_{16}$ to $Ar_{19}$ may be the same or different, and represent a substituted or unsubstituted aromatic hydrocarbon group, a substituted or unsubstituted aromatic heterocyclic group, or a substituted or unsubstituted condensed polycyclic aromatic group.)

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{16}$ to $Ar_{19}$ in the general formula (1a) or the general formula (1b) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

In the general formula (1a), $Ar_1$ and $Ar_{16}$ are preferably the same group, and $Ar_2$ and $Ar_{17}$ are preferably the same group.

In the general formula (1b), $Ar_1$, $Ar_{16}$, and $Ar_{18}$ are preferably the same group, and $Ar_2$, $Ar_{17}$, and $Ar_{19}$ are preferably the same group.

In the general formula (1), the "substituent" in the "substituted aromatic hydrocarbon group", the "substituted aromatic heterocyclic group", or the "substituted condensed polycyclic aromatic group" represented by $Ar_1$ to $Ar_4$ is preferably a deuterium atom, a linear or branched alkyl group of 1 to 6 carbon atoms that may have a substituent, a linear or branched alkenyl group of 2 to 6 carbon atoms that may have a substituent, a "substituted or unsubstituted aromatic hydrocarbon group", or a "substituted or unsubstituted condensed polycyclic aromatic group", more preferably a deuterium atom, a phenyl group, a biphenylyl group, a naphthyl group, or a vinyl group. Further, a case where these groups bind to each other via a single bond to form a condensed aromatic ring is also preferable.

In the hole injection layer of the organic EL device of the present invention, examples of the electron acceptor doped in the arylamine compound represented by the above general formula (1) include trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative (refers to JP-A-2011-100621, for example), and a radialene derivative represented by the above general formula (2) is preferably used.

$Ar_5$ to $Ar_7$ in the general formula (2) are preferably an "aromatic hydrocarbon group", a "condensed polycyclic aromatic group", or a pyridyl group, more preferably a phenyl group, a biphenylyl group, a terphenylyl group, a naphthyl group, a phenanthrenyl group, a fluorenyl group, or a pyridyl group, and the "electron acceptor group" is preferably a fluorine atom, a chlorine atom, a cyano group, or a trifluoromethyl group.

An embodiment in which $Ar_5$ to $Ar_7$ in the general formula (2) are at least partially, preferably completely substituted with an "electron acceptor group" is preferable.

$Ar_5$ to $Ar_9$ in the general formula (2) are preferably a phenyl group or a pyridyl group completely substituted with a fluorine atom, a chlorine atom, a cyano group, or a trifluoromethyl group such as a tetrafluoropyridyl group, a tetrafluoro-(trifluoromethyl)phenyl group, a cyano-tetrafluorophenyl group, dichloro-difluoro-(trifluoromethyl)phenyl group, or a pentafluorophenyl group.

The "aromatic heterocyclic group" in the "substituted or unsubstituted aromatic heterocyclic group" represented by $B_1$ in the general formula (3) is preferably a nitrogen-containing aromatic heterocyclic group such as a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzoimidazolyl group, a pyrazolyl group, or a carbolinyl group, more preferably a pyridyl group, a pyrimidinyl group, a quinolyl group, an isoquinolyl group, an indolyl group, a pyrazolyl group, a benzoimidazolyl group, or a carbolinyl group.

p and q in the general formula (3) maintains a relationship that the sum of p and q (p+q) is 9, and p represents 7 or 8, and q represents 1 or 2.

$A_1$ in the general formula (3) is preferably a "divalent group of a substituted or unsubstituted aromatic hydrocarbon" or a "divalent group of a substituted or unsubstituted condensed polycyclic aromatic", more preferably a divalent group that results from the removal of two hydrogen atoms from benzene, biphenyl, naphthalene, or phenanthrene.

As the compound having an anthracene ring structure represented by the general formula (3), a compound having an anthracene ring structure represented by the following general formula (3a), general formula (3b), or general formula (3c) is more preferably used.

[Chemical Formula 10]

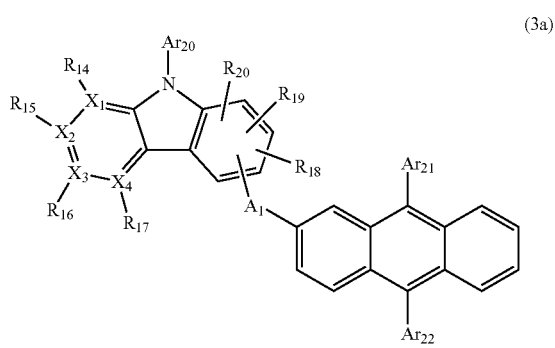

(3a)

(In the formula, $A_1$ represents the same meaning as described in the above general formula (3), $Ar_{20}$, $Ar_{21}$, and $Ar_{22}$ may be the same or different, and represent a substituted or unsubstituted aromatic hydrocarbon group, a substituted or unsubstituted aromatic heterocyclic group, or a substituted or unsubstituted condensed polycyclic aromatic group, $R_{14}$ to $R_{20}$ may be the same or different, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, and may bind to each other via a single bond, a substituted or unsubstituted methylene group, an oxygen atom, or a sulfur atom to form a ring, and $X_1$, $X_2$, $X_3$, and $X_4$ represent a carbon atom or a nitrogen atom, and only one of $X_1$, $X_2$, $X_3$, and $X_4$ is a nitrogen atom, and the nitrogen atom in this case does not have a hydrogen atom or a substituent of $R_{14}$ to $R_{17}$.)

[Chemical Formula 11]

(3b)

(In the formula, $A_1$ represents the same meaning as described in the above general formula (3), and $Ar_{23}$, $Ar_{24}$, and $Ar_{25}$ may be the same or different, and represent a substituted or unsubstituted aromatic hydrocarbon group, a substituted or unsubstituted aromatic heterocyclic group, or a substituted or unsubstituted condensed polycyclic aromatic group.)

[Chemical Formula 12]

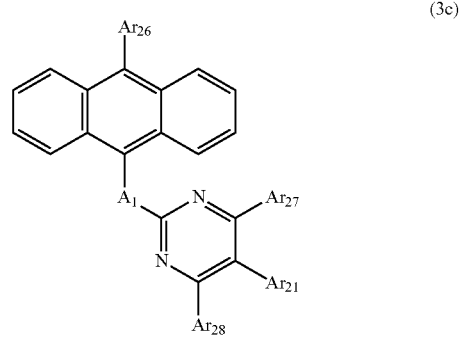

(3c)

(In the formula, $A_1$ represents the same meaning as described in the above general formula (3), $Ar_{26}$, $Ar_{27}$, and $Ar_{28}$ may be the same or different, and represent a substituted or unsubstituted aromatic hydrocarbon group, a substituted or unsubstituted aromatic heterocyclic group, or a substituted or unsubstituted condensed polycyclic aromatic group, $R_{21}$ represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group.)

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{20}$, $Ar_{21}$, and $Ar_{22}$ in the general formula (3a) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

Specific examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_{14}$ to $R_{20}$ in the general formula (3a) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group, and these groups may bind to each other via a single bond, a substituted or unsubstituted methylene group, an oxygen atom, or a sulfur atom to form a ring.

Specific examples of the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_{14}$ to $R_{20}$ in the general formula (3a) include a deuterium atom, a cyano group, a nitro group; halogen atoms such as a fluorine atom, a chlorine atom, a bromine atom, and an iodine atom; linear or branched alkyloxy groups of 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; and other groups, and these substituents may be further substituted with a substituent exemplified above. Further, these substituents may bind to each other via a single bond, a substituted or unsubstituted methylene group, an oxygen atom, or a sulfur atom to form a ring.

Specific examples of the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_{14}$ to $R_{20}$ in the general formula (3a) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_{14}$ to $R_{20}$ in the above general formula (3a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{14}$ to $R_{20}$ in the general formula (3a) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

Specific examples of the "aryloxy group" in the "substituted or unsubstituted aryloxy group" represented by $R_{14}$ to $R_{20}$ in the general formula (3a) include a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group, and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

In the general formula (3a), $X_1$, $X_2$, $X_3$, and $X_4$ represent a carbon atom or a nitrogen atom, and only one of $X_1$, $X_2$, $X_3$, and $X_4$ is a nitrogen atom (the rest are each a carbon atom), and the nitrogen atom in this case does not have a hydrogen atom or a substituent of $R_{14}$ to $R_{17}$. That is, it means that in the case where $X_1$ is a nitrogen atom, $R_{14}$, in the case where $X_2$ is a nitrogen atom, $R_{15}$, in the case where $X_3$ is a nitrogen atom, $R_{16}$, and in the case where $X_4$ is a nitrogen atom, $R_{17}$ is not present.

In the general formula (3a), $X_3$ is preferably a nitrogen atom ($X_1$, $X_2$, and $X_4$ are each a carbon atom), and in this case, a hydrogen atom or a substituent of $R_{16}$ is not present.

Further, as for the bonding position of the linking group $L_1$, $L_1$ preferably binds at a position corresponding to the para position of the nitrogen atom of a pyridoindole ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{23}$, $Ar_{24}$, and $Ar_{25}$ in the general formula (3b) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{26}$, $Ar_{27}$, and $Ar_{28}$ in the general formula (3c) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

Examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_{21}$ in the general formula (3c) include the same groups exemplified as the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_{14}$ to $R_{20}$ in the above general formula (3a).

Further, these groups may have a substituent, and examples of the substituent include the same substituents exemplified as the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_{14}$ to $R_{20}$ in the above general formula (3a), and possible embodiments may also be the same embodiments as the exemplified embodiments.

Examples of the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_{21}$ in the general formula (3c) include the same groups exemplified as the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_{14}$ to $R_{20}$ in the above general formula (3a).

Further, these groups may have a substituent, and examples of the substituent include the same substituents exemplified as the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_{14}$ to $R_{20}$ in the above general formula (3a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{21}$ in the general formula (3c) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

Examples of the "aryloxy group" in the "substituted or unsubstituted aryloxy group" represented by $R_{21}$ in the general formula (3c) include the same groups exemplified as the "aryloxy group" in the "substituted or unsubstituted aryloxy group" represented by $R_{14}$ to $R_{20}$ in the above general formula (3a).

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

$Ar_8$ in the general formula (4) is preferably a phenyl group, a biphenylyl group, a naphthyl group, an anthracenyl group, an acenaphthenyl group, a phenanthrenyl group, a fluorenyl group, an indenyl group, a pyrenyl group, a perylenyl group, a fluoranthenyl group, or a triphenylenyl group, more preferably a phenyl group, a biphenylyl group, a naphthyl group, an anthracenyl group, a phenanthrenyl group, a pyrenyl group, a fluoranthenyl group, or a triphenylenyl group. Here, the phenyl group preferably has a substituted or unsubstituted condensed polycyclic aromatic group as a substituent, more preferably has a substituent selected from a naphthyl group, an anthracenyl group, a phenanthrenyl group, a pyrenyl group, a fluoranthenyl group, or a triphenylenyl group.

$Ar_9$ in the general formula (4) is preferably a phenyl group that has a substituent, and the substituent in this case is preferably an aromatic hydrocarbon group such as a phenyl group, a biphenylyl group, or a terphenylyl group, or a condensed polycyclic aromatic group such as a naphthyl group, an anthracenyl group, an acenaphthenyl group, a phenanthrenyl group, a fluorenyl group, an indenyl group, a pyrenyl group, a perylenyl group, a fluoranthenyl group, or a triphenylenyl group, more preferably a phenyl group, a naphthyl group, an anthracenyl group, a phenanthrenyl group, a pyrenyl group, a fluoranthenyl group, or a triphenylenyl group.

$Ar_{10}$ in the general formula (4) is preferably a phenyl group that has a substituent, and the substituent in this case is preferably an aromatic hydrocarbon group such as a phenyl group, a biphenylyl group, or a terphenylyl group, or a condensed polycyclic aromatic group such as a naphthyl group, an anthracenyl group, an acenaphthenyl group, a phenanthrenyl group, a fluorenyl group, an indenyl group, a pyrenyl group, a perylenyl group, a fluoranthenyl group, or a triphenylenyl group, more preferably a phenyl group, a naphthyl group, an anthracenyl group, a phenanthrenyl group, a pyrenyl group, a fluoranthenyl group, or a triphenylenyl group.

It is preferable that in the general formula (4), $Ar_8$ and $Ar_9$ are not the same from the viewpoint of stability as a thin film. Here, when $Ar_8$ and $Ar_9$ are the same group, they may have a different substituent or the substitution position may be different.

In the general formula (4), $Ar_9$ and $Ar_{10}$ may be the same group, however, there is a risk that crystallization is likely to occur due to an increase in symmetry of the molecule as a whole, and from the viewpoint of stability as a thin film, $Ar_9$ and $Ar_{10}$ are preferably different groups, and $Ar_9$ and $Ar_{10}$ are not simultaneously a hydrogen atom.

Further, it is preferable that one of $Ar_9$ and $Ar_{10}$ is a hydrogen atom.

Example of the compound having a pyrimidine ring structure represented by the general formula (4) include compounds having a pyrimidine ring structure represented by the following general formula (4a) and general formula (4b) in which a bonding pattern of a substituent is different.

[Chemical Formula 13]

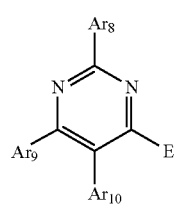

(4a)

(In the formula, $Ar_8$, $Ar_9$, $Ar_{10}$, and E represent the same meanings as described in the above general formula (4).)

[Chemical Formula 14]

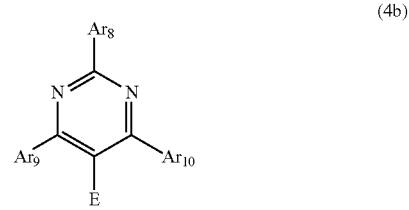

(4b)

(In the formula, $Ar_8$, $Ar_9$, $Ar_{10}$, and E represent the same meanings as described in the above general formula (4).)

$Ar_{11}$ in the structural formula (5) is preferably a nitrogen-containing heterocyclic group such as a triazinyl group, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzoimidazolyl group, a pyrazolyl group, a naphthyridinyl group, a phenanthrolinyl group, an acridinyl group, or a carbolinyl group, more preferably a triazinyl group, a pyridyl group, a pyrimidinyl group, a quinolyl group, an isoquinolyl group, an indolyl group, a quinoxalinyl group, a benzoimidazolyl group, a naphthyridinyl group, a phenanthrolinyl group, or an acridinyl group, particularly preferably a pyridyl group, a pyrimidinyl group, a quinolyl group, an isoquinolyl group, an indolyl group, a quinoxalinyl group, a benzoimidazolyl group, a phenanthrolinyl group, or an acridinyl group.

In the structural formula (5), a bonding position of $Ar_{11}$ in the benzene ring is preferably a meta position with respect to a bonding position of the pyrimidine ring shown in the general formula (4) as shown in the following structural formula (5a) from the viewpoint of stability as a thin film.

[Chemical Formula 15]

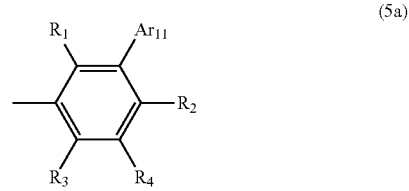

(5a)

(In the formula, $Ar_{11}$, and $R_1$ to $R_4$ represent the same meanings as described in the above structural formula (5).)

$Ar_{12}$ and $Ar_{13}$ in the general formula (6) are preferably a "substituted or unsubstituted aromatic hydrocarbon group", a "substituted or unsubstituted condensed polycyclic aromatic group", or a pyridyl group, a dibenzothienyl group, a carbazolyl group, or a dibenzofuranyl group, more preferably a phenyl group, a biphenylyl group, a terphenylyl group, a naphthyl group, an anthracenyl group, a phenanthrenyl group, a fluorenyl group, an indenyl group, a pyrenyl group, a pyridyl group, a carbazolyl group, or a dibenzofuranyl group, particularly preferably a phenyl group, a biphenylyl group, a terphenylyl group, a naphthyl group, an anthracenyl group, a phenanthrenyl group, or a fluorenyl group.

Then, the substituent that these groups may have is preferably an "aromatic hydrocarbon group", an "aromatic heterocyclic group", or a "condensed polycyclic aromatic group" such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a pyridyl group, a triazinyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, or an acridinyl group, more preferably a phenyl group, a biphenylyl group, a naphthyl group, an anthracenyl group, a phenanthrenyl group, a fluorenyl group, a pyrenyl group, a pyridyl group, a triazinyl group, a pyrimidinyl group, a quinolyl group, an isoquinolyl group, an indolyl group, a carbazolyl group, a quinoxalinyl group, a benzoimidazolyl group, a pyrazolyl group, a phenanthrolinyl group, or an acridinyl group, particularly preferably a phenyl group, a naphthyl group, an anthracenyl group, a pyridyl group, a quinolyl group, or an isoquinolyl group.

$L_1$ in the general formula (6) is preferably a "divalent group of a substituted or unsubstituted aromatic hydrocarbon", a "divalent group of a substituted or unsubstituted condensed polycyclic aromatic", or a pyridylene group or a bipyridylene group, more preferably a divalent group derived from benzene, biphenyl, naphthalene, anthracene, fluorene, phenanthrene, pyrene, or pyridine, particularly preferably a divalent group derived from benzene, naphthalene, or pyridine.

$L_2$ in the general formula (6) is preferably a single bond, or a divalent group derived from naphthalene, anthracene, fluorene, phenanthrene, or pyrene, more preferably a single bond, or a divalent group derived from naphthalene or anthracene.

$B_2$ in the general formula (6) is preferably a nitrogen-containing aromatic heterocyclic group such as a pyridyl group, a bipyridyl group, a triazinyl group, a pyrimidinyl group, a pyrrolyl group, a quinolyl group, an isoquinolyl group, an indolyl group, a carbazolyl group, a carbolinyl group, a benzoxazolyl group, a benzothiazolyl group, a quinoxalinyl group, a benzoimidazolyl group, a pyrazolyl group, a naphthyridinyl group, a phenanthrolinyl group, or an acridinyl group, more preferably a pyridyl group, a bipyridyl group, a pyrimidinyl group, a quinolyl group, an isoquinolyl group, an indolyl group, a carbolinyl group, a quinoxalinyl group, a benzoimidazolyl group, a naphthyridinyl group, or a phenanthrolinyl group, particularly preferably a pyridyl group, a quinolyl group, or an isoquinolyl group.

In the general formula (6), when $L_1$ is a divalent group that results from the removal of two hydrogen atoms from substituted or unsubstituted benzene and $L_2$ is a single bond, $B_2$ is preferably a nitrogen-containing aromatic heterocyclic group having a condensed polycyclic structure such as a pyridyl group, a bipyridyl group, a quinolyl group, an isoquinolyl group, an indolyl group, a carbazolyl group, a carbolinyl group, a benzoxazolyl group, a benzothiazolyl group, a quinoxalinyl group, a benzoimidazolyl group, a naphthyridinyl group, a phenanthrolinyl group, or an acridinyl group, more preferably a pyridyl group, a bipyridyl group, a quinolyl group, an isoquinolyl group, an indolyl group, a carbolinyl group, a quinoxalinyl group, a benzo-imidazolyl group, a naphthyridinyl group, or a phenanthrolinyl group, particularly preferably a pyridyl group, a bipyridyl group, a quinolyl group, or an isoquinolyl group.

In the general formula (6), when $B_2$ is a pyridyl group or a bipyridyl group and $L_2$ is a single bond, $L_1$ is more preferably a divalent group that results from the removal of two hydrogen atoms from benzene, biphenyl, naphthalene, anthracene, fluorene, phenanthrene, or pyrene, or a single bond, particularly preferably a divalent group that results from the removal of two hydrogen atoms from benzene or biphenyl, or a single bond.

$A_2$ in the general formula (7) is preferably a "divalent group of a substituted or unsubstituted aromatic hydrocarbon" or a single bond, more preferably a divalent group that results from the removal of two hydrogen atoms from benzene, biphenyl, or naphthalene, or a single bond, particularly preferably a single bond.

$Ar_{14}$ and $Ar_{15}$ in the general formula (7) are preferably a phenyl group, a biphenylyl group, a naphthyl group, a fluorenyl group, an indenyl group, a pyridyl group, a dibenzofuranyl group, or a pyridobenzofuranyl group.

$Ar_{14}$ and $Ar_{15}$ in the general formula (7) may bind to each other directly or through substituents included in these groups via a single bond, a substituted or unsubstituted methylene group, an oxygen atom, or a sulfur atom to form a ring.

It is preferable that at least one of $R_5$ to $R_8$ in the general formula (7) is a "disubstituted amino group substituted with a group selected from an aromatic hydrocarbon group, an aromatic heterocyclic group, or a condensed polycyclic aromatic group", and the "aromatic hydrocarbon group", the "aromatic heterocyclic group", or the "condensed polycyclic aromatic group" in this case is preferably a phenyl group, a biphenylyl group, a naphthyl group, a fluorenyl group, an indenyl group, a pyridyl group, a dibenzofuranyl group, or a pyridobenzofuranyl group.

An embodiment in which adjacent two or all of $R_5$ to $R_8$ in the general formula (7) are a vinyl group and adjacent two vinyl groups bind to each other via a single bond to form a condensed ring, that is, an embodiment in which a naphthalene ring or a phenanthrene ring is formed along with the benzene ring to which $R_5$ to $R_8$ bind is also preferable.

An embodiment in which in the general formula (7), one of $R_5$ to $R_8$ is an "aromatic hydrocarbon group" and binds to the benzene ring to which $R_5$ to $R_8$ bind via a substituted or unsubstituted methylene group, an oxygen atom, or a sulfur atom to form a ring is preferable. An embodiment in which the "aromatic hydrocarbon group" in this case is a phenyl group and binds to the benzene ring to which $R_5$ to $R_8$ bind via an oxygen atom or a sulfur atom to form a ring, that is, an embodiment in which a dibenzofuran ring or a dibenzothiophene ring is formed along with the benzene ring to which $R_5$ to $R_8$ bind is particularly preferable.

An embodiment in which in the general formula (7), one of $R_9$ to $R_{11}$ is an "aromatic hydrocarbon group" and binds to the benzene ring to which $R_9$ to $R_{11}$ bind via a substituted or unsubstituted methylene group, an oxygen atom, or a sulfur atom to form a ring is preferable. An embodiment in which the "aromatic hydrocarbon group" in this case is a phenyl group and binds to the benzene ring to which $R_9$ to $R_{11}$ bind via an oxygen atom or a sulfur atom to form a ring, that is, an embodiment in which a dibenzofuran ring or a dibenzothiophene ring is formed is particularly preferable.

As described above, in the amine derivatives having a condensed ring structure represented by the general formula (7), as the embodiment in which these groups represented by $R_5$ to $R_{11}$ bind to each other to form a ring, or the embodiment in which $R_5$ to $R_{11}$ bind to the benzene ring to which $R_5$ to $R_{11}$ bind to form a ring, an embodiment represented by the following general formula (7a-a), (7a-b), (7b-a), (7b-b), (7b-c), (7b-d), (7c-a), or (7c-b) is preferably used.

[Chemical Formula 16]

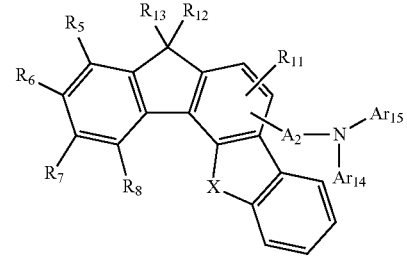
(7a-a)

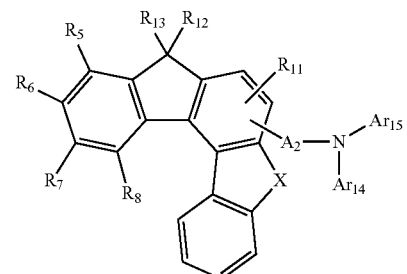
(7a-b)

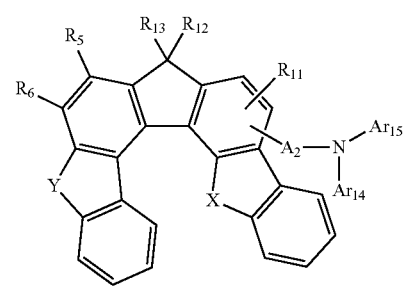
(7b-a)

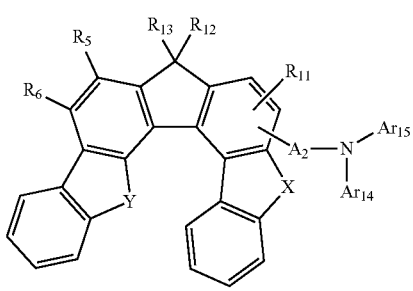
(7b-b)

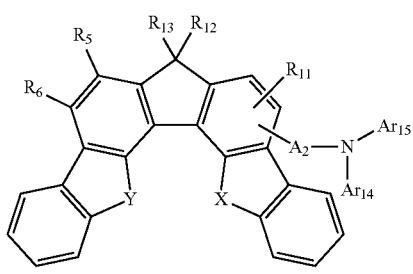
(7b-c)

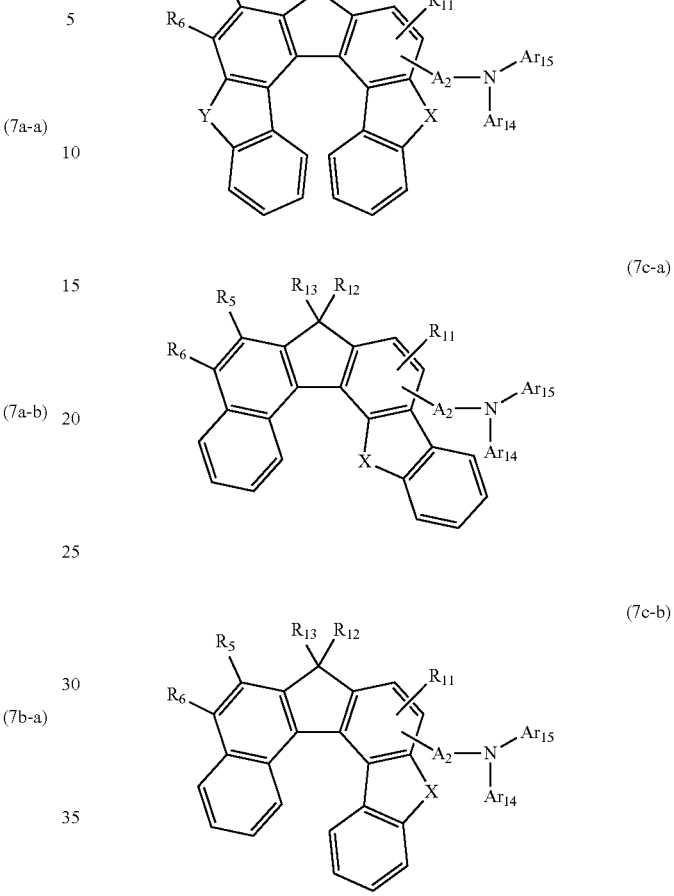
(7b-d)
(7c-a)
(7c-b)

(In the formula, X and Y may be the same or different, and represent an oxygen atom or a sulfur atom, $A_2$, $Ar_{14}$, $Ar_{15}$, $R_5$ to $R_8$, $R_{11}$, and $R_{12}$ to $R_{13}$ represent the same meanings as described in the above general formula (7).)

$R_{12}$ and $R_{13}$ in the general formula (7) are preferably a "substituted or unsubstituted aromatic hydrocarbon group", a "substituted or unsubstituted oxygen-containing aromatic heterocyclic group", or a "substituted or unsubstituted condensed polycyclic aromatic group", more preferably a phenyl group, a naphthyl group, a phenanthrenyl group, a pyridyl group, a quinolyl group, an isoquinolyl group, or a dibenzofuranyl group, particularly preferably a phenyl group.

Then, an embodiment in which $R_{12}$ and $R_{13}$ bind to each other via a single bond, or a linking group such as a substituted or unsubstituted methylene group, an oxygen atom, a sulfur atom, or a monosubstituted amino group to form a ring is preferable, and an embodiment in which $R_{12}$ and $R_{13}$ bind to each other via a single bond is particularly preferable.

As described above, in the amine derivatives having a condensed ring structure represented by the general formula (7), as the embodiment in which $R_{12}$ and $R_{13}$ bind to each other to form a ring, an embodiment represented by the following general formula (7a-a1), (7a-b1), (7b-a1), (7b-b1), (7b-c1), (7b-d1), (7c-a1), or (7c-b1) is preferably used.

[Chemical Formula 17]

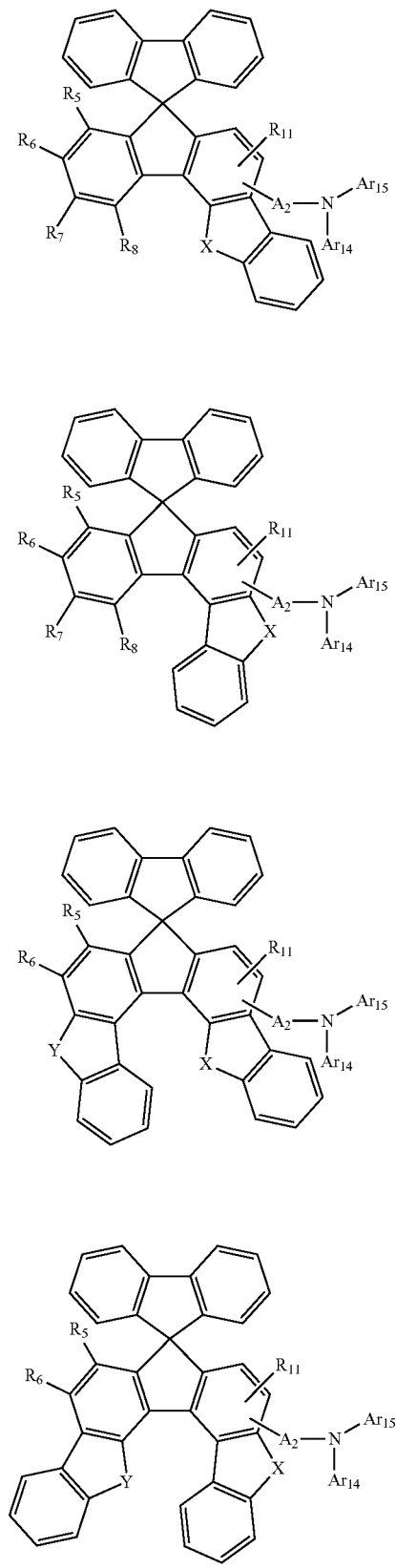

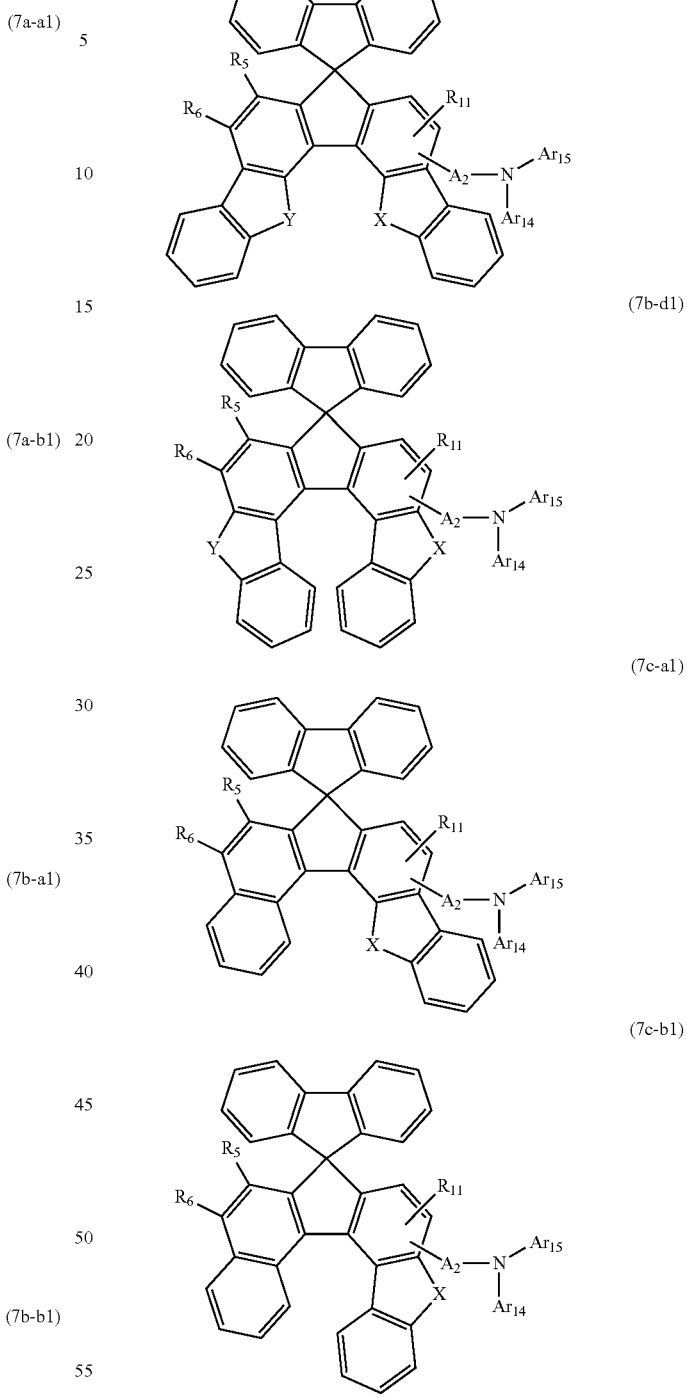

(In the formula, X and Y may be the same or different, and represent an oxygen atom or a sulfur atom, and $A_2$, $Ar_{14}$, $Ar_{15}$, $R_5$ to $R_8$, and $R_{11}$ represent the same meanings as described in the above general formula (7).)

The arylamine compounds of the general formula (1), for preferred use in the organic EL device of the present invention, can be used as a constitutive material of a hole injection layer or a hole transport layer of an organic EL device. The arylamine compounds of the general formula (1)

have high hole mobility and are therefore preferred compounds as material of a hole injection layer or a hole transport layer.

The radialene derivatives of the general formula (2) for preferred use in the organic EL device of the present invention are preferred compounds as a p-doping material into a material commonly used for a hole injection layer or a hole transport layer of an organic EL device.

The compounds of the general formula (3) having an anthracene ring structure, for preferable use in the organic EL device of the present invention, are preferred compounds as a constitutive material of an electron transport layer of an organic EL device.

The compounds of the general formula (4) having a pyrimidine ring structure, for preferable use in the organic EL device of the present invention, are preferred compounds as a constitutive material of an electron transport layer of an organic EL device.

The compounds of the general formula (6) having a benzotriazole ring structure, for preferable use in the organic EL device of the present invention, are preferred compounds as a constitutive material of an electron transport layer of an organic EL device.

The amine derivatives of the general formula (7) having a condensed ring structure, for preferred use in the organic EL device of the present invention, can be used as a constitutive material of a light emitting layer of an organic EL device. The amine derivatives of the general formula (2) having a condensed ring structure excel in luminous efficiency compared with conventional materials and are therefore preferred compounds as dopant material of a light emitting layer.

In the organic EL device of the present invention, materials for an organic EL device having excellent hole injection and transport performances, stability as a thin film, and durability are combined while taking carrier balance into consideration, and therefore, compared with the conventional organic EL devices, hole transport efficiency to the hole transport layer from the anode is improved (and further, a specific arylamine compound (having a specific structure) is used in the hole transport layer), and as a result, luminous efficiency is improved and also durability of the organic EL device can be improved while maintaining low driving voltage.

Thus, an organic EL device having low driving voltage, high luminous efficiency, and a long lifetime can be attained.

Effects of the Invention

The organic EL device of the present invention can achieve an organic EL device having excellent hole injection and transport performances, low driving voltage, and high luminous efficiency by selecting a specific arylamine compound (having a specific structure) capable of effectively exhibiting hole injection and transport roles as a material of a hole injection layer and p-doping the compound with an electron acceptor so that holes can be efficiently injected and transported into a hole transport layer from an electrode, and thus, hole injection and transport efficiency into a light emitting layer can be improved.

Further, an organic EL device having low driving voltage, high luminous efficiency, and a long lifetime can be realized by selecting a specific arylamine compound (having a specific structure) without p-doping as a material of the hole transport layer, and combining the compound so that carrier balance can be refined.

According to the present invention, luminous efficiency, particularly durability can be improved while maintaining low driving voltage of the conventional organic EL device.

BRIEF DESCRIPTION OF THE DRAWINGS

FIG. 1 is a diagram illustrating the configuration of the organic EL devices of Examples 61 and 72 and Comparative Examples 1 to 8.

MODE FOR CARRYING OUT THE INVENTION

The following presents specific examples of preferred compounds among the arylamine compounds of the general formula (1) preferably used in the organic EL device of the present invention. The present invention, however, is not restricted to these compounds.

[Chemical Formula 18]

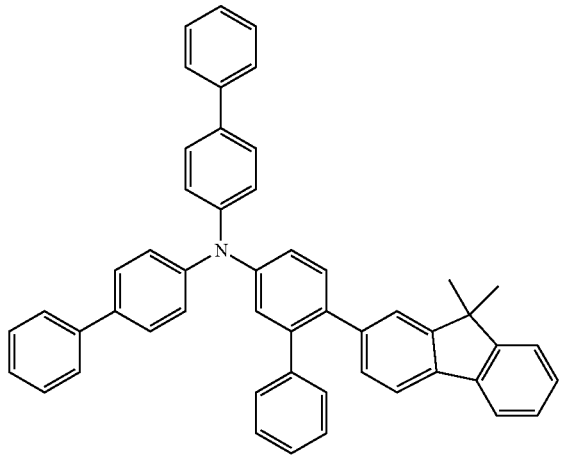

(1-1)

[Chemical Formula 19]

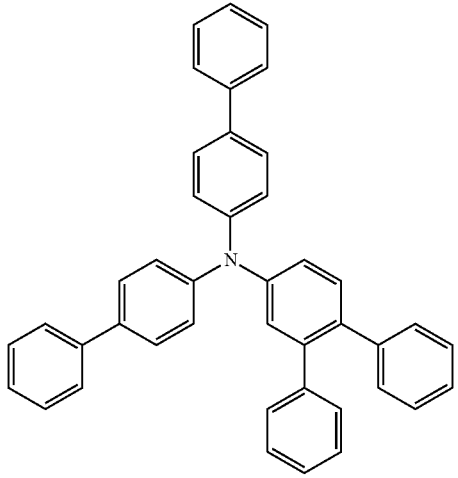

(1-2)

[Chemical Formula 20]
(1-3)
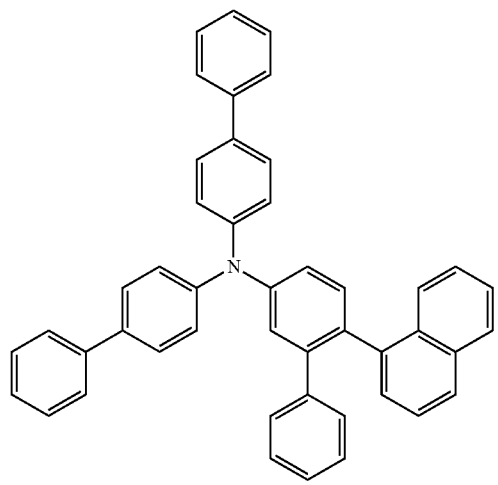
[Chemical Formula 21]
(1-4)
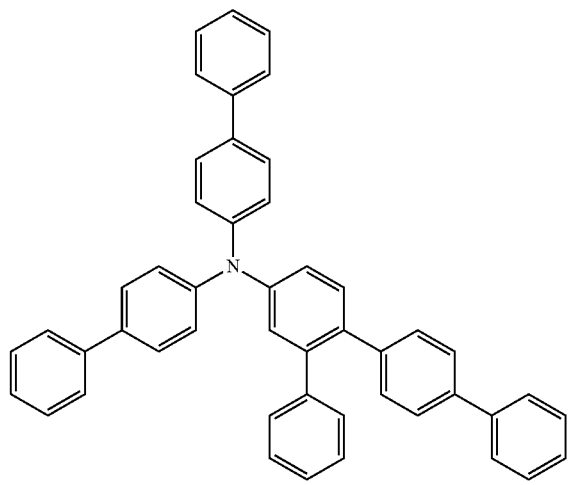
[Chemical Formula 22]
(1-5)
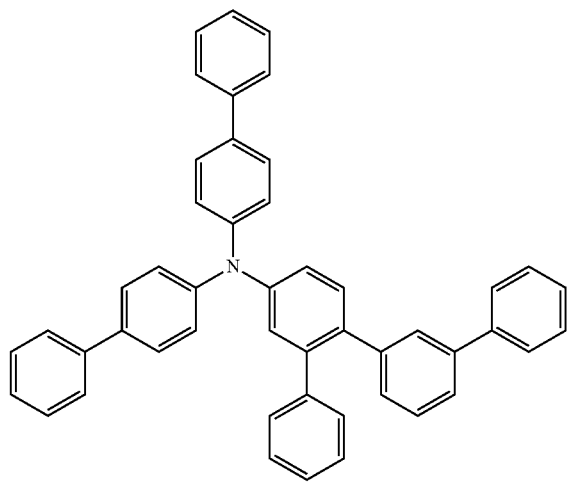
[Chemical Formula 23]
(1-6)
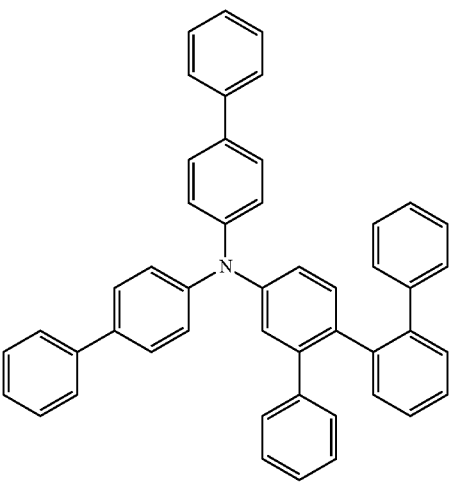
[Chemical Formula 24]
(1-7)
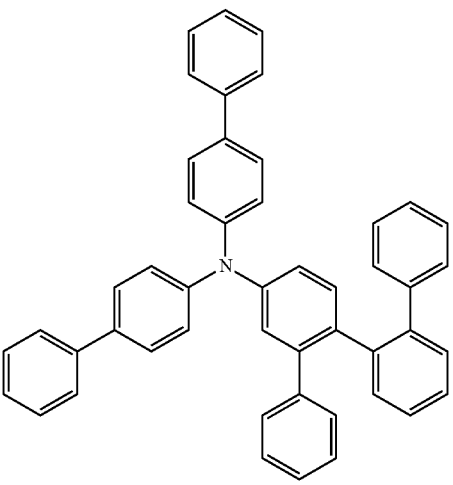
[Chemical Formula 25]
(1-8)
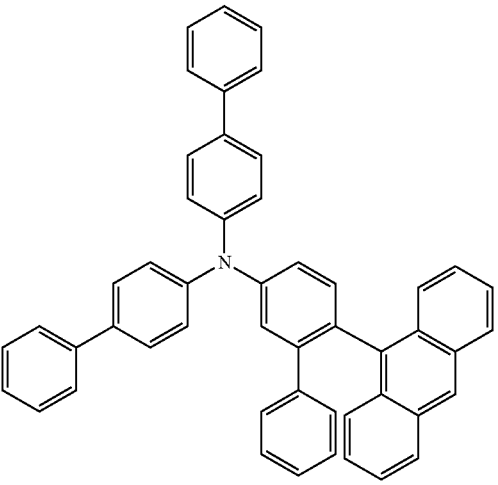

[Chemical Formula 26]
(1-9)
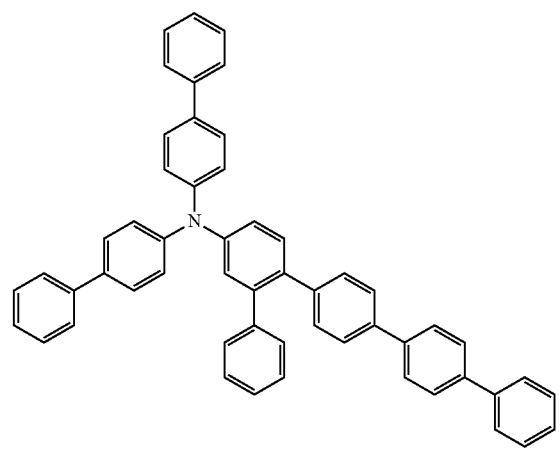
[Chemical Formula 27]
(1-10)
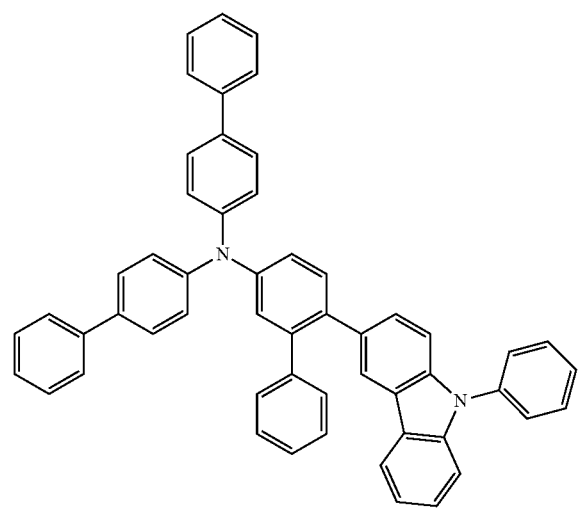
[Chemical Formula 28]
(1-11)
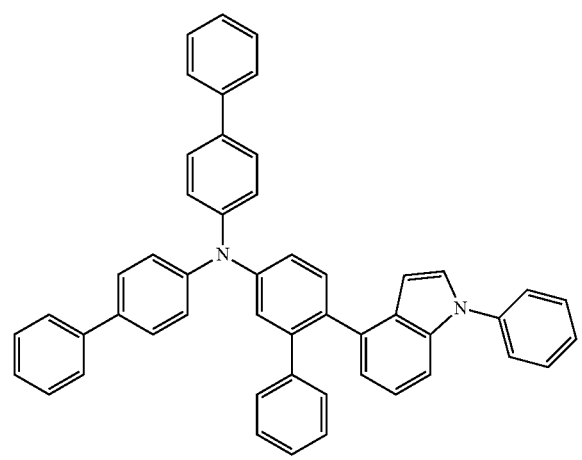
[Chemical Formula 29]
(1-12)
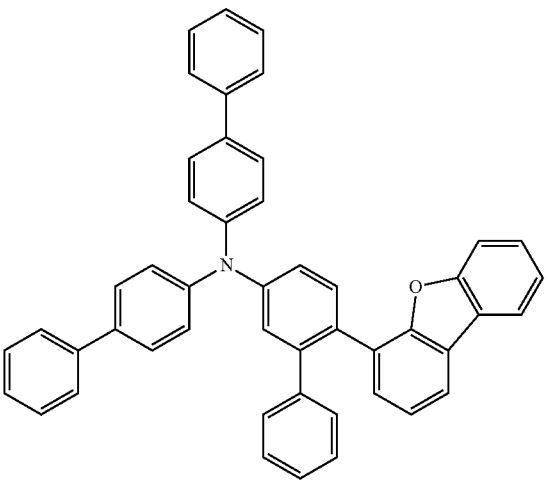
[Chemical Formula 30]
(1-13)
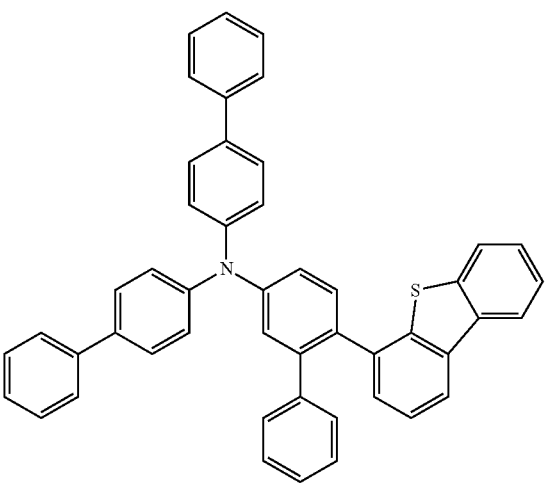
[Chemical Formula 31]
(1-14)
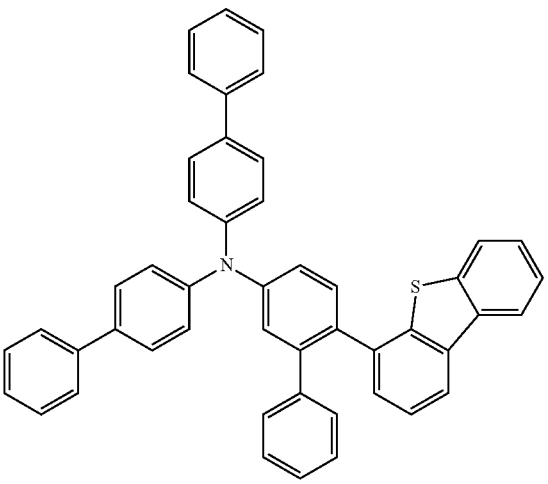

[Chemical Formula 32]
(1-15)
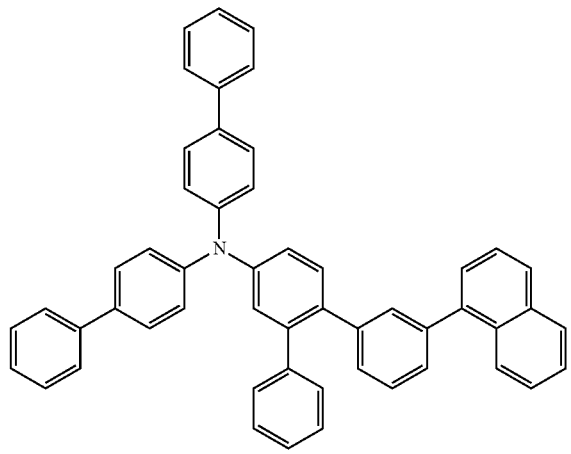
[Chemical Formula 33]
(1-16)
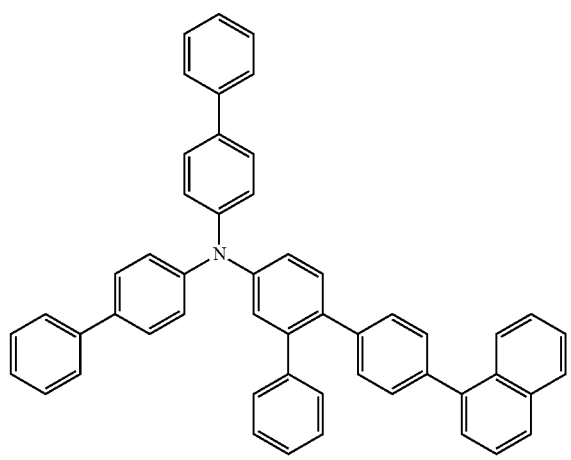
[Chemical Formula 34]
(1-17)
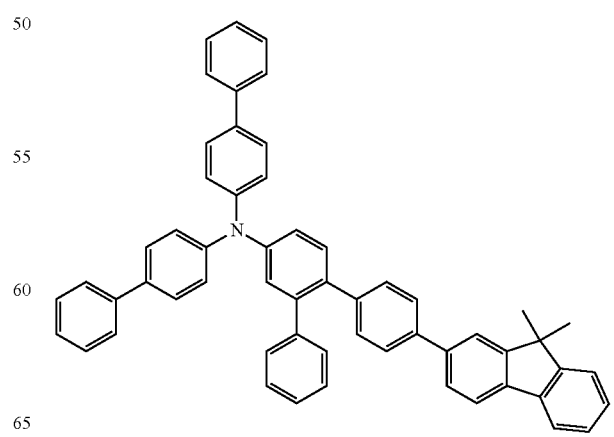
[Chemical Formula 35]
(1-18)
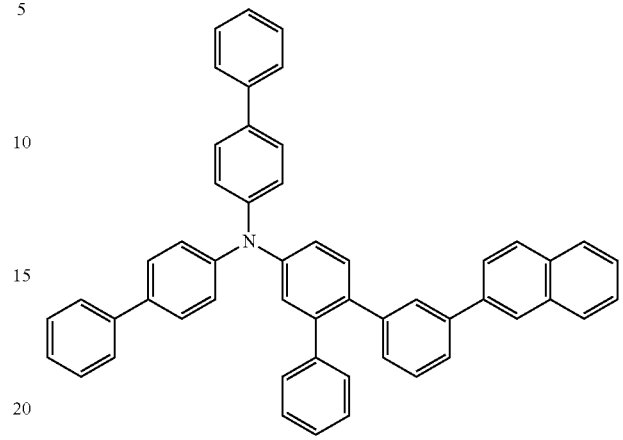
[Chemical Formula 36]
(1-19)
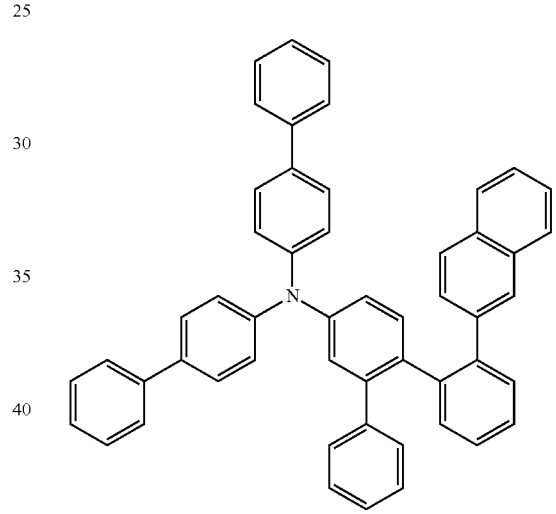
[Chemical Formula 37]
(1-20)

-continued
[Chemical Formula 38]
(1-21)
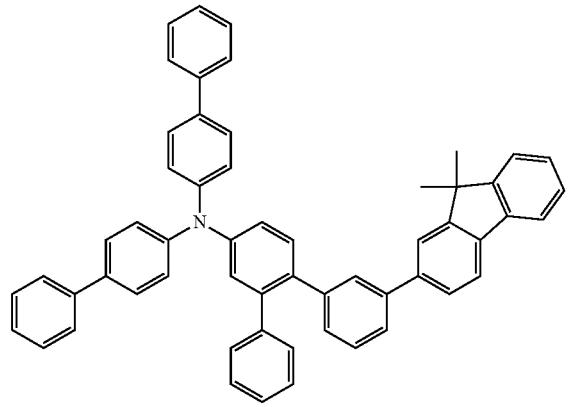
[Chemical Formula 39]
(1-22)
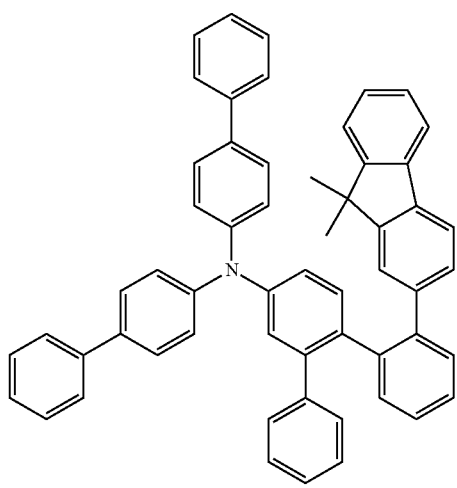
[Chemical Formula 40]
(1-23)
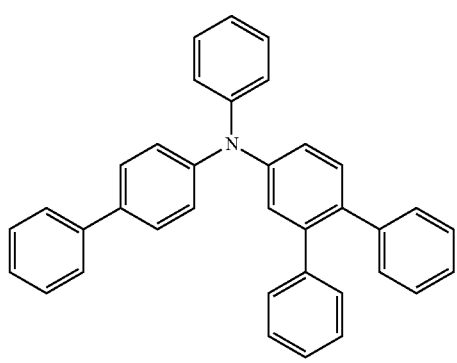
[Chemical Formula 41]
(1-24)
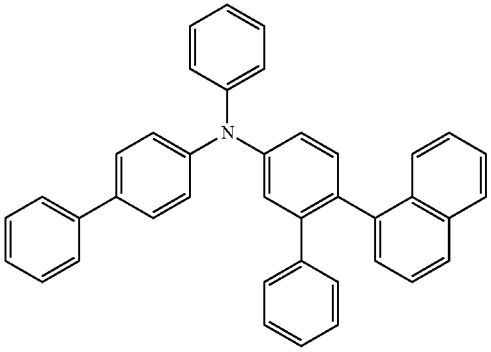
[Chemical Formula 42]
(1-25)
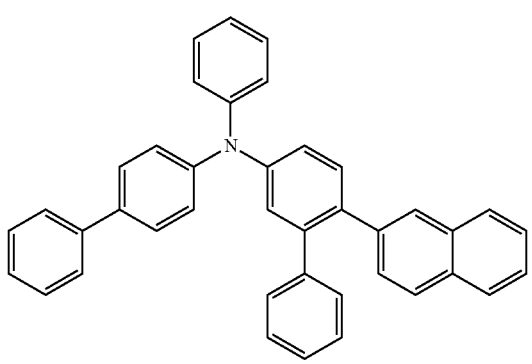
[Chemical Formula 43]
(1-26)
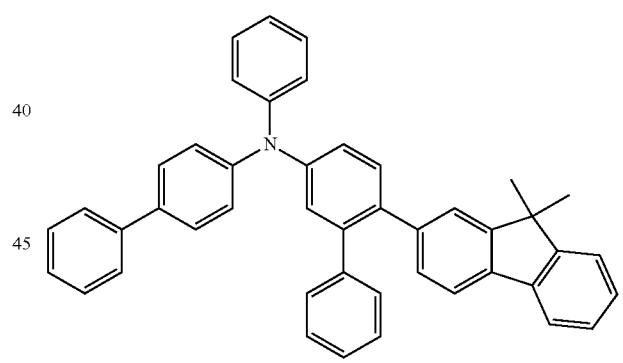
[Chemical Formula 44]
(1-27)
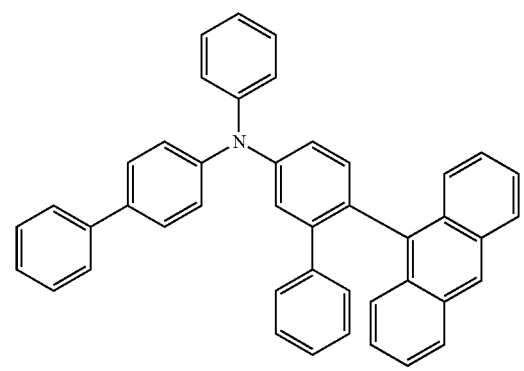

[Chemical Formula 45] (1-28)
[Chemical Formula 46] (1-29)
[Chemical Formula 47] (1-30)
[Chemical Formula 48] (1-31)
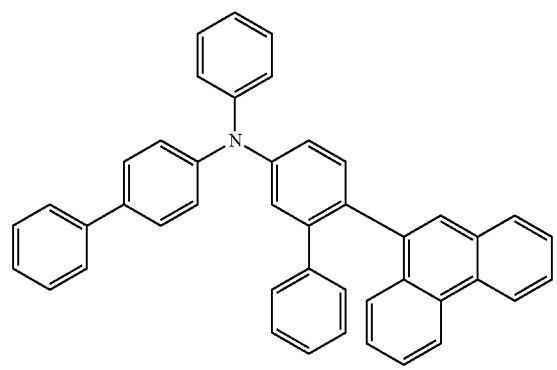
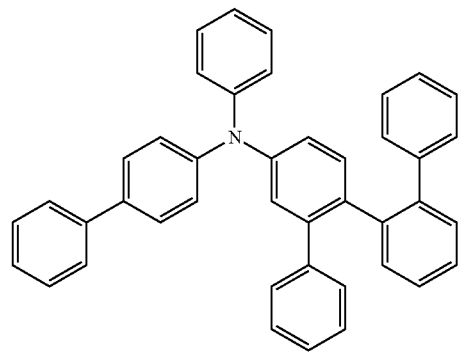
[Chemical Formula 49] (1-32)
[Chemical Formula 50] (1-33)
[Chemical Formula 51] (1-34)
[Chemical Formula 52] (1-35)
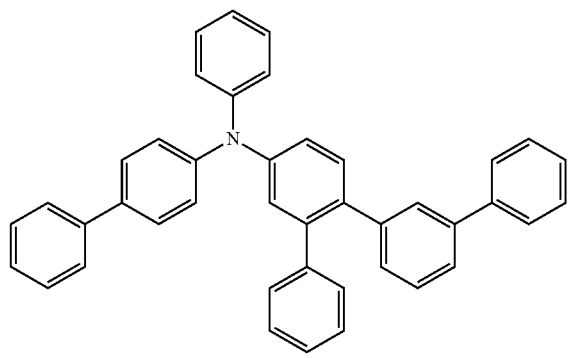
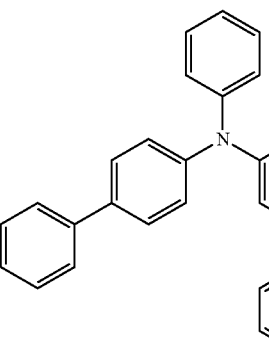

[Chemical Formula 53]
(1-36)
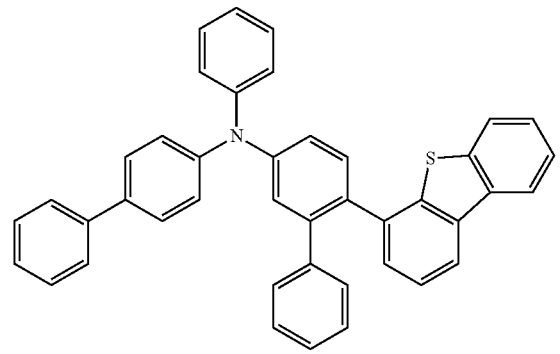
[Chemical Formula 54]
(1-37)
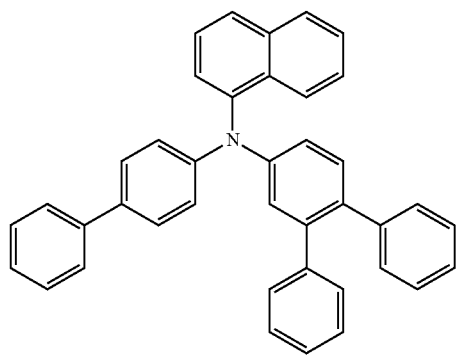
[Chemical Formula 55]
(1-38)
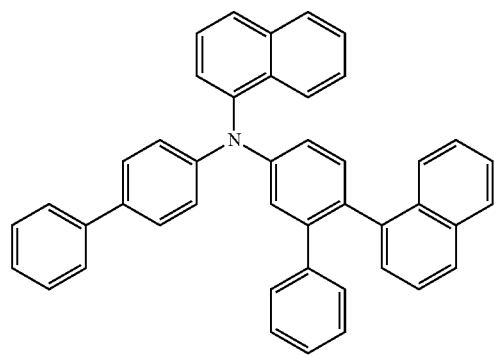
[Chemical Formula 56]
(1-39)
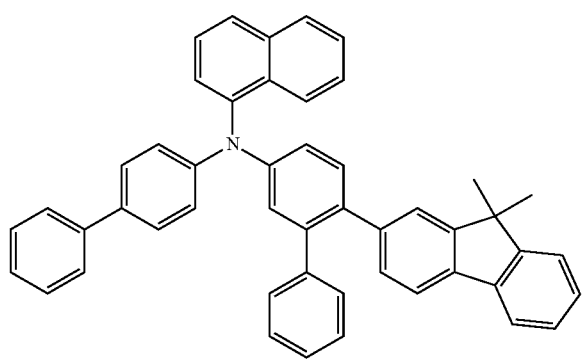
[Chemical Formula 57]
(1-40)
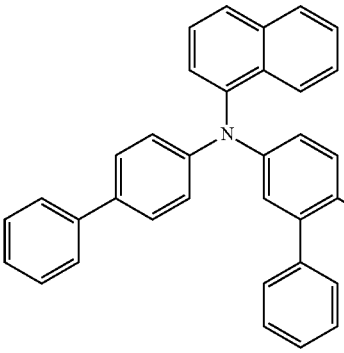
[Chemical Formula 58]
(1-41)
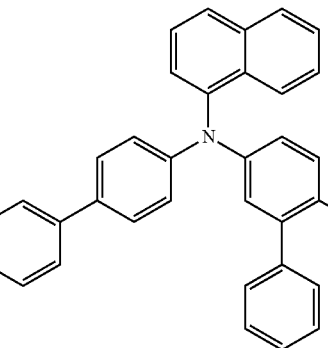
[Chemical Formula 59]
(1-42)
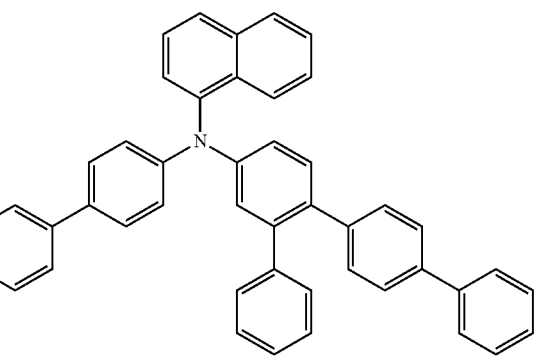
[Chemical Formula 60]
(1-43)
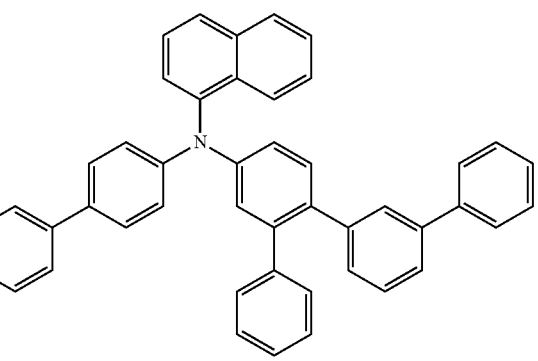

[Chemical Formula 61]
(1-44)
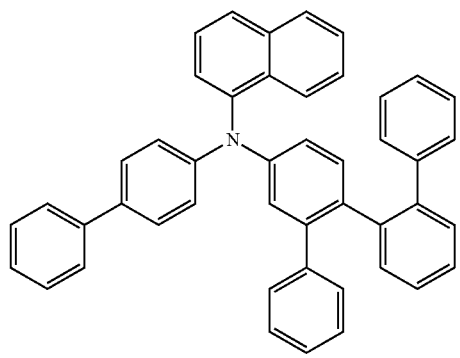
[Chemical Formula 62]
(1-45)
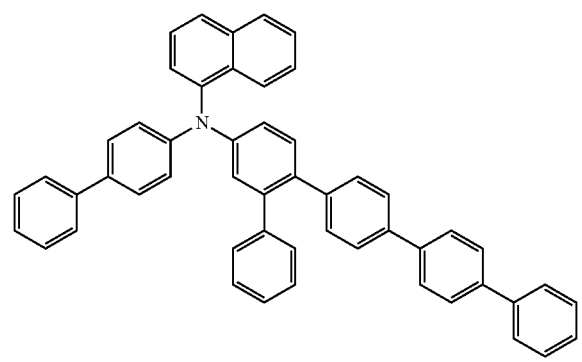
[Chemical Formula 63]
(1-46)
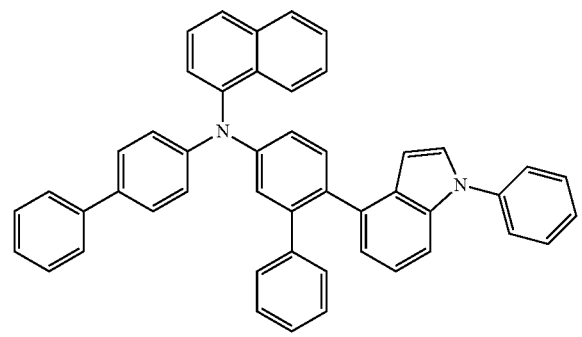
[Chemical Formula 64]
(1-47)
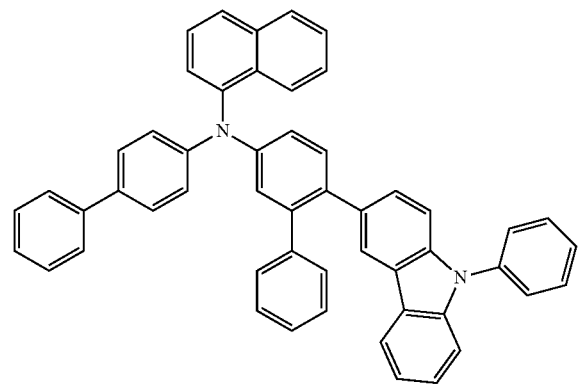
[Chemical Formula 65]
(1-48)
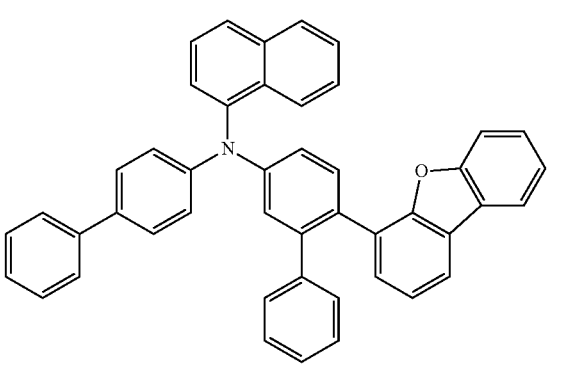
[Chemical Formula 66]
(1-49)
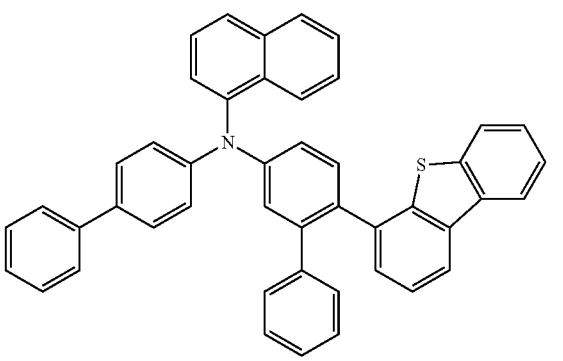
[Chemical Formula 67]
(1-50)
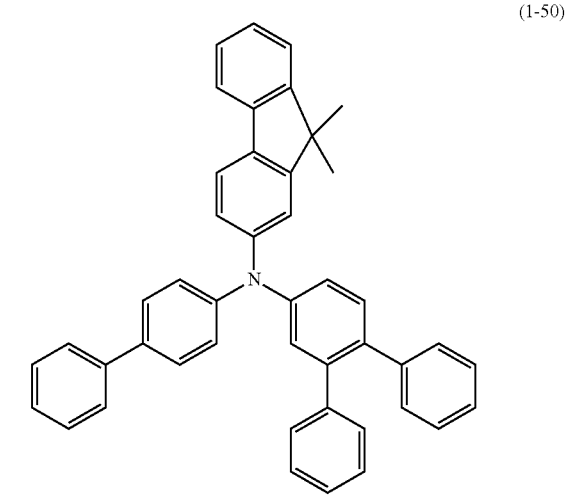

[Chemical Formula 68]
(1-51)
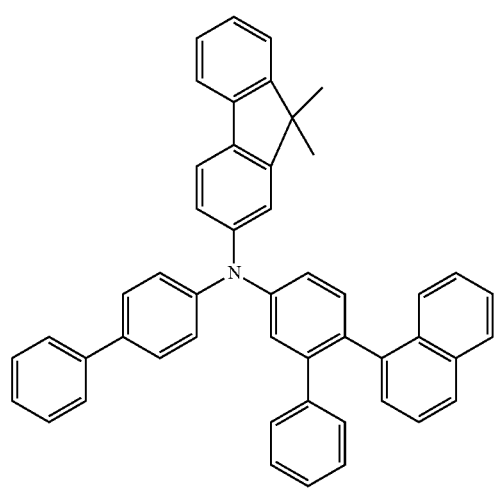
[Chemical Formula 69]
(1-52)
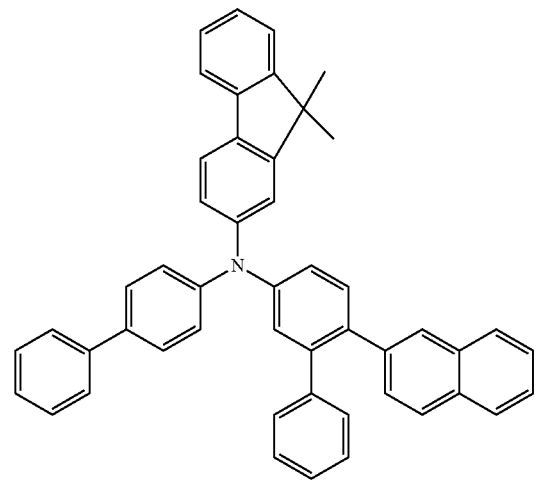
[Chemical Formula 70]
(1-53)
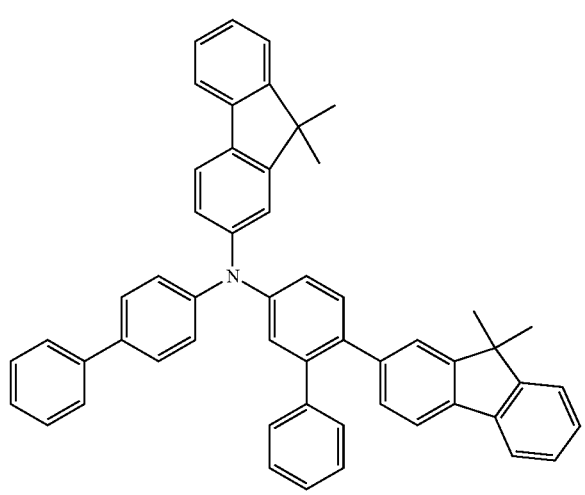
[Chemical Formula 71]
(1-54)
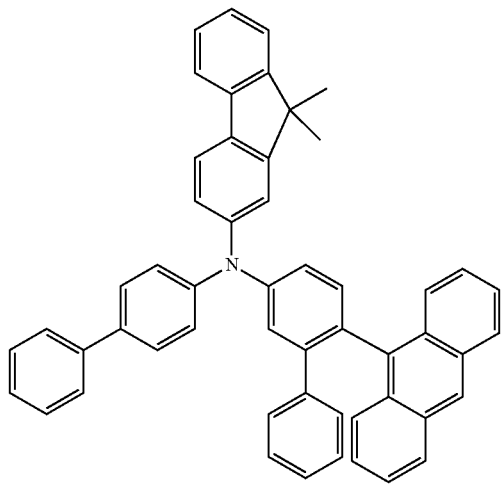
[Chemical Formula 72]
(1-55)
[Chemical Formula 73]
(1-56)
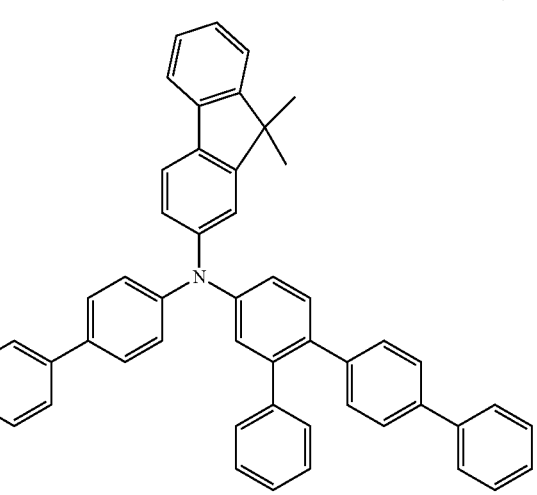

[Chemical Formula 74]
(1-57)
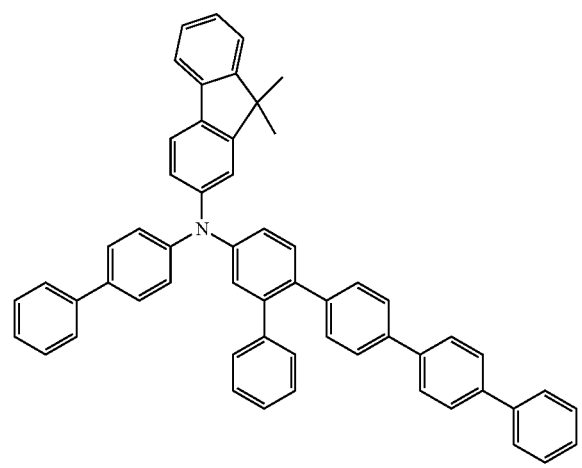
[Chemical Formula 75]
(1-58)
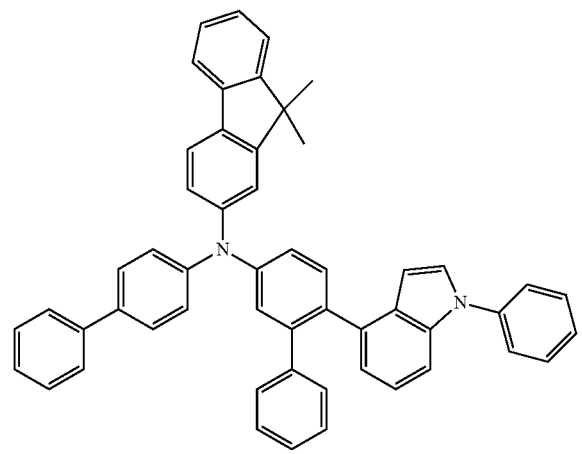
[Chemical Formula 76]
(1-59)
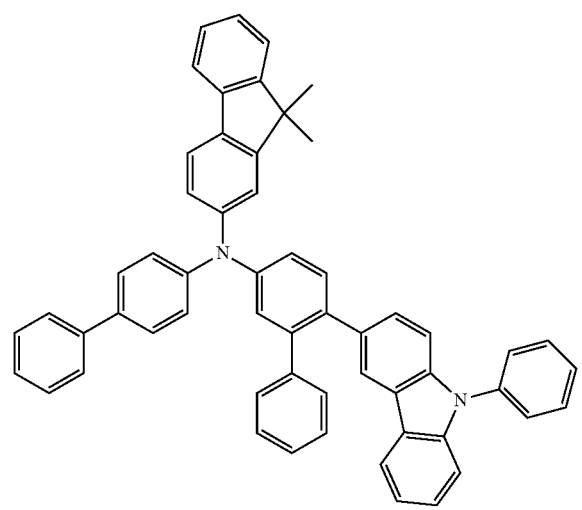
[Chemical Formula 77]
(1-60)
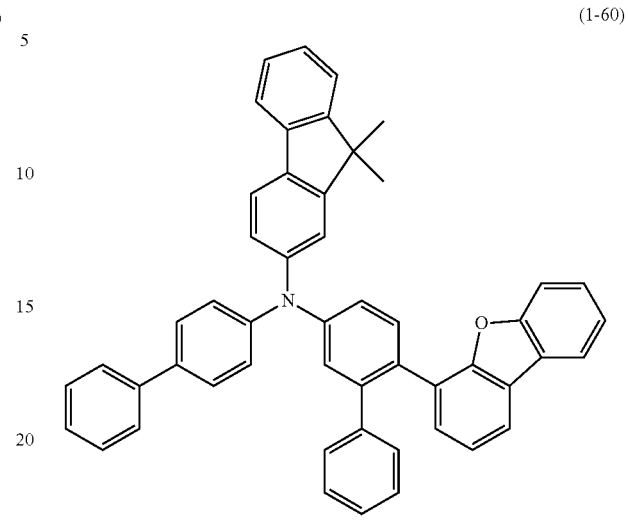
[Chemical Formula 78]
(1-61)
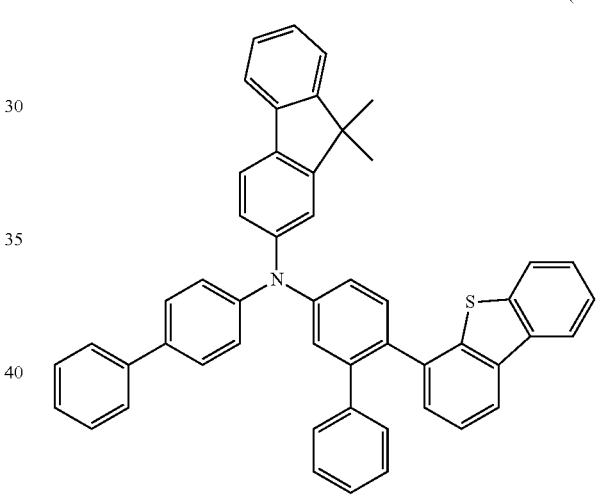
[Chemical Formula 79]
(1-62)
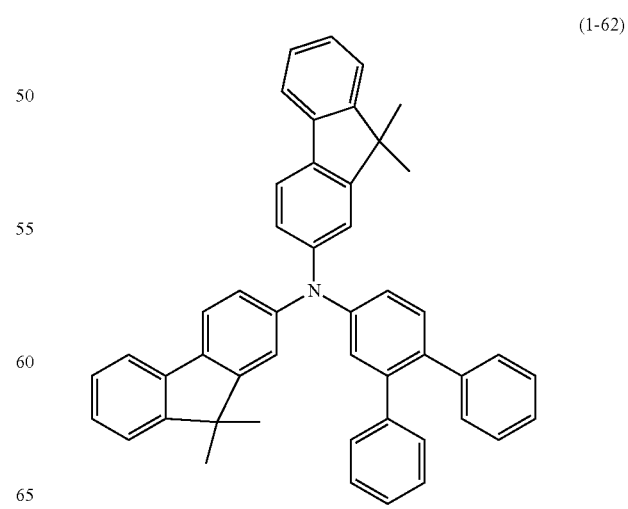

[Chemical Formula 80]
(1-63)
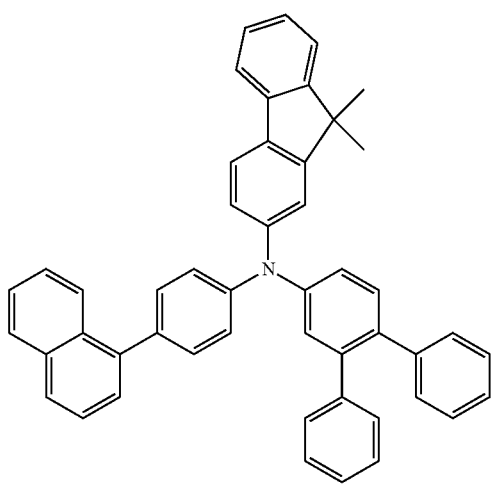
[Chemical Formula 81]
(1-64)
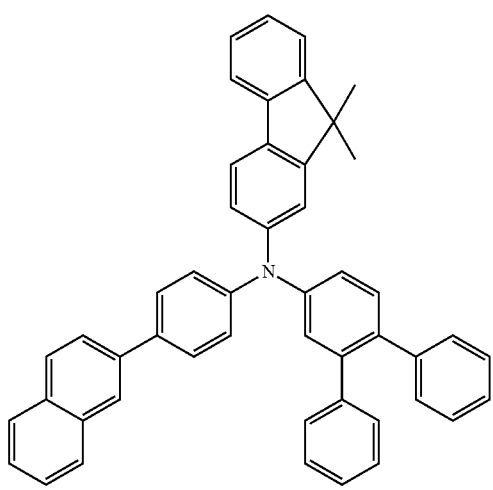
[Chemical Formula 82]
(1-65)
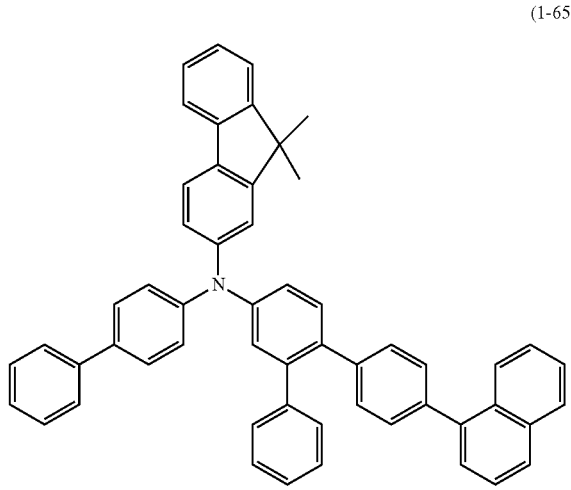
[Chemical Formula 83]
(1-66)
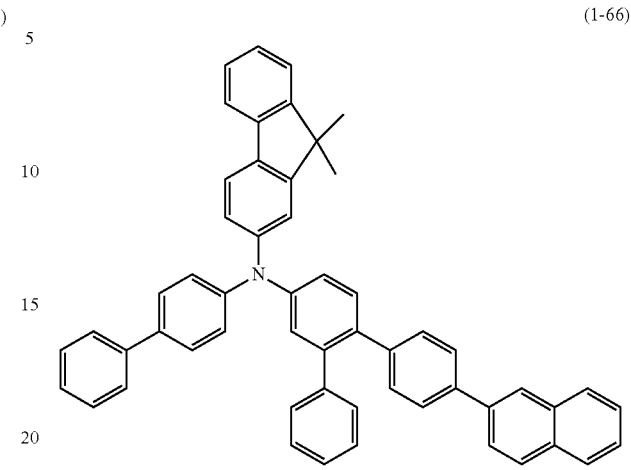
[Chemical Formula 84]
(1-67)
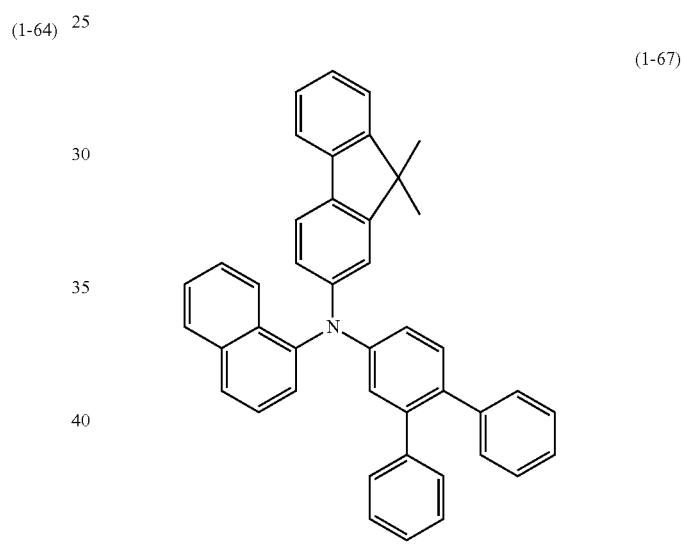
[Chemical Formula 85]
(1-68)
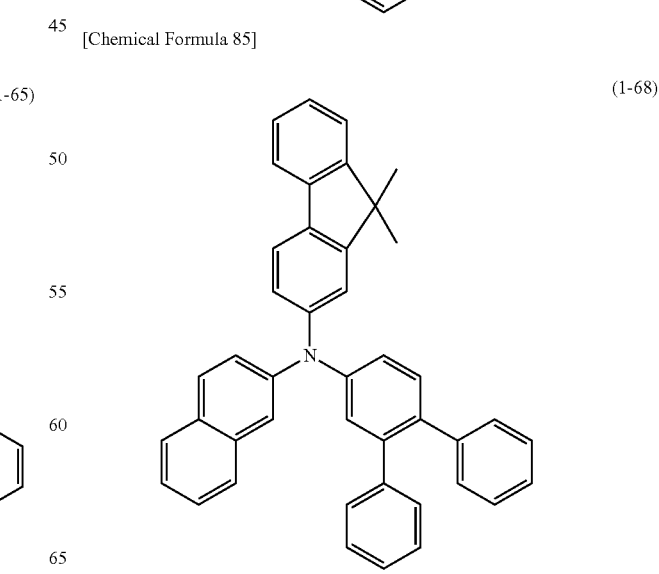

[Chemical Formula 86]
(1-69)
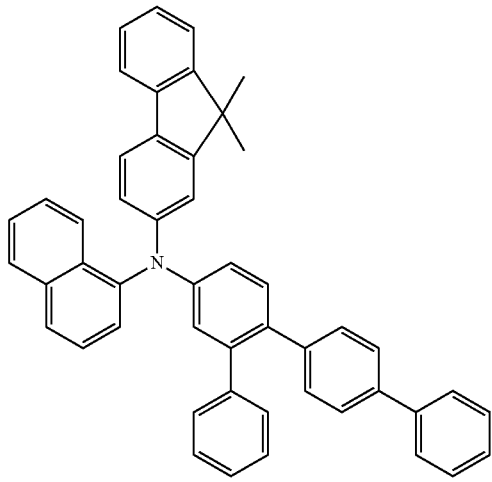
[Chemical Formula 87]
(1-70)
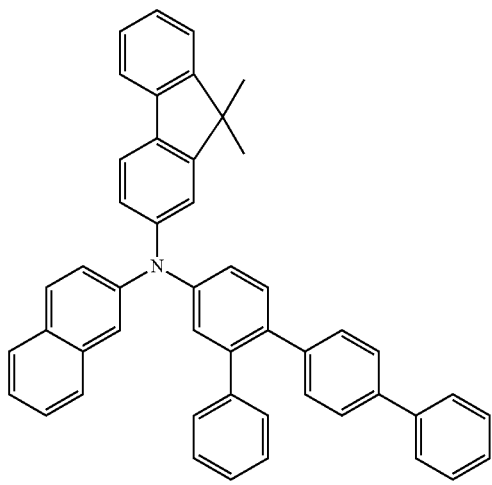
[Chemical Formula 88]
(1-71)
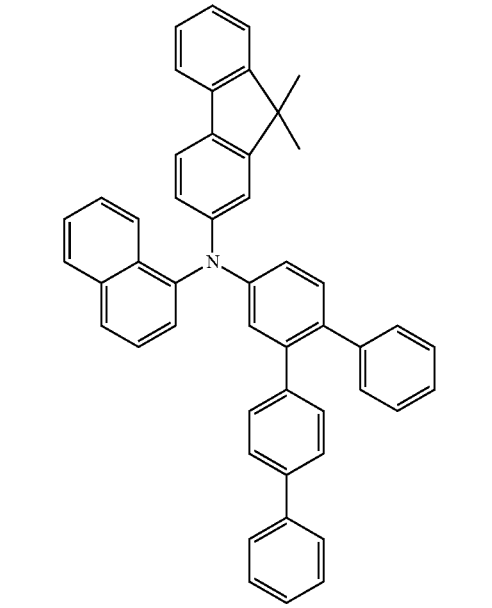
[Chemical Formula 89]
(1-72)
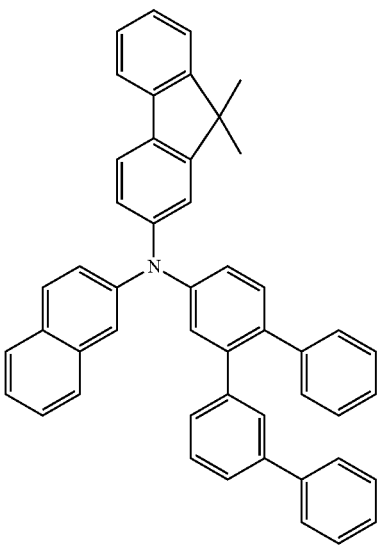
[Chemical Formula 90]
(1-73)
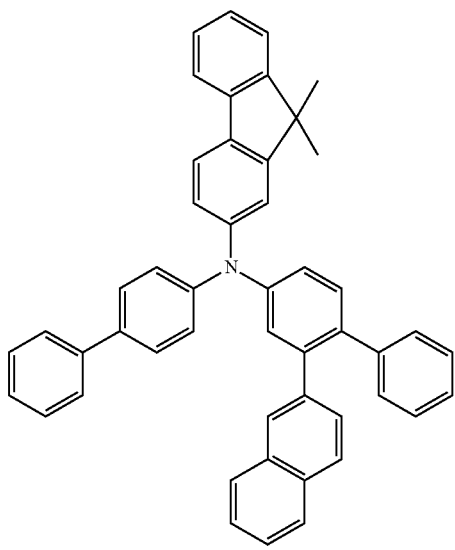
[Chemical Formula 91]
(1-74)
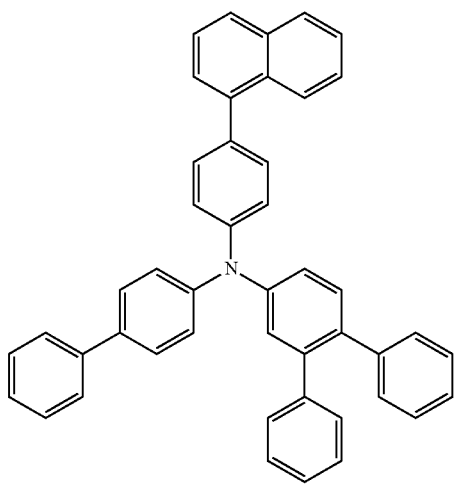

[Chemical Formula 92]
(1-75)
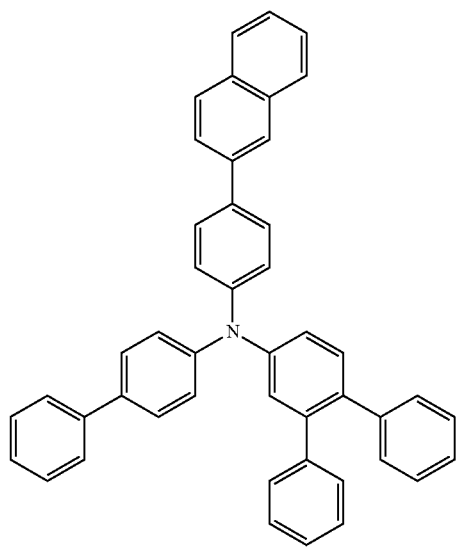
[Chemical Formula 93]
(1-76)
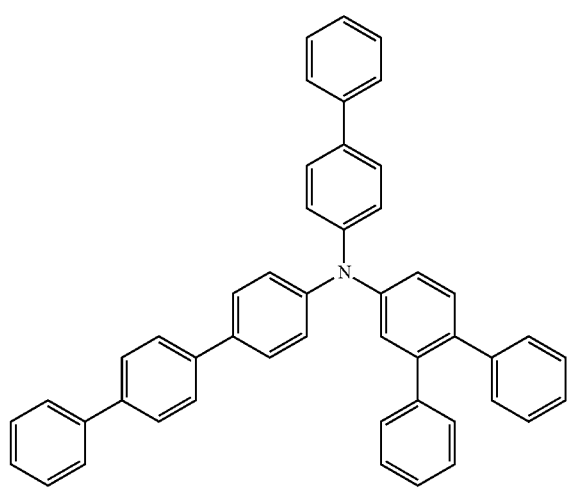
[Chemical Formula 94]
(1-77)
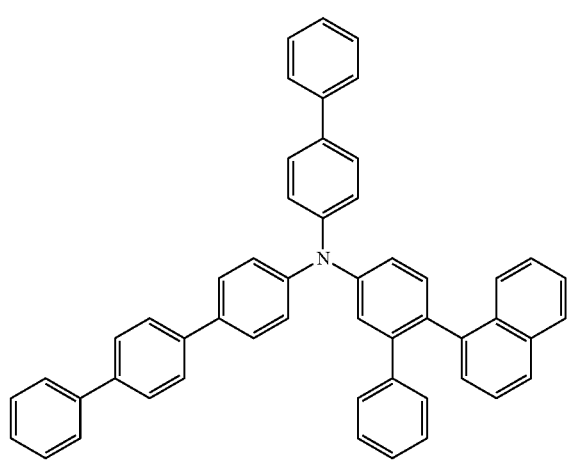
[Chemical Formula 95]
(1-78)
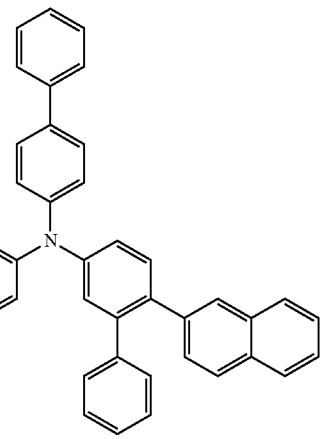
[Chemical Formula 96]
(1-79)
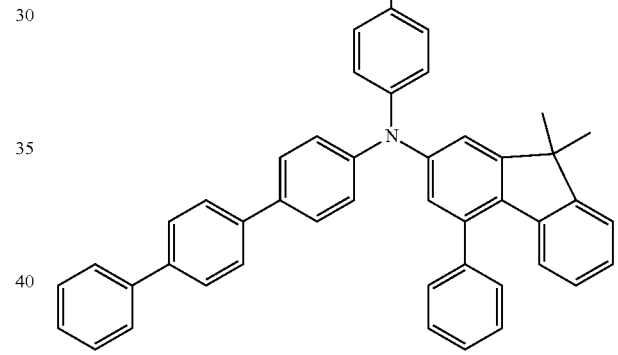
[Chemical Formula 97]
(1-80)
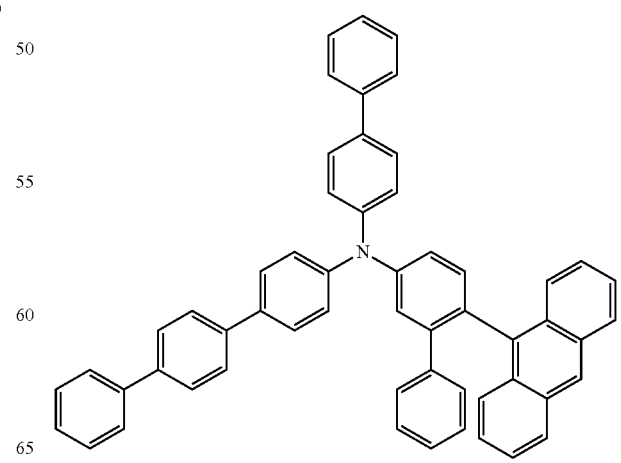

-continued
[Chemical Formula 98]
(1-81)
[Chemical Formula 99]
(1-82)
[Chemical Formula 100]
(1-83)
-continued
[Chemical Formula 101]
(1-84)
[Chemical Formula 102]
(1-85)
[Chemical Formula 103]
(1-86)
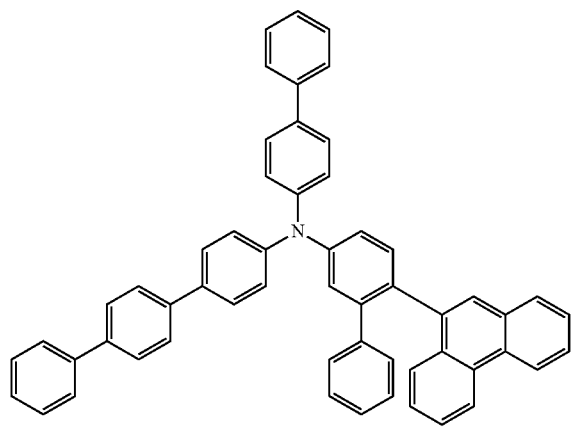
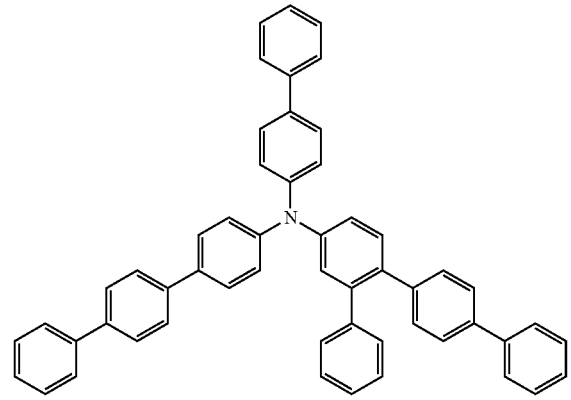

[Chemical Formula 104]
(1-87)
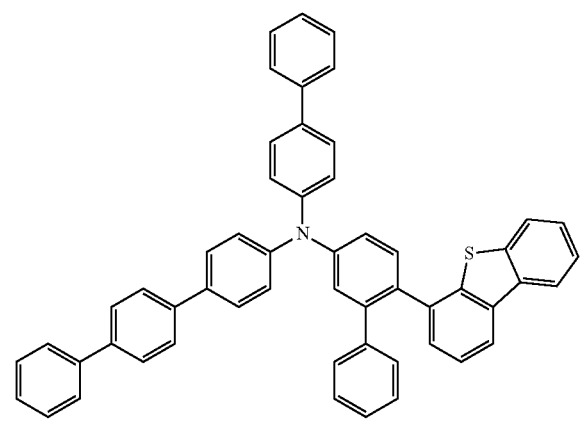
[Chemical Formula 105]
(1-88)
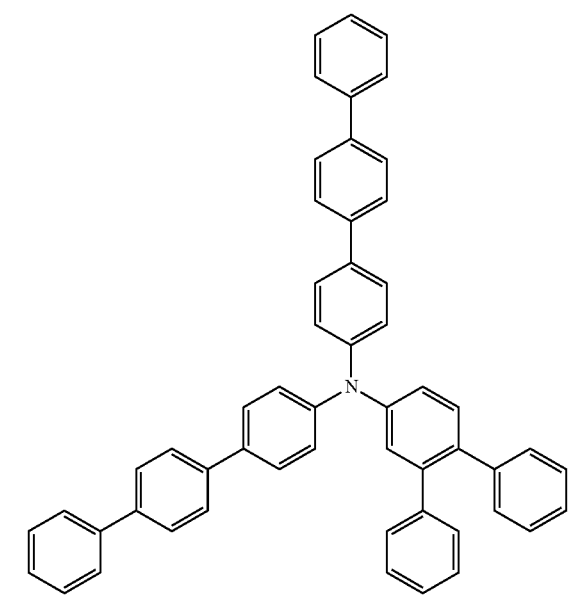
[Chemical Formula 106]
(1-89)
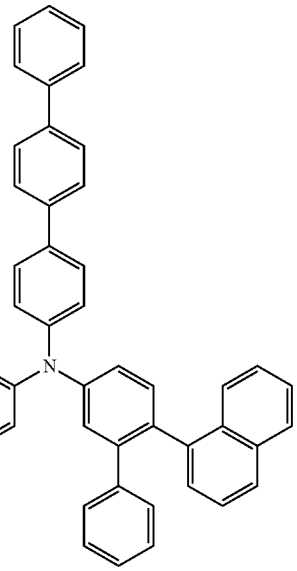
[Chemical Formula 107]
(1-90)
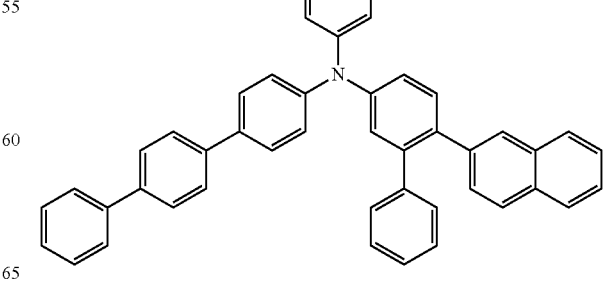

[Chemical Formula 108]
(1-91)
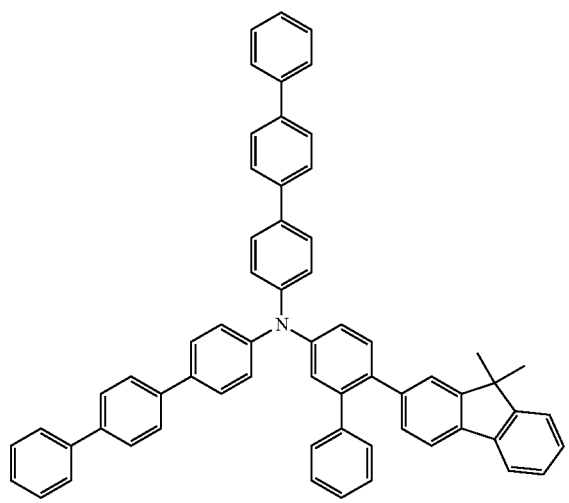
[Chemical Formula 109]
(1-92)
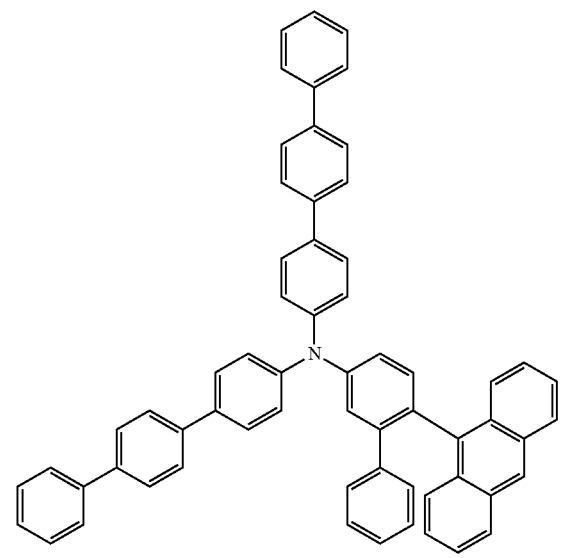
[Chemical Formula 110]
(1-93)
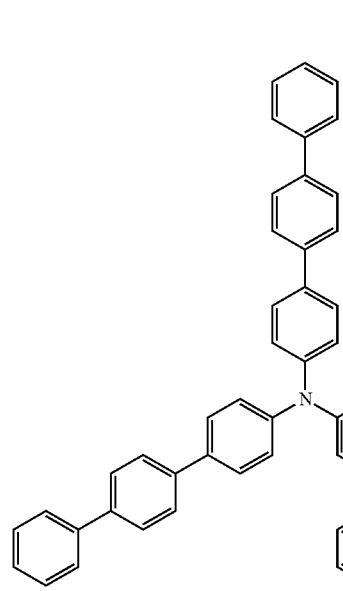
[Chemical Formula 111]
(1-94)
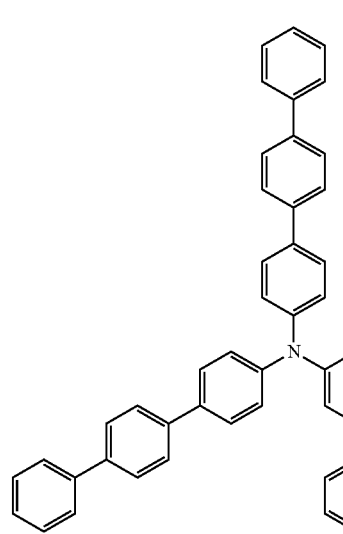

[Chemical Formula 112]
(1-95)
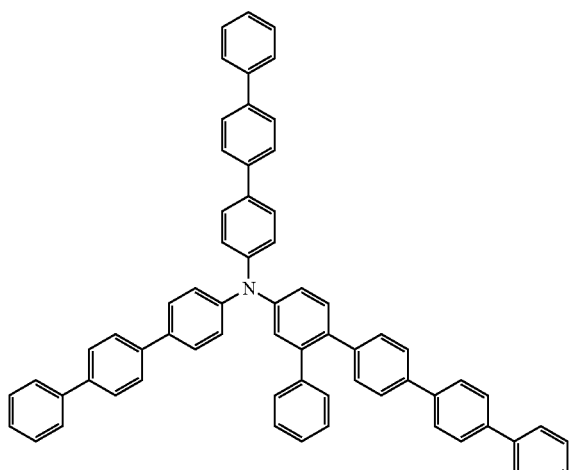
[Chemical Formula 113]
(1-96)
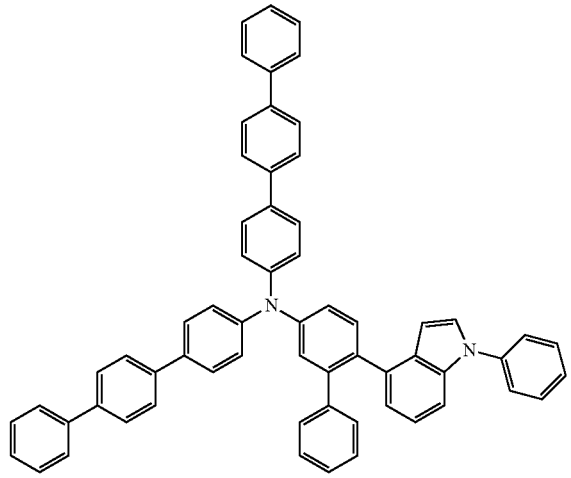
[Chemical Formula 114]
(1-97)
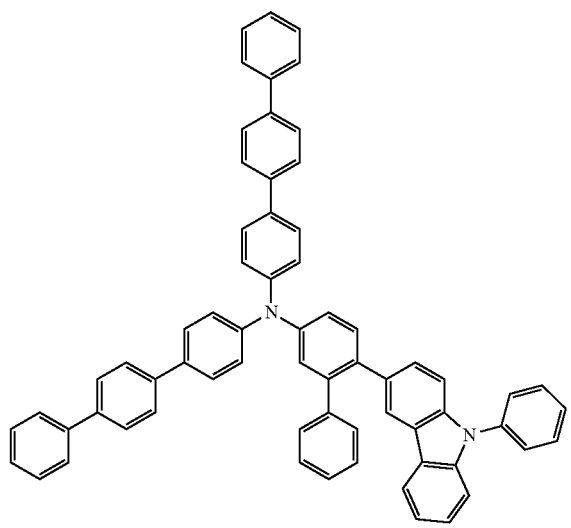
[Chemical Formula 115]
(1-98)
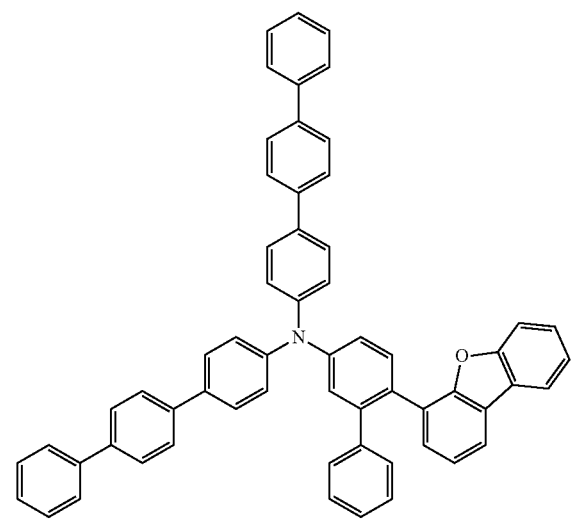
[Chemical Formula 116]
(1-99)
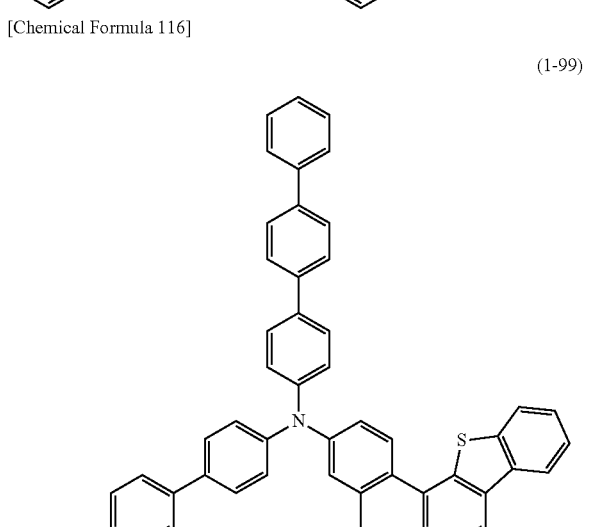
[Chemical Formula 117]
(1-100)
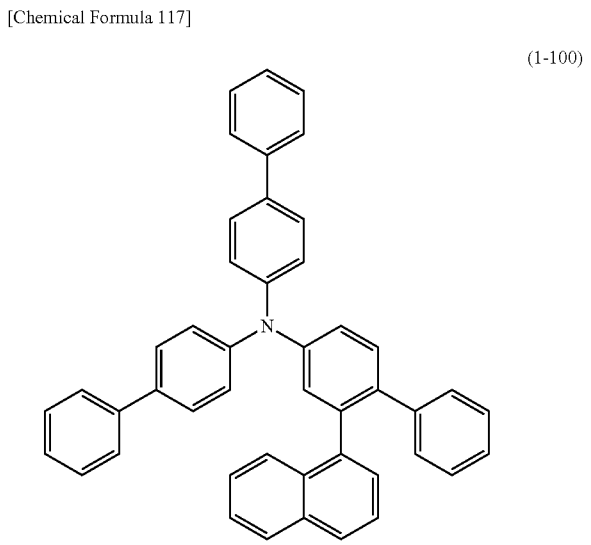

[Chemical Formula 118]
(1-101)
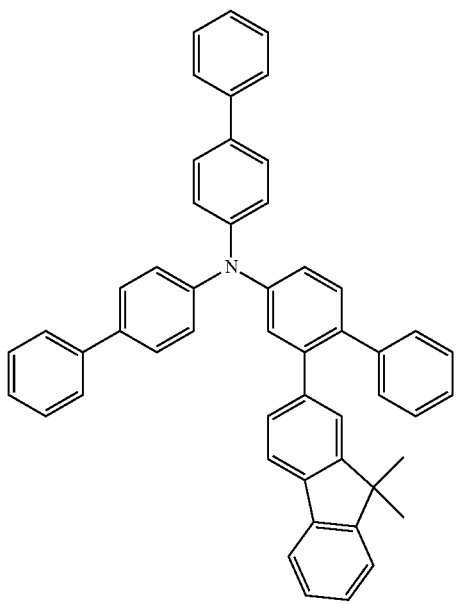
[Chemical Formula 119]
(1-102)
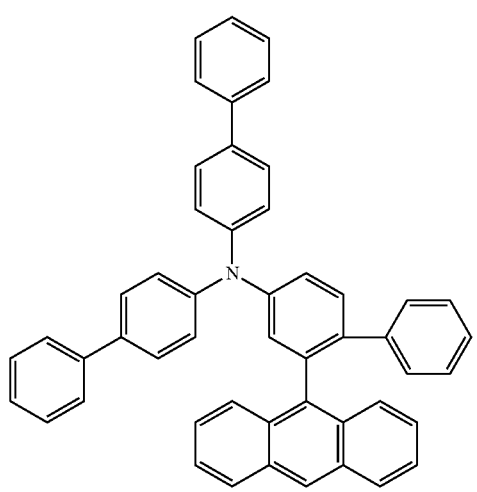
[Chemical Formula 120]
(1-103)
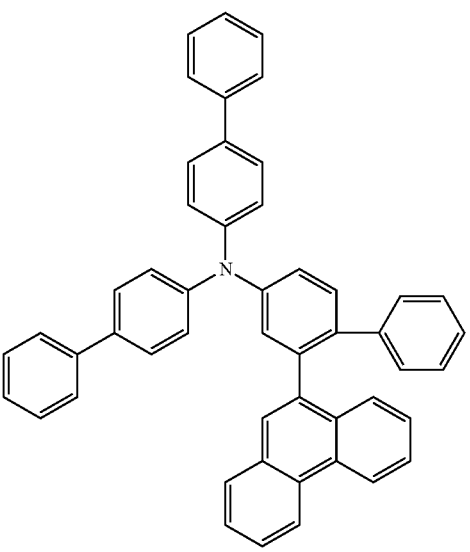
[Chemical Formula 121]
(1-104)
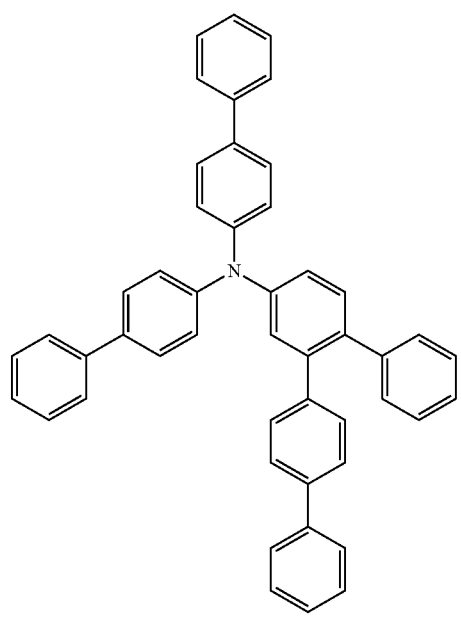

[Chemical Formula 122]
(1-105)
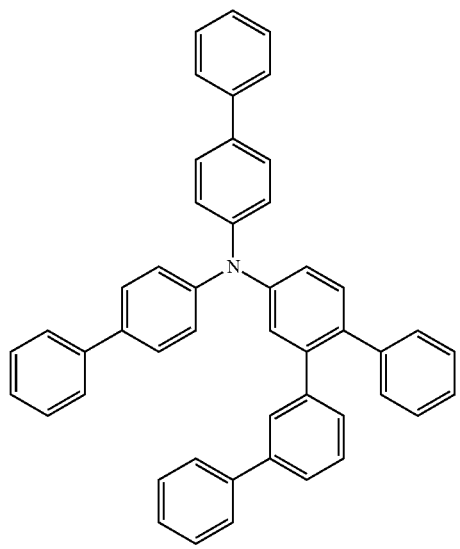
[Chemical Formula 123]
(1-106)
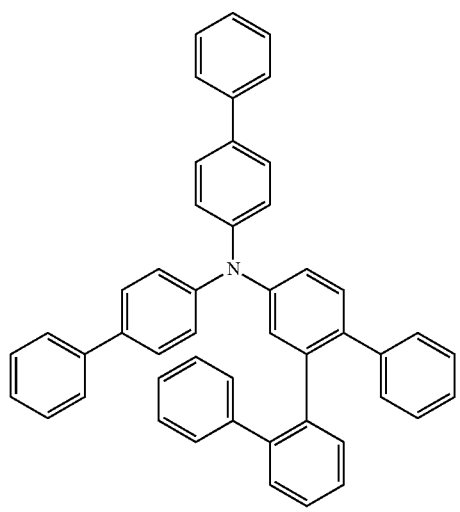
[Chemical Formula 124]
(1-107)
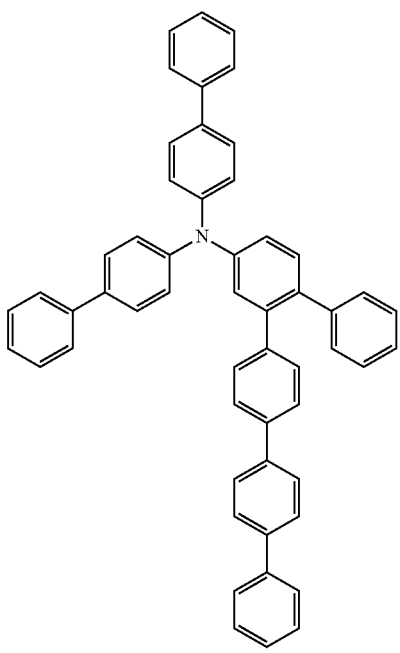
[Chemical Formula 125]
(1-108)
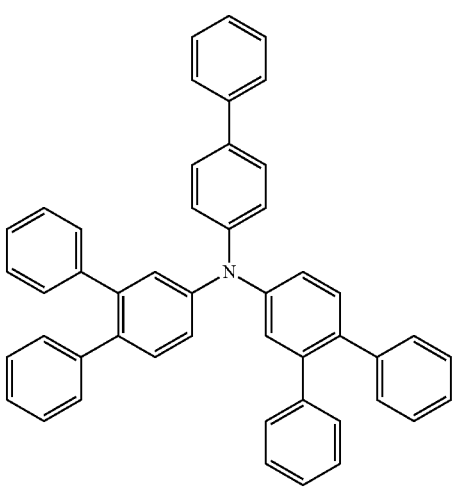

[Chemical Formula 126]
(1-109)
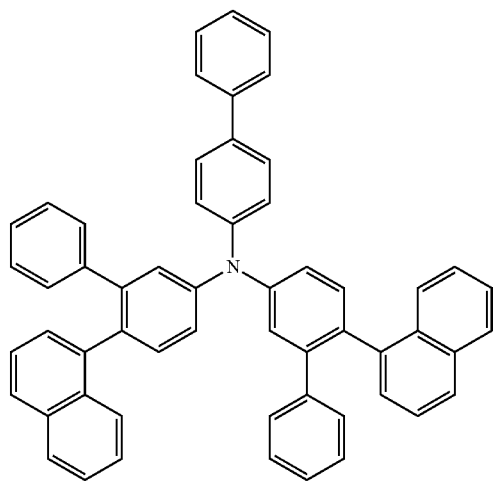
[Chemical Formula 127]
(1-110)
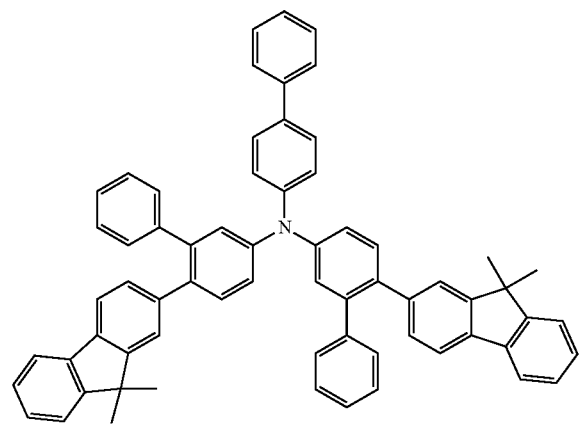
[Chemical Formula 128]
(1-111)
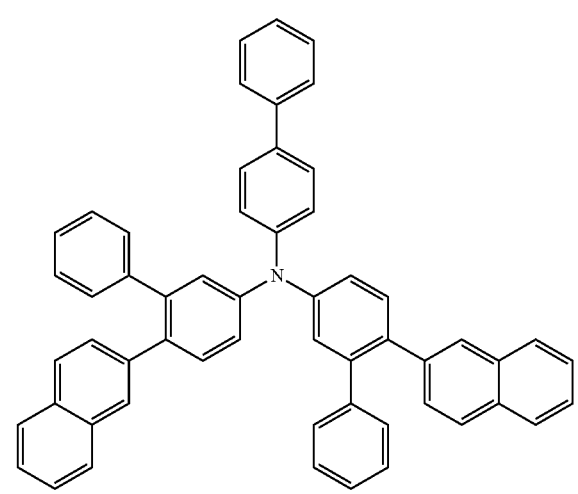
[Chemical Formula 129]
(1-112)
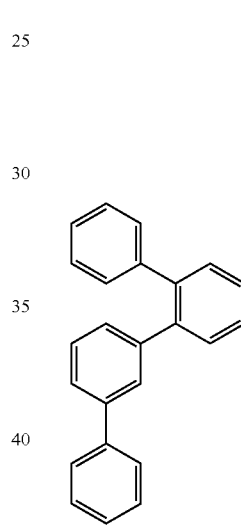
[Chemical Formula 130]
(1-113)
[Chemical Formula 131]
(1-114)
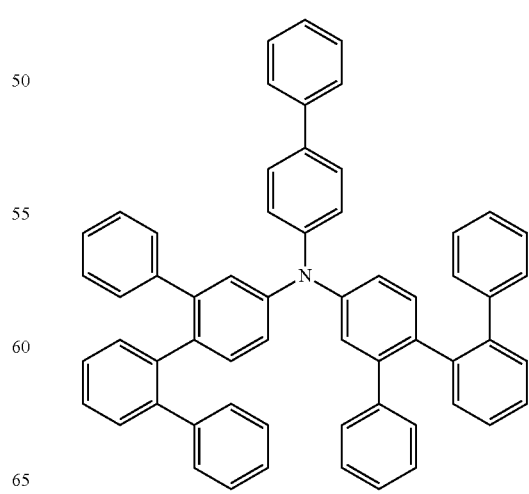

77
-continued
[Chemical Formula 132]
(1-115)
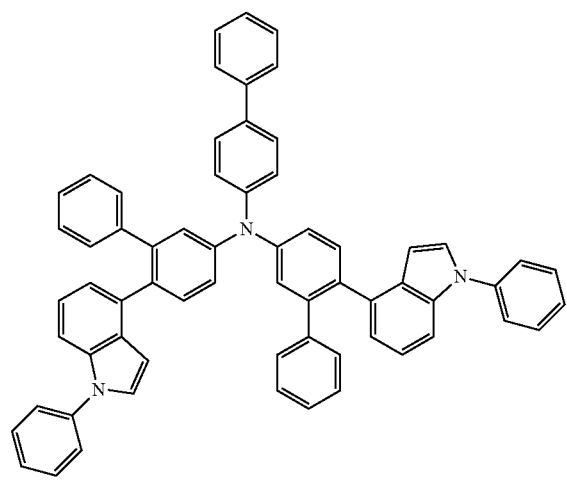
[Chemical Formula 133]
(1-116)
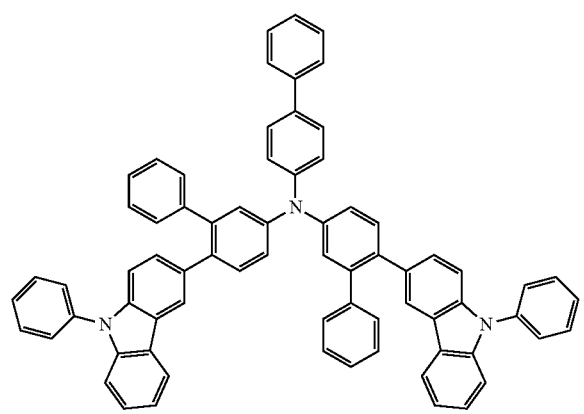
[Chemical Formula 134]
(1-117)
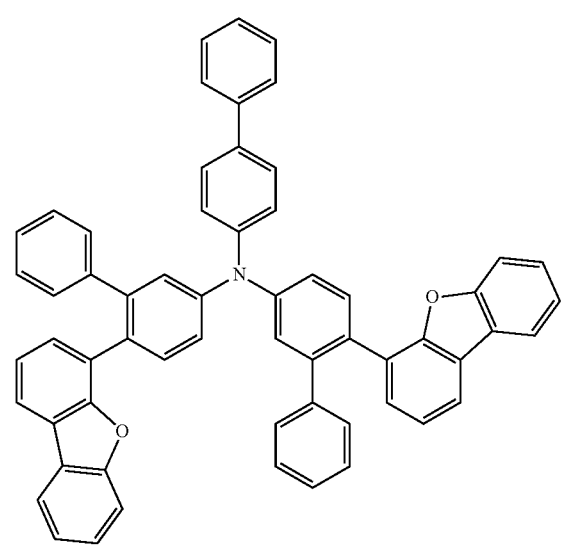
78
-continued
[Chemical Formula 135]
(1-118)
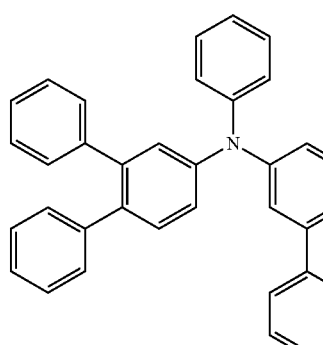
[Chemical Formula 136]
(1-119)
[Chemical Formula 137]
(1-120)
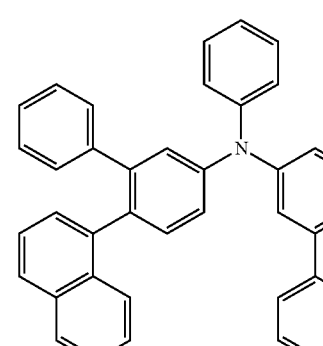

-continued
[Chemical Formula 138]
(1-121)
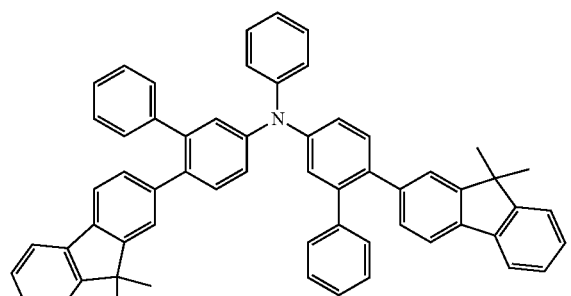
[Chemical Formula 139]
(1-122)
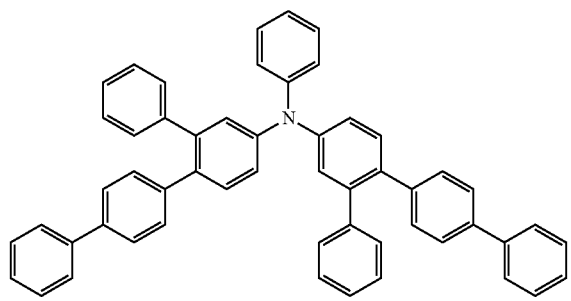
[Chemical Formula 140]
(1-123)
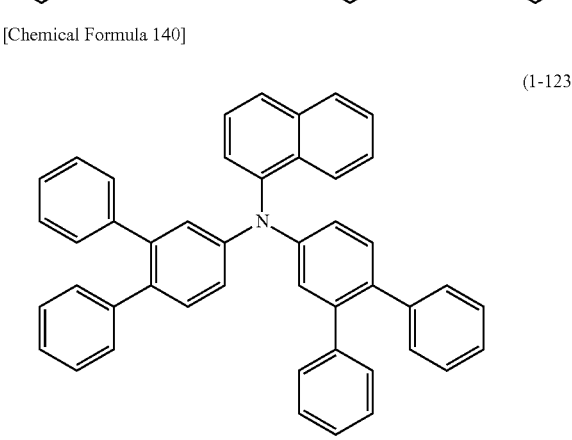
[Chemical Formula 141]
(1-124)
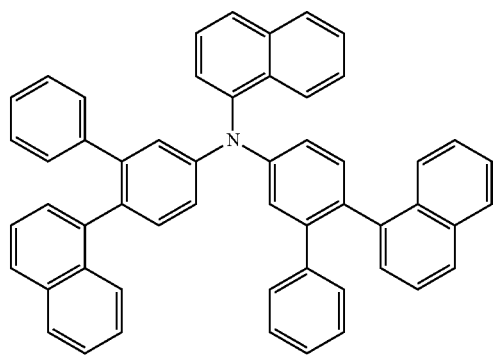
-continued
[Chemical Formula 142]
(1-125)
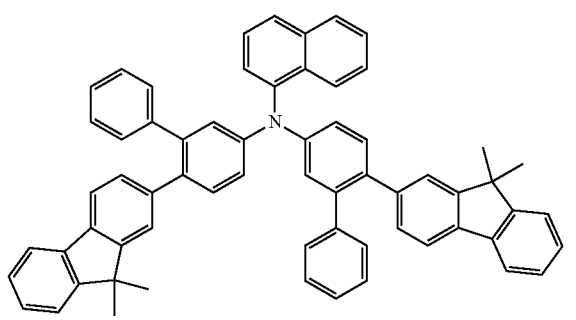
[Chemical Formula 143]
(1-126)
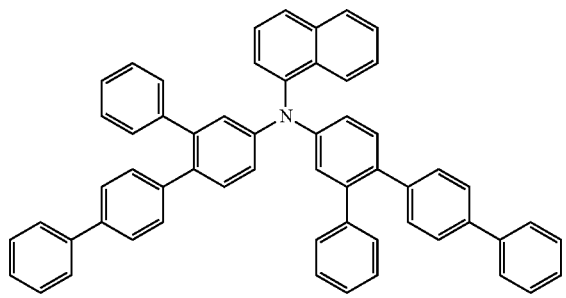
[Chemical Formula 144]
(1-127)
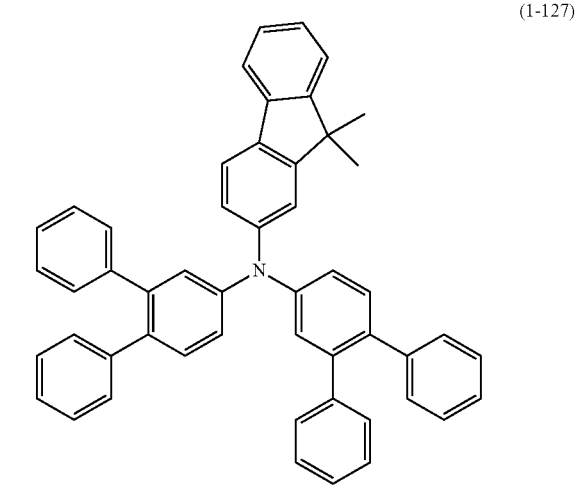

[Chemical Formula 145]
(1-128)
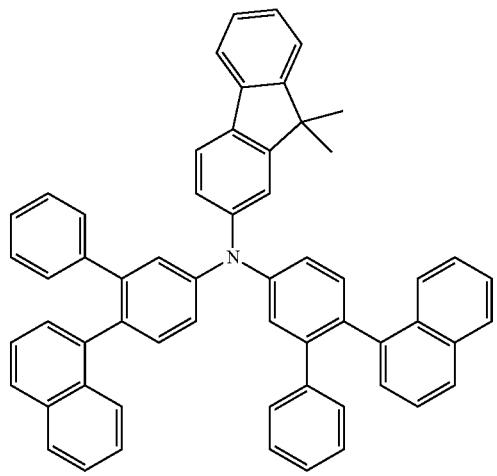
[Chemical Formula 146]
(1-129)
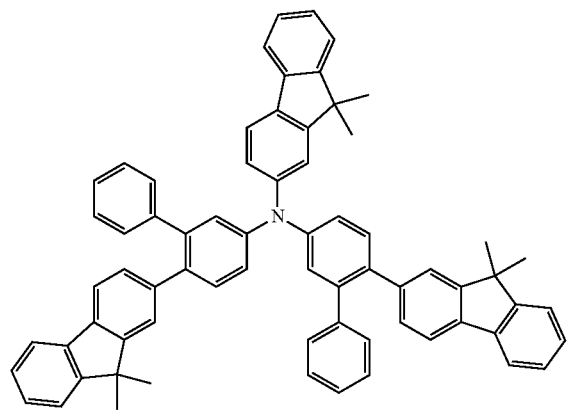
[Chemical Formula 147]
(1-130)
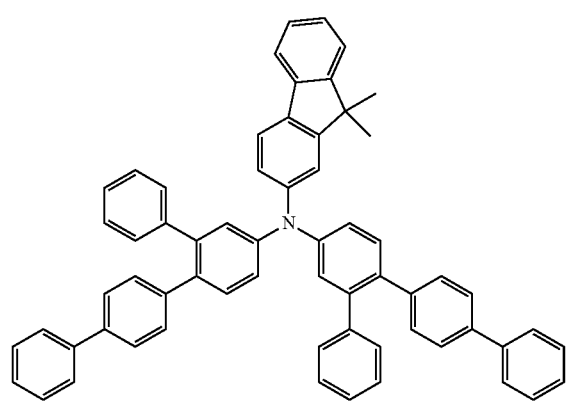
[Chemical Formula 148]
(1-131)
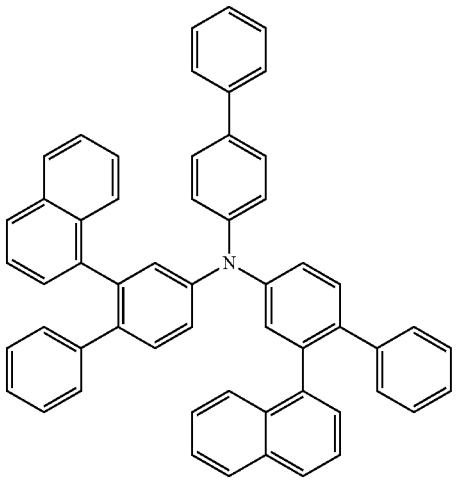
[Chemical Formula 149]
(1-132)
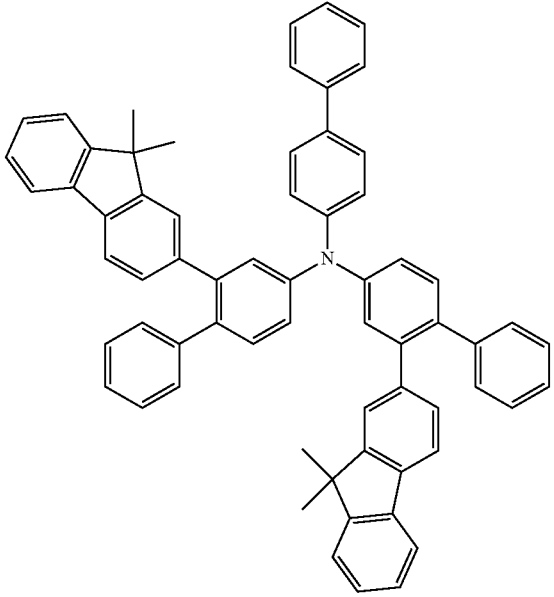
[Chemical Formula 150]
(1-133)
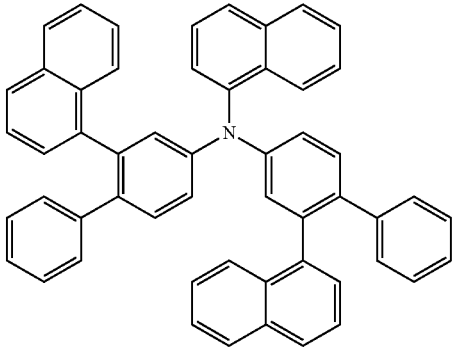

-continued
[Chemical Formula 151]
(1-134)
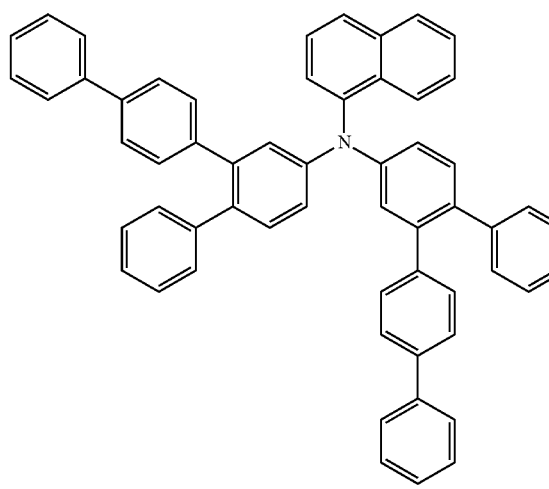
[Chemical Formula 152]
(1-135)
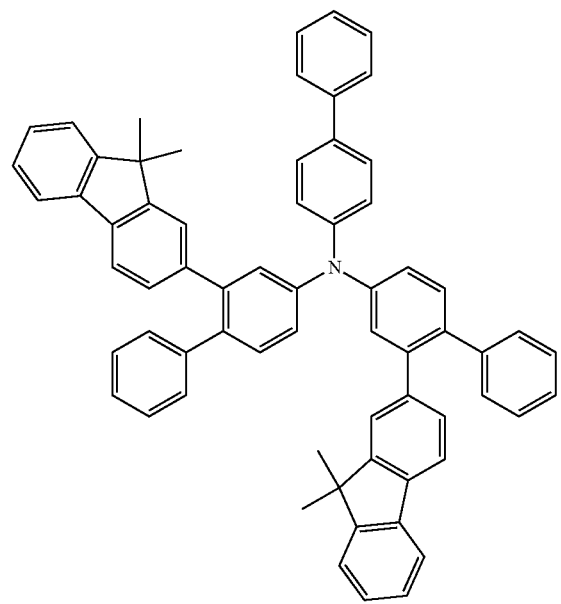
[Chemical Formula 153]
(1-136)
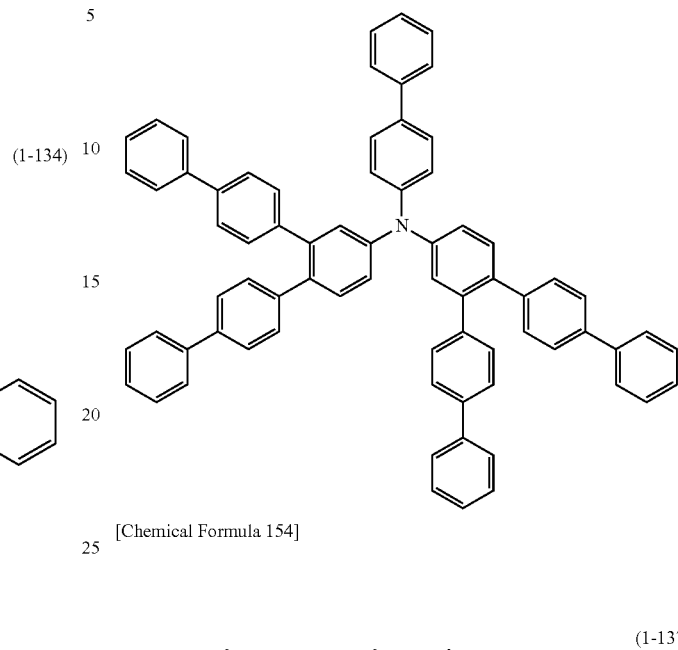
[Chemical Formula 154]
(1-137)
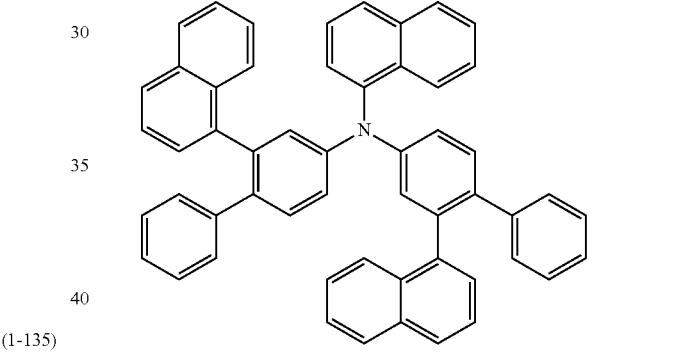
[Chemical Formula 155]
(1-138)
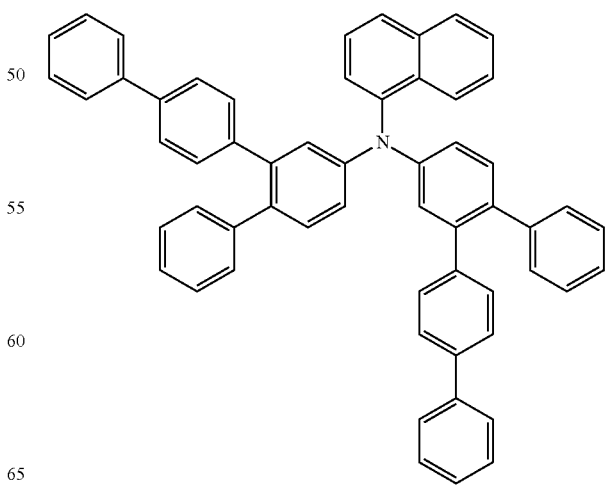

[Chemical Formula 156]
(1-139)
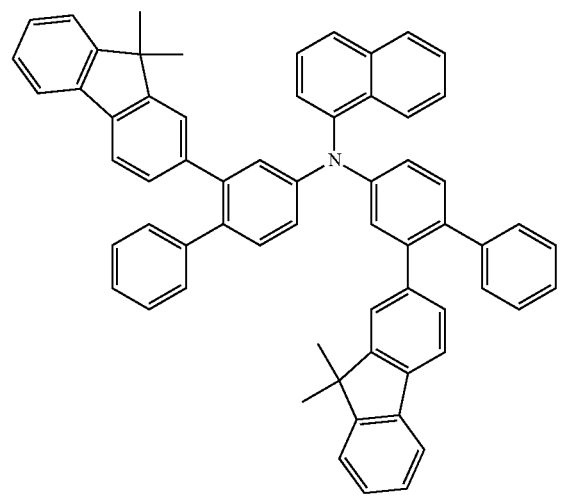
[Chemical Formula 157]
(1-140)
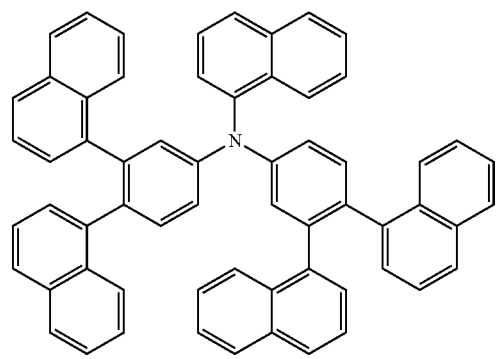
[Chemical Formula 158]
(1-141)
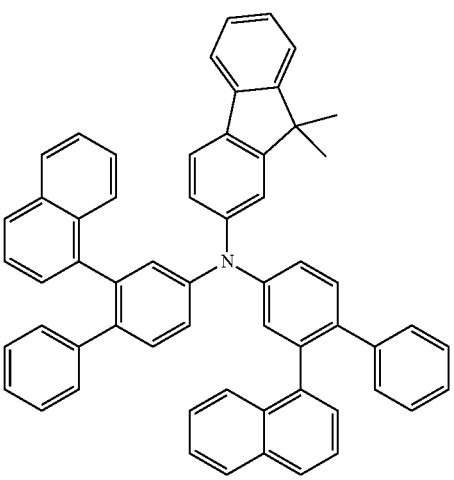
[Chemical Formula 159]
(1-142)
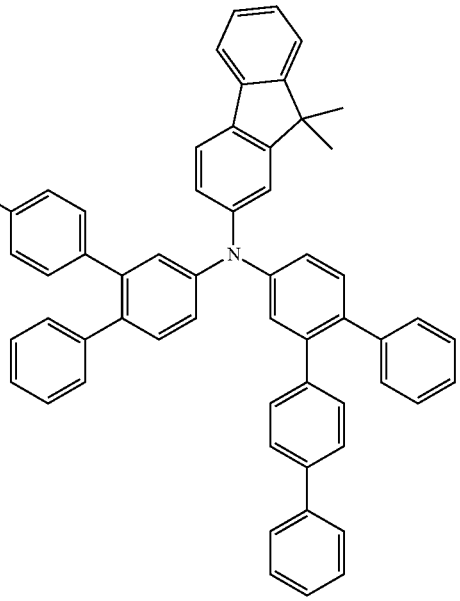
[Chemical Formula 160]
(1-143)
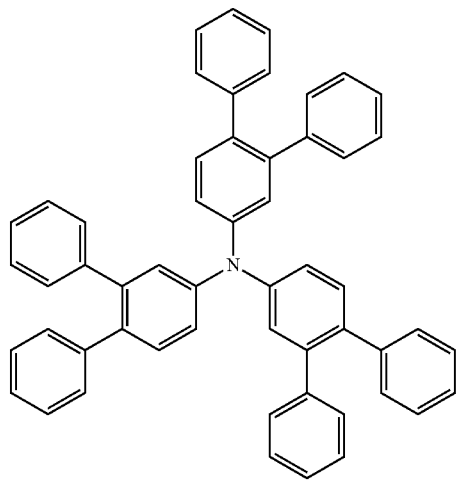
[Chemical Formula 161]
(1-144)
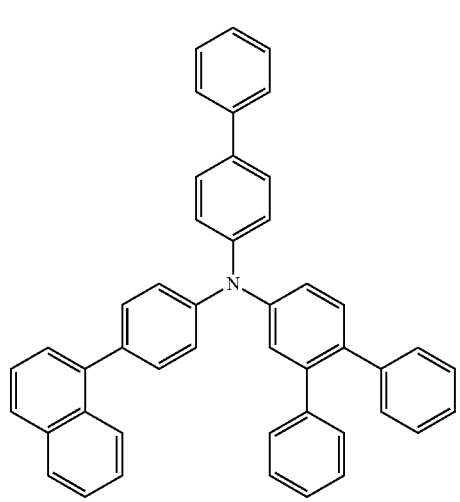

[Chemical Formula 162]
(1-145)
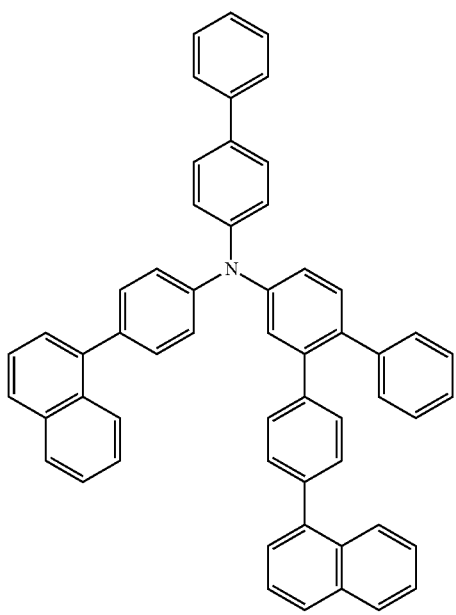
[Chemical Formula 163]
(1-146)
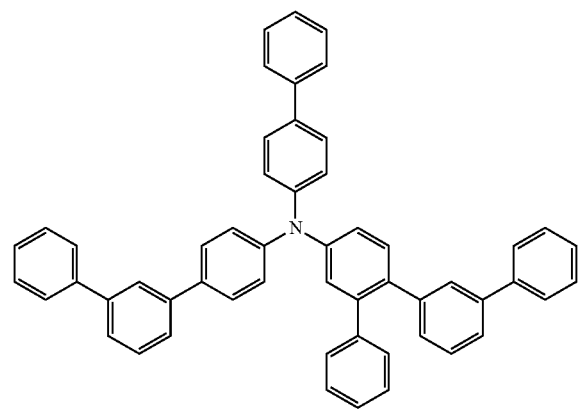
[Chemical Formula 164]
(1-147)
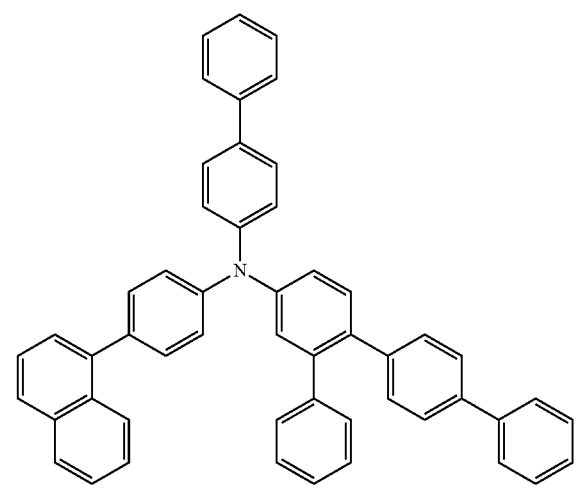
[Chemical Formula 165]
(1-148)
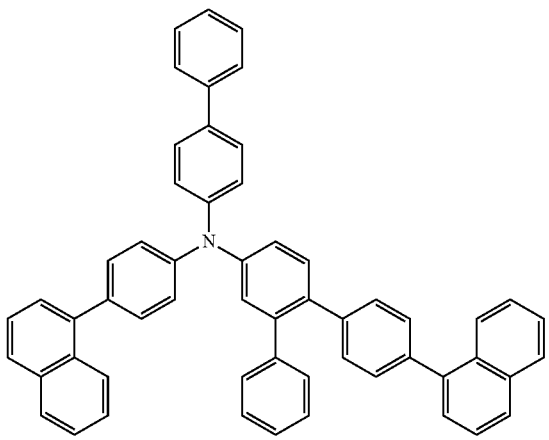
[Chemical Formula 166]
(1-149)
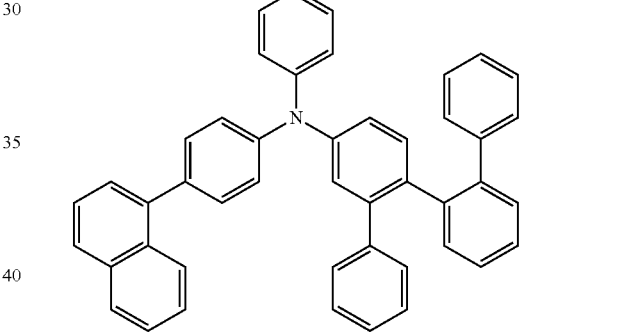
[Chemical Formula 167]
(1-150)
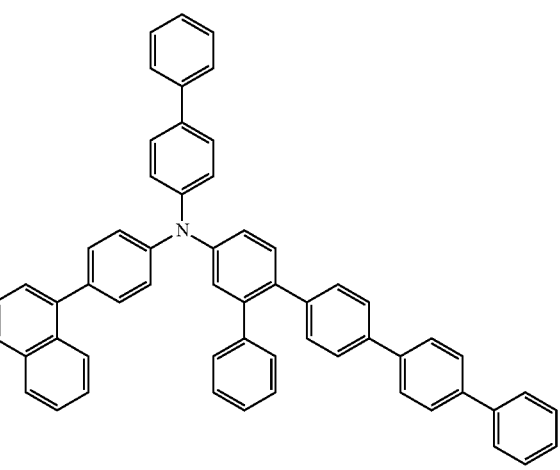

[Chemical Formula 168]
(1-151)
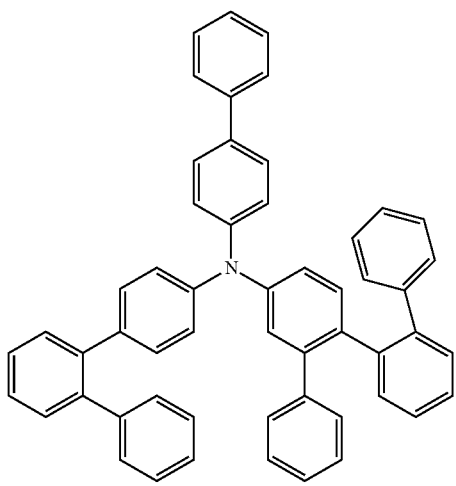
[Chemical Formula 169]
(1-152)
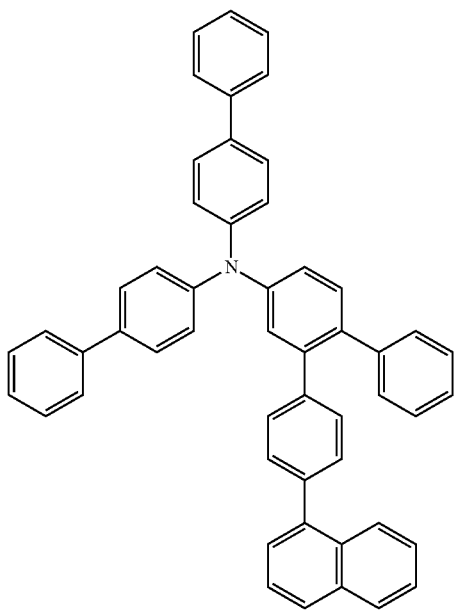
[Chemical Formula 170]
(1-153)
[Chemical Formula 171]
(1-154)
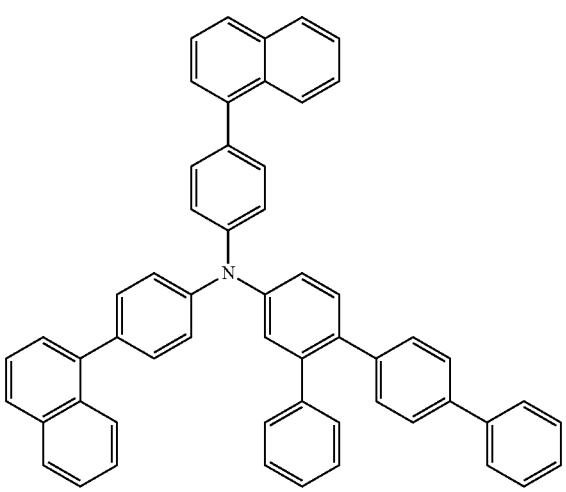
[Chemical Formula 172]
(1-155)

[Chemical Formula 173]
(1-156)
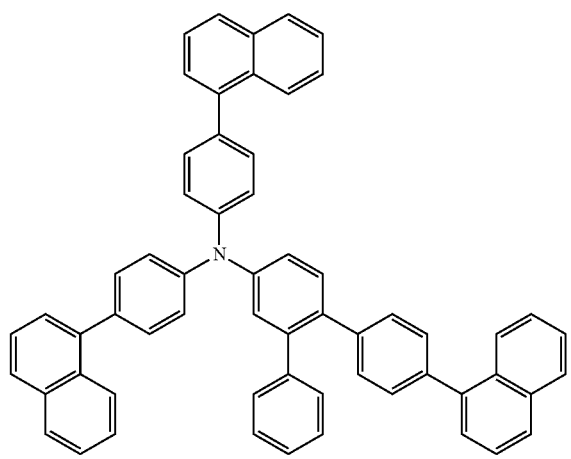
[Chemical Formula 174]
(1-157)
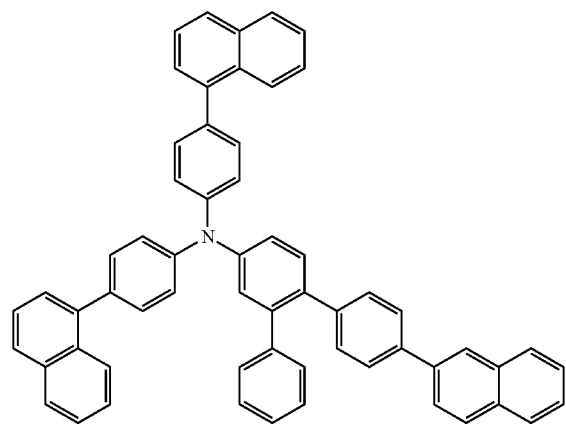
[Chemical Formula 175]
(1-158)
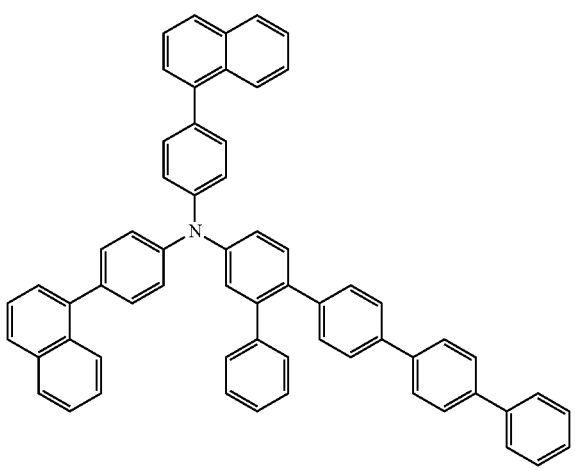
[Chemical Formula 176]
(1-159)
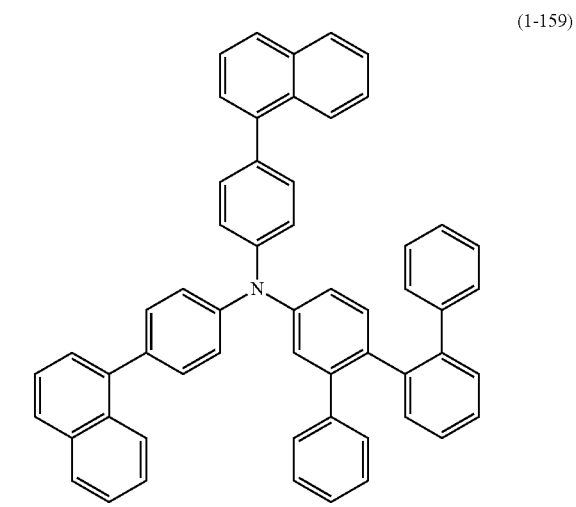
[Chemical Formula 177]
(1-160)
[Chemical Formula 178]
(1-161)
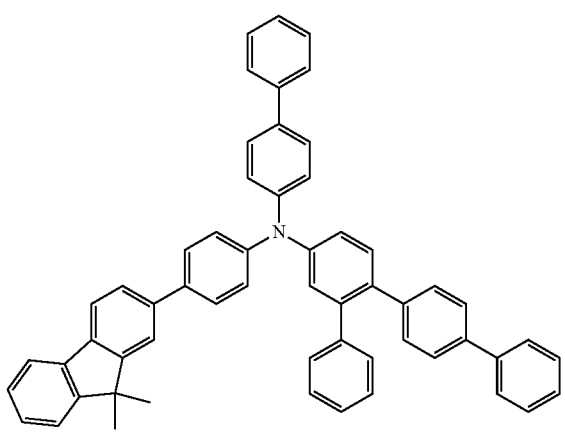

[Chemical Formula 179]
(1-162)
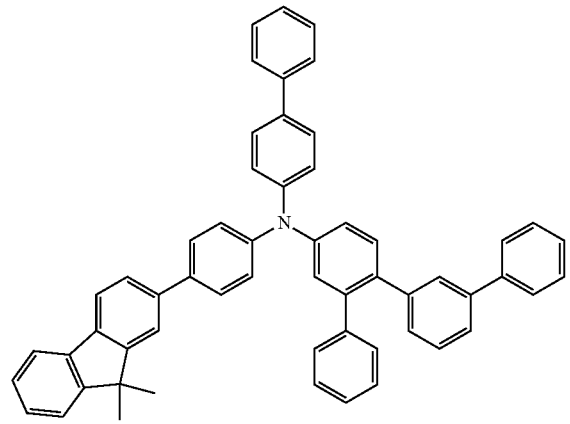
[Chemical Formula 180]
(1-163)
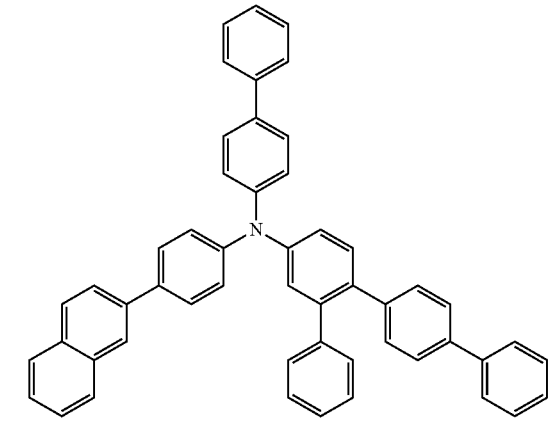
[Chemical Formula 181]
(1-164)
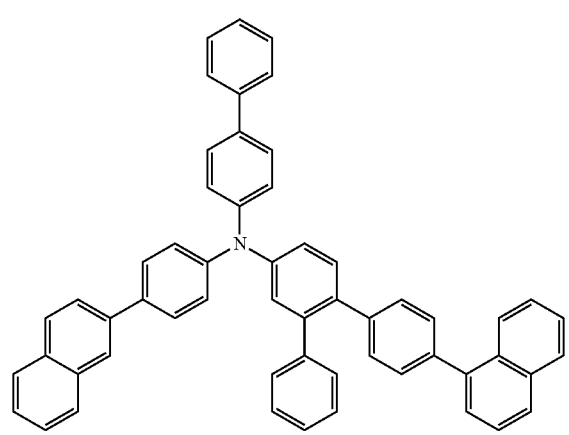
[Chemical Formula 182]
(1-165)
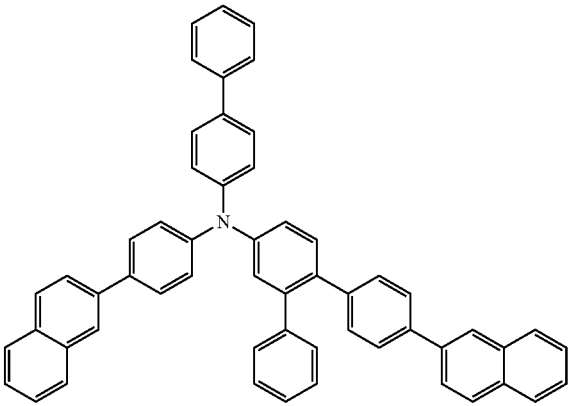
[Chemical Formula 183]
(1-166)
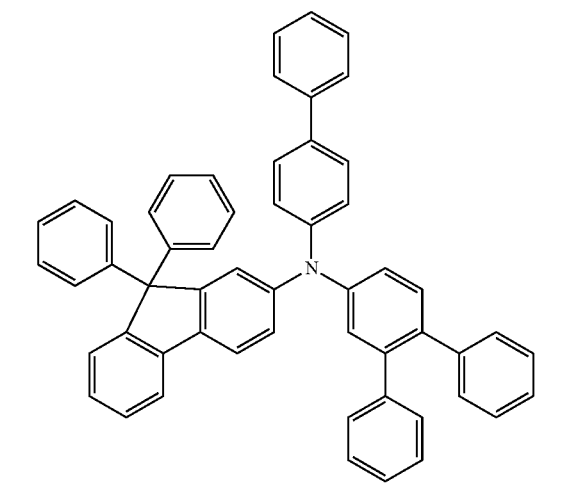
[Chemical Formula 184]
(1-167)
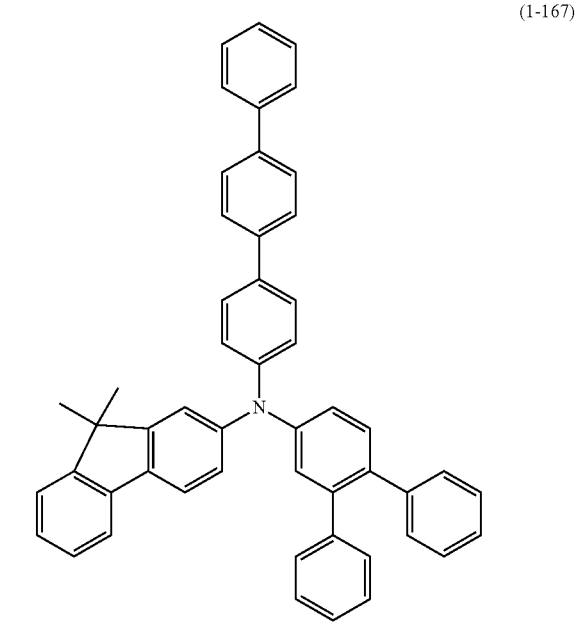

[Chemical Formula 185]
(1-168)
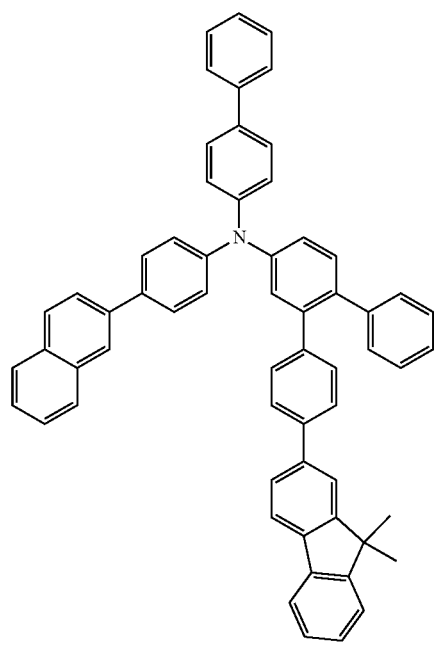
[Chemical Formula 186]
(1-169)
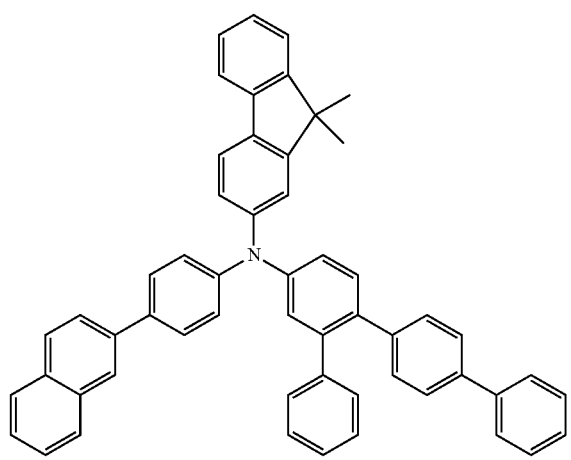
[Chemical Formula 187]
(1-170)
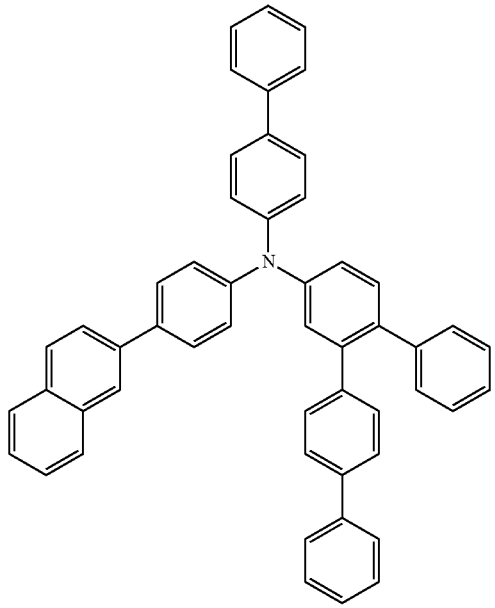
[Chemical Formula 188]
(1-171)
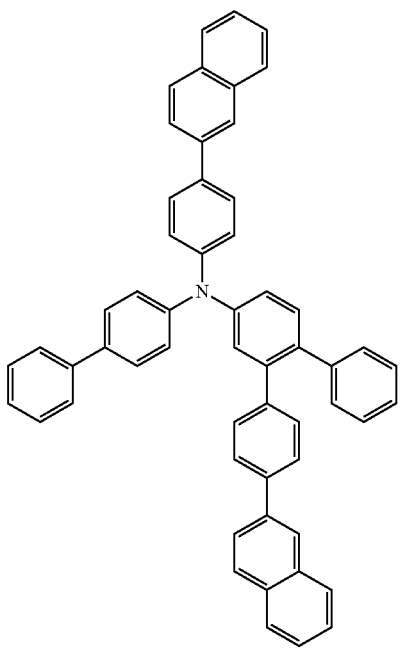

[Chemical Formula 189]
(1-172)
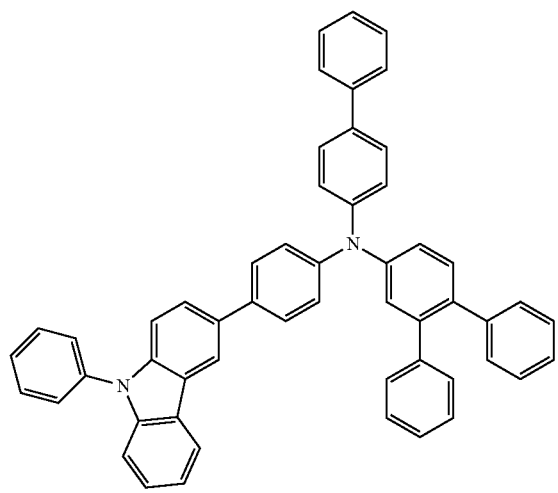
[Chemical Formula 190]
(1-173)
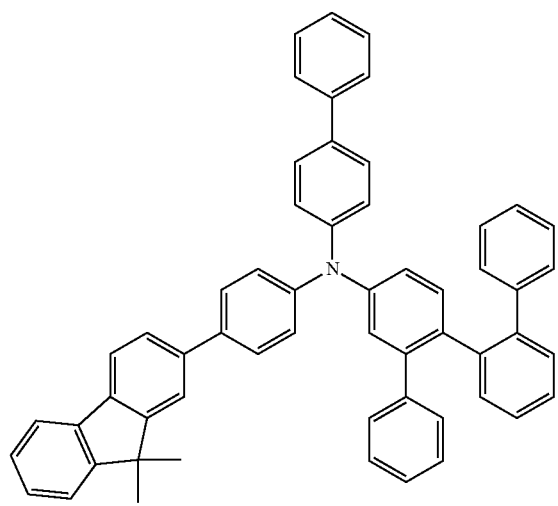
[Chemical Formula 191]
(1-174)
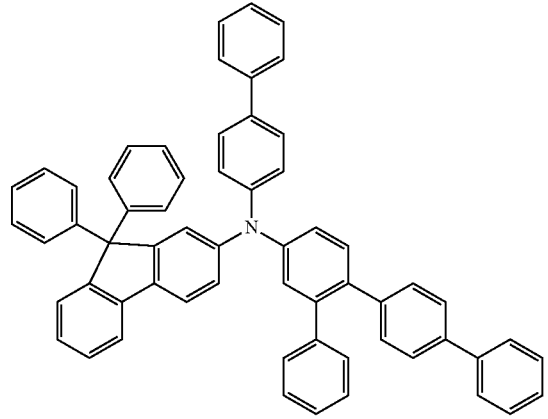
[Chemical Formula 192]
(1-175)
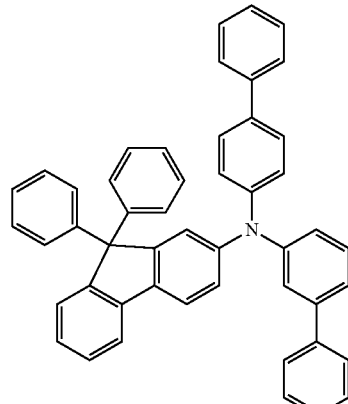
[Chemical Formula 193]
(1-176)
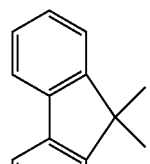
[Chemical Formula 194]
(1-177)
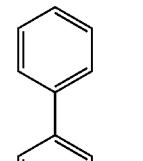

[Chemical Formula 195]
(1-178)
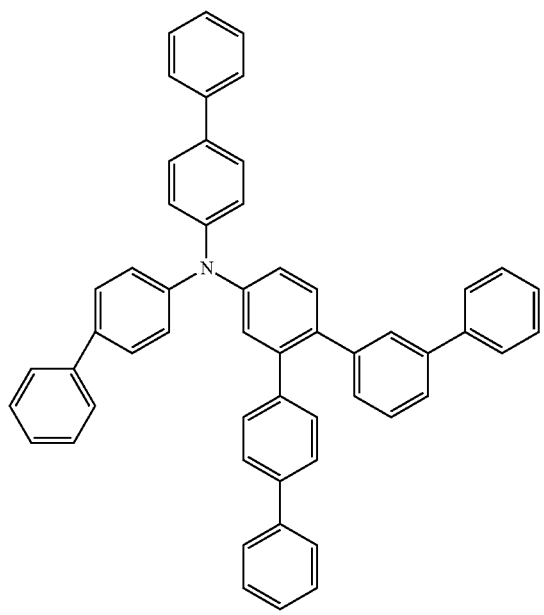
[Chemical Formula 196]
(1-179)
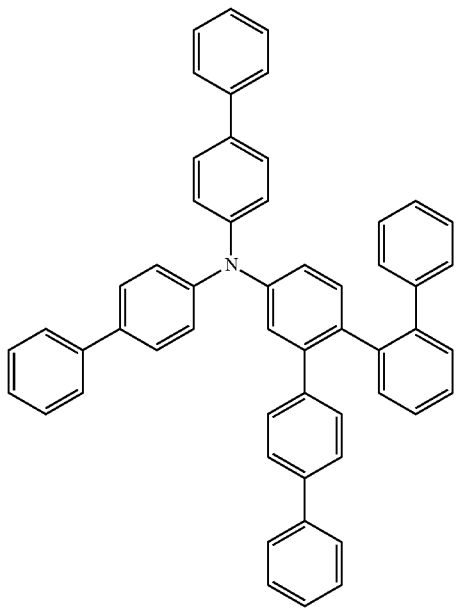
[Chemical Formula 197]
(1-180)
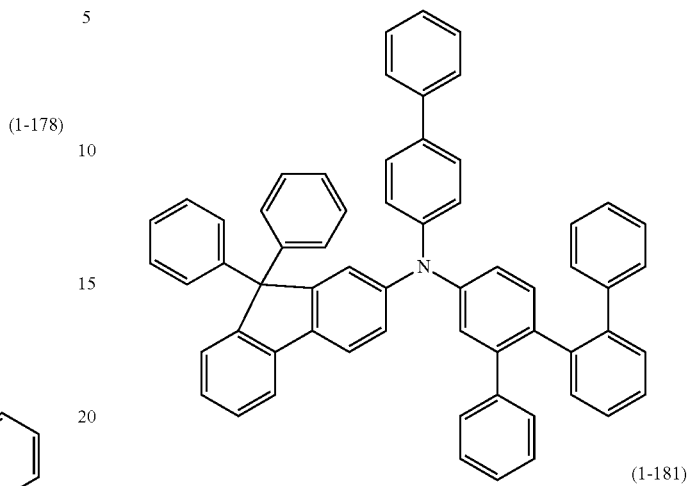
[Chemical Formula 198]
(1-181)
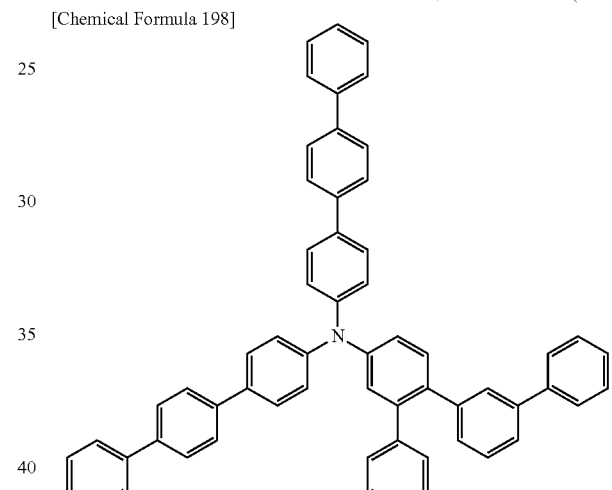
[Chemical Formula 199]
(1-182)
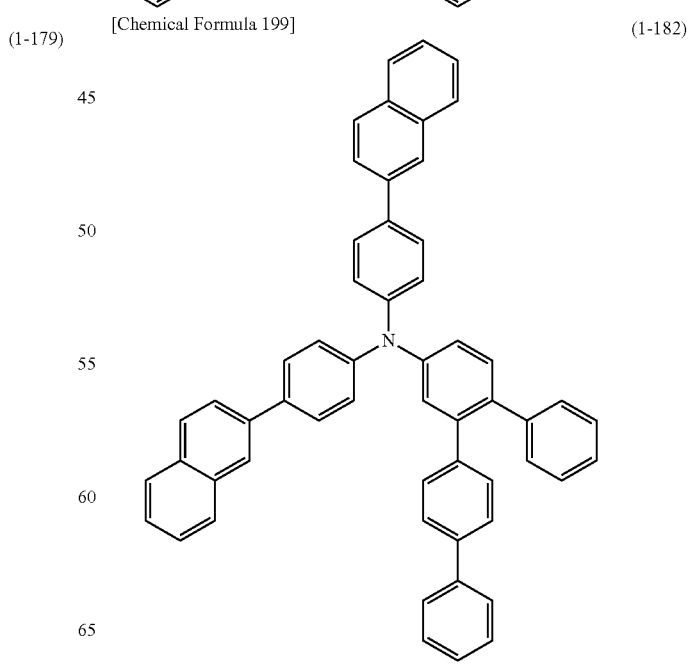

101
-continued
[Chemical Formula 200]
(1-183)
[Chemical Formula 201]
(1-184)
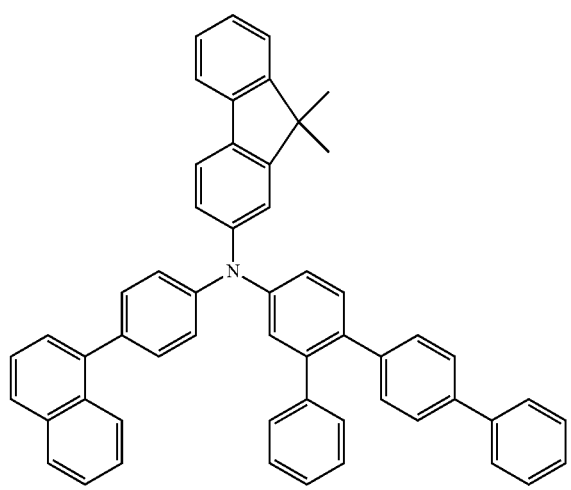
[Chemical Formula 202]
(1-1845)
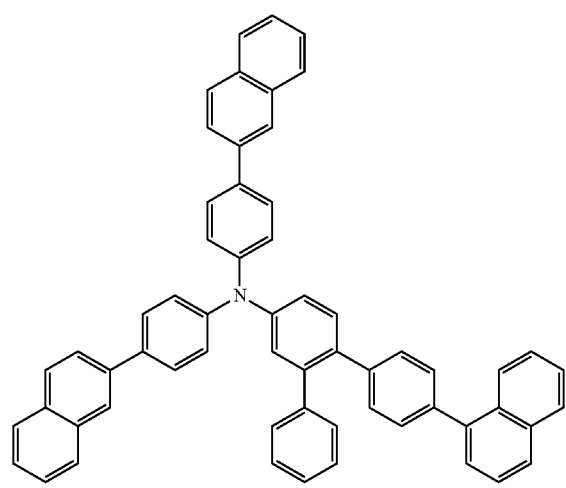
102
-continued
[Chemical Formula 203]
(1-186)
[Chemical Formula 204]
(1-187)
[Chemical Formula 205]
(1-188)
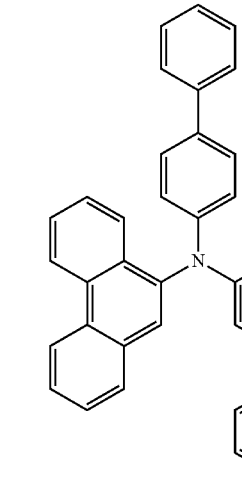

[Chemical Formula 206]
(1-189)
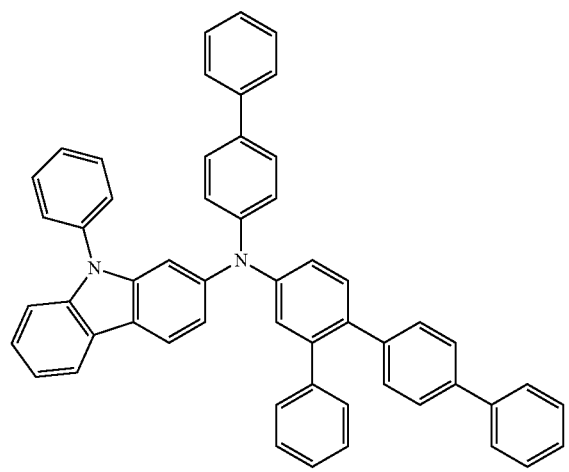
[Chemical Formula 207]
(1-190)
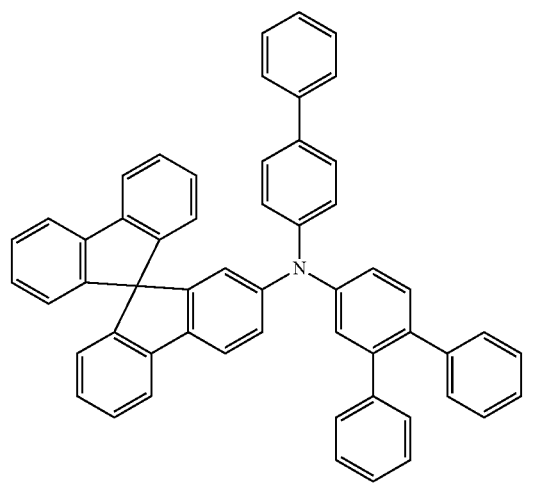
[Chemical Formula 208]
(1-191)
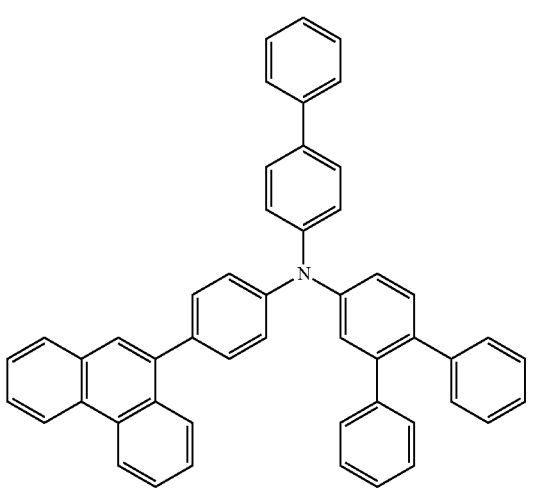
[Chemical Formula 209]
(1-192)
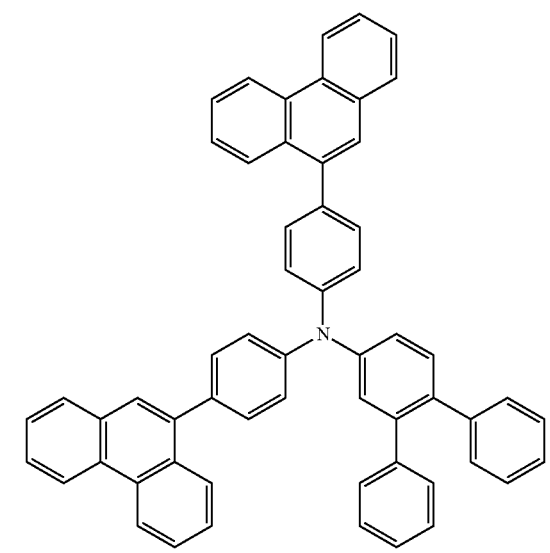
[Chemical Formula 210]
(1-193)
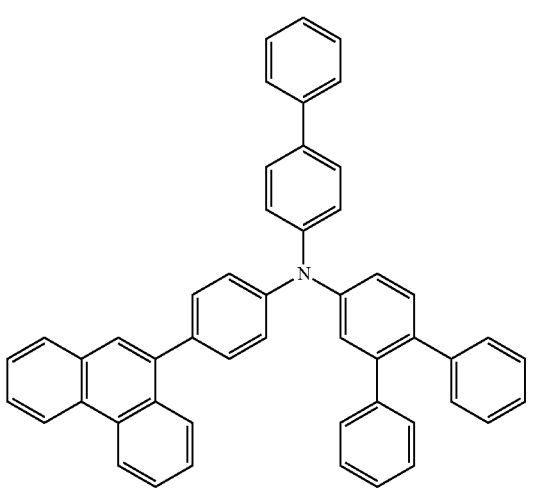
[Chemical Formula 211]
(1-194)
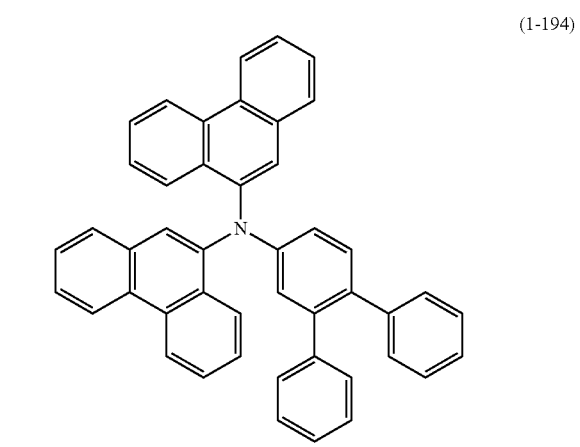

[Chemical Formula 212]
(1-195)
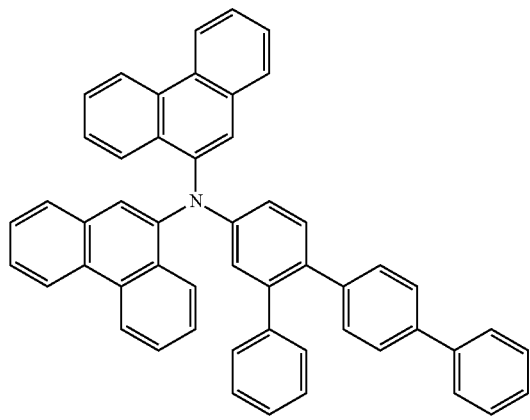
[Chemical Formula 213]
(1-196)
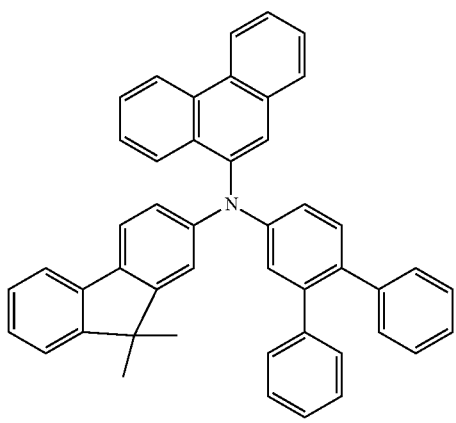
[Chemical Formula 214]
(1-197)
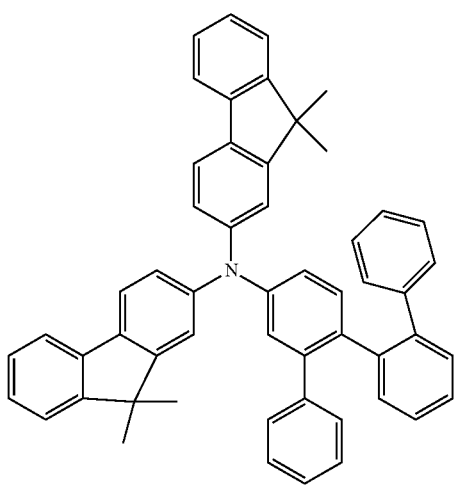
[Chemical Formula 215]
(1-198)
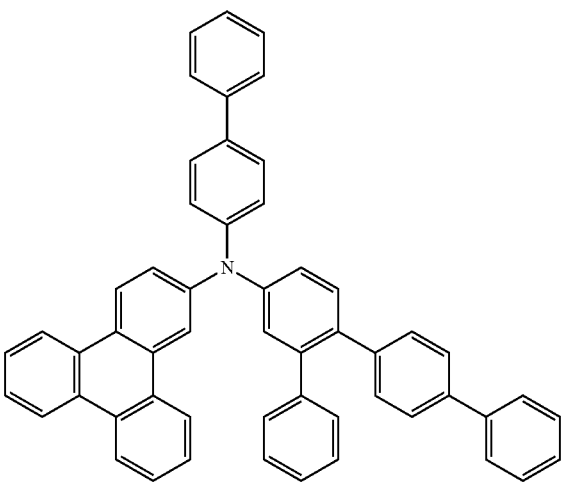
[Chemical Formula 216]
(1-199)
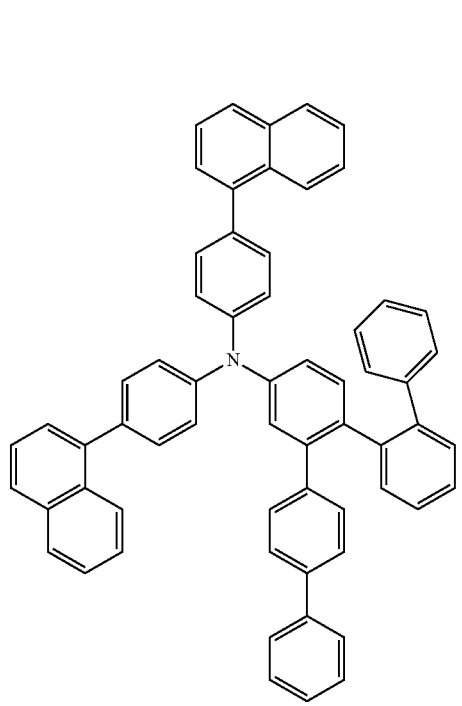

[Chemical Formula 217]
(1-200)
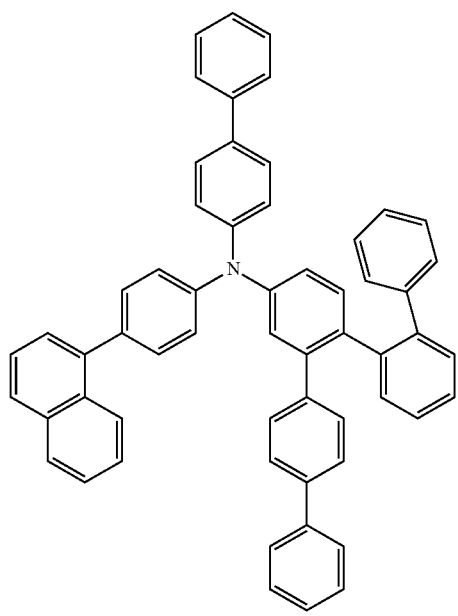
[Chemical Formula 218]
(1-201)
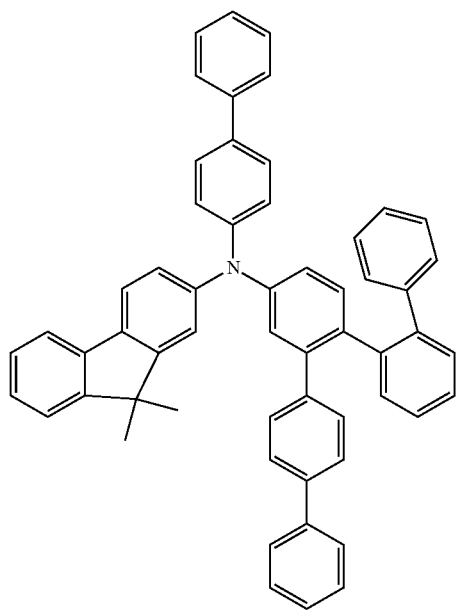
[Chemical Formula 219]
(1-202)
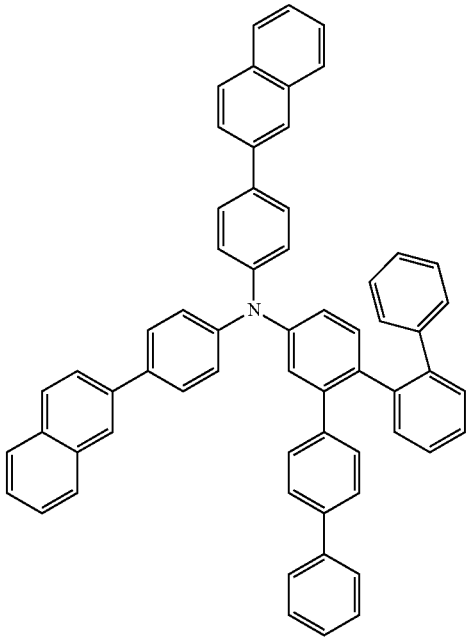
[Chemical Formula 220]
(1-203)
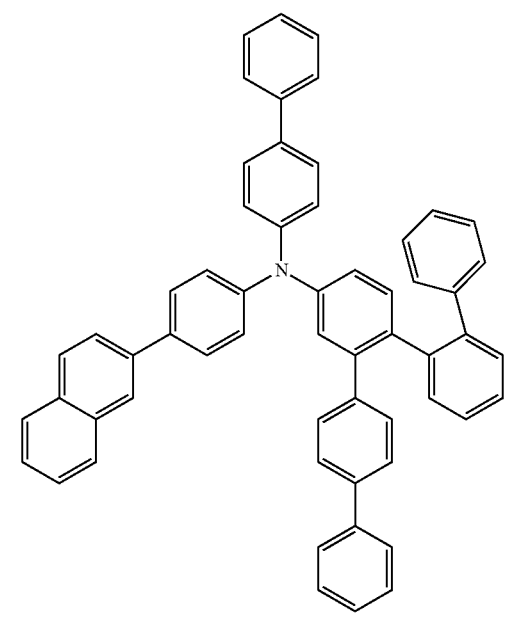

[Chemical Formula 221]
(1-204)
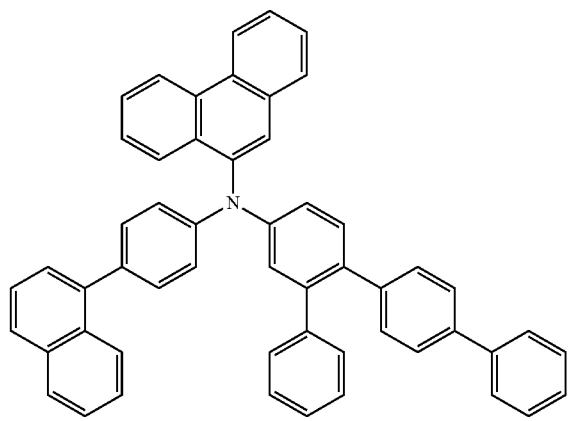
[Chemical Formula 222]
(1-205)
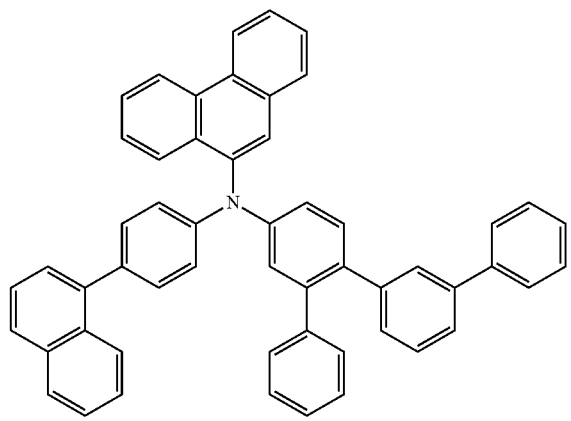
[Chemical Formula 223]
(1-206)
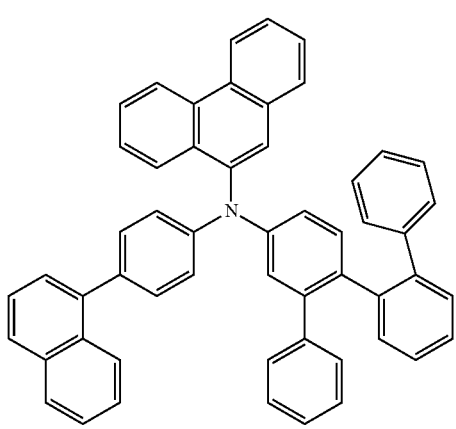
[Chemical Formula 224]
(1-207)
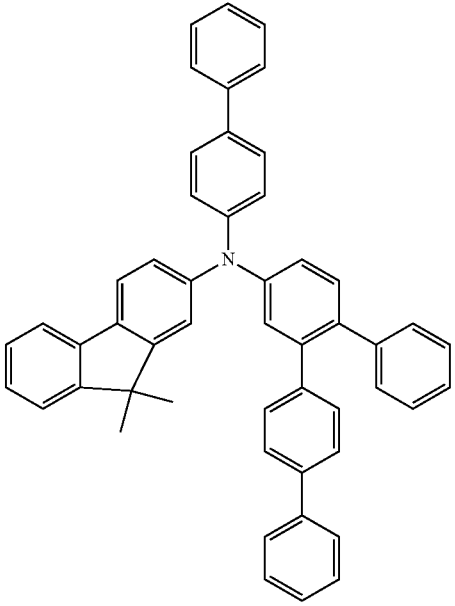
[Chemical Formula 225]
(1-208)
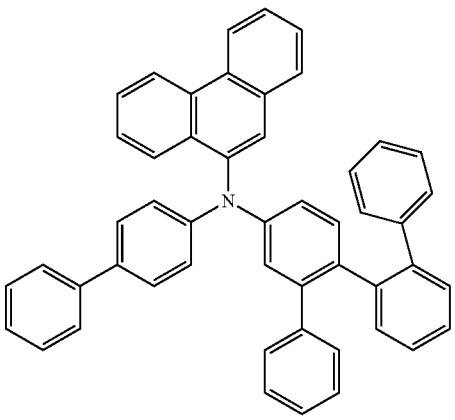
[Chemical Formula 226]
(1-209)

[Chemical Formula 227]
(1-210)
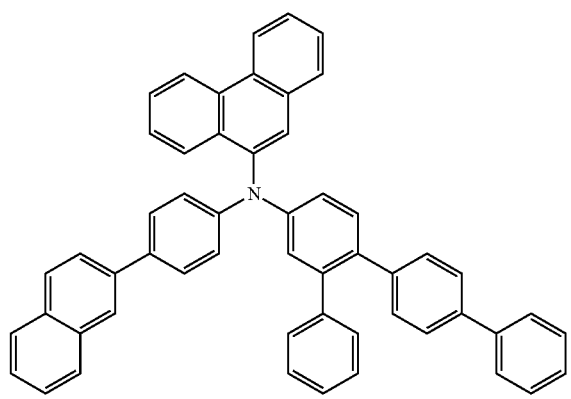
[Chemical Formula 228]
(1-211)
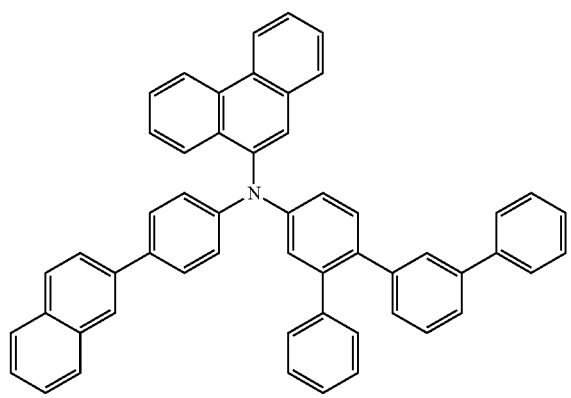
[Chemical Formula 229]
(1-212)
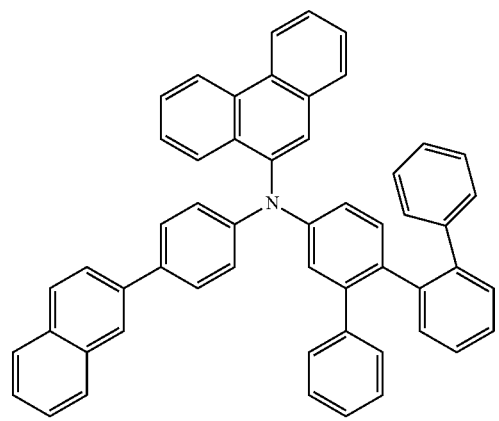
[Chemical Formula 230]
(1-213)
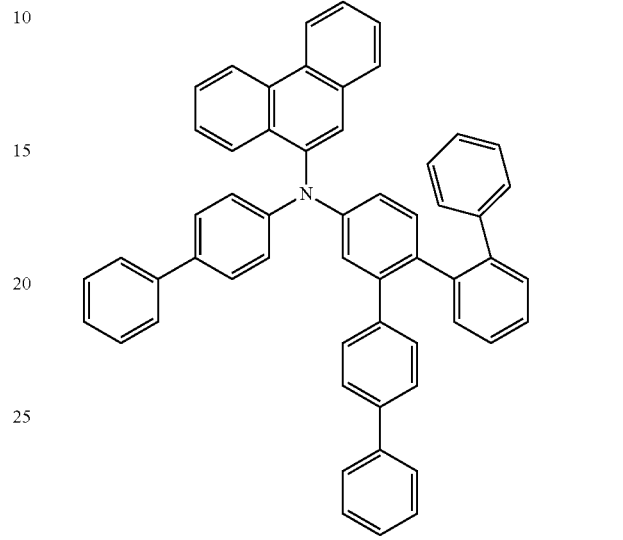
[Chemical Formula 231]
(1-214)
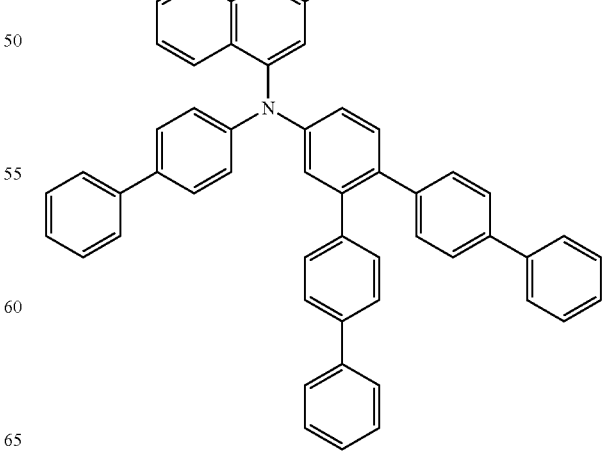

-continued

[Chemical Formula 232]

(1-215)

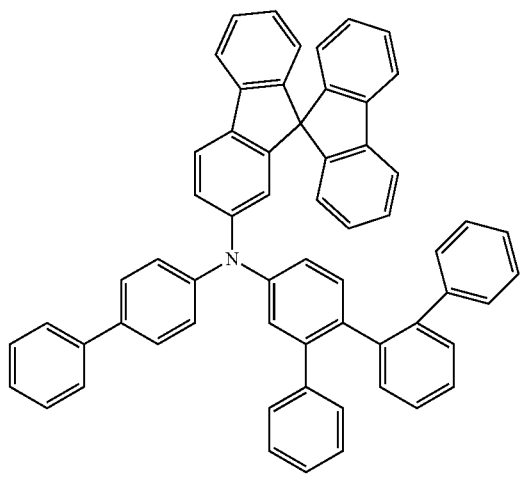

[Chemical Formula 233]

(1-216)

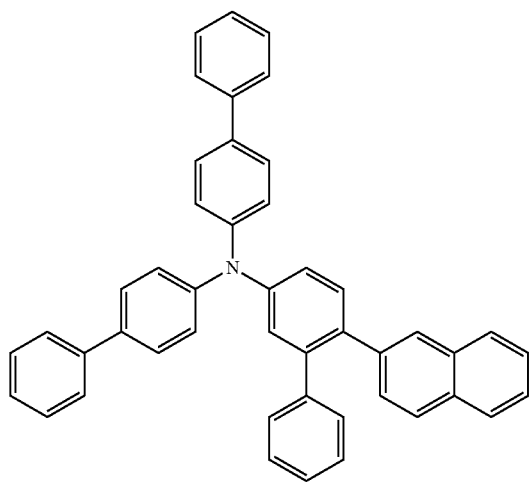

[Chemical Formula 234]

(1-217)

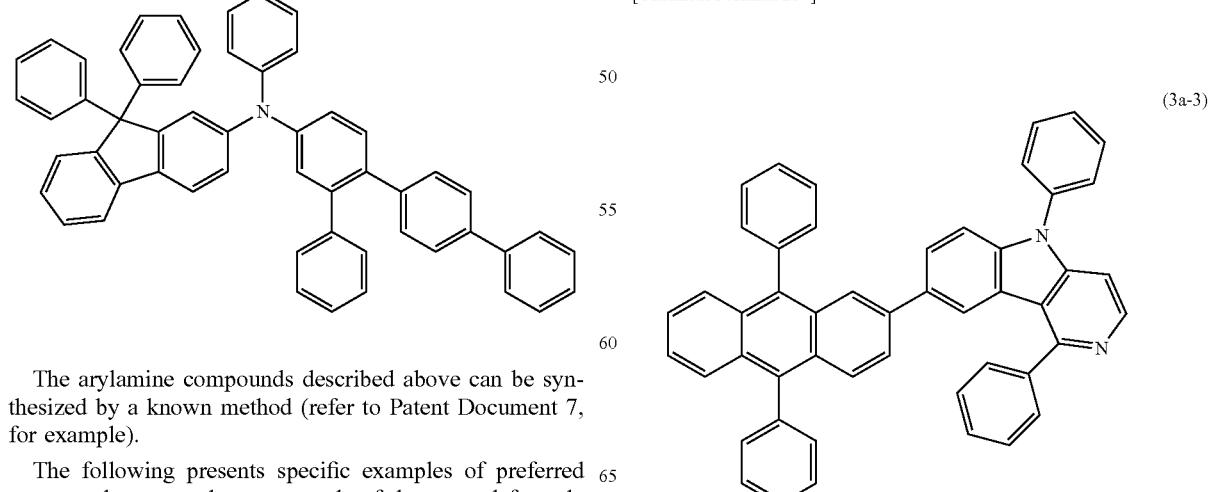

The arylamine compounds described above can be synthesized by a known method (refer to Patent Document 7, for example).

The following presents specific examples of preferred compounds among the compounds of the general formula (3a) preferably used in the organic EL device of the present invention and having an anthracene ring structure. The present invention, however, is not restricted to these compounds.

[Chemical Formula 235]

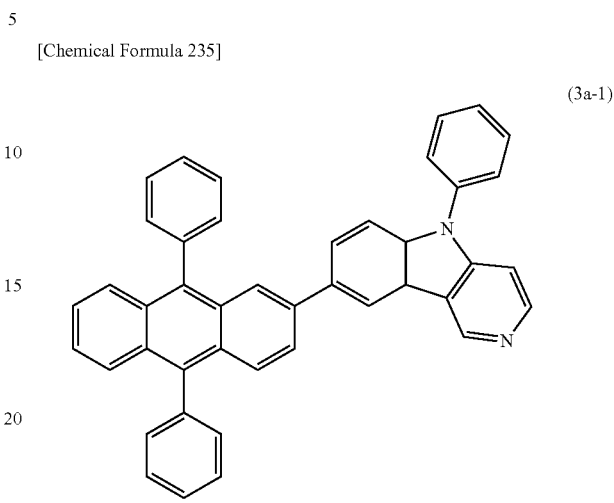

[Chemical Formula 236]

[Chemical Formula 237]

[Chemical Formula 238]
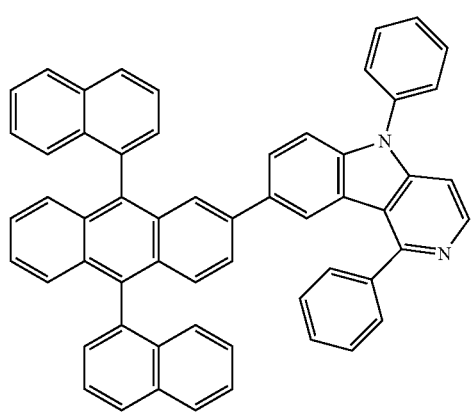
(3a-4)
[Chemical Formula 239]
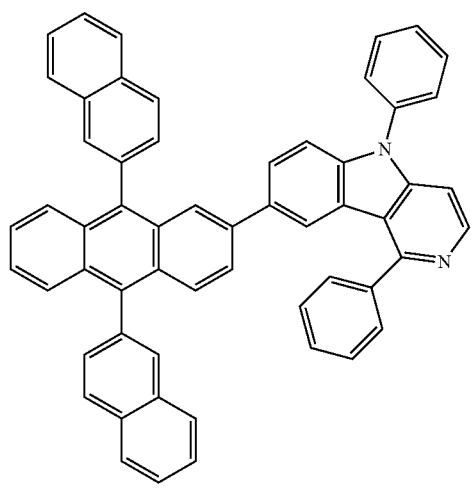
(3a-5)
[Chemical Formula 240]
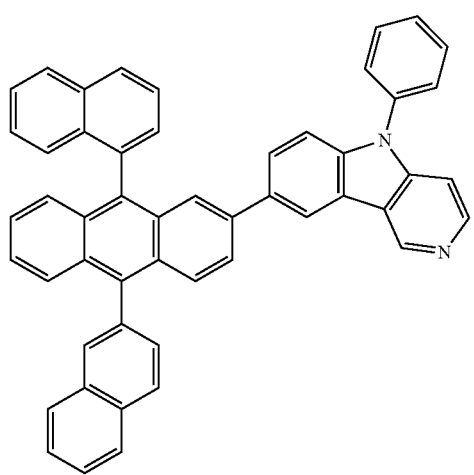
(3a-6)
[Chemical Formula 241]
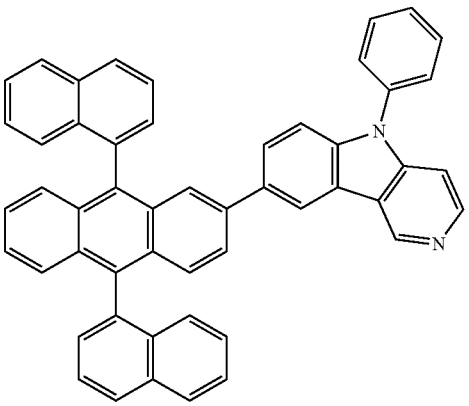
(3a-7)
[Chemical Formula 242]
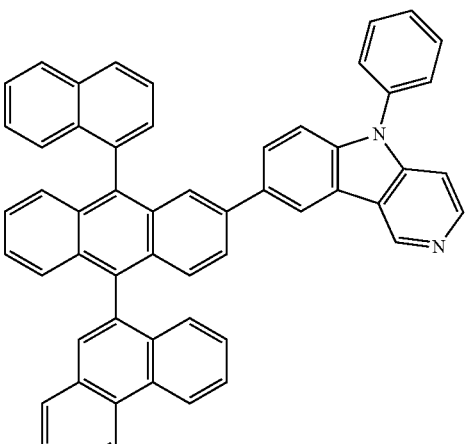
(3a-8)
[Chemical Formula 243]
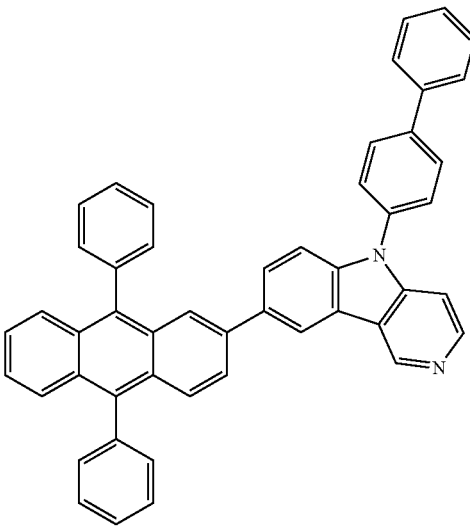
(3a-9)

[Chemical Formula 244]
(3a-10)
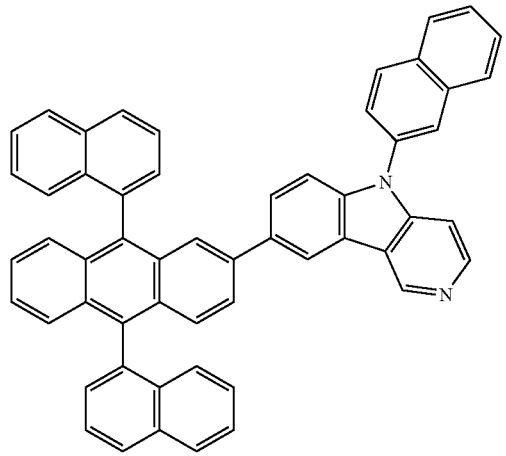
[Chemical Formula 245]
(3a-11)
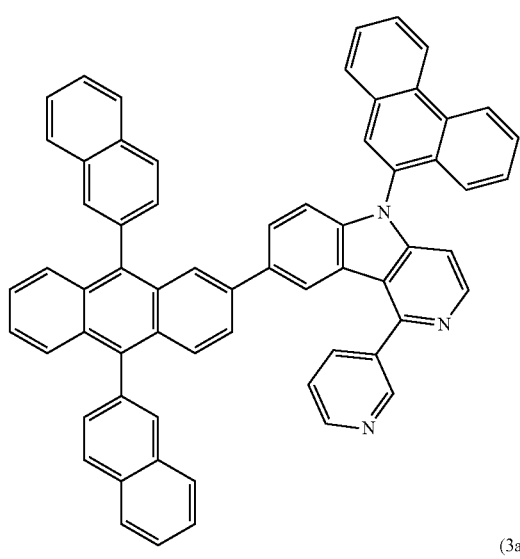
[Chemical Formula 246]
(3a-12)
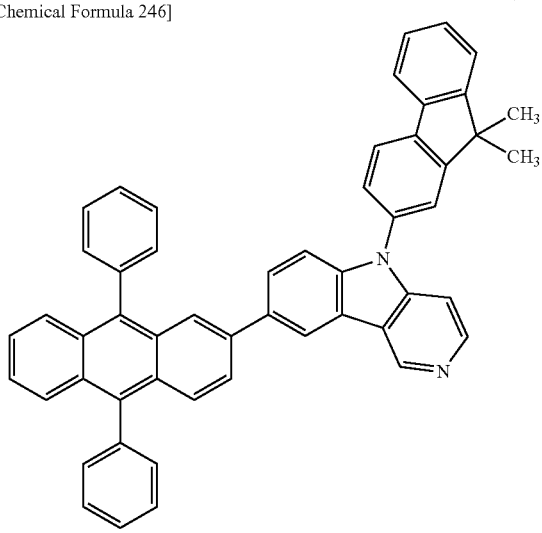
[Chemical Formula 247]
(3a-13)
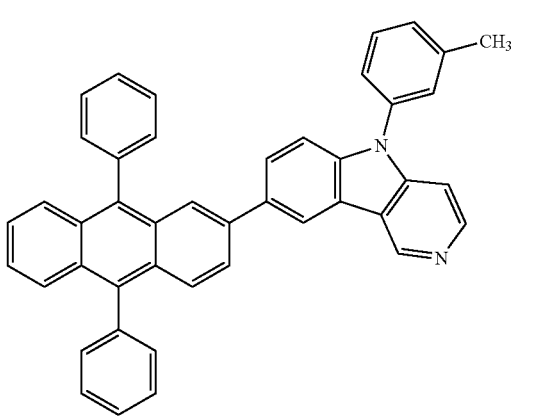
[Chemical Formula 248]
(3a-14)
[Chemical Formula 249]
(3a-15)
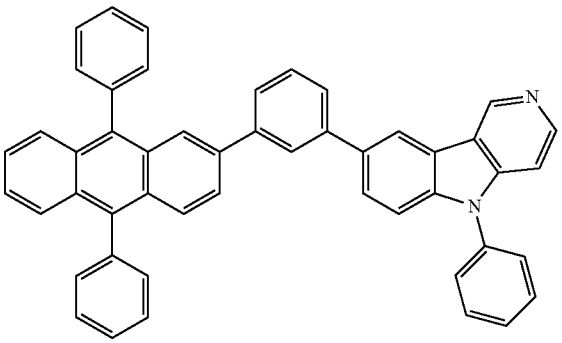

[Chemical Formula 250]

(3a-16)

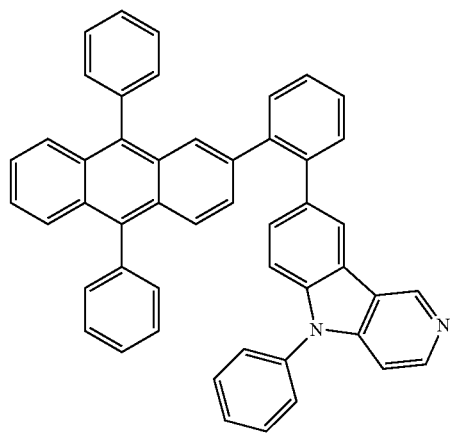

[Chemical Formula 251]

(3a-17)

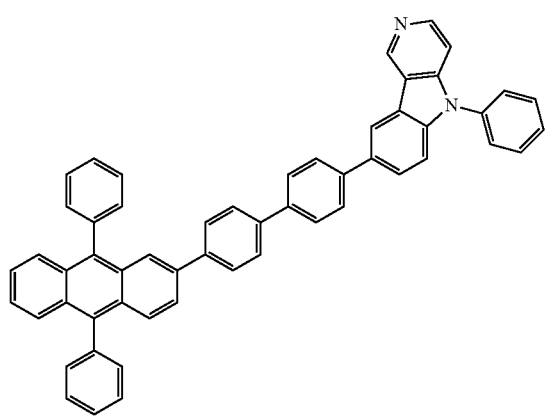

[Chemical Formula 252]

(3a-18)

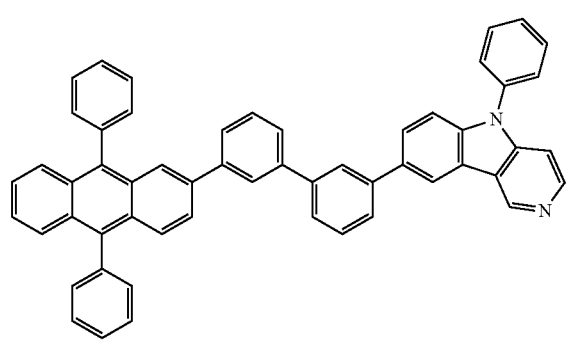

[Chemical Formula 253]

(3a-19)

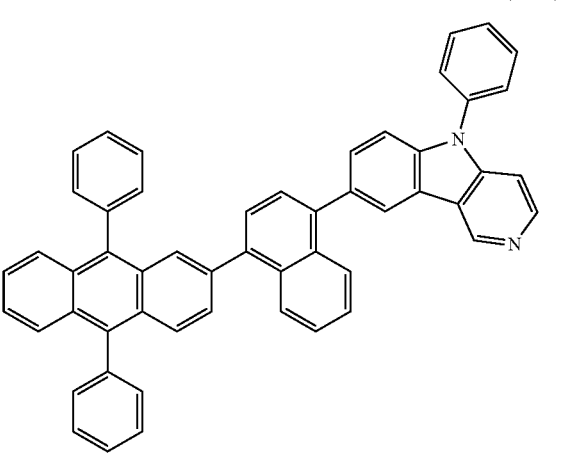

[Chemical Formula 254]

(3a-20)

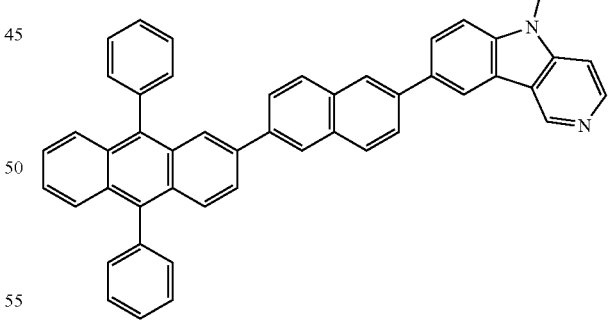

The following presents specific examples of preferred compounds among the compounds of the general formula (3b) preferably used in the organic EL device of the present invention and having an anthracene ring structure. The present invention, however, is not restricted to these compounds.

[Chemical Formula 255]
(3b-1)
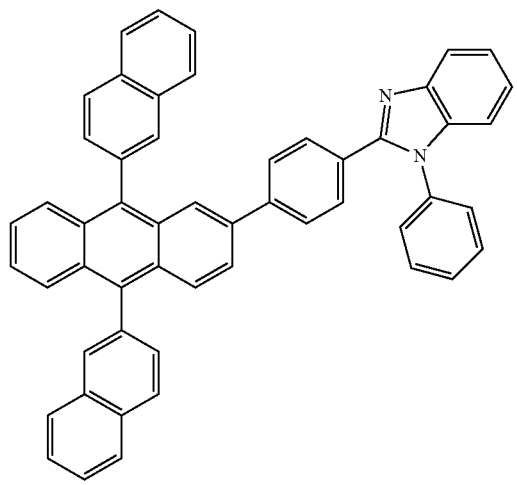
[Chemical Formula 256]
(3b-2)
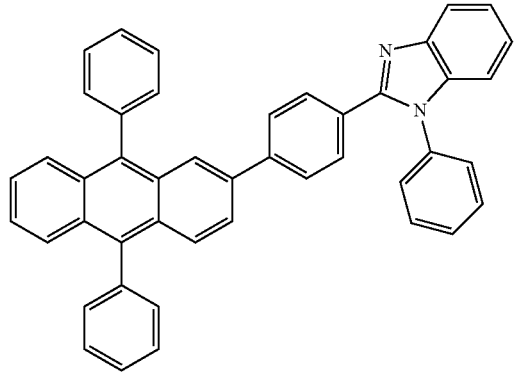
[Chemical Formula 257]
(3b-3)
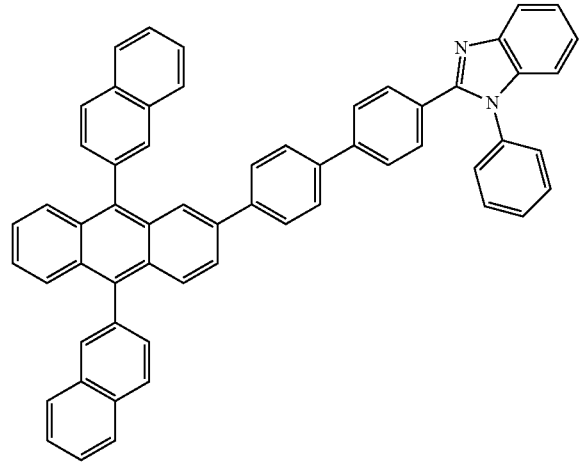
[Chemical Formula 258]
(3b-4)
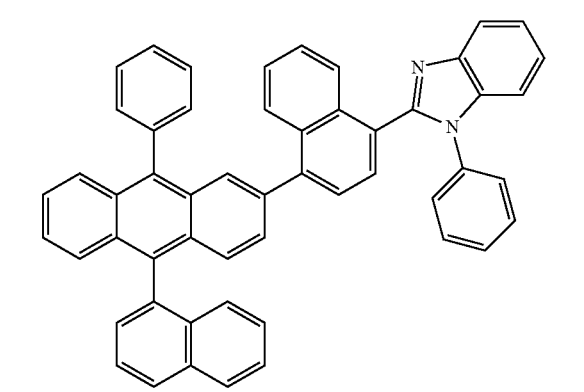
[Chemical Formula 259]
(3b-5)
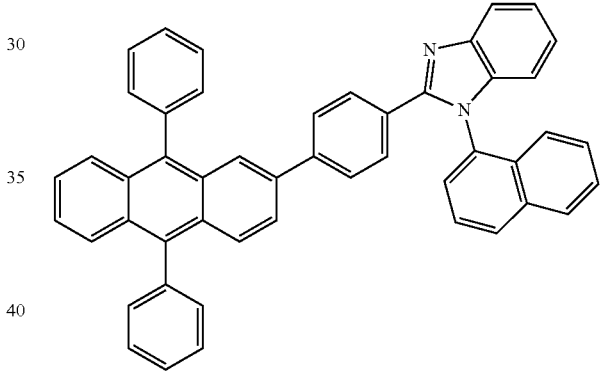
[Chemical Formula 260]
(3b-6)
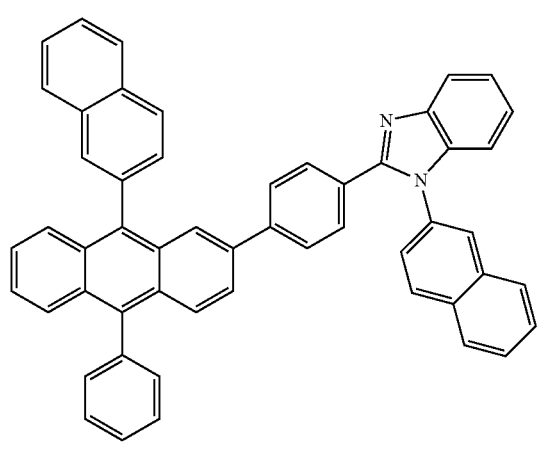

-continued
[Chemical Formula 261]
(3b-7)
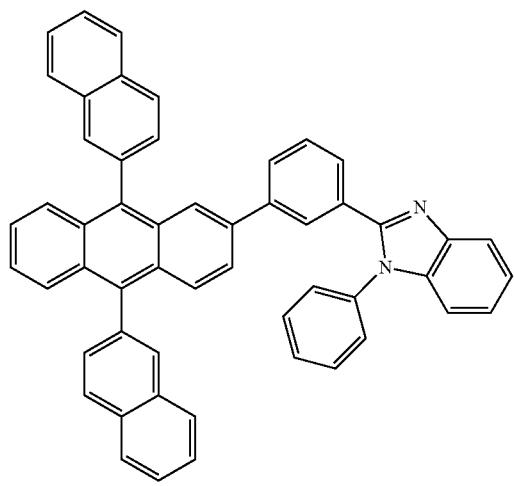
[Chemical Formula 262]
(3b-8)
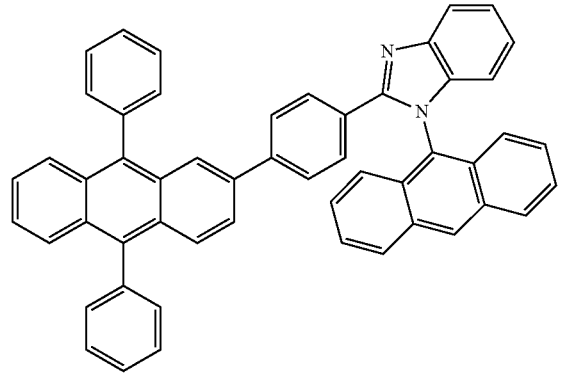
[Chemical Formula 263]
(3b-9)
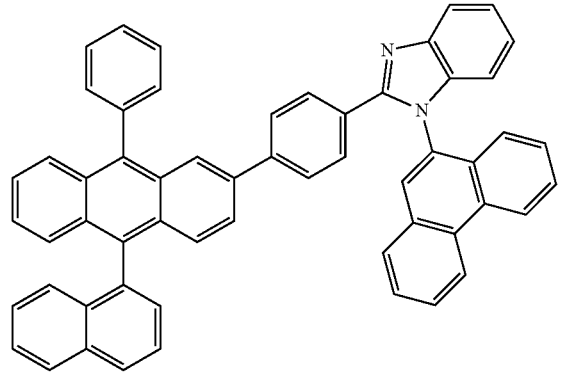
-continued
[Chemical Formula 264]
(3b-10)
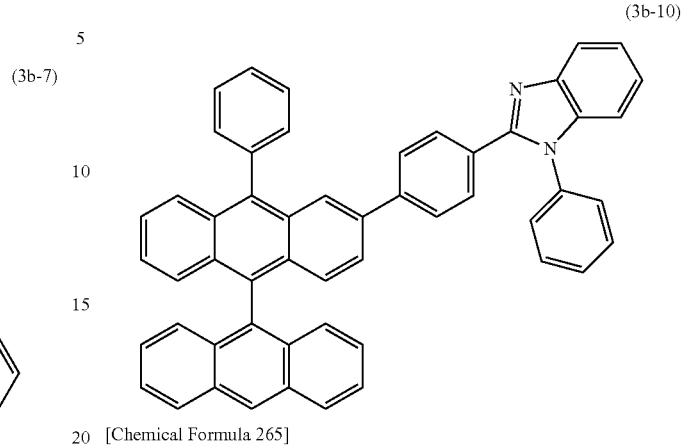
[Chemical Formula 265]
(3b-11)
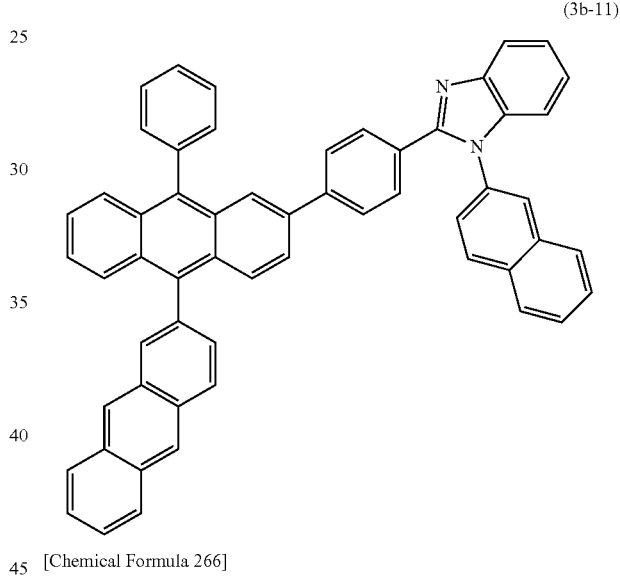
[Chemical Formula 266]
(3b-12)
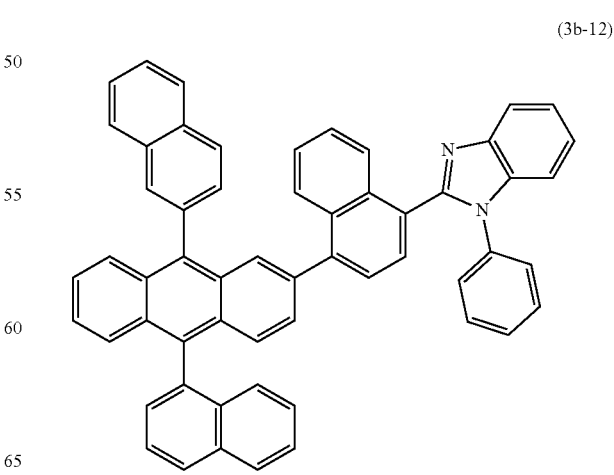

[Chemical Formula 267]

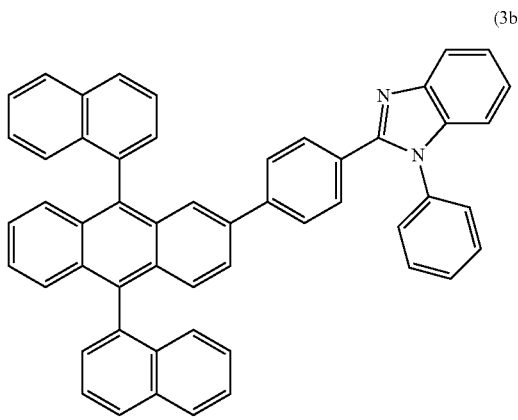

(3b-13)

[Chemical Formula 268]

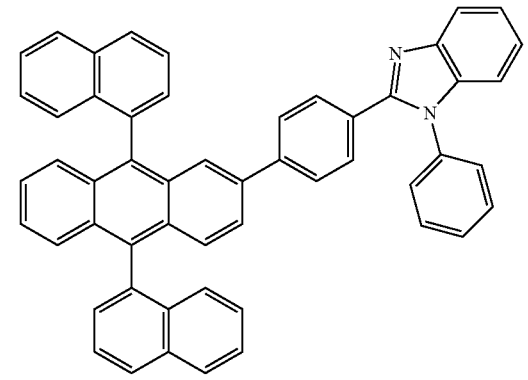

(3b-14)

[Chemical Formula 269]

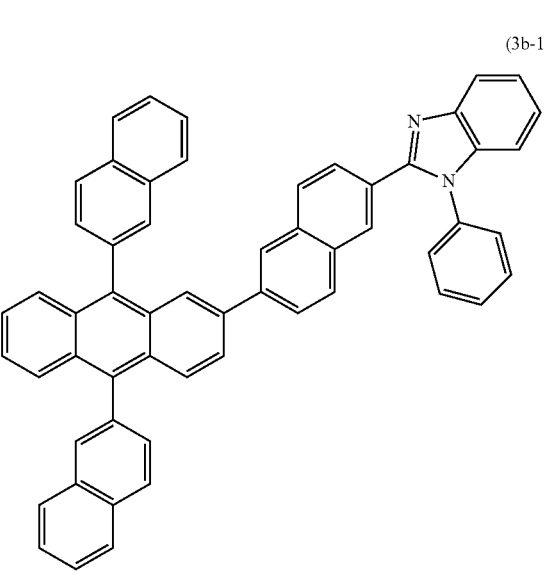

(3b-15)

[Chemical Formula 270]

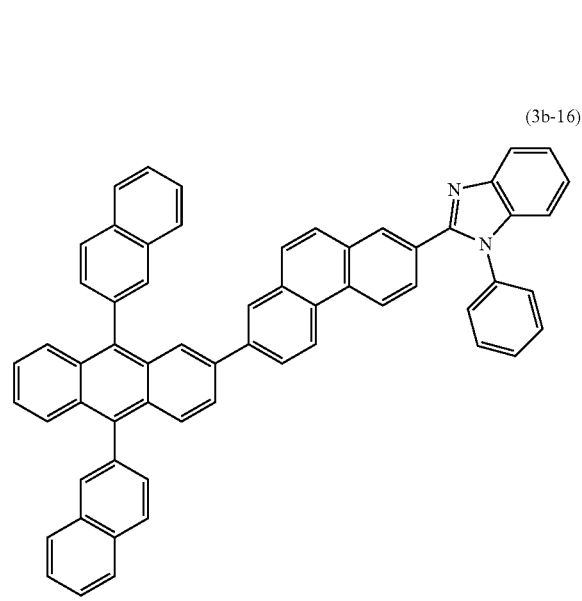

(3b-16)

The following presents specific examples of preferred compounds among the compounds of the general formula (3c) preferably used in the organic EL device of the present invention and having an anthracene ring structure. The present invention, however, is not restricted to these compounds.

[Chemical Formula 271]

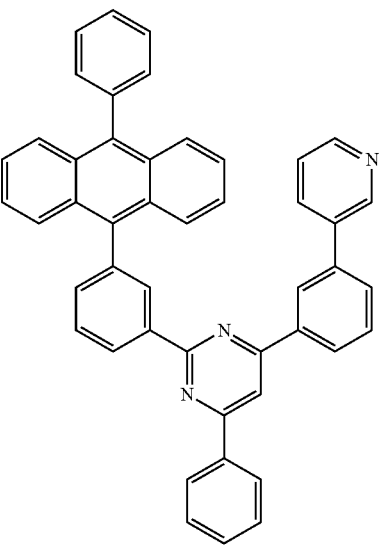

(3c-1)

[Chemical Formula 272]
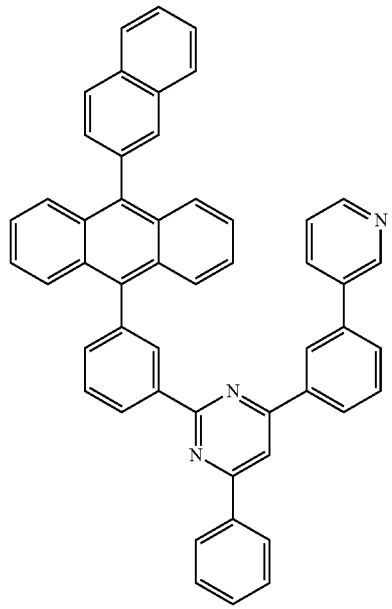
(3c-2)
[Chemical Formula 273]
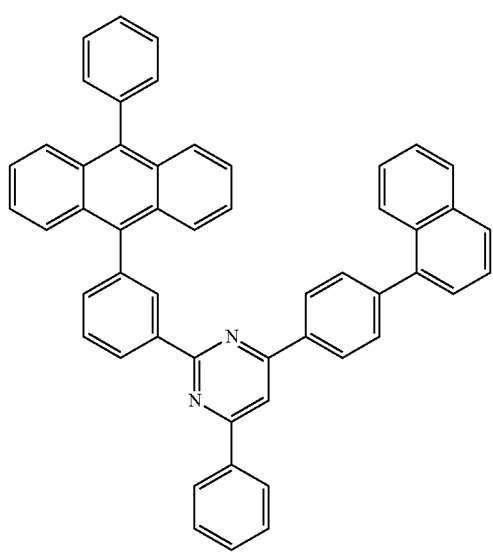
(3c-3)
[Chemical Formula 274]
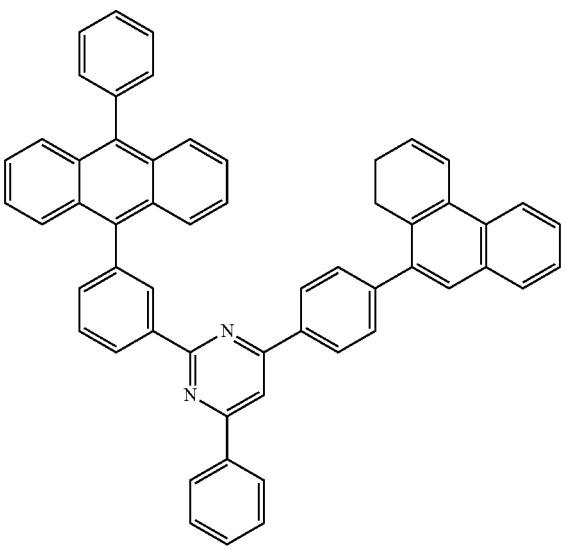
(3c-4)
[Chemical Formula 275]
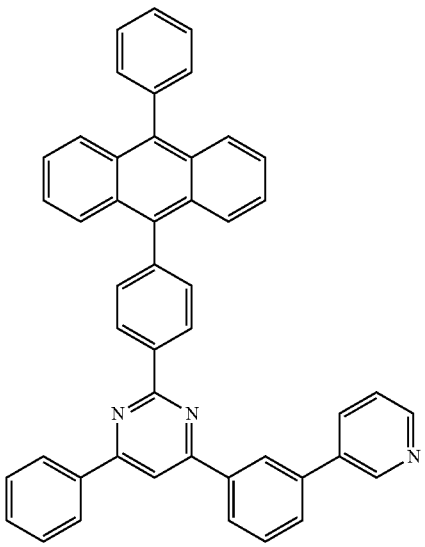
(3c-5)

[Chemical Formula 276]
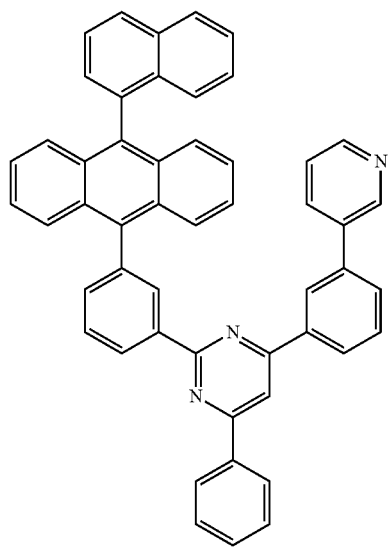
(3c-6)
[Chemical Formula 277]
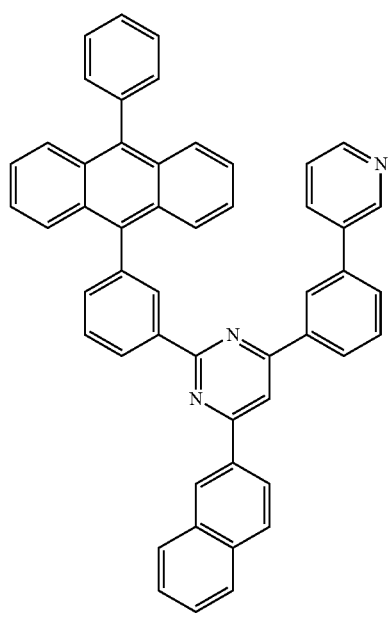
(3c-7)
[Chemical Formula 278]
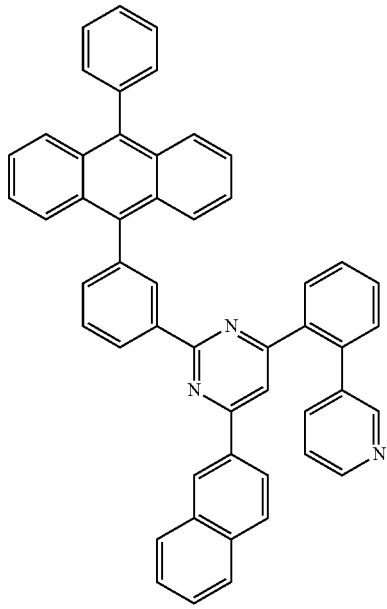
(3c-8)
[Chemical Formula 279]
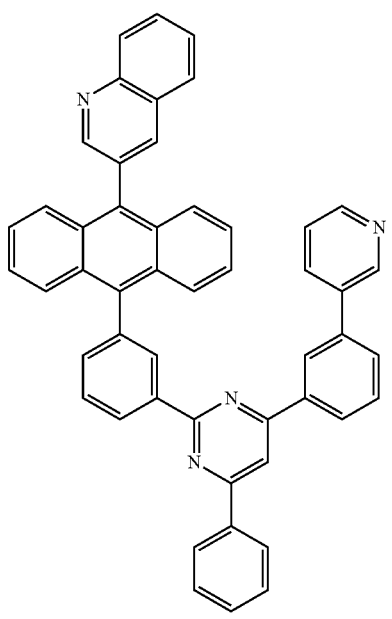
(3c-9)

[Chemical Formula 280]
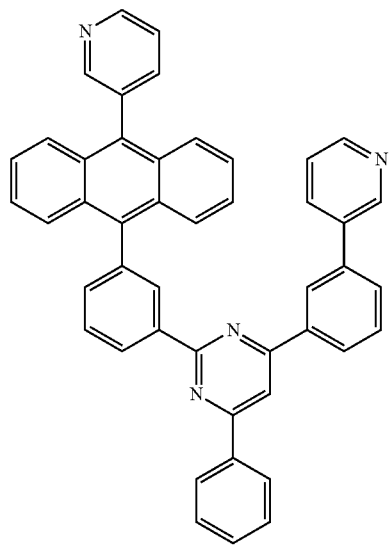
(3c-10)
[Chemical Formula 281]
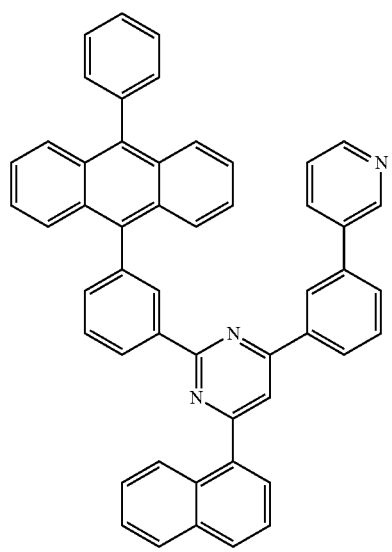
(3c-11)
[Chemical Formula 282]
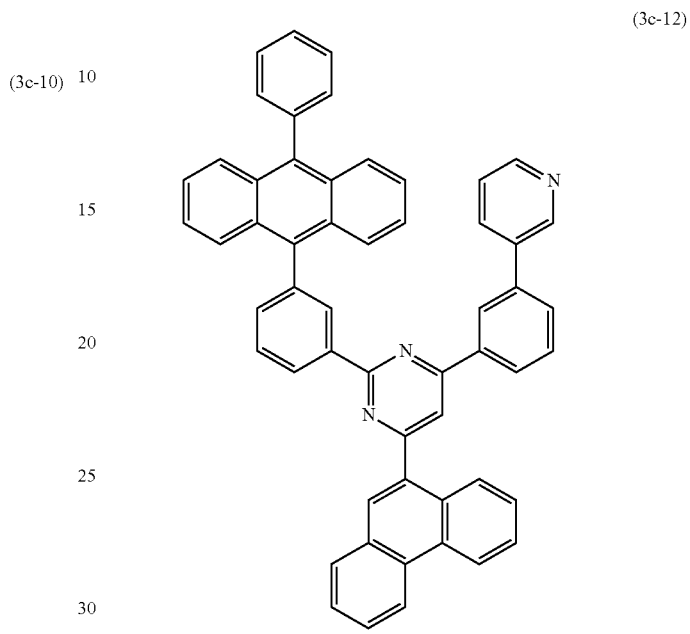
(3c-12)
[Chemical Formula 283]
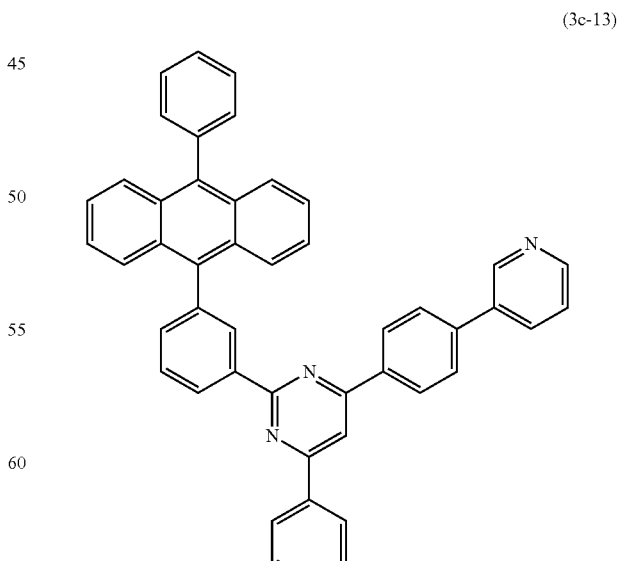
(3c-13)

[Chemical Formula 284]
(3c-14)
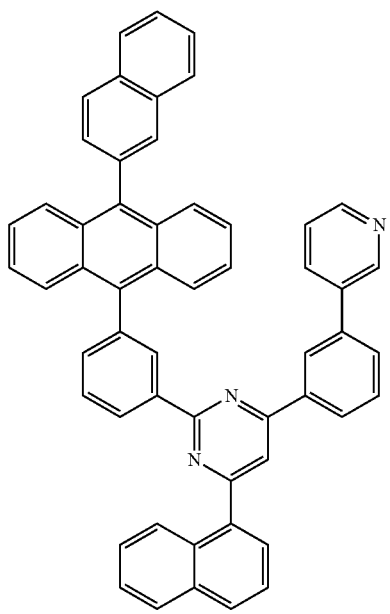
[Chemical Formula 285]
(3c-15)
[Chemical Formula 286]
(3c-16)
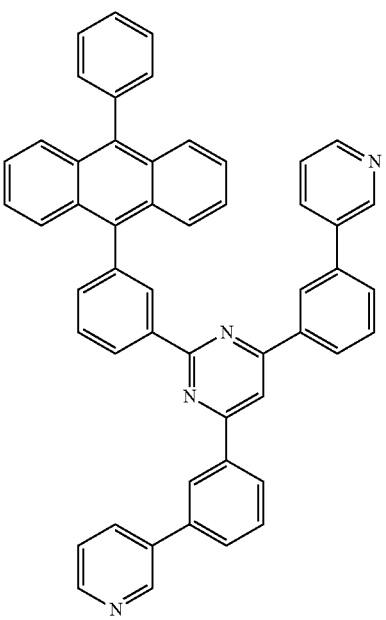
[Chemical Formula 287]
(3c-17)
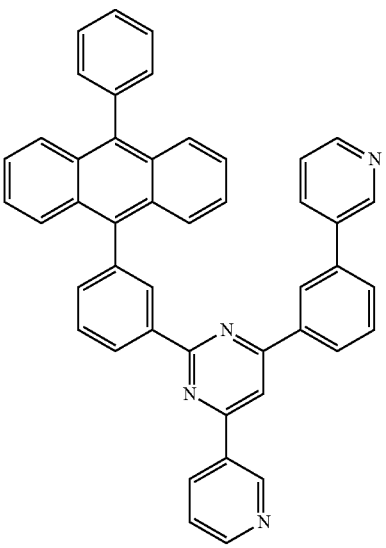

[Chemical Formula 288]
(3c-18)
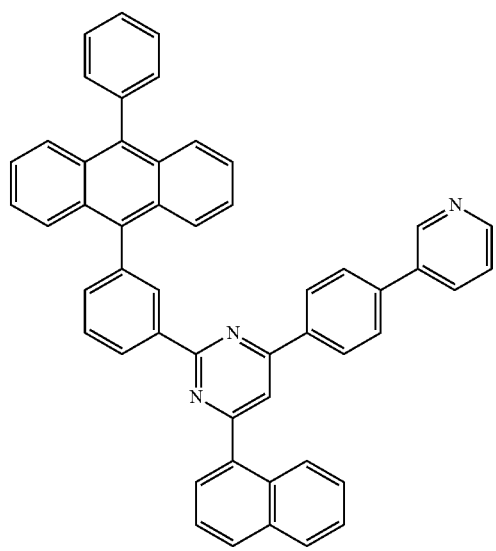
[Chemical Formula 289]
(3c-19)
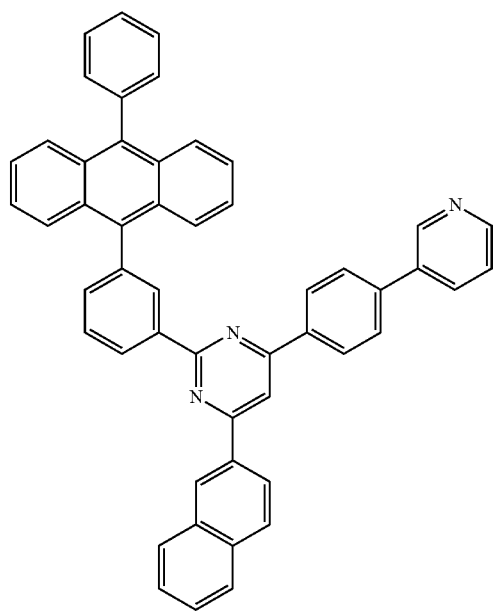
[Chemical Formula 290]
(3c-20)
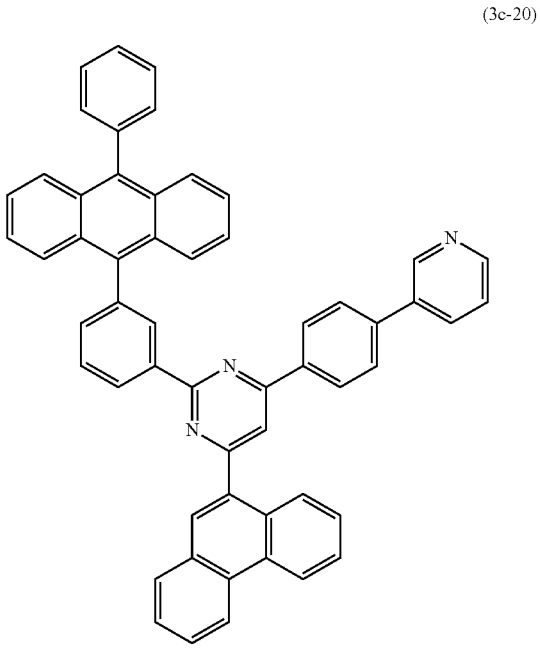
[Chemical Formula 291]
(3c-21)
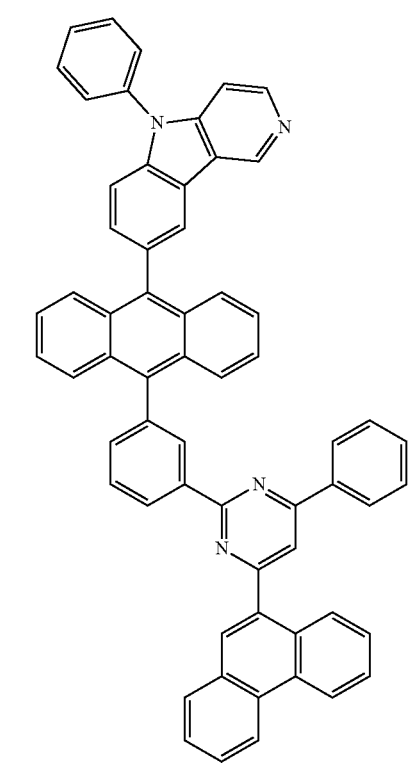

[Chemical Formula 292]
(3c-22)
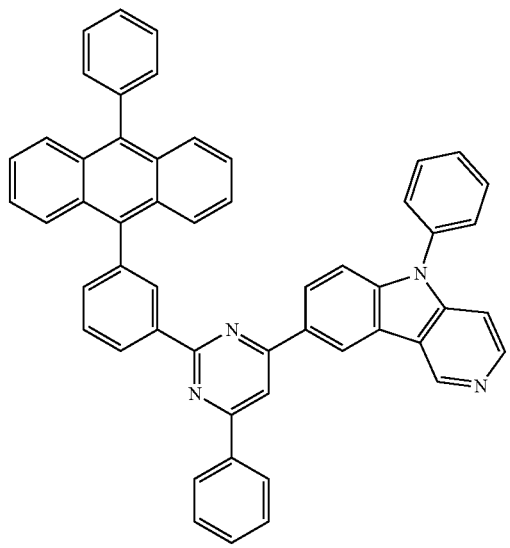
[Chemical Formula 293]
(3c-23)
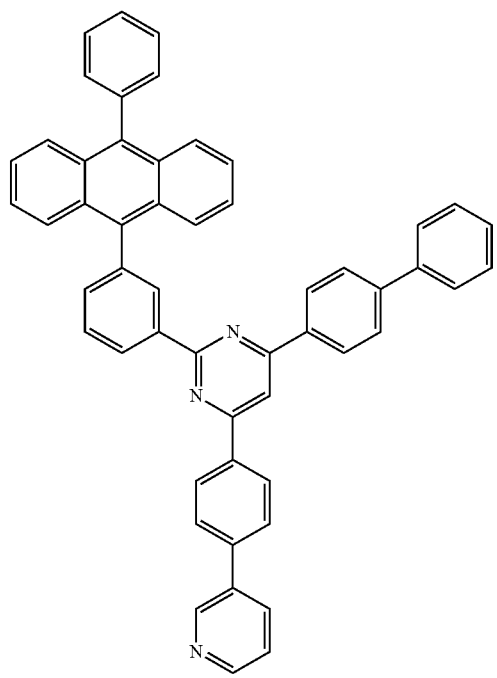
[Chemical Formula 294]
(3c-24)
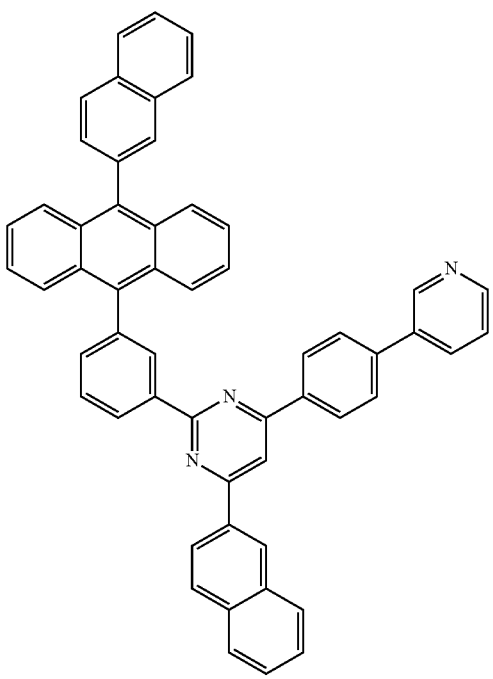
[Chemical Formula 295]
(3c-25)
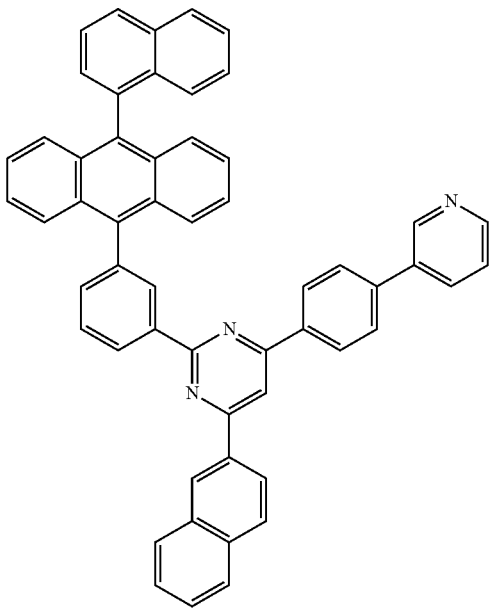

[Chemical Formula 296]
(3c-26)
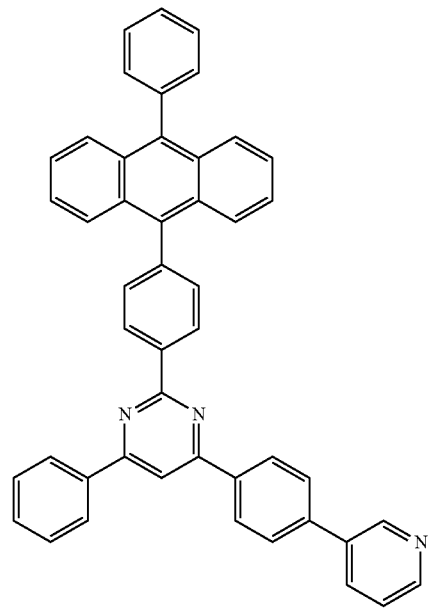
[Chemical Formula 297]
(3c-27)
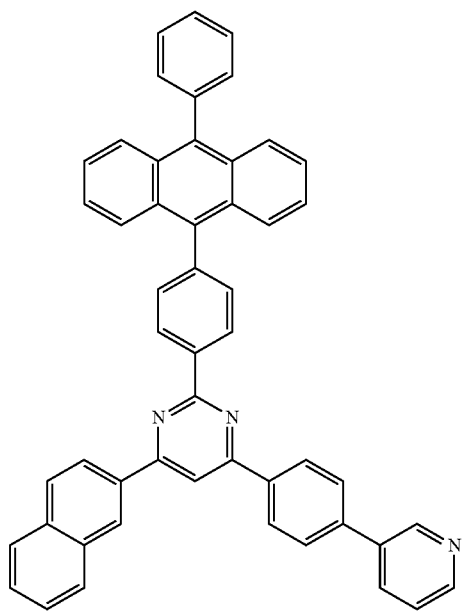
[Chemical Formula 298]
(3c-28)
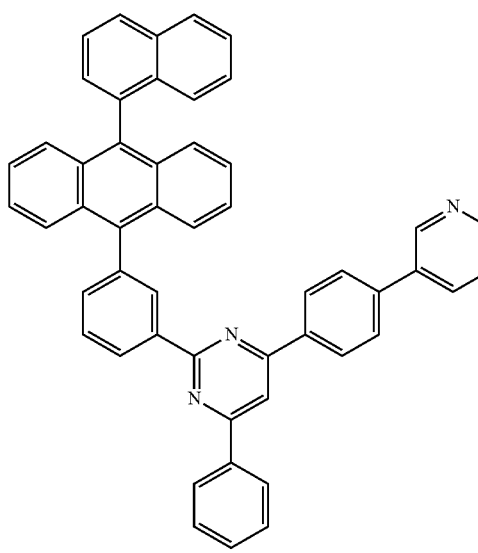
[Chemical Formula 299]
(3c-29)
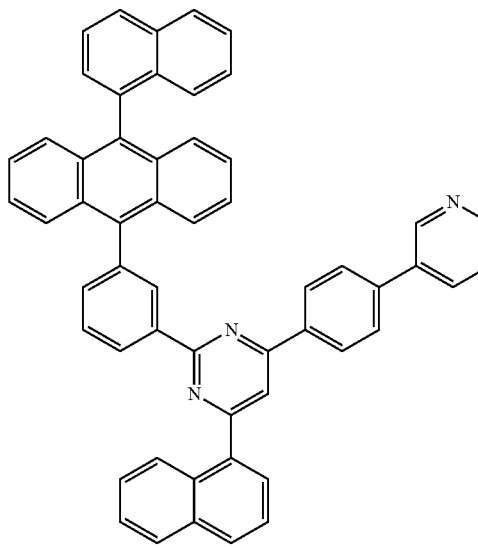

[Chemical Formula 300]

(3c-30)

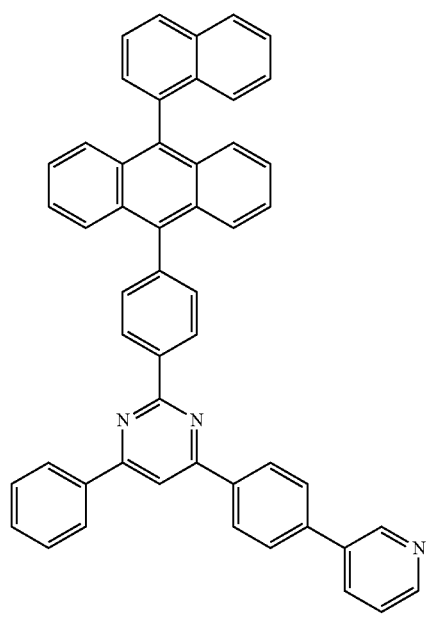

The compounds having an anthracene ring structure described above can be synthesized by a known method (refer to Patent Documents 8 to 10, for example).

The following presents specific examples of preferred compounds among the compounds of the general formula (4) preferably used in the organic EL device of the present invention and having a pyrimidine ring structure. The present invention, however, is not restricted to these compounds.

[Chemical Formula 301]

(4-1)

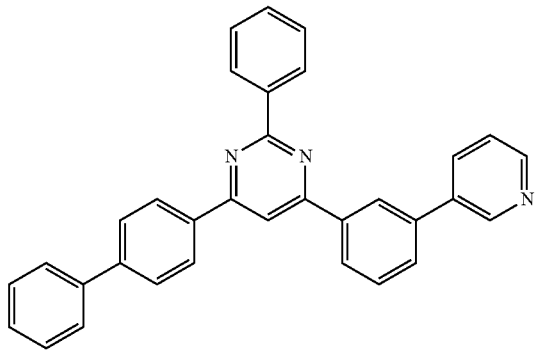

[Chemical Formula 302]

(4-2)

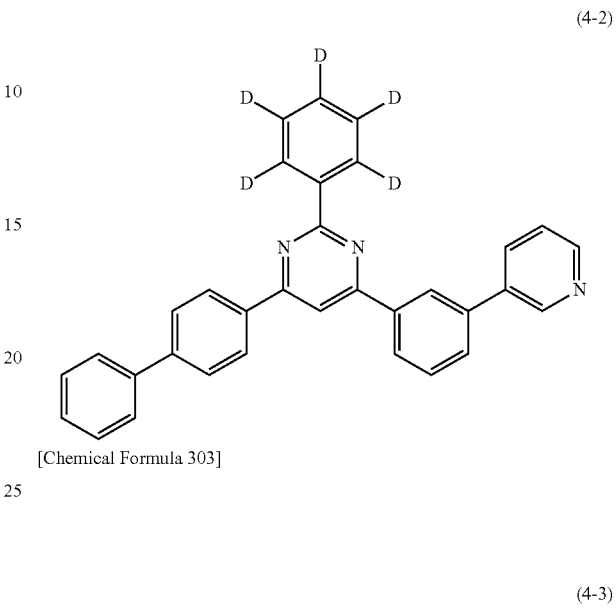

[Chemical Formula 303]

(4-3)

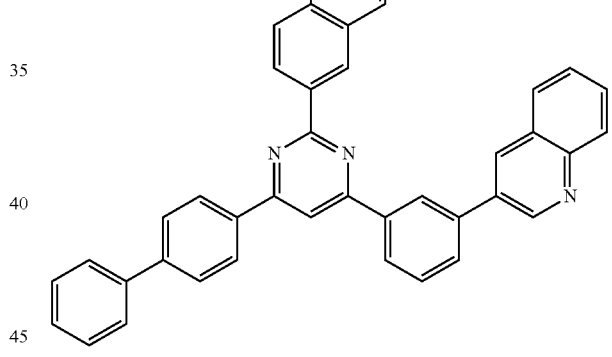

[Chemical Formula 304]

(4-4)

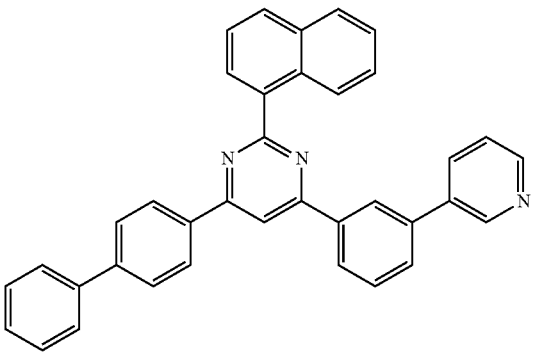

[Chemical Formula 305]
(4-5)
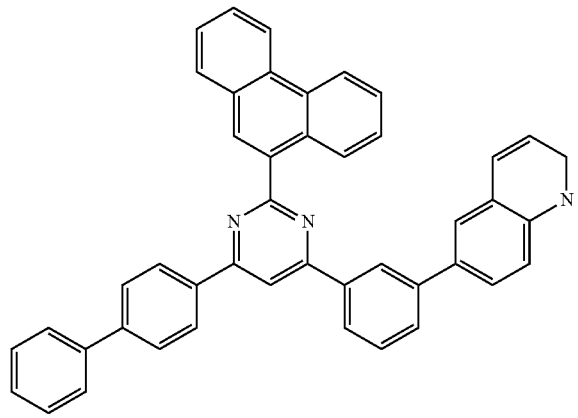
[Chemical Formula 306]
(4-6)
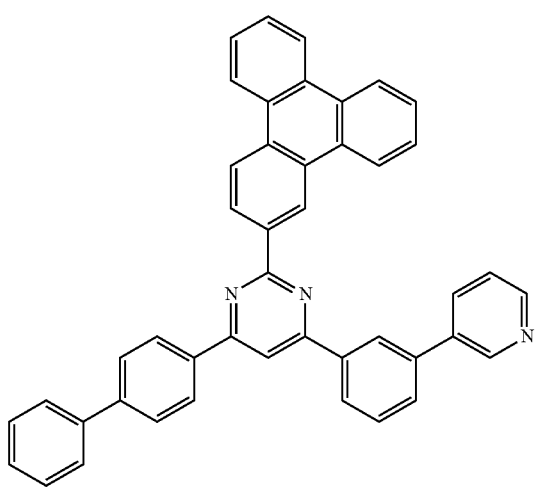
[Chemical Formula 307]
(4-7)
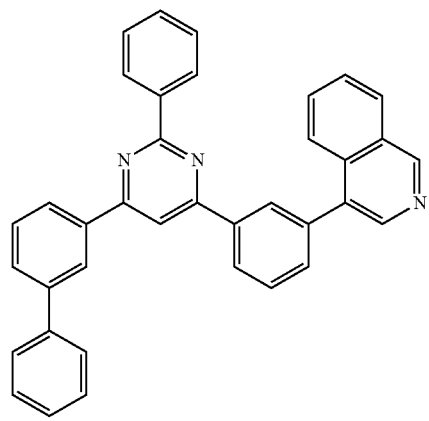
[Chemical Formula 308]
(4-8)
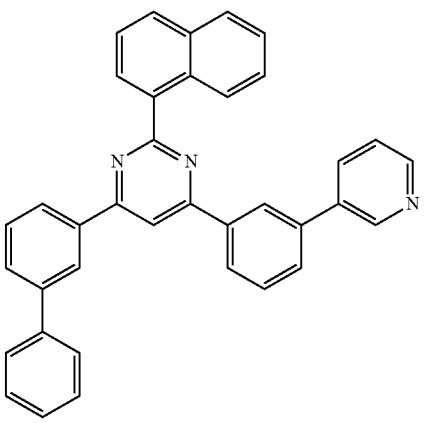
[Chemical Formula 309]
(4-9)
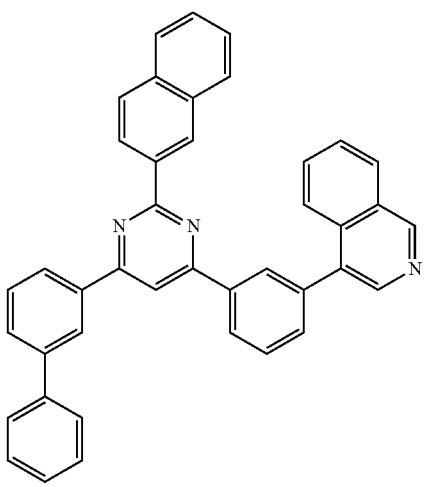
[Chemical Formula 310]
(4-10)

[Chemical Formula 311]
(4-11)
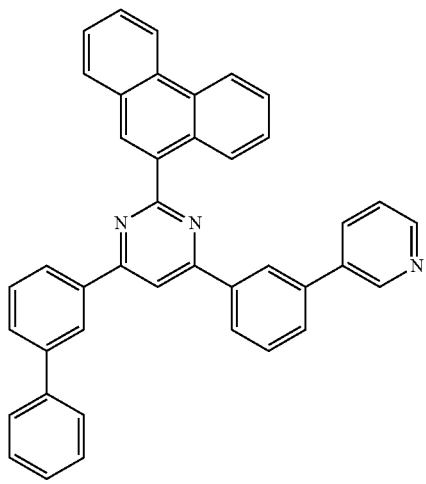
[Chemical Formula 312]
(4-12)
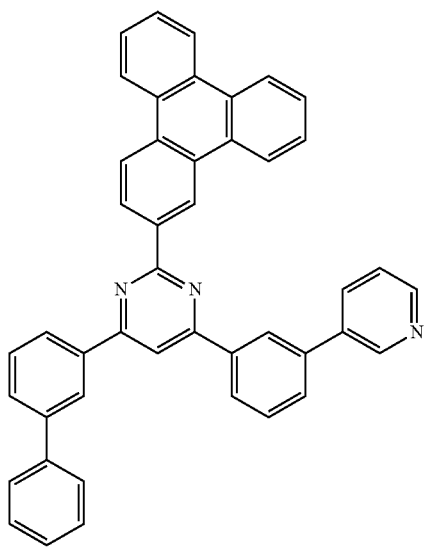
[Chemical Formula 313]
(4-13)
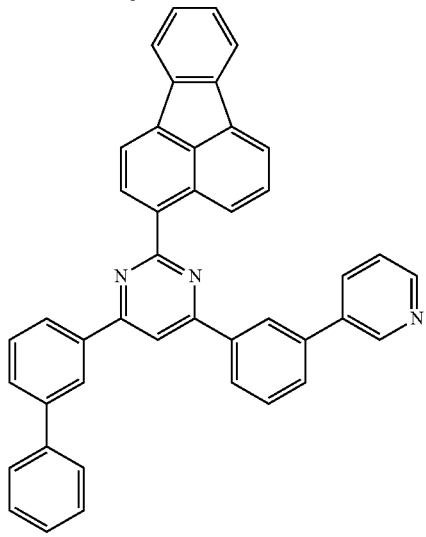
[Chemical Formula 314]
(4-14)
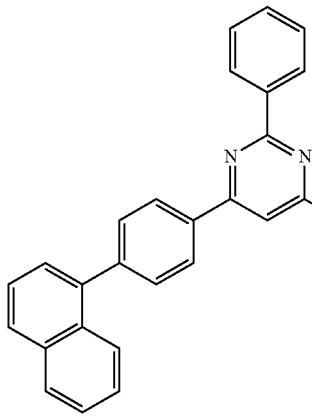
[Chemical Formula 315]
(4-15)
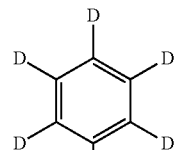
[Chemical Formula 316]
(4-16)
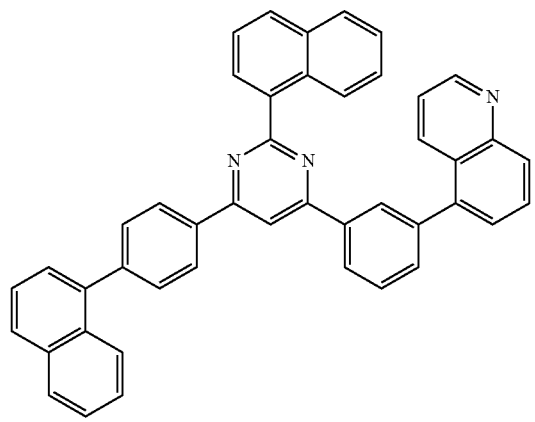

[Chemical Formula 317]
(4-17)
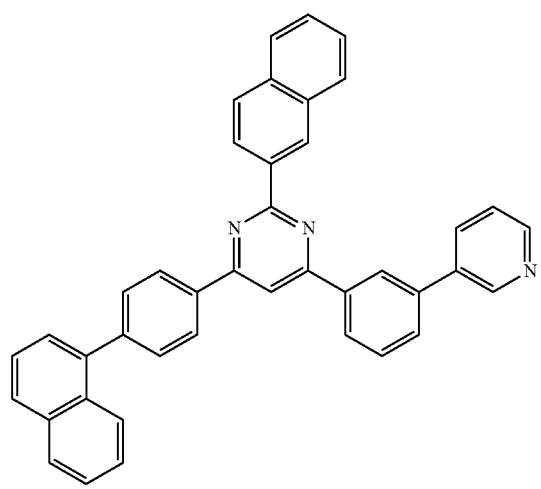
[Chemical Formula 318]
(4-18)
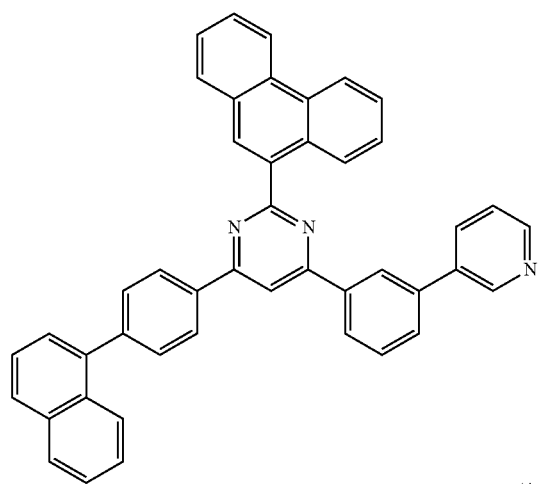
[Chemical Formula 319]
(4-19)
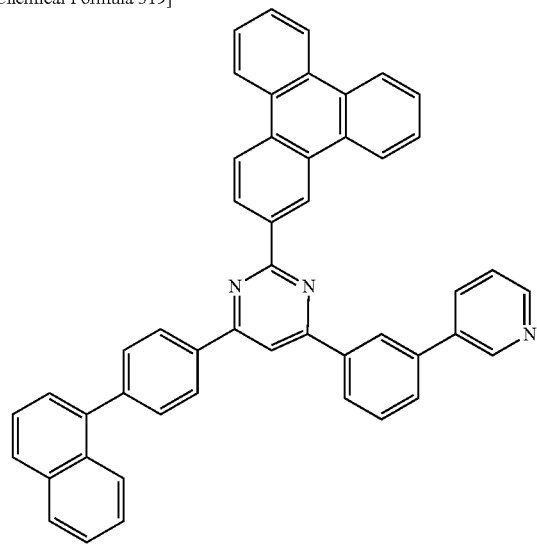
[Chemical Formula 320]
(4-20)
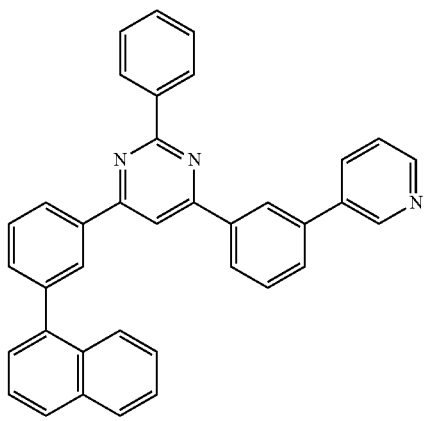
[Chemical Formula 321]
(4-21)
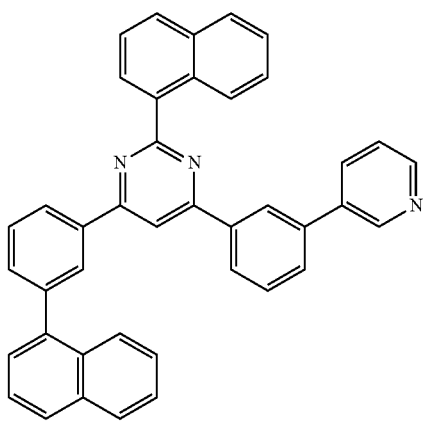
[Chemical Formula 322]
(4-22)
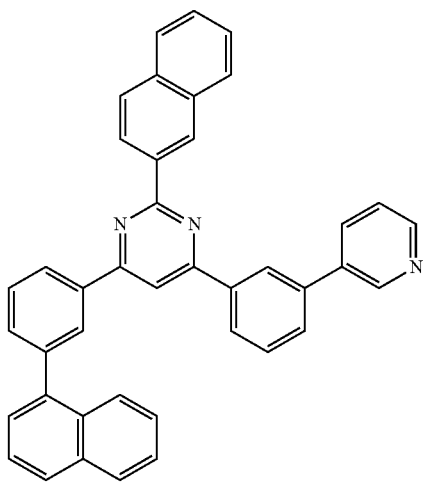

[Chemical Formula 323]
(4-23)
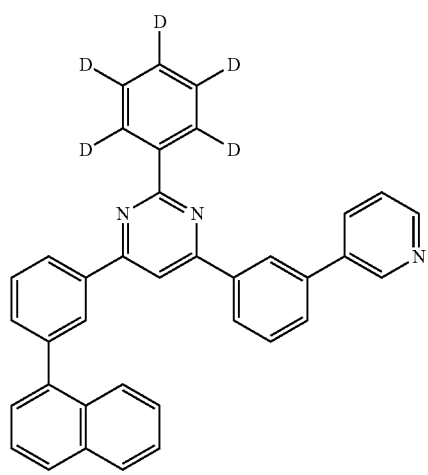
[Chemical Formula 324]
(4-24)
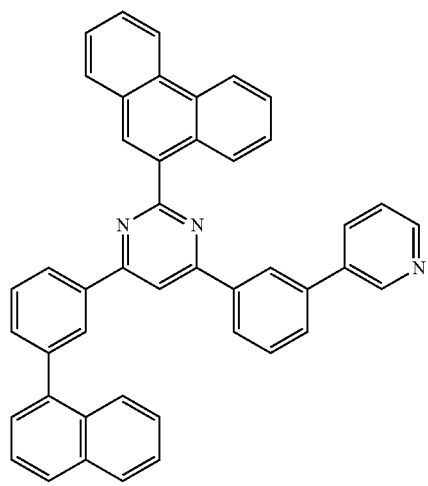
[Chemical Formula 325]
(4-25)
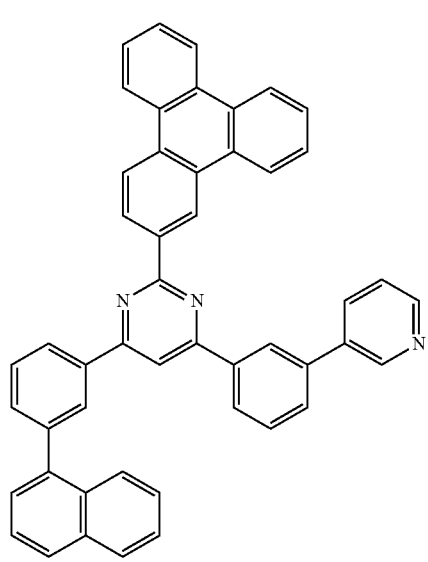
[Chemical Formula 326]
(4-26)
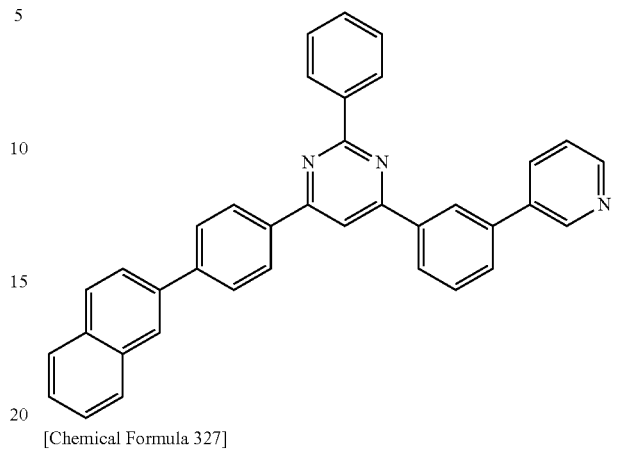
[Chemical Formula 327]
(4-27)
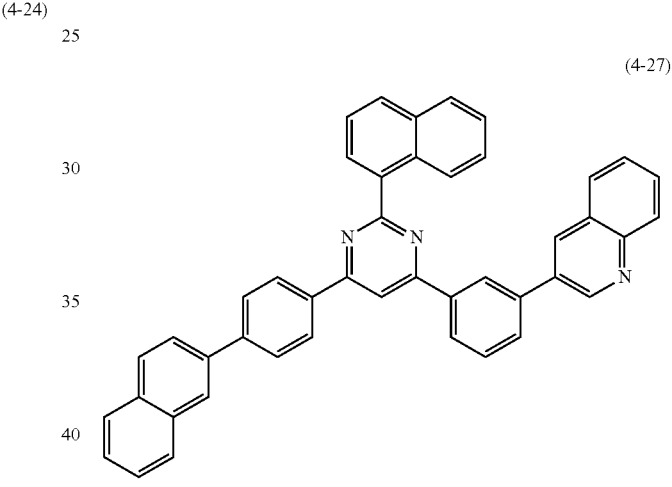
[Chemical Formula 328]
(4-28)
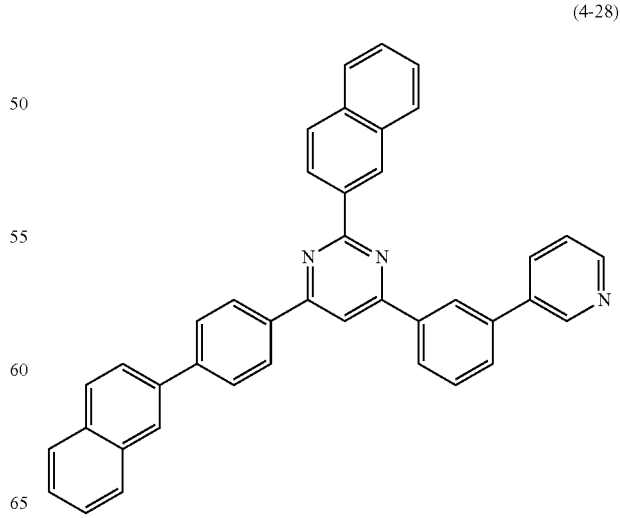

[Chemical Formula 329]
(4-29)
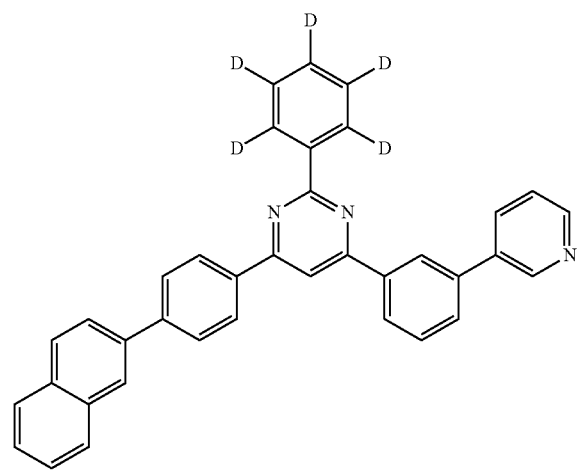
[Chemical Formula 330]
(4-30)
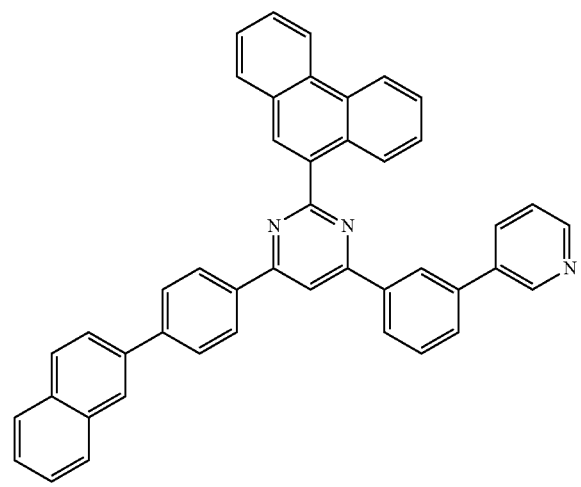
[Chemical Formula 331]
(4-31)
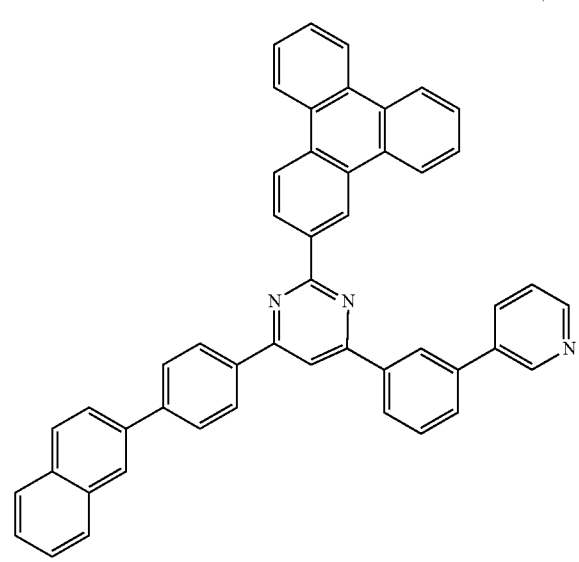
[Chemical Formula 332]
(4-32)
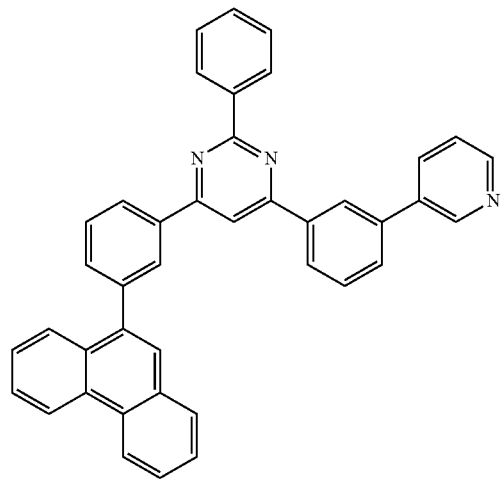
[Chemical Formula 333]
(4-33)
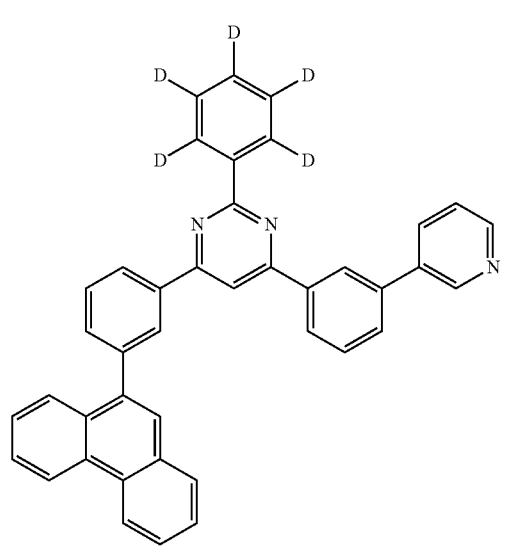
[Chemical Formula 334]
(4-34)
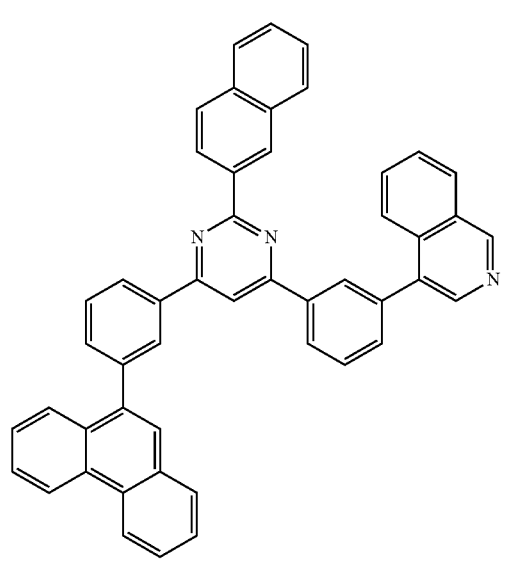

[Chemical Formula 335]
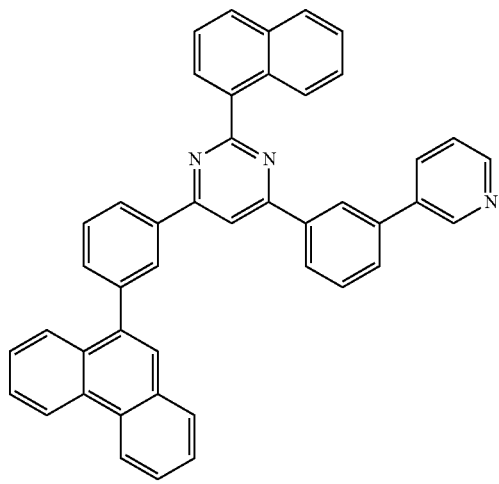
(4-35)
[Chemical Formula 336]
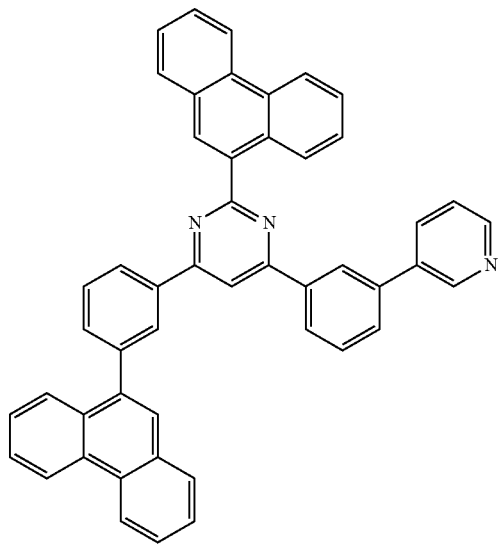
(4-36)
[Chemical Formula 337]
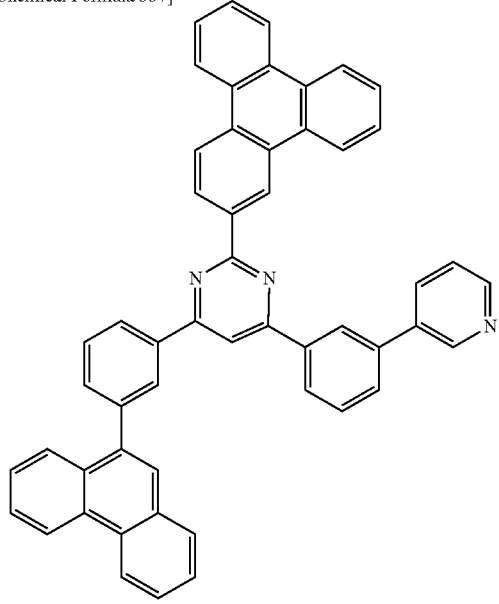
(4-37)
[Chemical Formula 338]
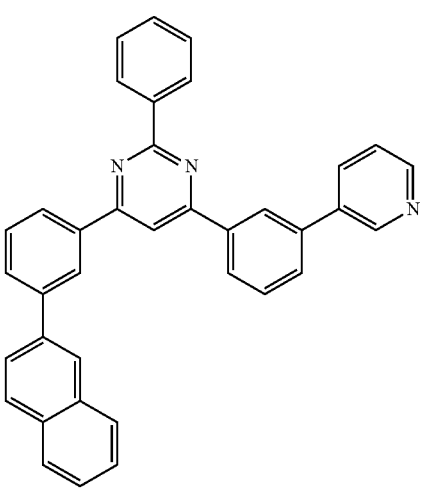
(4-38)
[Chemical Formula 339]
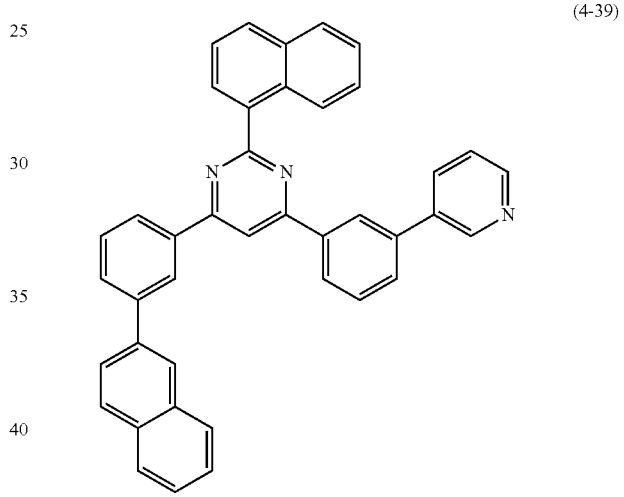
(4-39)
[Chemical Formula 340]
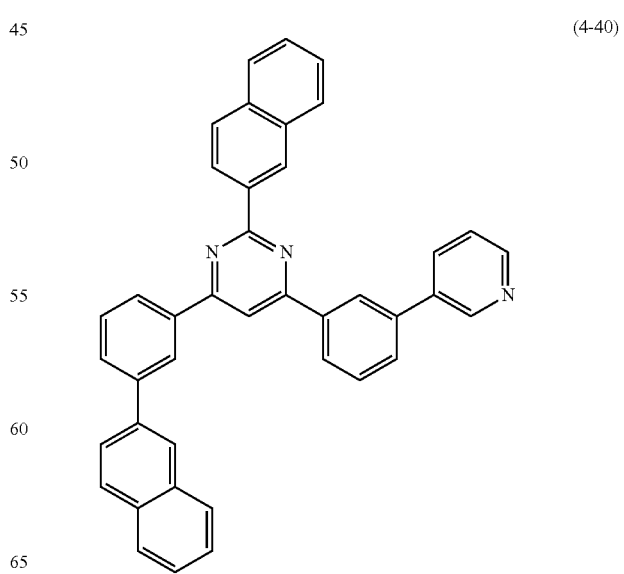
(4-40)

[Chemical Formula 341]
(4-41)
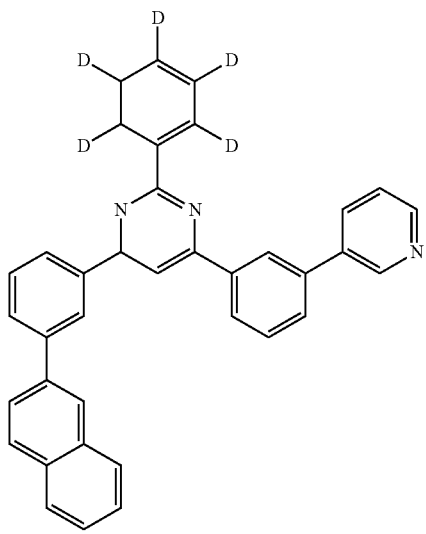
[Chemical Formula 342]
(4-42)
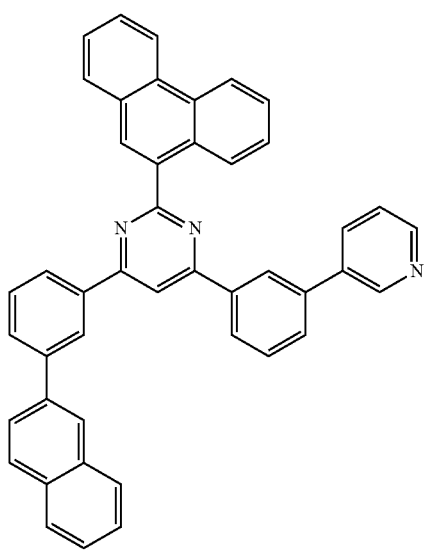
[Chemical Formula 343]
(4-43)
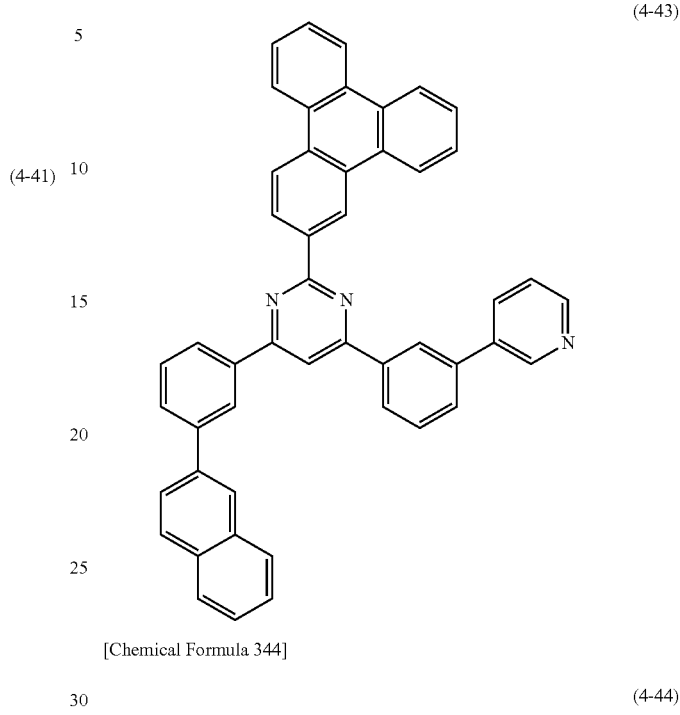
[Chemical Formula 344]
(4-44)
[Chemical Formula 345]
(4-45)
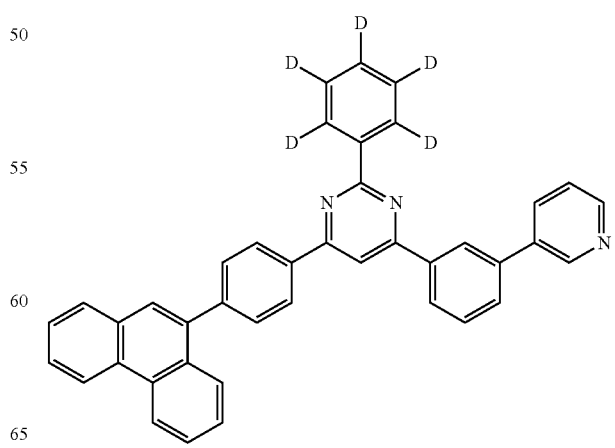

[Chemical Formula 346]
(4-46)
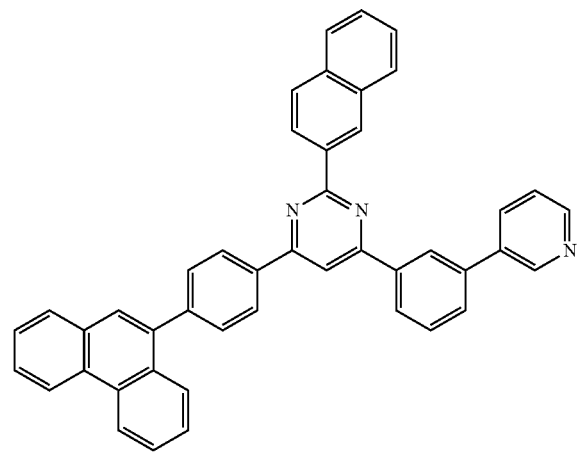
[Chemical Formula 347]
(4-47)
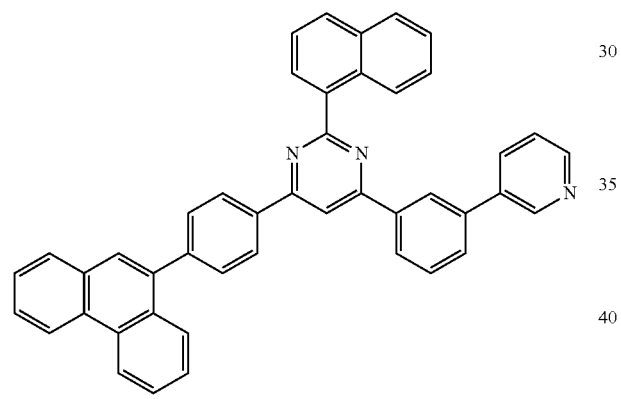
[Chemical Formula 348]
(4-48)
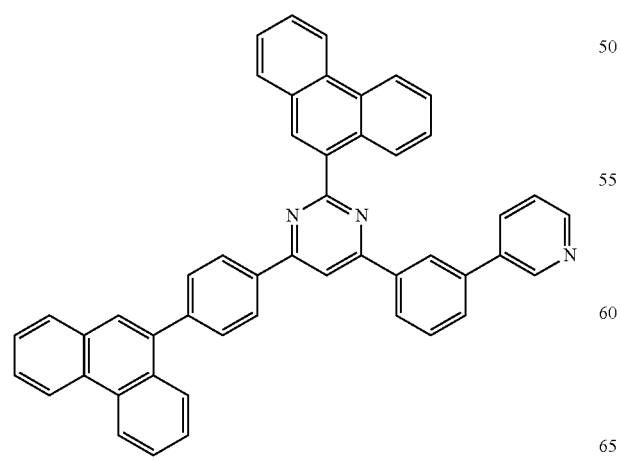
[Chemical Formula 349]
(4-49)
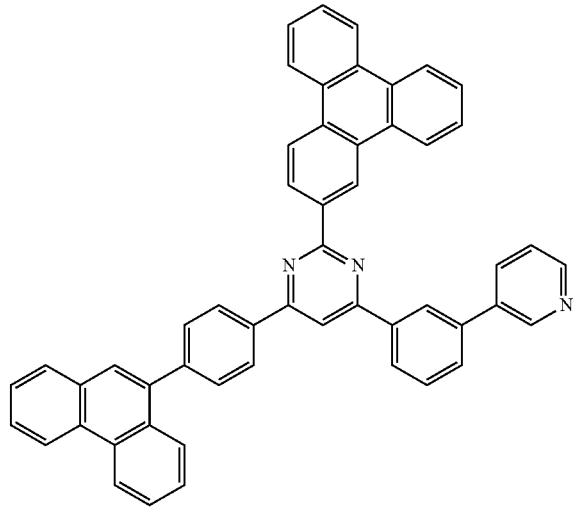
[Chemical Formula 350]
(4-50)
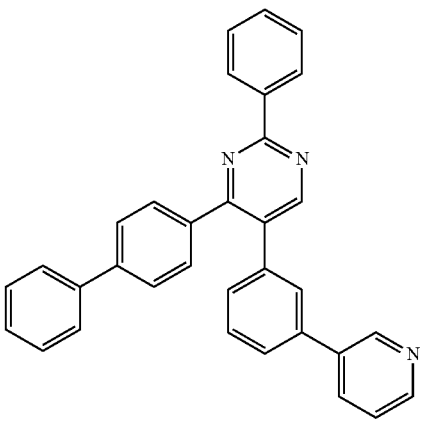
[Chemical Formula 351]
(4-51)
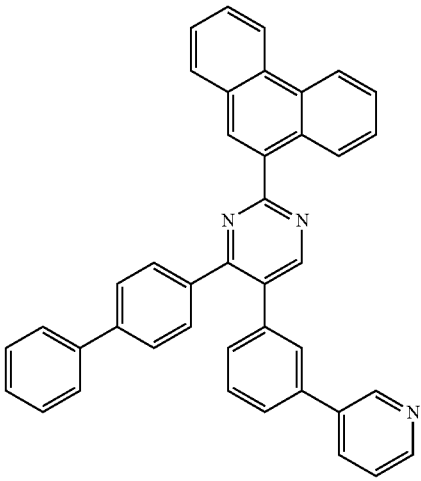

[Chemical Formula 352]
(4-52)
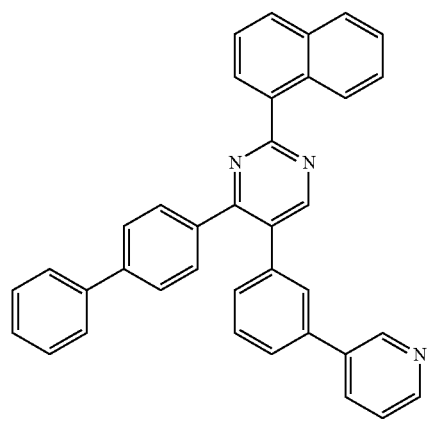
[Chemical Formula 353]
(4-53)
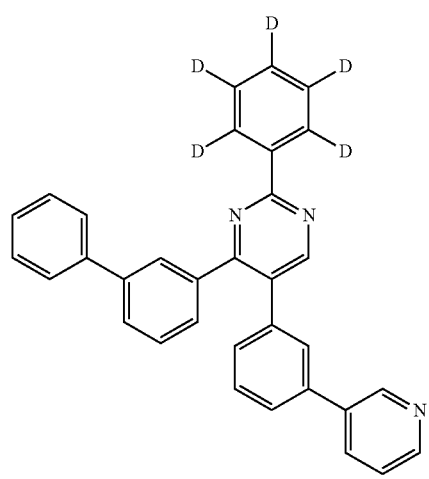
[Chemical Formula 354]
(4-54)
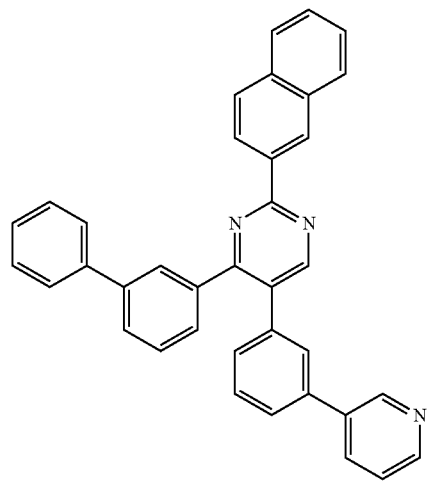
[Chemical Formula 355]
(4-55)
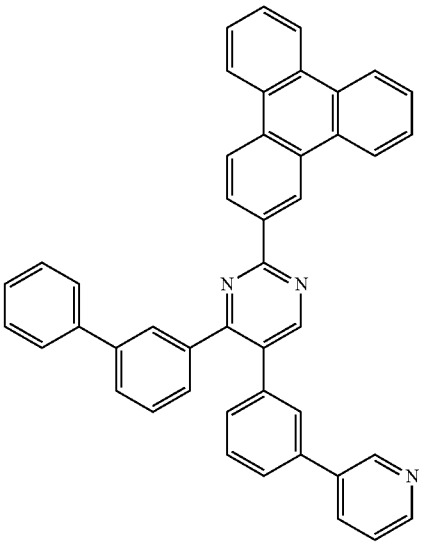
[Chemical Formula 356]
(4-56)
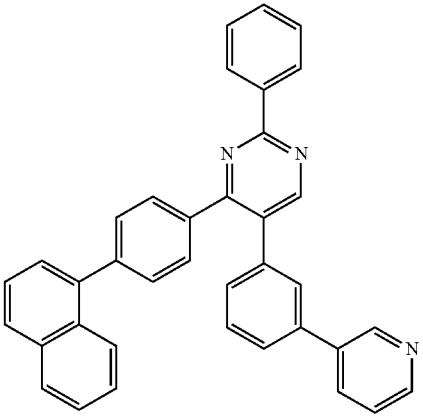
[Chemical Formula 357]
(4-57)
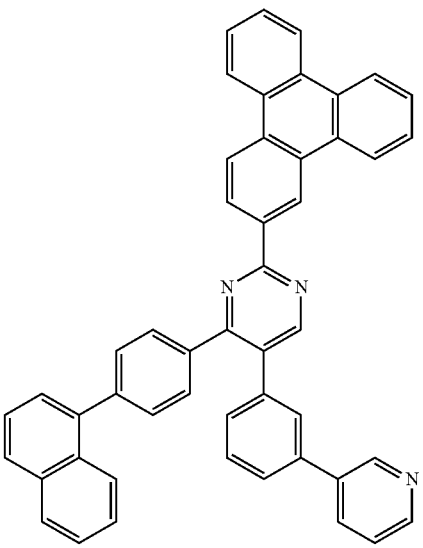

[Chemical Formula 358]
(4-58)
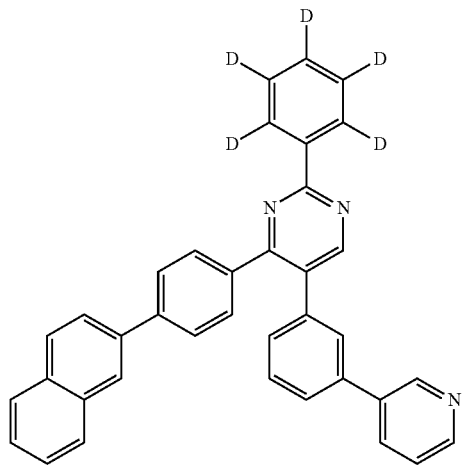
[Chemical Formula 359]
(4-59)
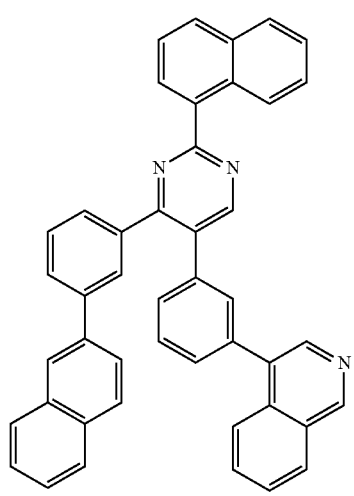
[Chemical Formula 360]
(4-60)
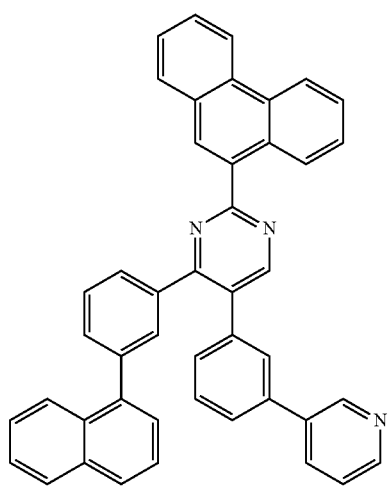
[Chemical Formula 361]
(4-61)
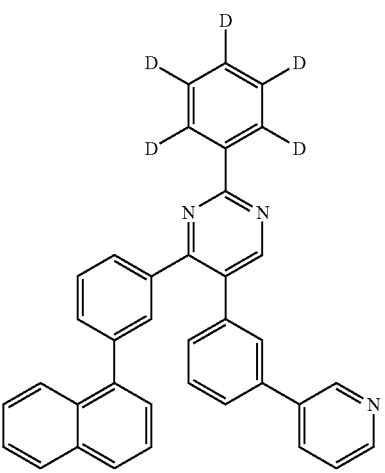
[Chemical Formula 362]
(4-62)
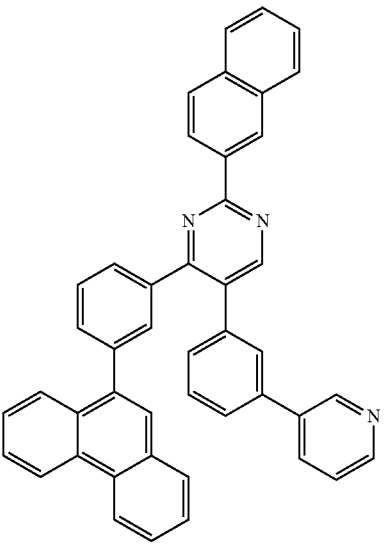
[Chemical Formula 363]
(4-63)
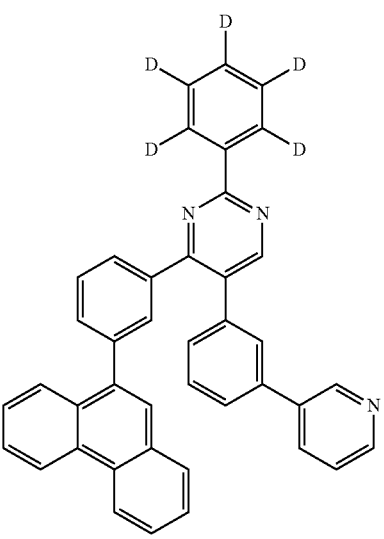

[Chemical Formula 364]
(4-64)
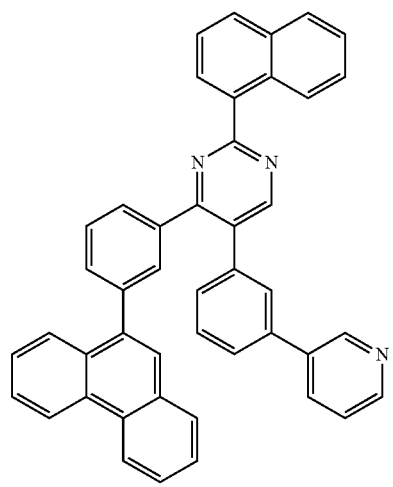
[Chemical Formula 365]
(4-65)
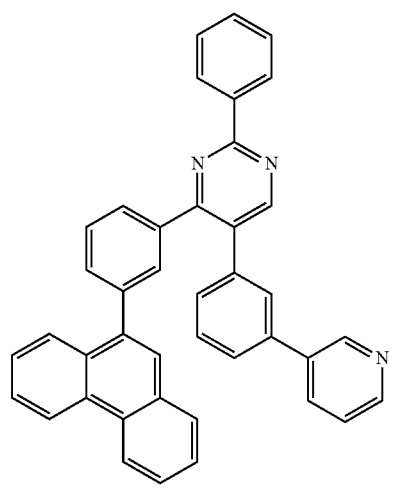
[Chemical Formula 366]
(4-66)
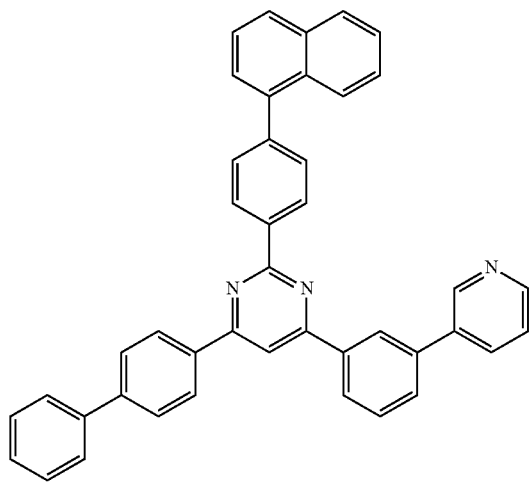
[Chemical Formula 367]
(4-67)
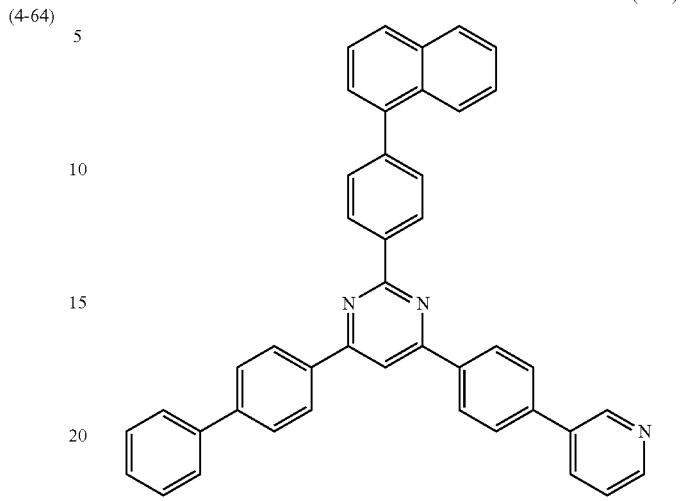
[Chemical Formula 368]
(4-68)
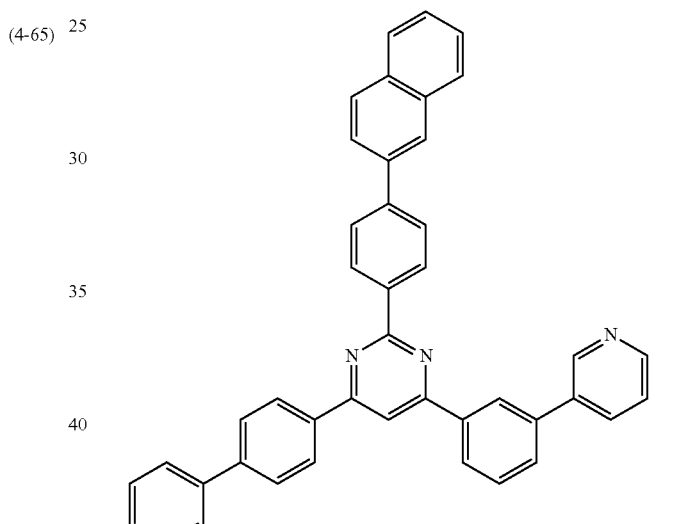
[Chemical Formula 369]
(4-69)
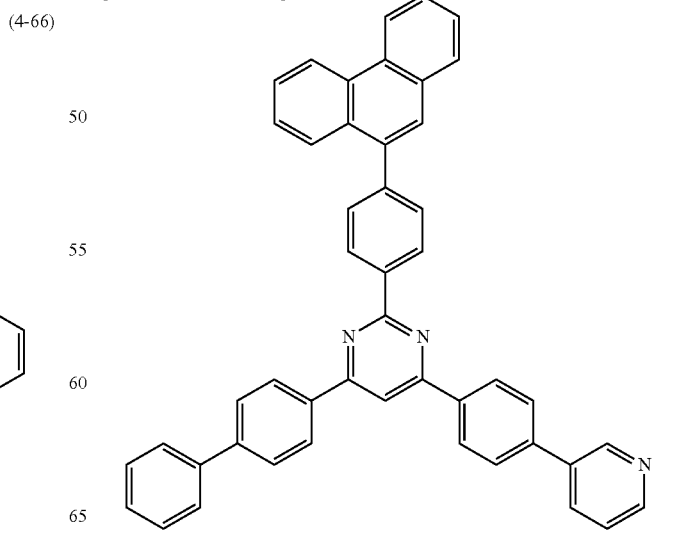

[Chemical Formula 370]
(4-70)
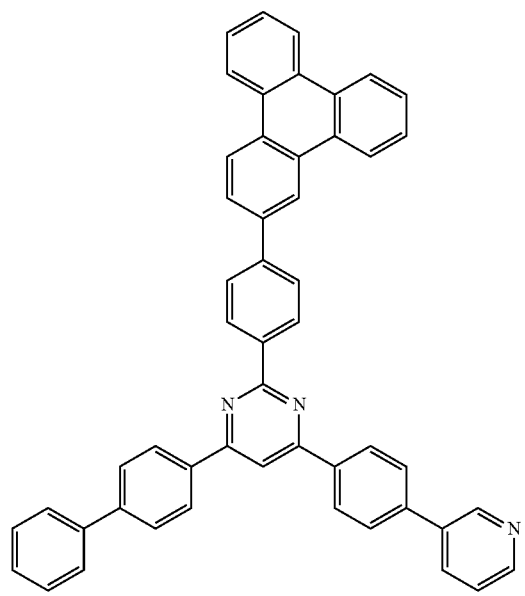
[Chemical Formula 371]
(4-71)
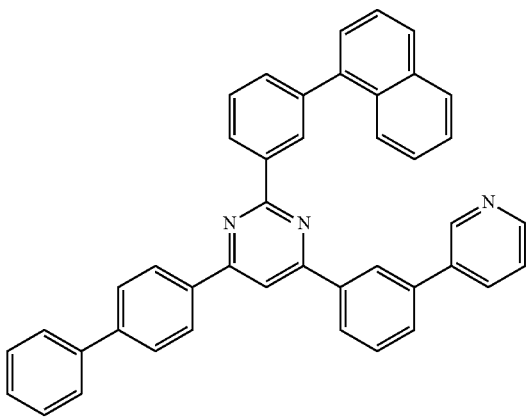
[Chemical Formula 372]
(4-72)
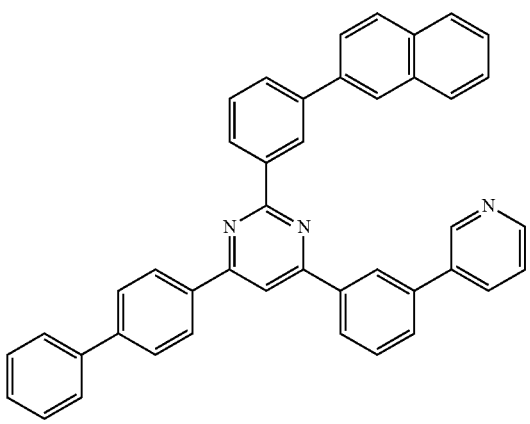
[Chemical Formula 373]
(4-73)
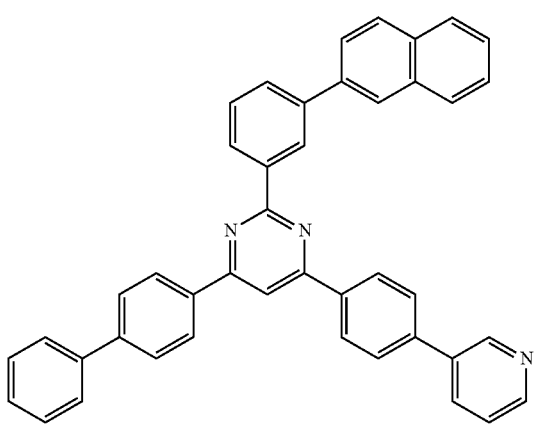
[Chemical Formula 374]
(4-74)
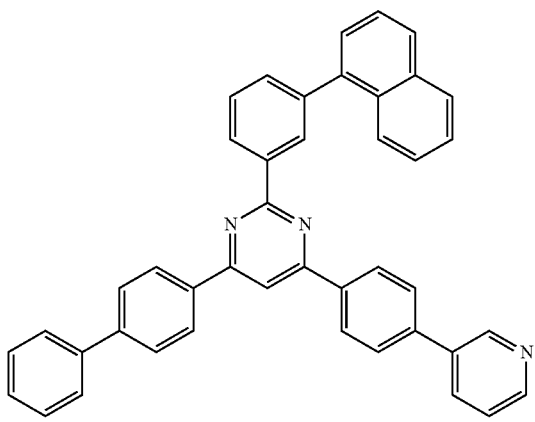
[Chemical Formula 375]
(4-75)
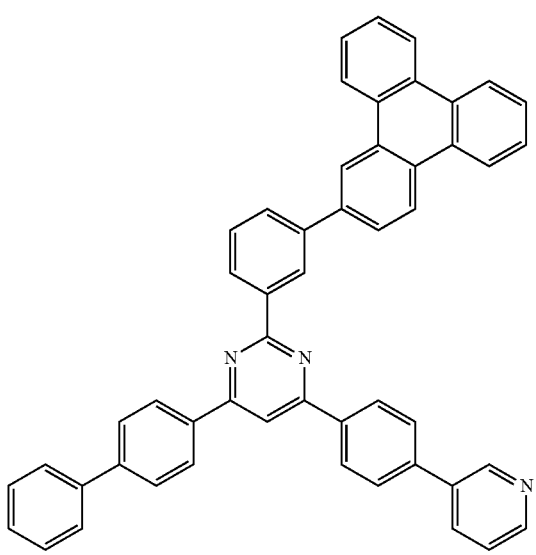

[Chemical Formula 376]
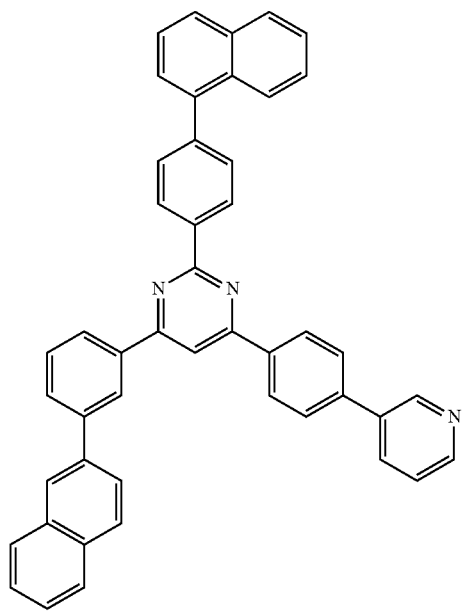
(4-76)
[Chemical Formula 377]
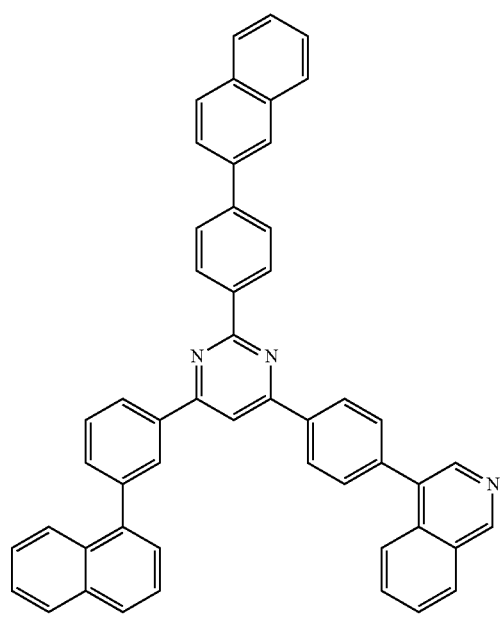
(4-77)
[Chemical Formula 378]
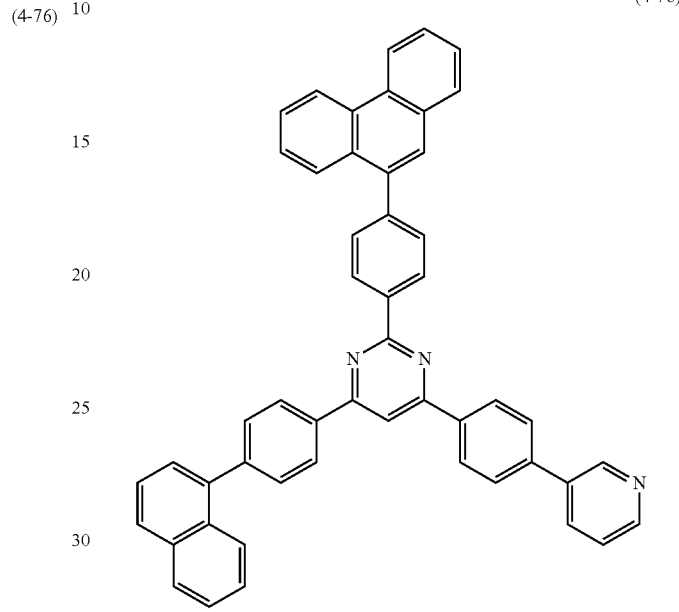
(4-78)
[Chemical Formula 379]
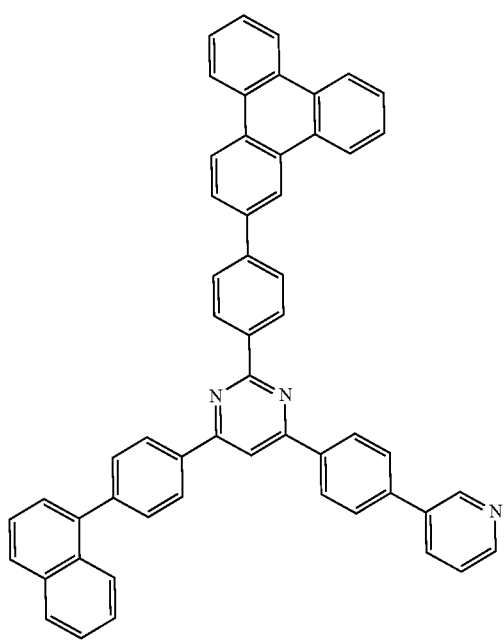
(4-79)

[Chemical Formula 380]
(4-80)
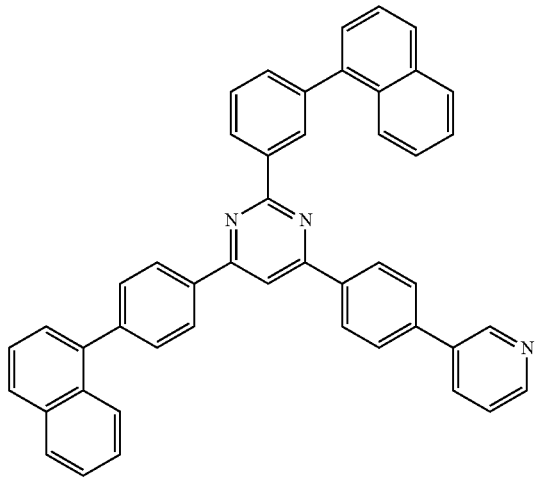
[Chemical Formula 381]
(4-81)
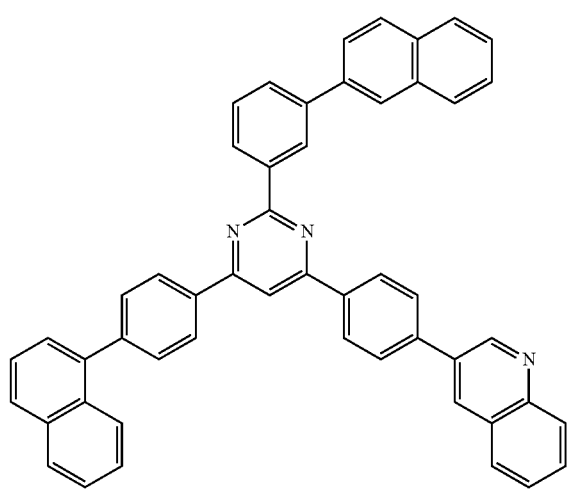
[Chemical Formula 382]
(4-82)
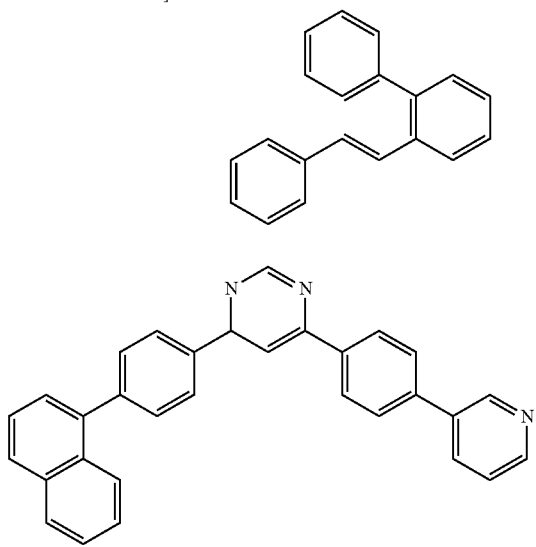
[Chemical Formula 383]
(4-83)
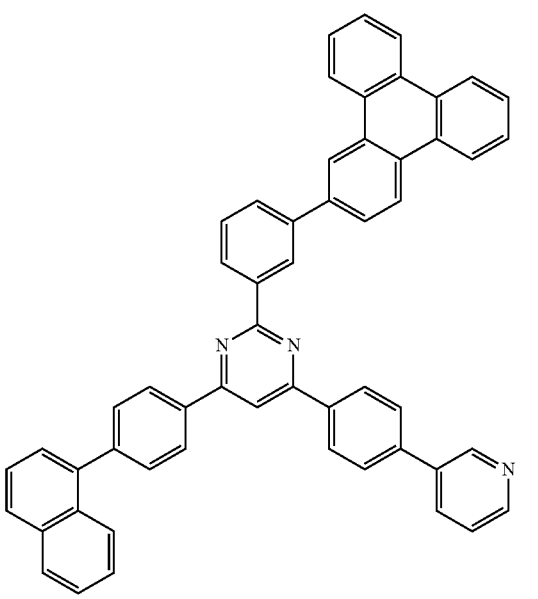
[Chemical Formula 384]
(4-84)
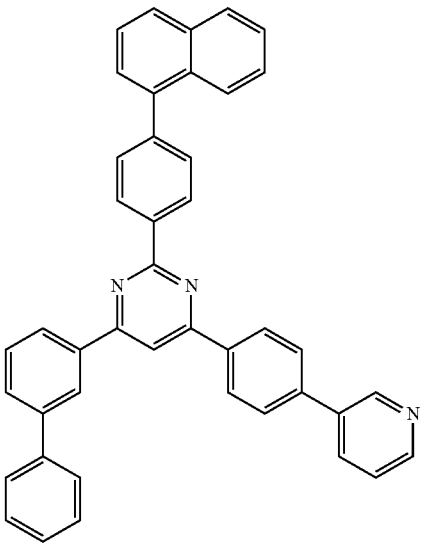

[Chemical Formula 385]
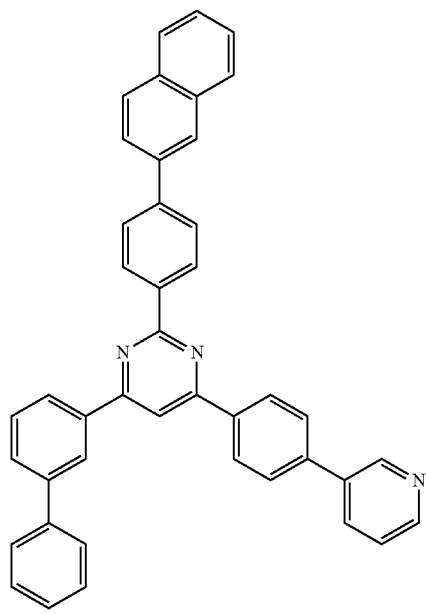
(4-85)
[Chemical Formula 386]
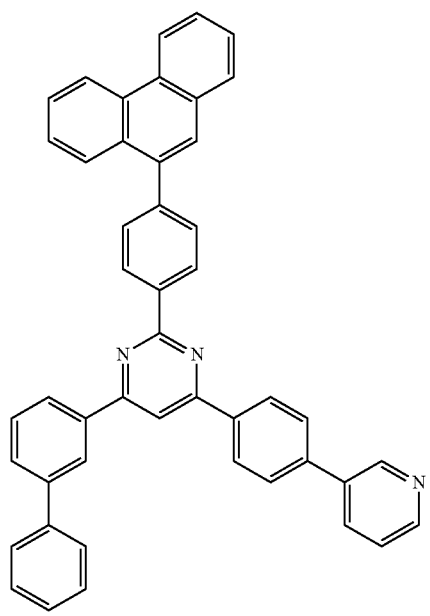
(4-86)
[Chemical Formula 387]
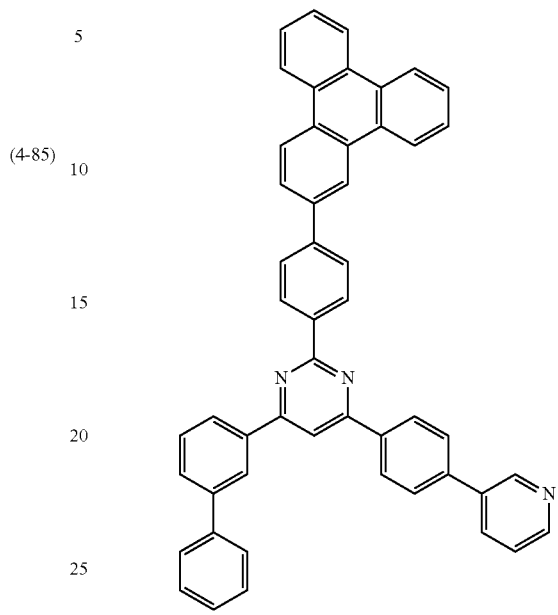
(4-87)
[Chemical Formula 388]
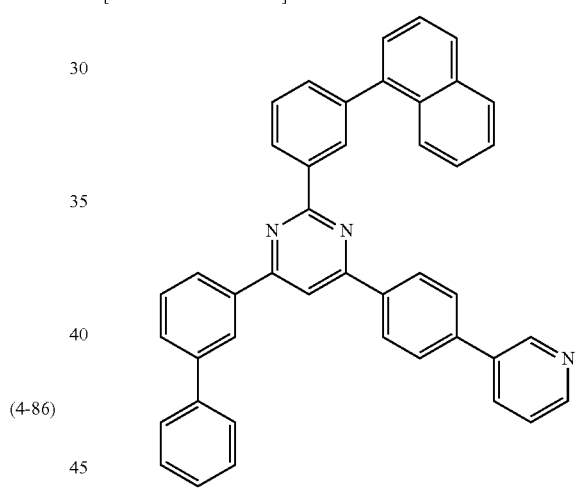
(4-88)
[Chemical Formula 389]
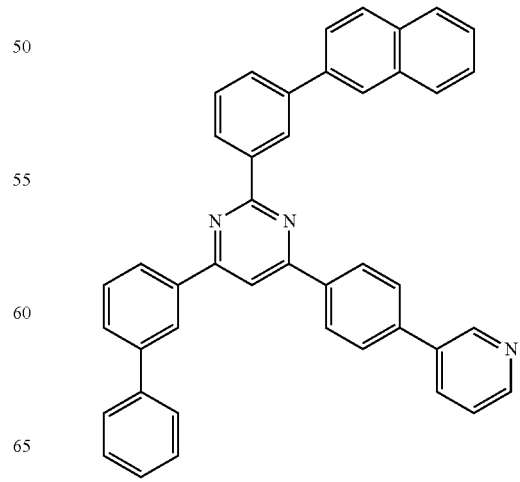
(4-89)

[Chemical Formula 390]
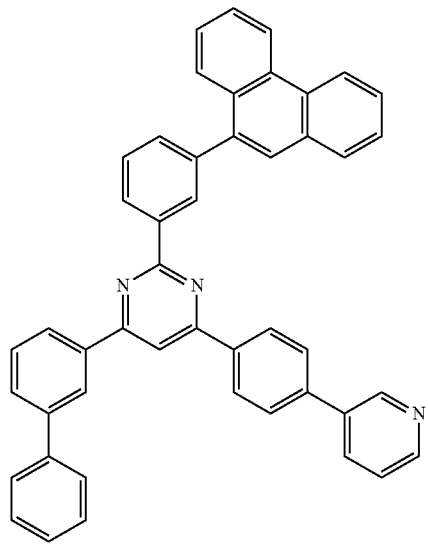
(4-90)
[Chemical Formula 391]
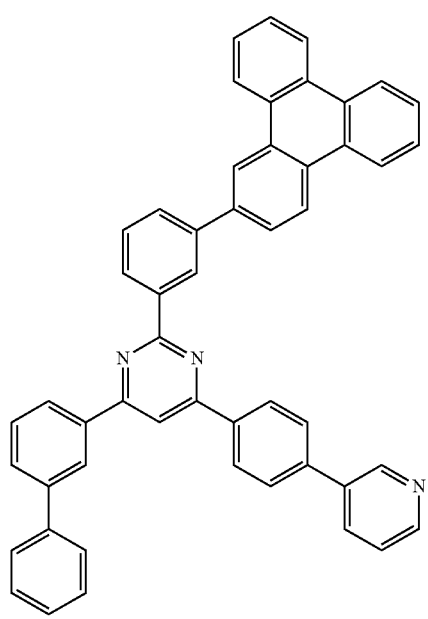
(4-91)
[Chemical Formula 392]
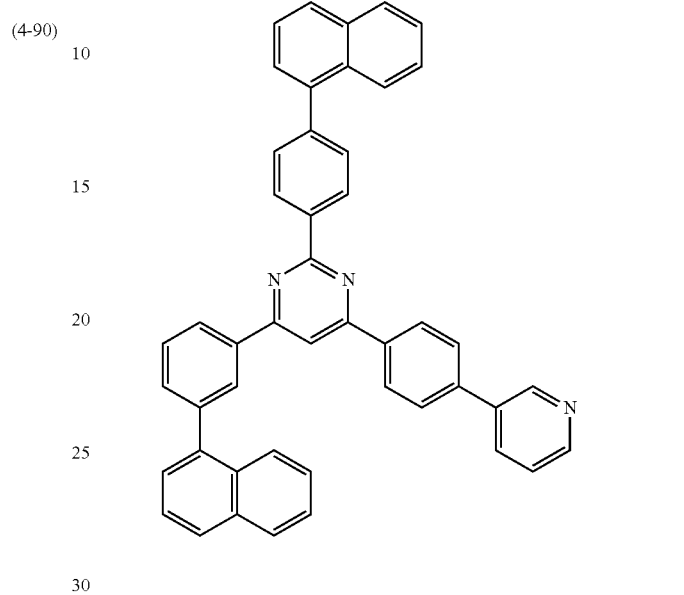
(4-92)
[Chemical Formula 393]
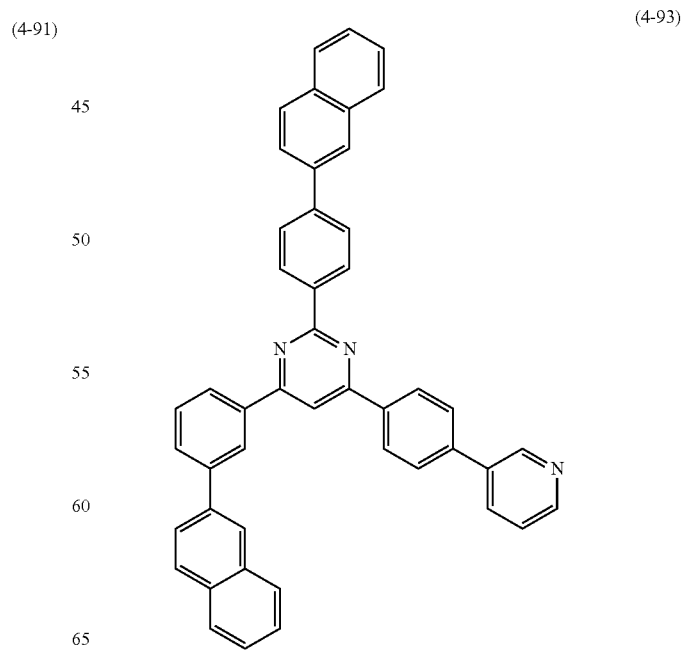
(4-93)

[Chemical Formula 394]
(4-94)
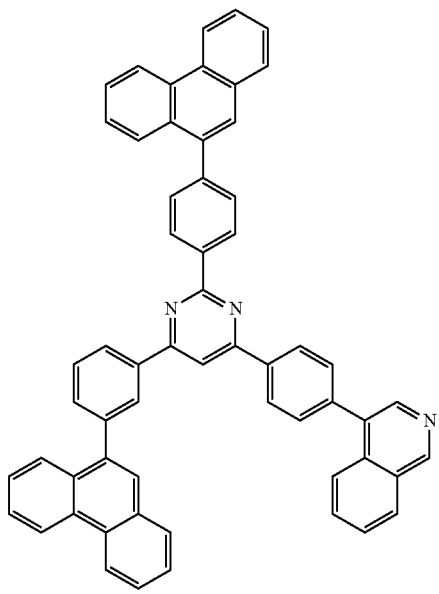
[Chemical Formula 395]
(4-95)
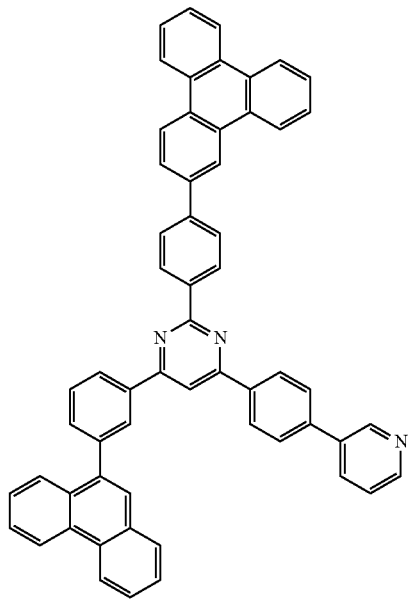
[Chemical Formula 396]
(4-96)
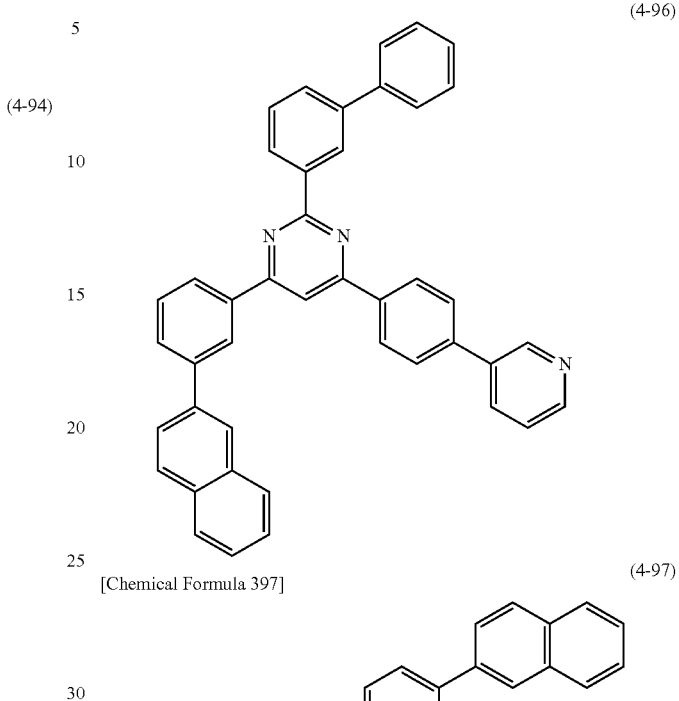
[Chemical Formula 397]
(4-97)
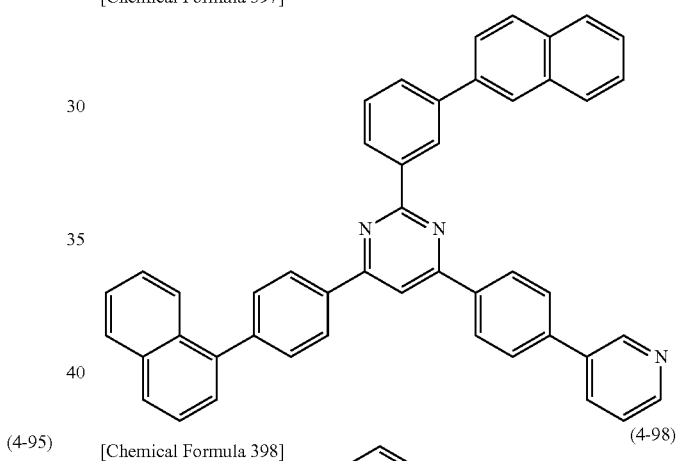
[Chemical Formula 398]
(4-98)
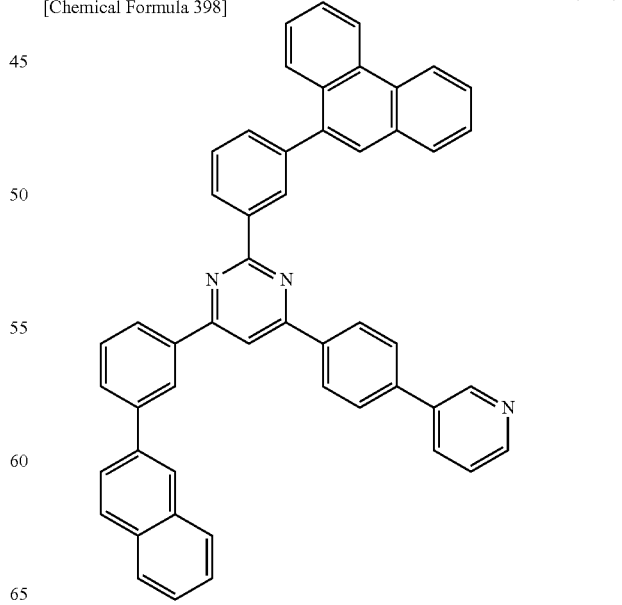

[Chemical Formula 399]
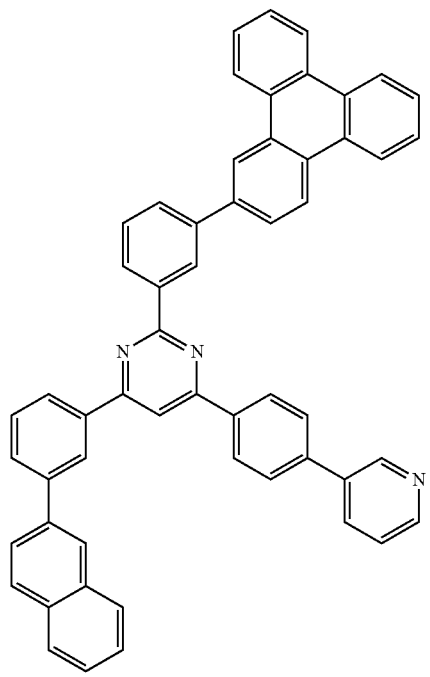
(4-99)
[Chemical Formula 400]
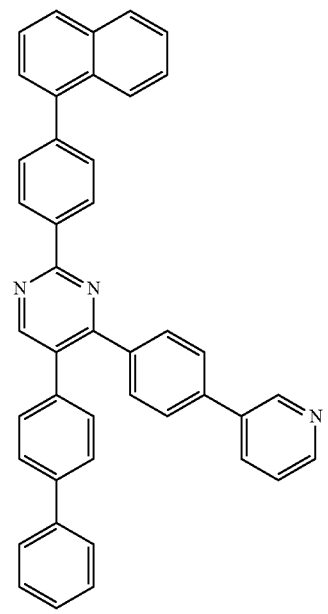
(4-100)
[Chemical Formula 401]
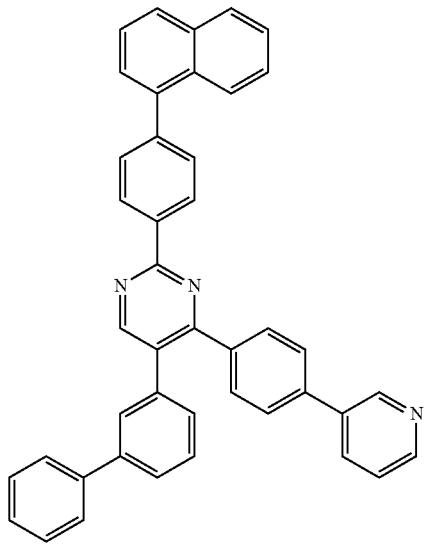
(4-101)
[Chemical Formula 402]
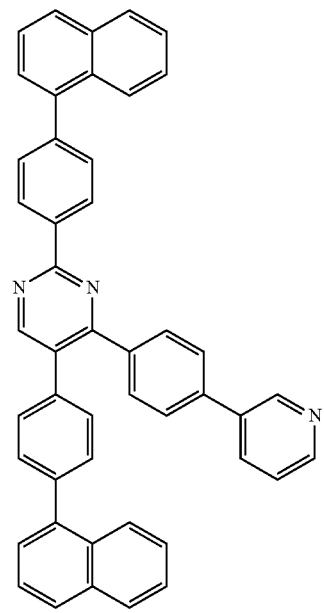
(4-102)

[Chemical Formula 403]

(4-103)

[Chemical Formula 404]

(4-104)

[Chemical Formula 405]

(4-105)

[Chemical Formula 406]

(4-106)

[Chemical Formula 407]
(4-107)
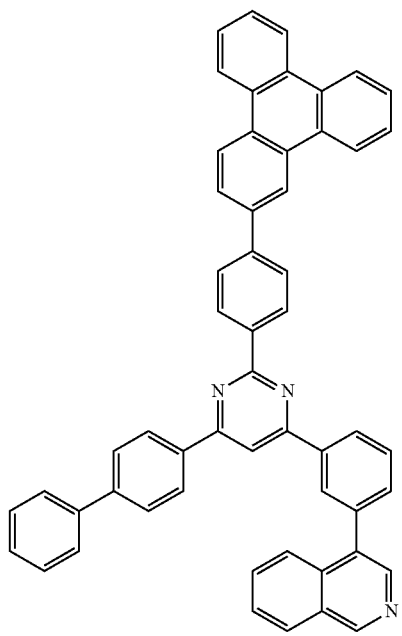
[Chemical Formula 408]
(4-108)
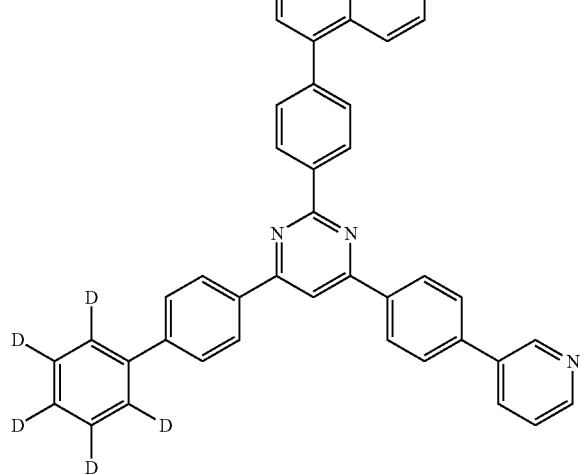
[Chemical Formula 409]
(4-109)
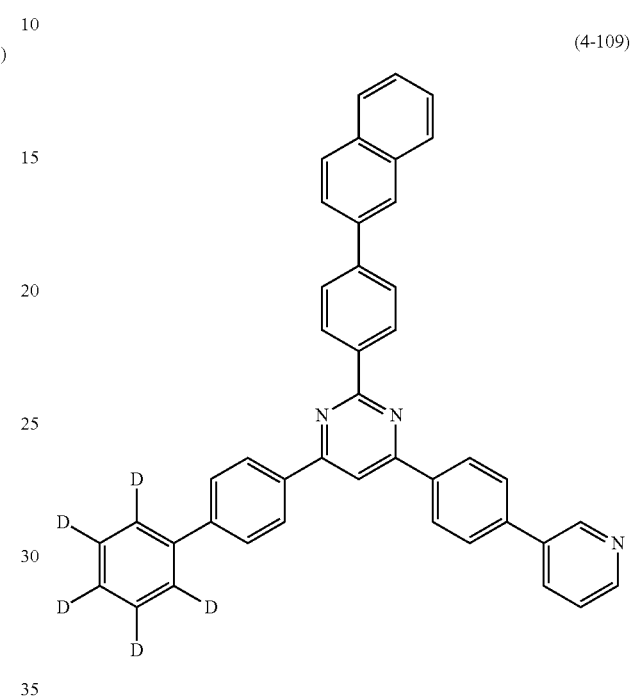
[Chemical Formula 410]
(4-110)
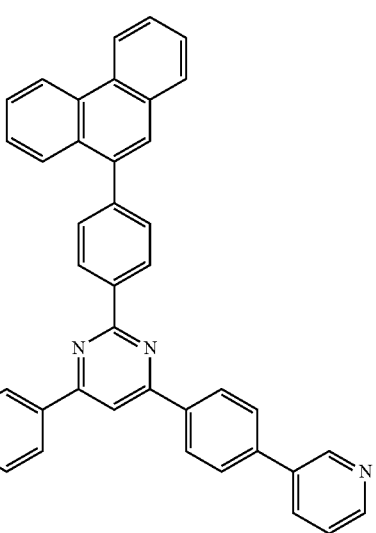

[Chemical Formula 411]
(4-111)
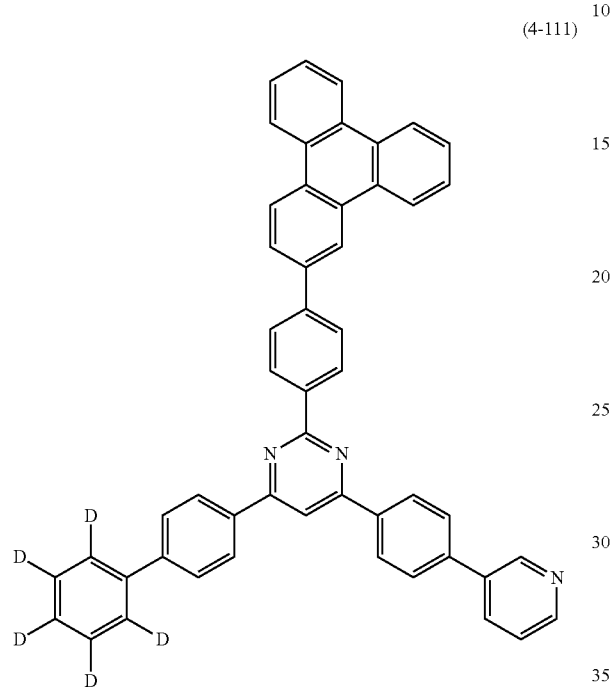
[Chemical Formula 412]
(4-112)
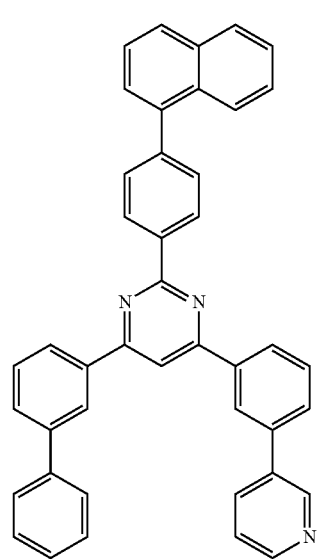
[Chemical Formula 413]
(4-113)
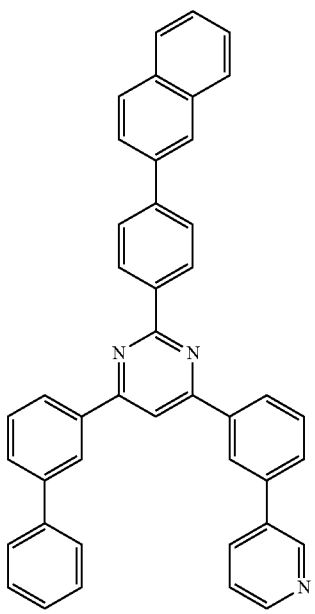
[Chemical Formula 414]
(4-114)
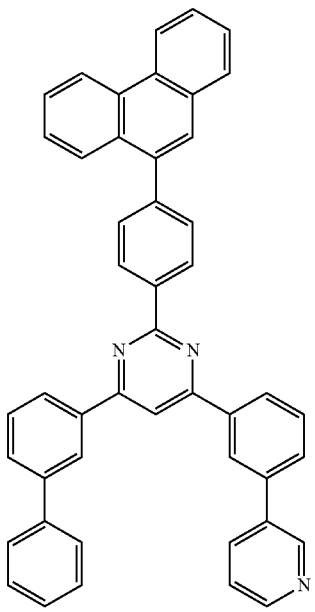

[Chemical Formula 415]
(4-115)
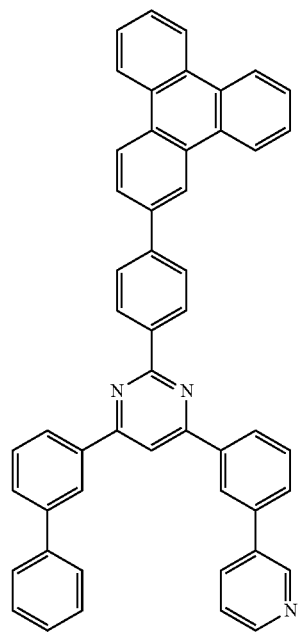
[Chemical Formula 416]
(4-116)
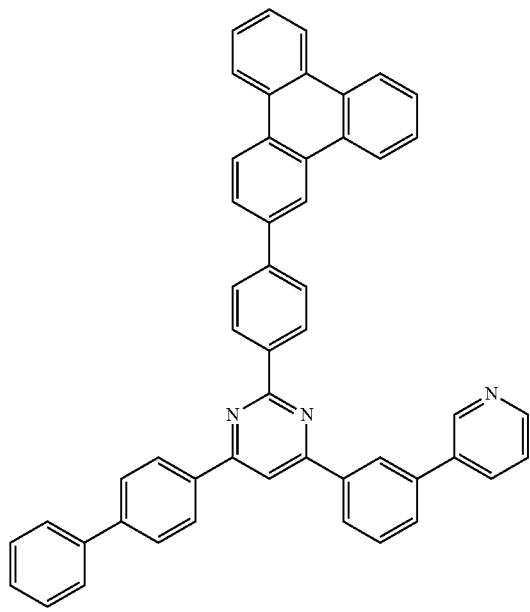
[Chemical Formula 417]
(4-117)
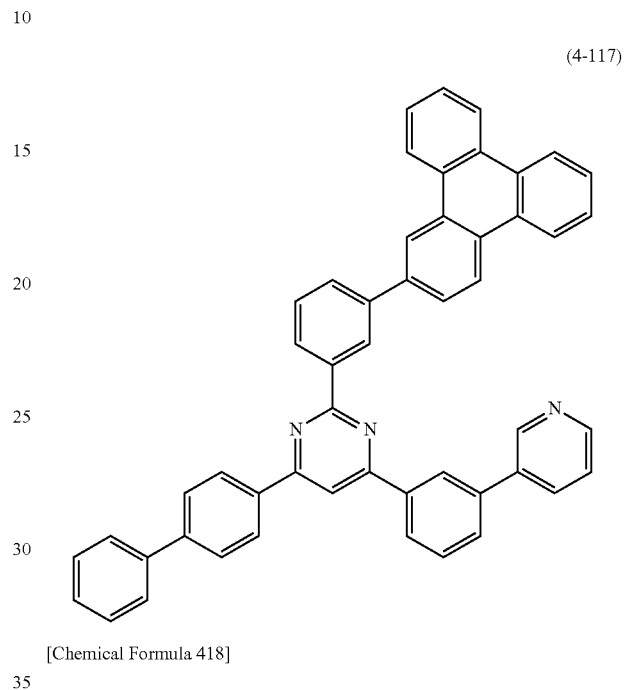
[Chemical Formula 418]
(4-118)
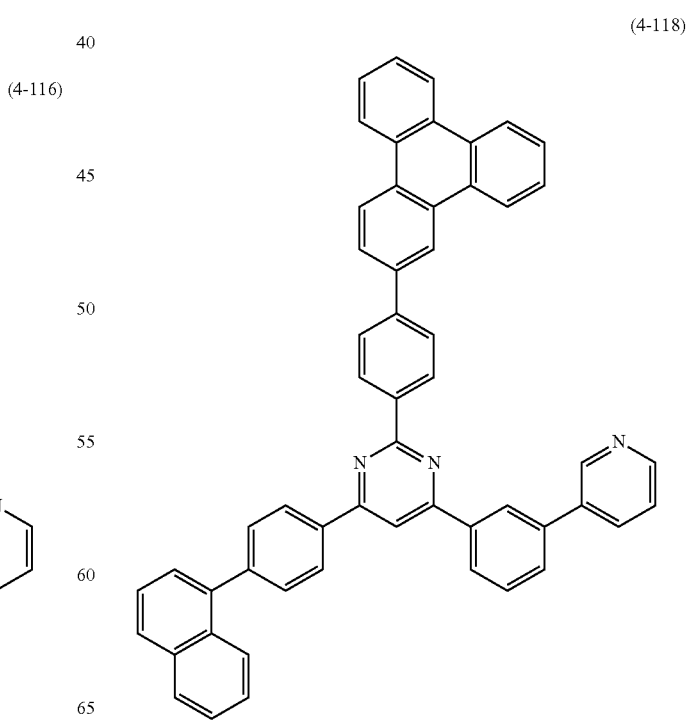

[Chemical Formula 419]
(4-119)
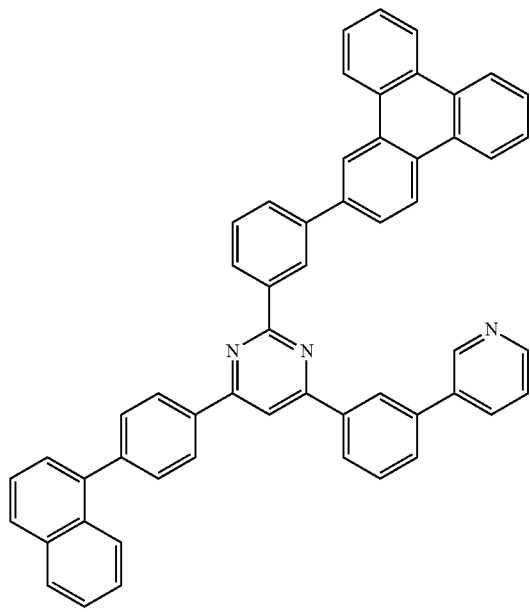
[Chemical Formula 420]
(4-120)
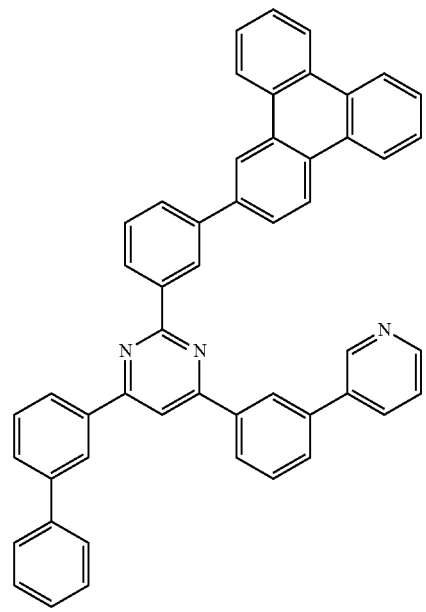
[Chemical Formula 421]
(4-121)
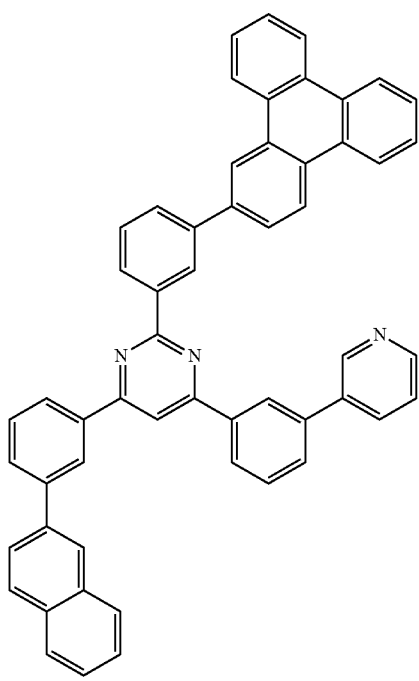
[Chemical Formula 422]
(4-122)
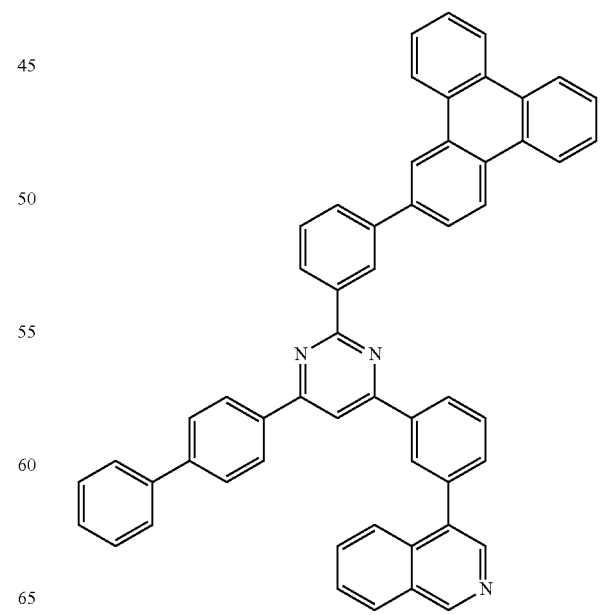

[Chemical Formula 423]
(4-123)
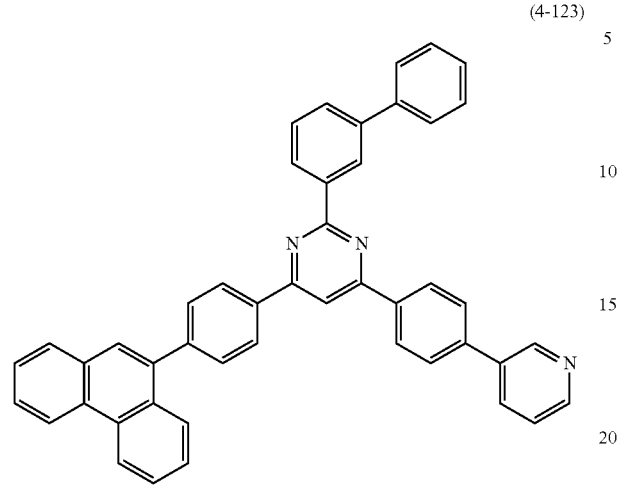
[Chemical Formula 424]
(4-124)
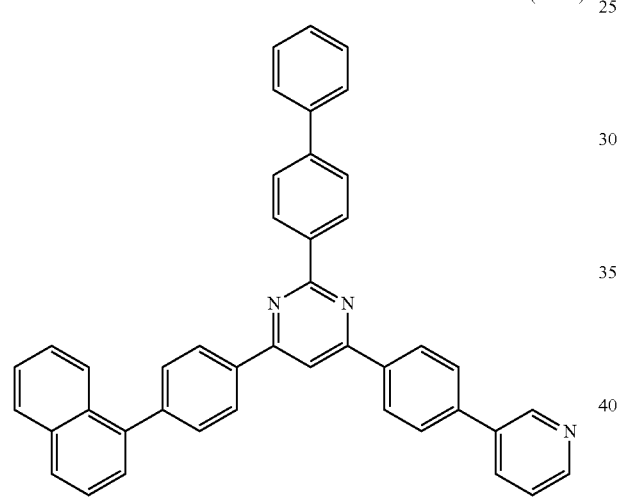
[Chemical Formula 425]
(4-125)
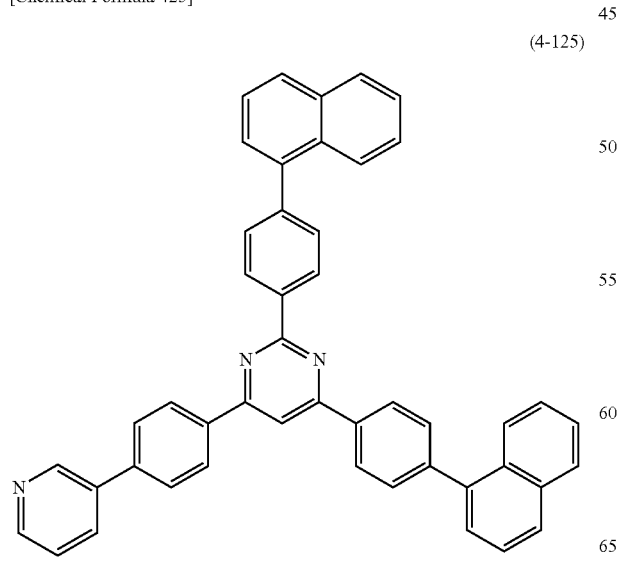
[Chemical Formula 426]
(4-126)
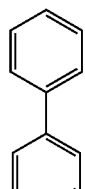
[Chemical Formula 427]
(4-127)
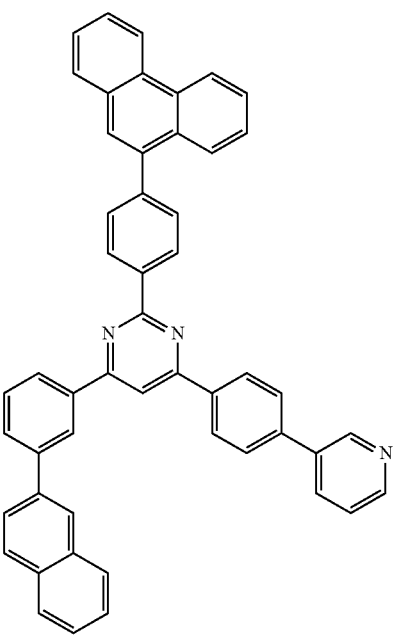

[Chemical Formula 428]
(4-128)
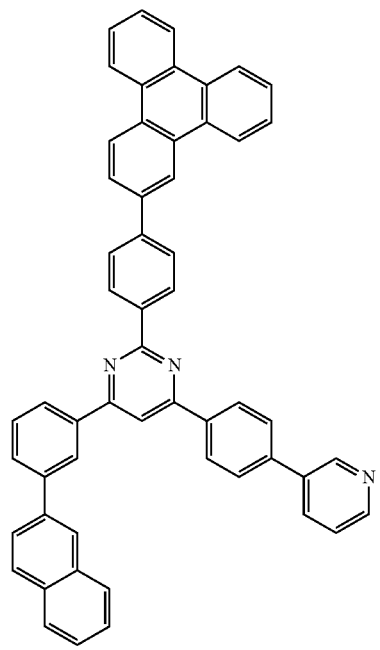
[Chemical Formula 429]
(4-129)
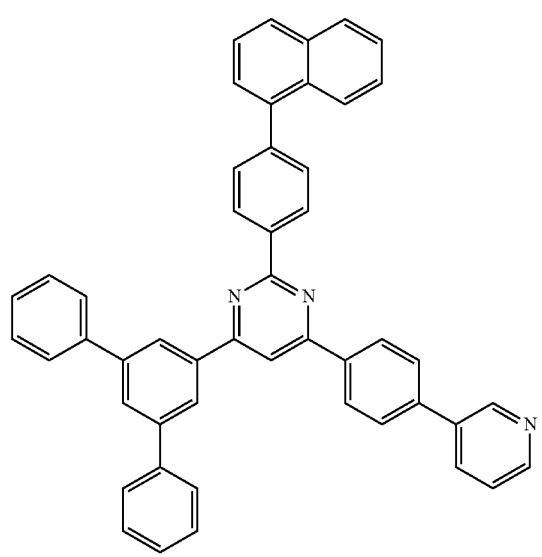
[Chemical Formula 430]
(4-130)
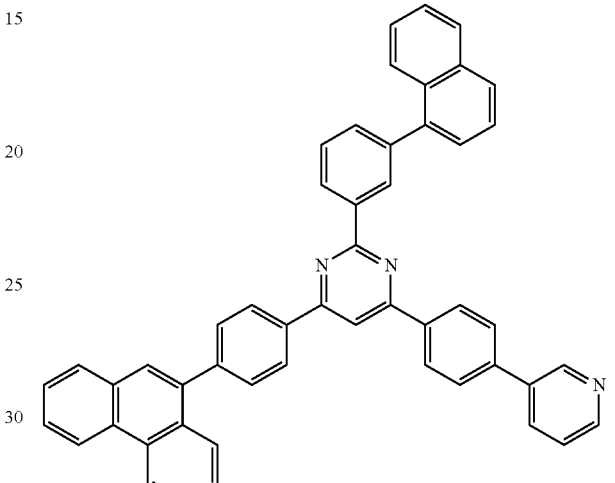
[Chemical Formula 431]
(4-131)
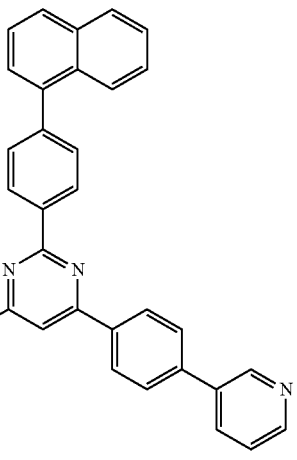

[Chemical Formula 432]
(4-132)
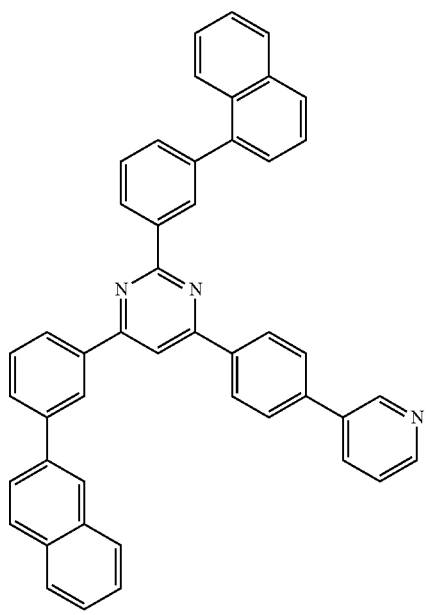
[Chemical Formula 433]
(4-133)
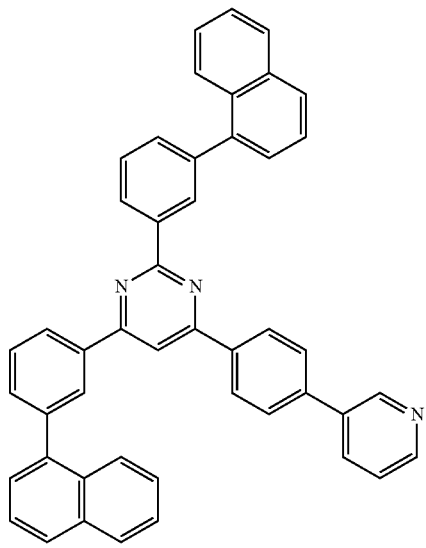
[Chemical Formula 434]
(4-134)
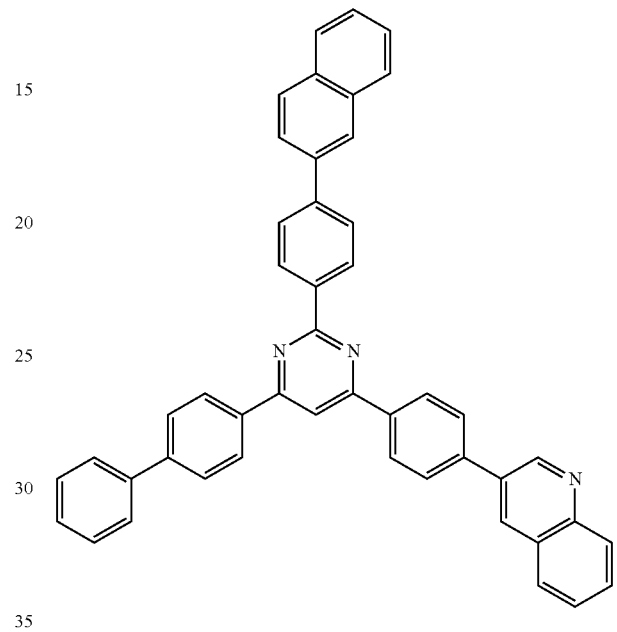
[Chemical Formula 435]
(4-135)
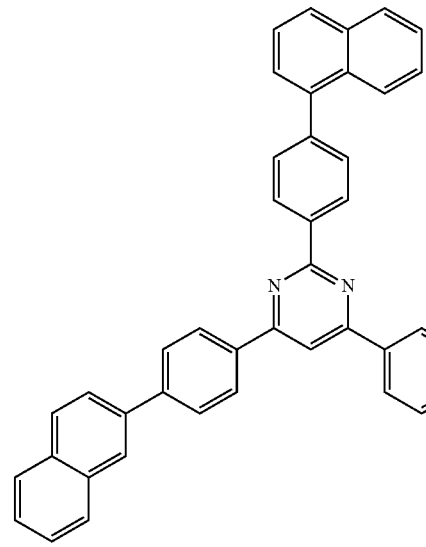

[Chemical Formula 436]
(4-136)
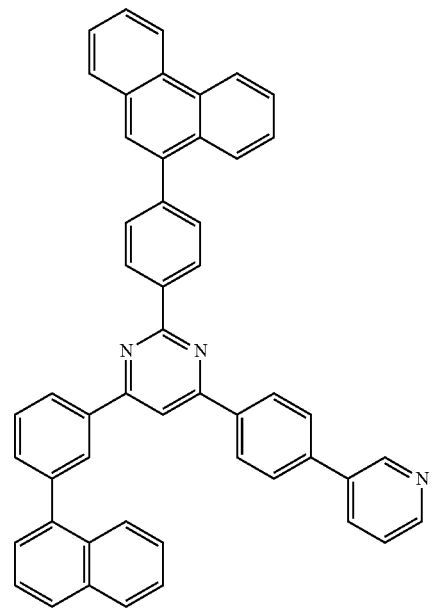
[Chemical Formula 437]
(4-137)
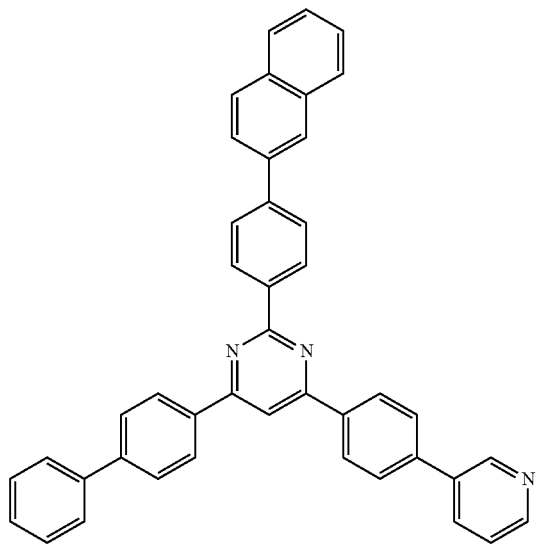
[Chemical Formula 438]
(4-138)
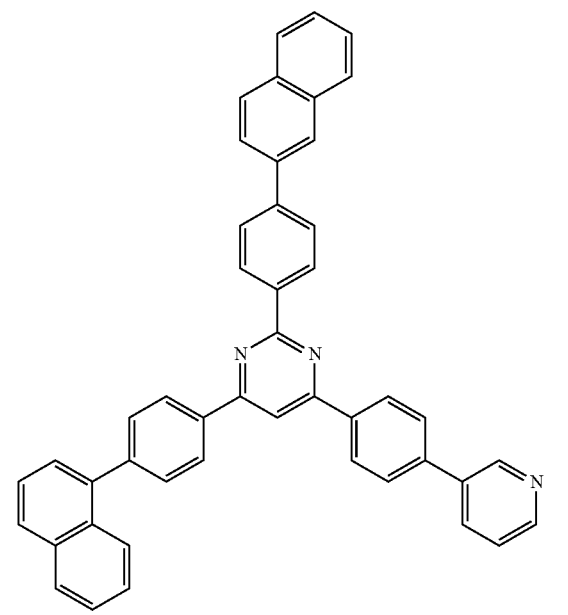
[Chemical Formula 439]
(4-139)
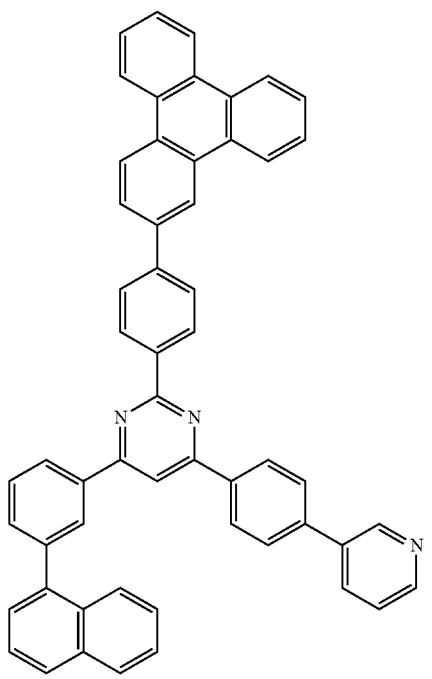

[Chemical Formula 440]
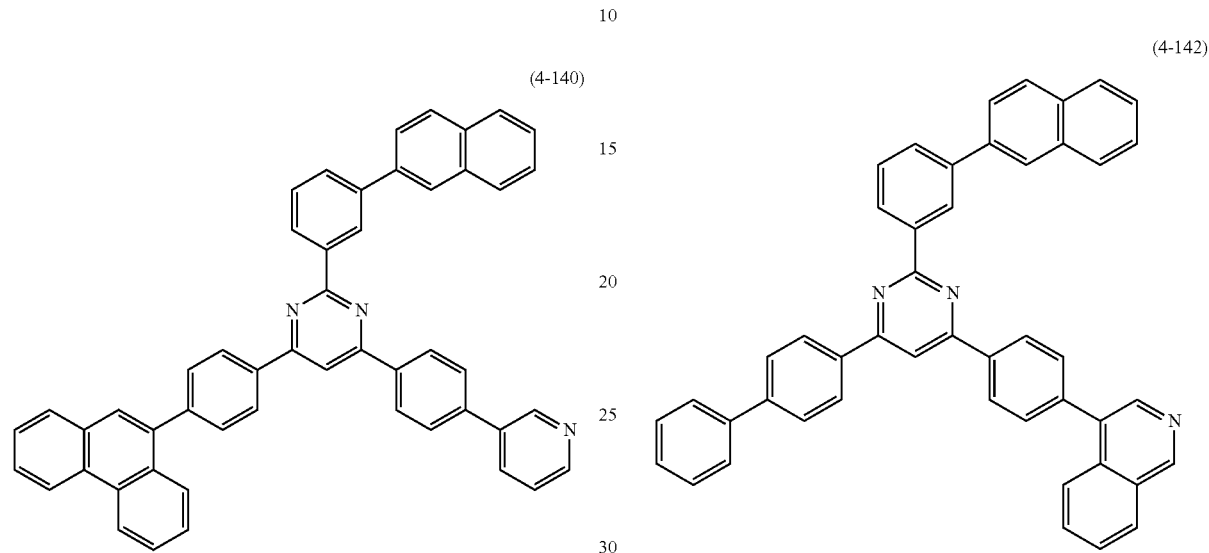
(4-140)
[Chemical Formula 441]
(4-141)
[Chemical Formula 442]
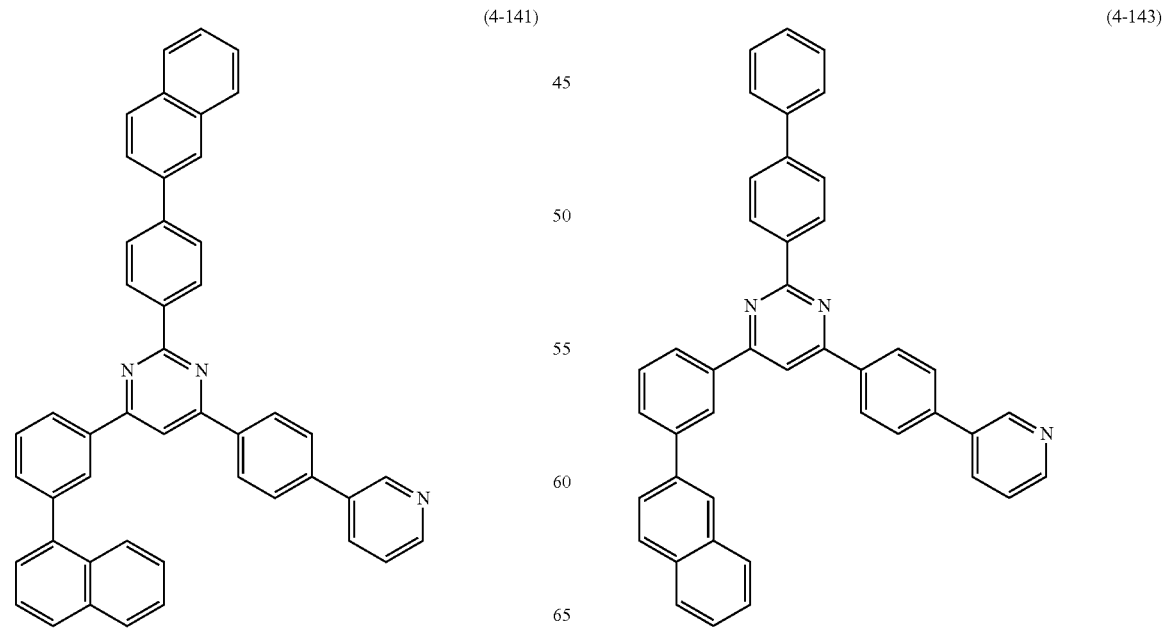
(4-142)
[Chemical Formula 443]
(4-143)

[Chemical Formula 444]
(4-144)
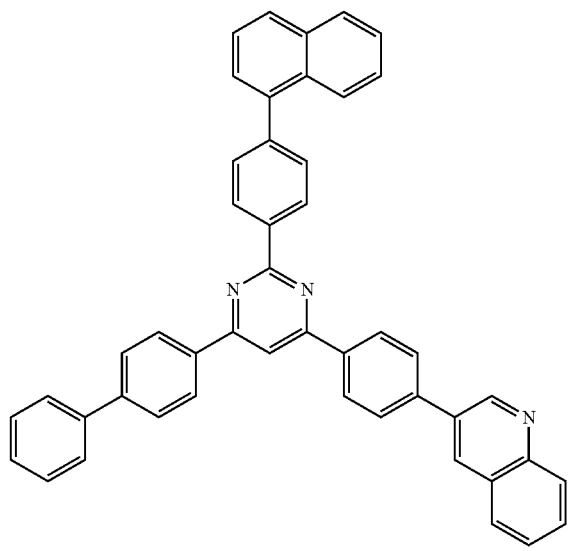
[Chemical Formula 445]
(4-145)
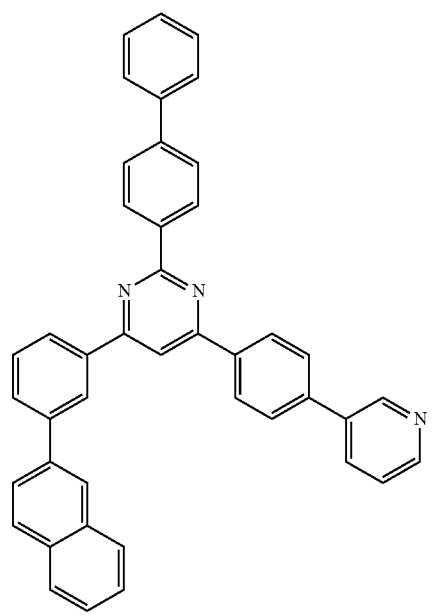
[Chemical Formula 446]
(4-146)
[Chemical Formula 447]
(4-147)
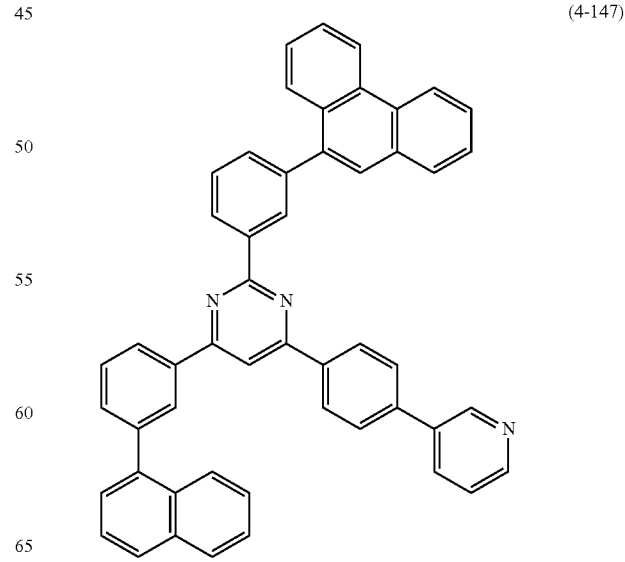

[Chemical Formula 448]
(4-148)
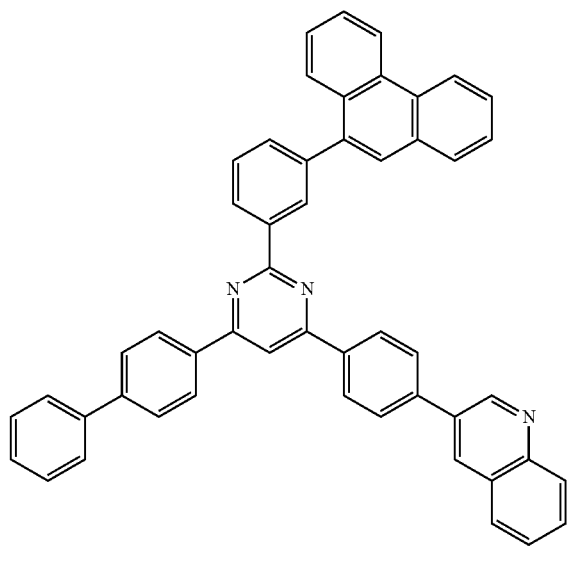
[Chemical Formula 449]
(4-149)
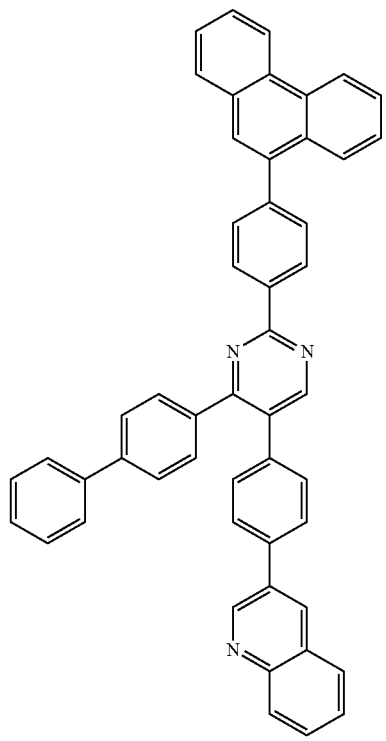
[Chemical Formula 450]
(4-150)
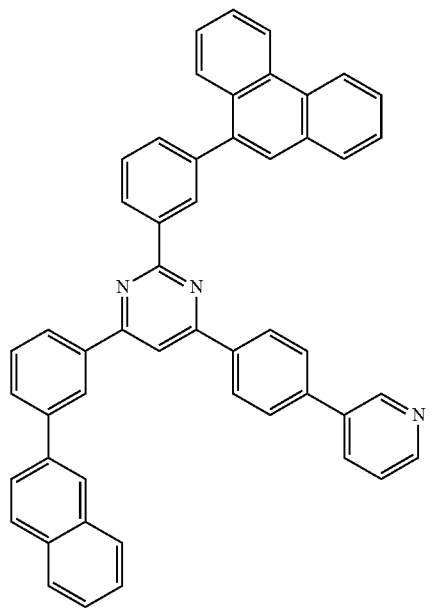
[Chemical Formula 451]
(4-151)
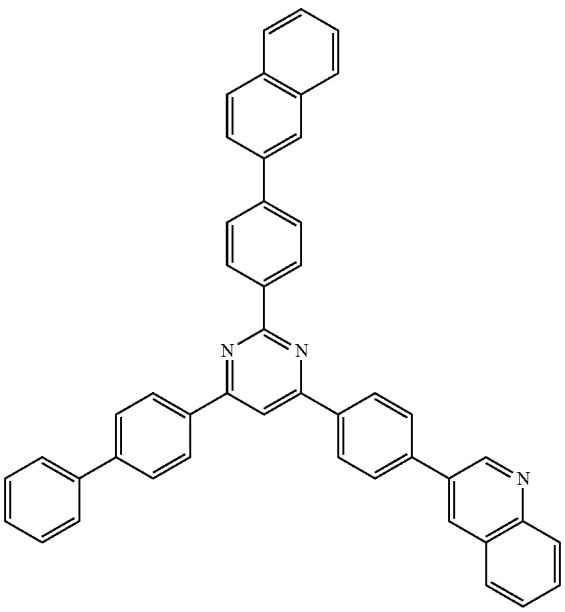

[Chemical Formula 452]
(4-152)
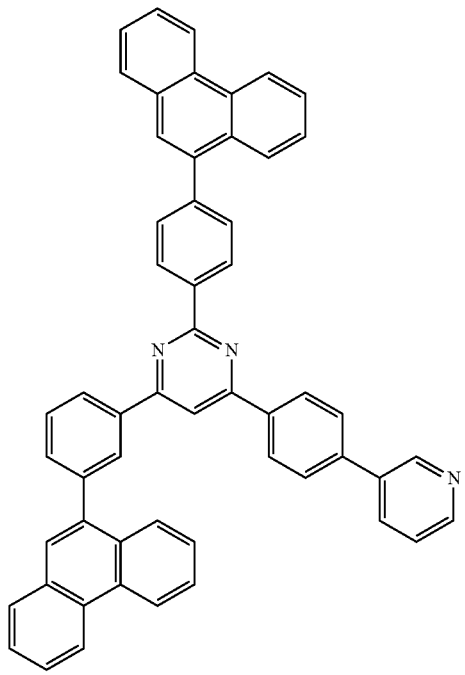
[Chemical Formula 453]
(4-153)
[Chemical Formula 454]
(4-154)
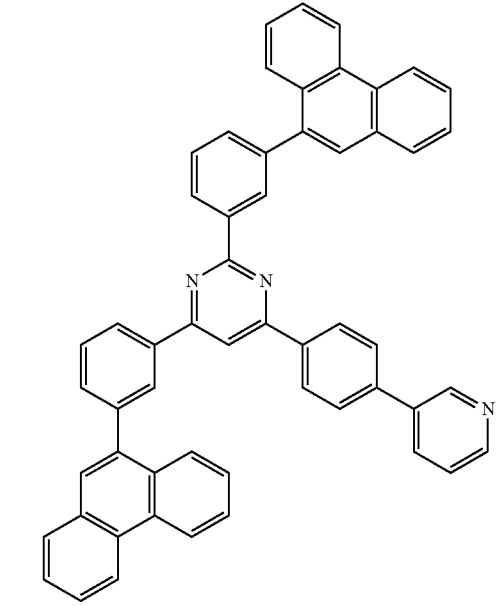
[Chemical Formula 455]
(4-155)
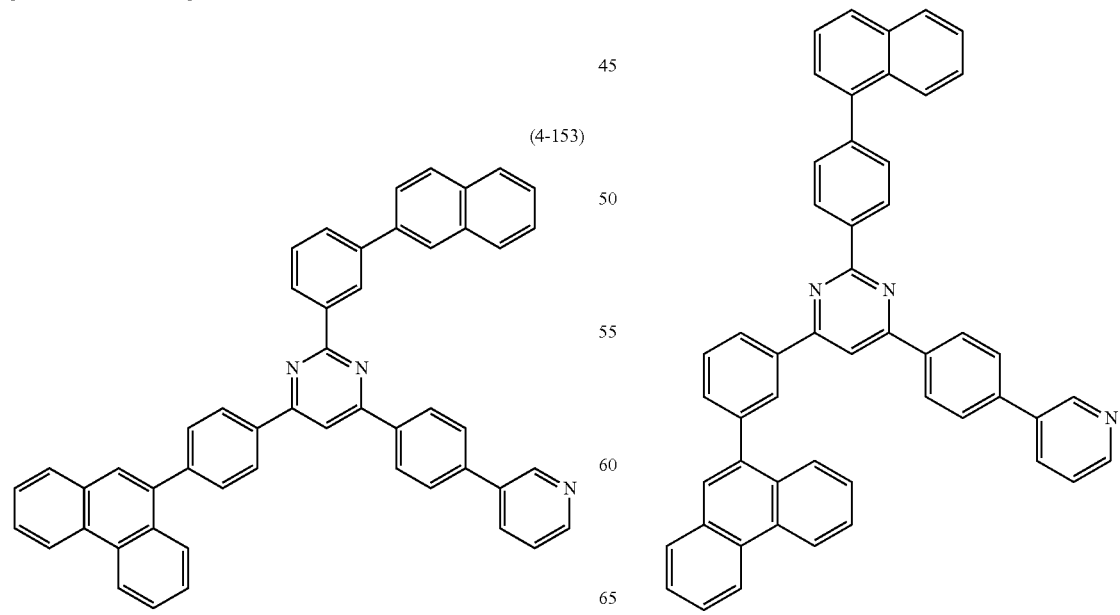

[Chemical Formula 456]
(4-156)
[Chemical Formula 457]
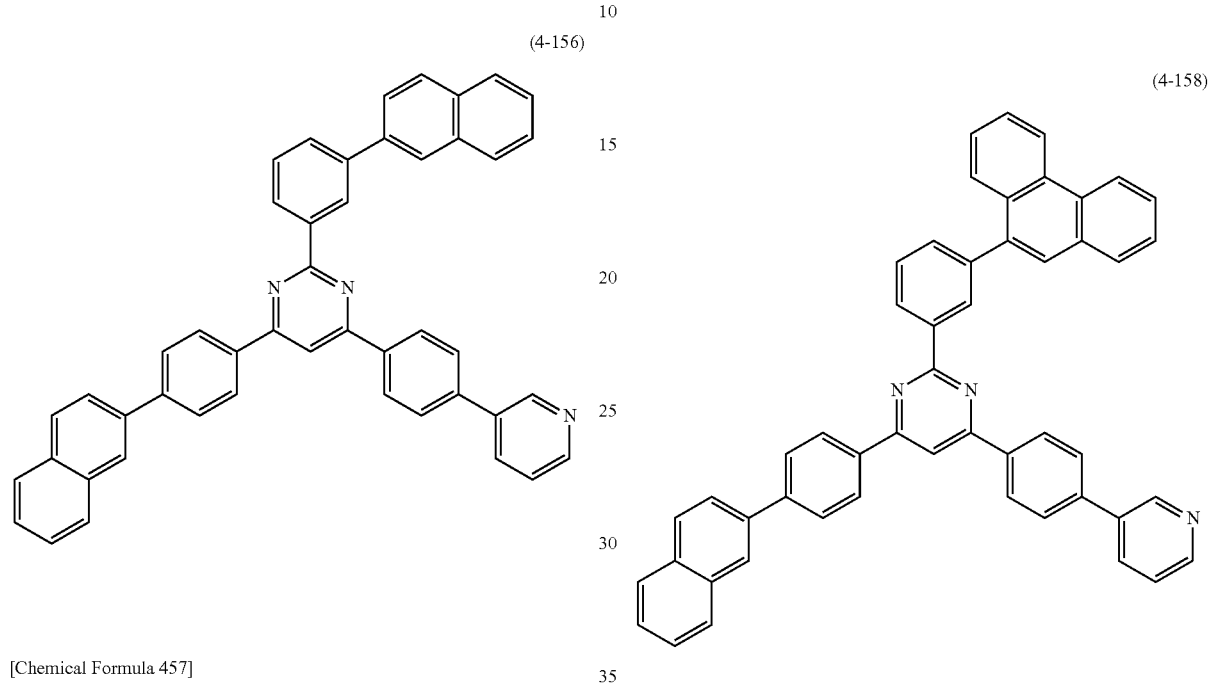
[Chemical Formula 458]
(4-158)
[Chemical Formula 459]
(4-159)
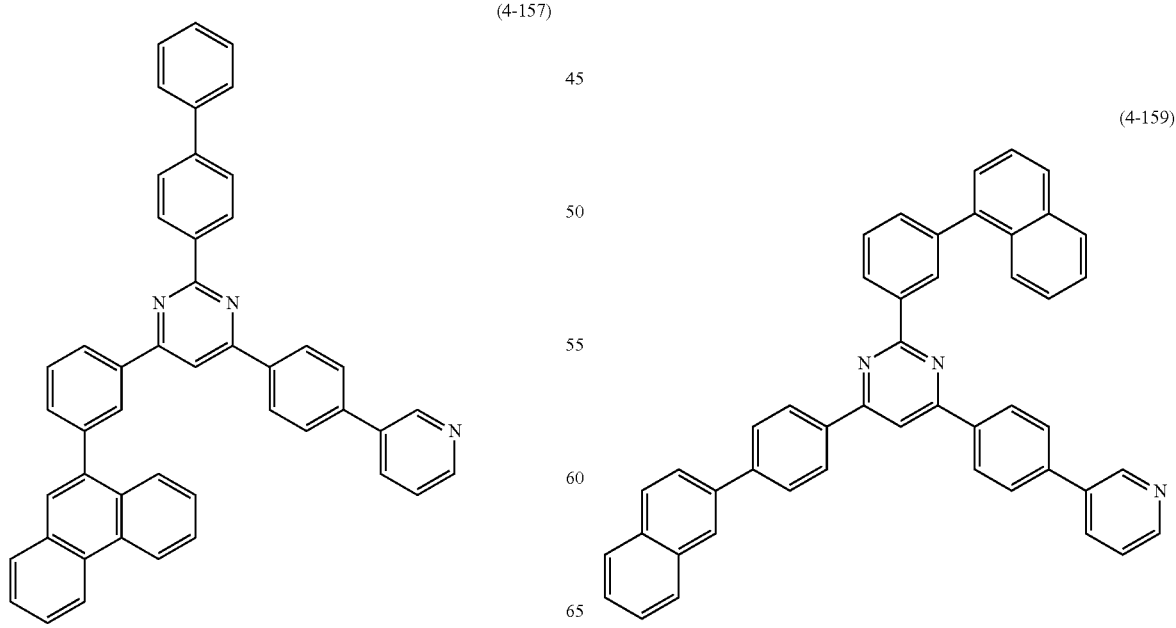

[Chemical Formula 460]
(4-160)
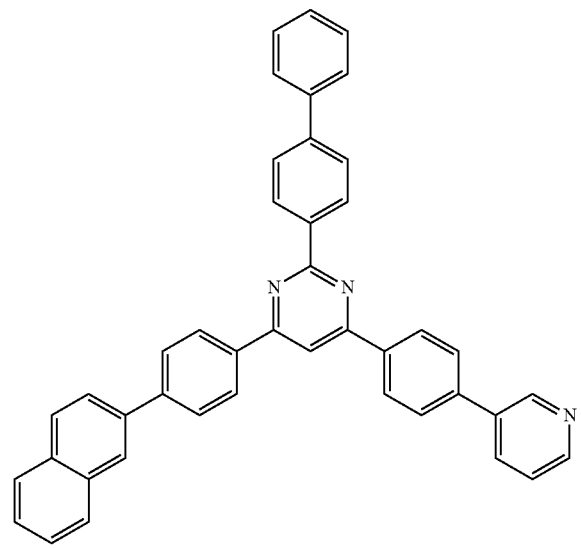
[Chemical Formula 461]
(4-161)
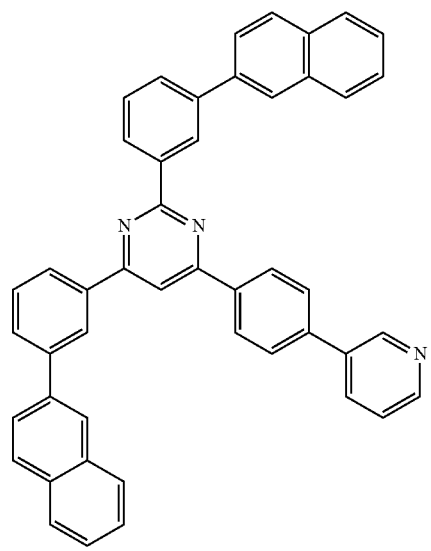
[Chemical Formula 462]
(4-162)
[Chemical Formula 463]
(4-163)
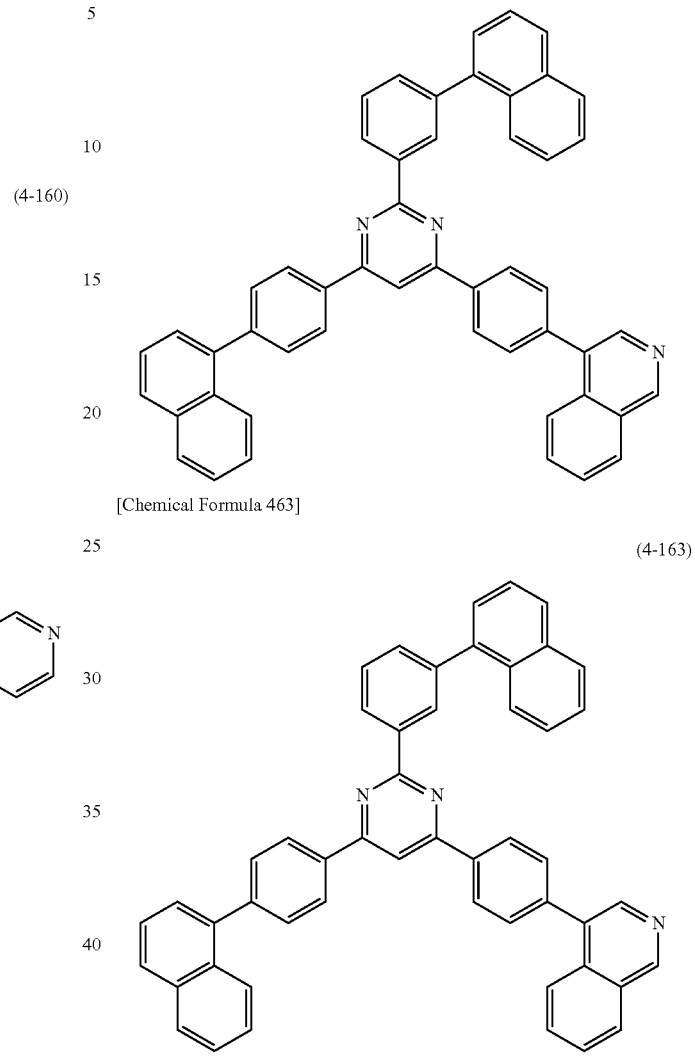
[Chemical Formula 464]
(4-164)
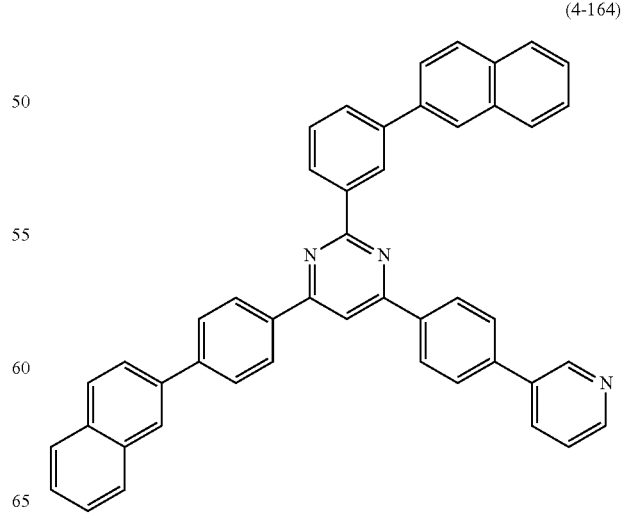

[Chemical Formula 465]
(4-165)
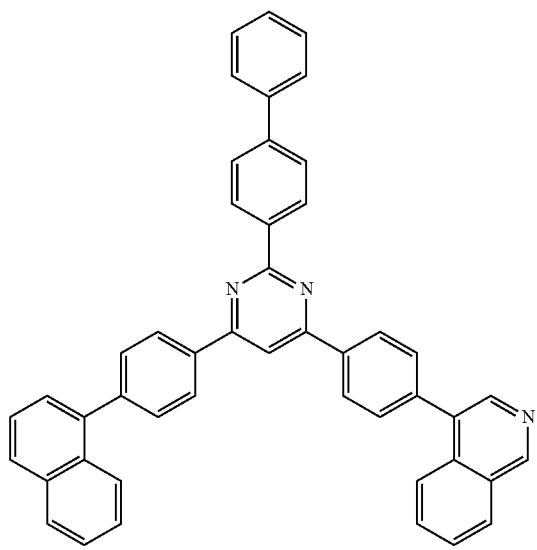
[Chemical Formula 466]
(4-166)
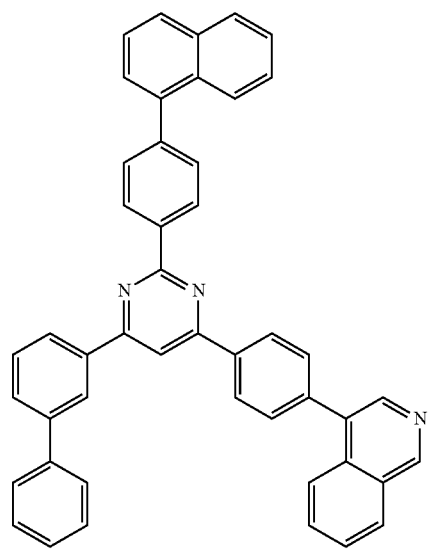
[Chemical Formula 467]
(4-167)
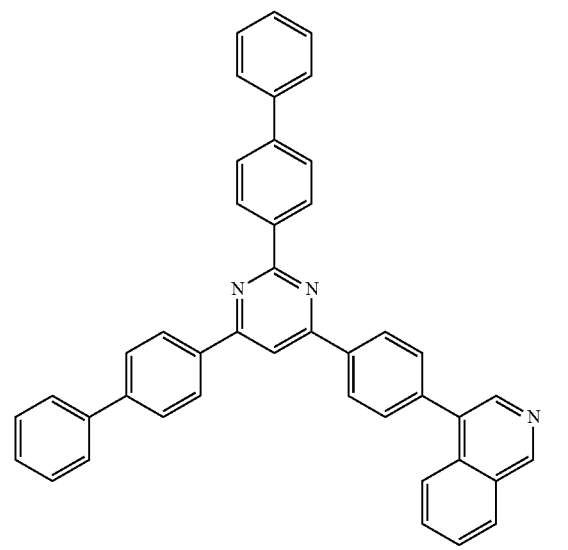
[Chemical Formula 468]
(4-168)
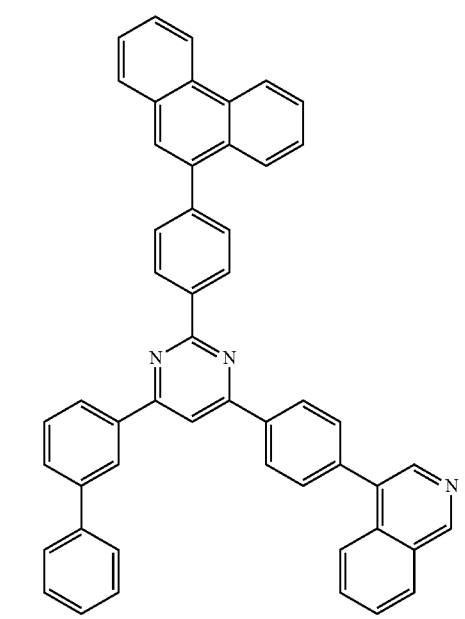

-continued
[Chemical Formula 469]
(4-169)
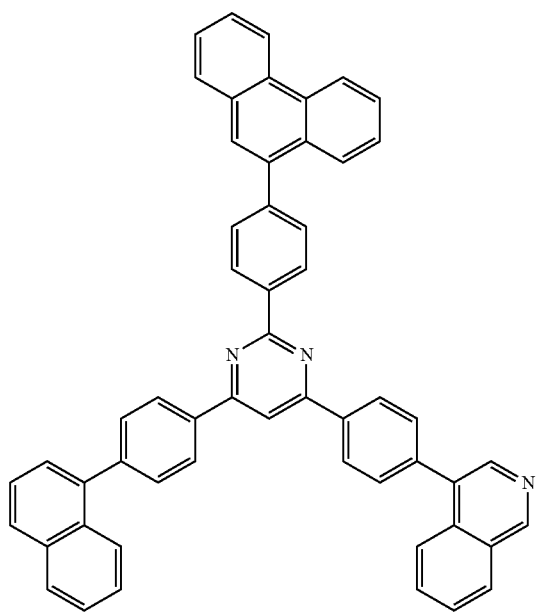
[Chemical Formula 470]
(4-170)
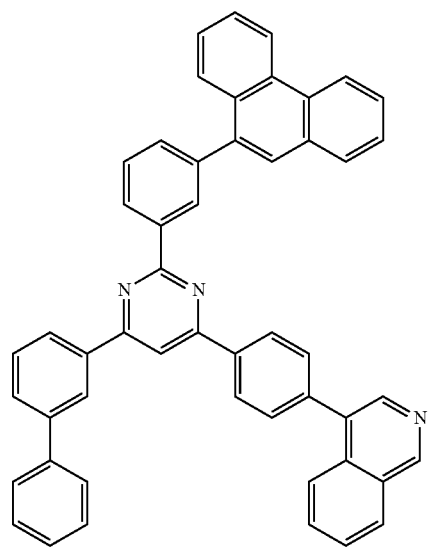
-continued
[Chemical Formula 471]
(4-171)
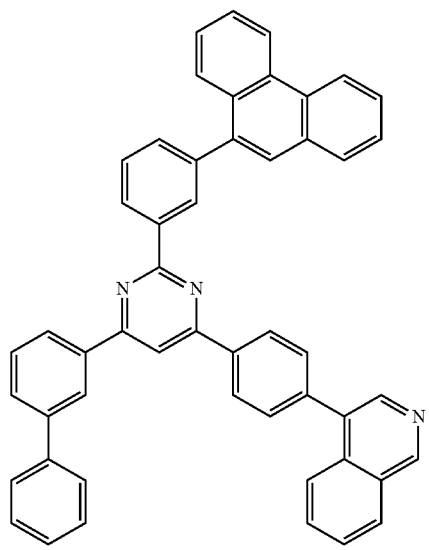
[Chemical Formula 472]
(4-172)
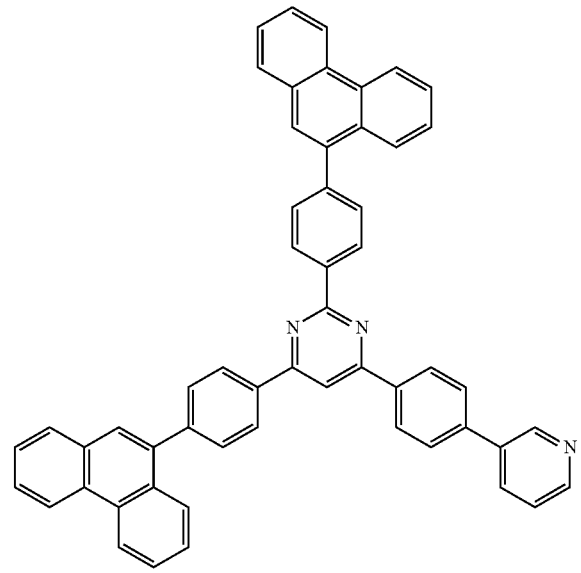

[Chemical Formula 473]
(4-173)
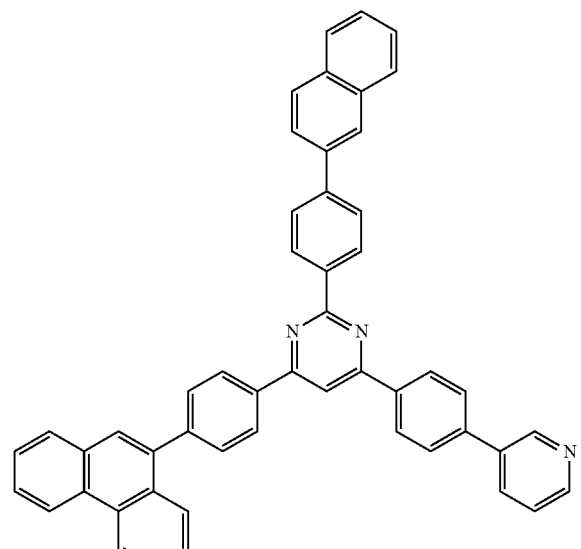
[Chemical Formula 474]
(4-174)
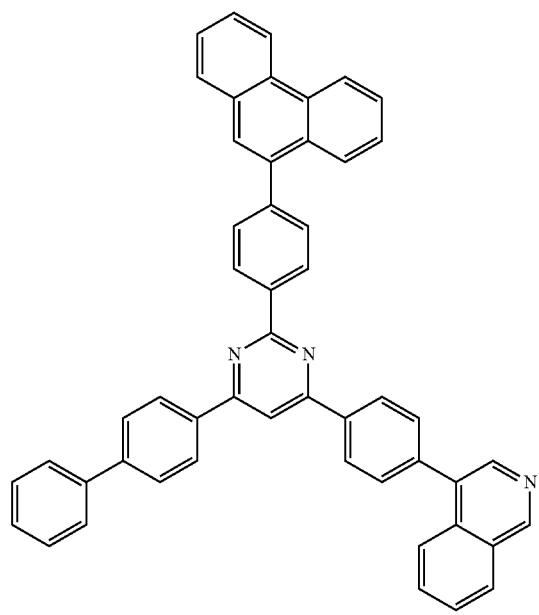
[Chemical Formula 475]
(4-175)
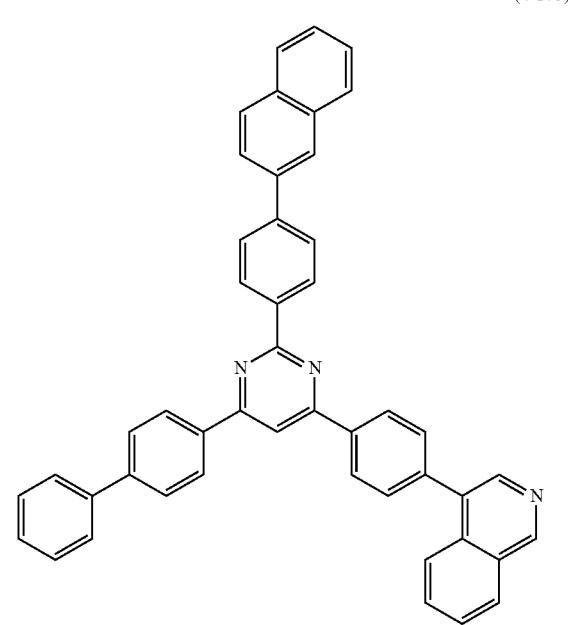
[Chemical Formula 476]
(4-176)
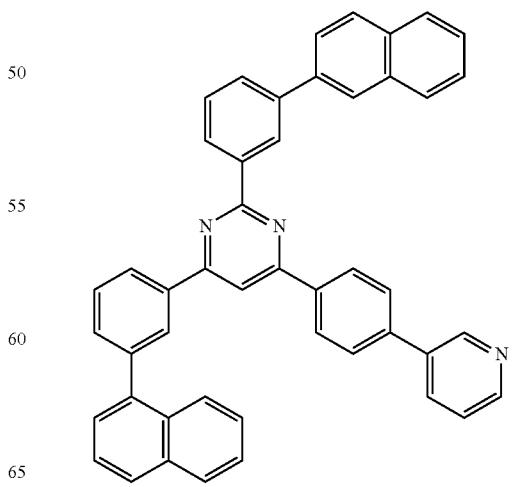

[Chemical Formula 477]
(4-177)
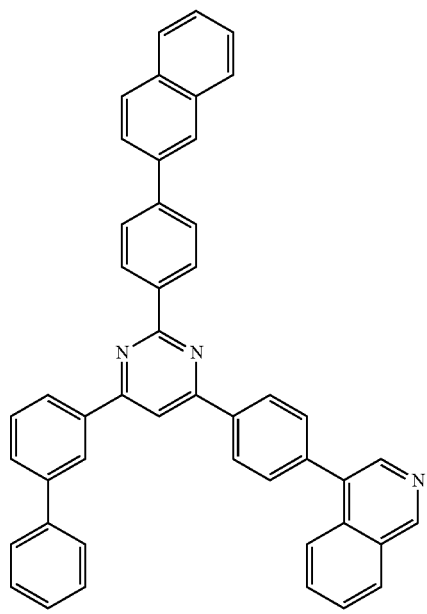
[Chemical Formula 478]
(4-178)
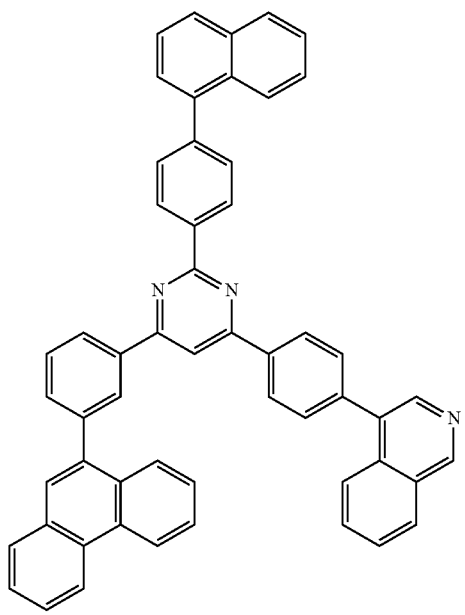
[Chemical Formula 479]
(4-179)
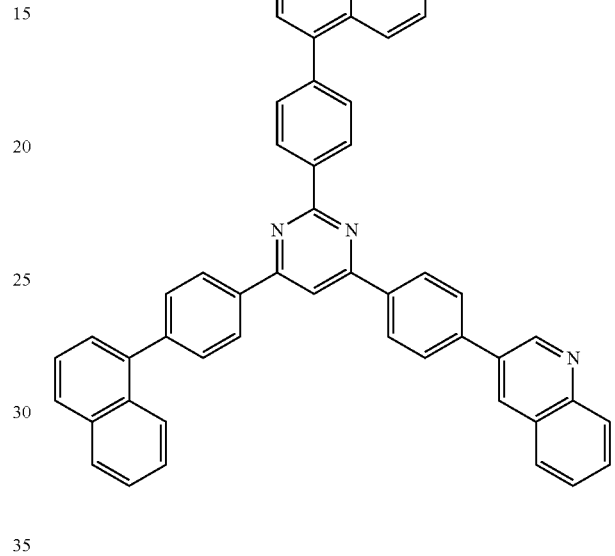
[Chemical Formula 480]
(4-180)
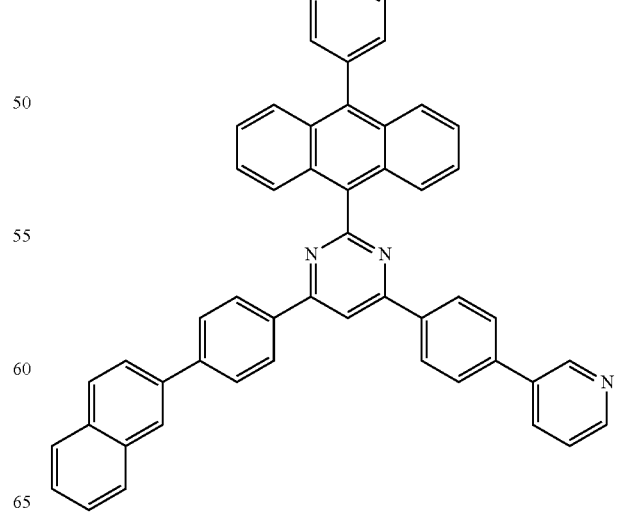

[Chemical Formula 481]
(4-181)
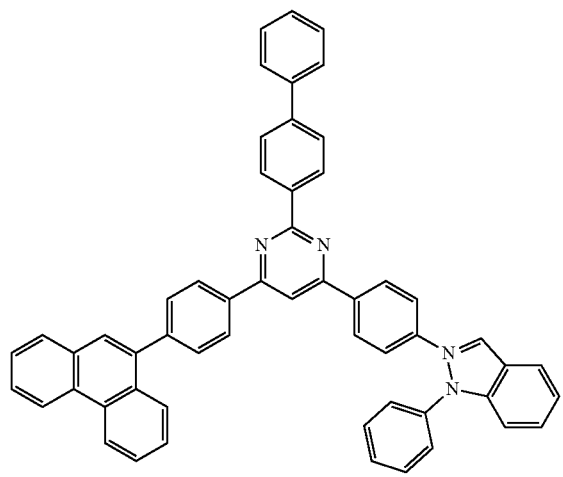
[Chemical Formula 482]
(4-182)
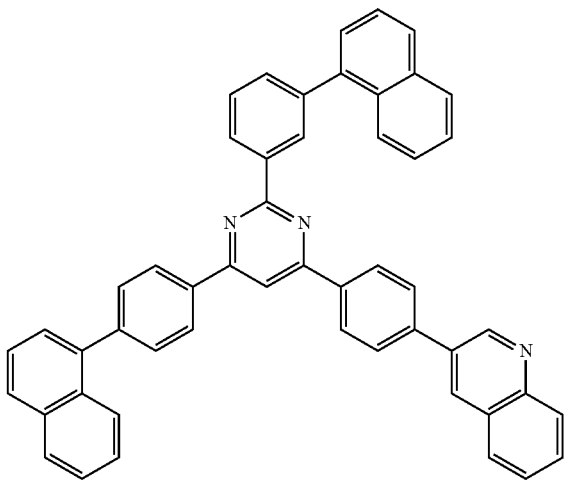
[Chemical Formula 483]
(4-183)
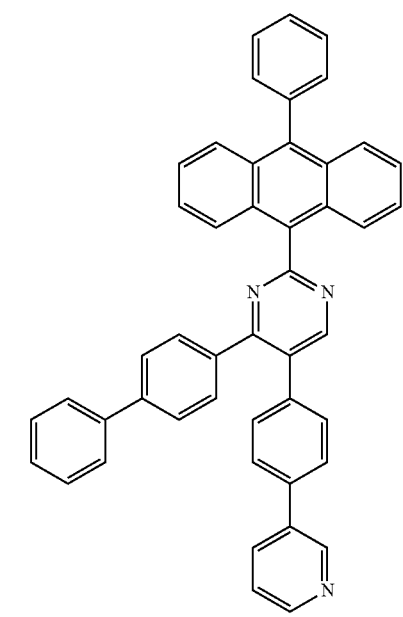
[Chemical Formula 484]
(4-184)
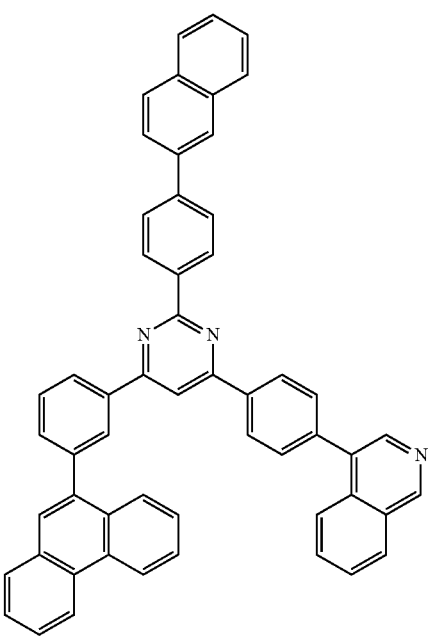

[Chemical Formula 485]
(4-185)
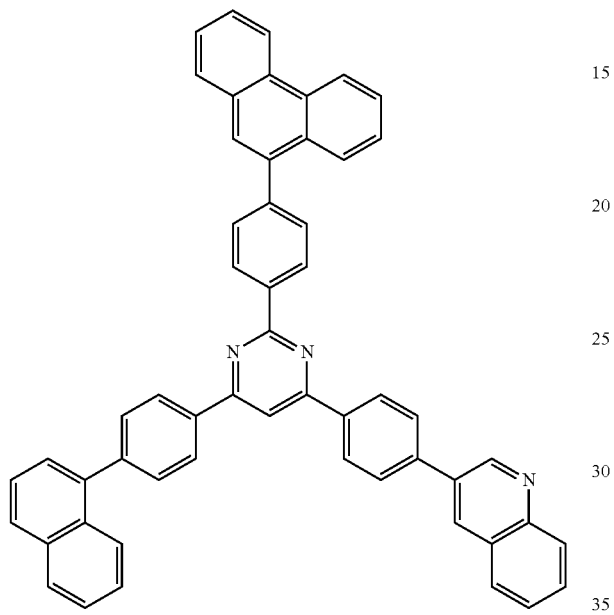
[Chemical Formula 486]
(4-186)
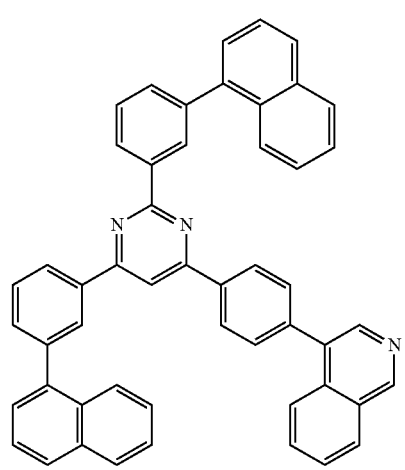
[Chemical Formula 487]
(4-187)
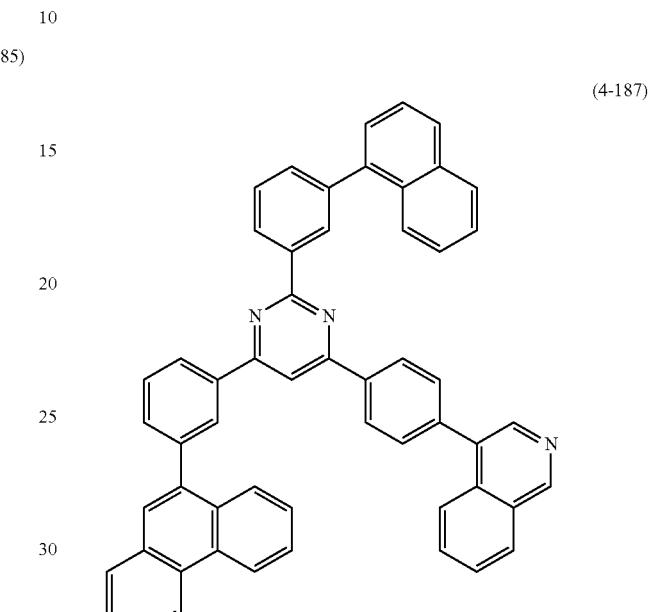
[Chemical Formula 488]
(4-188)
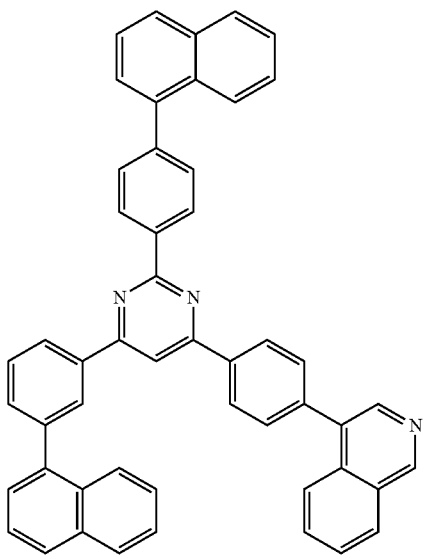

[Chemical Formula 489]
(4-189)
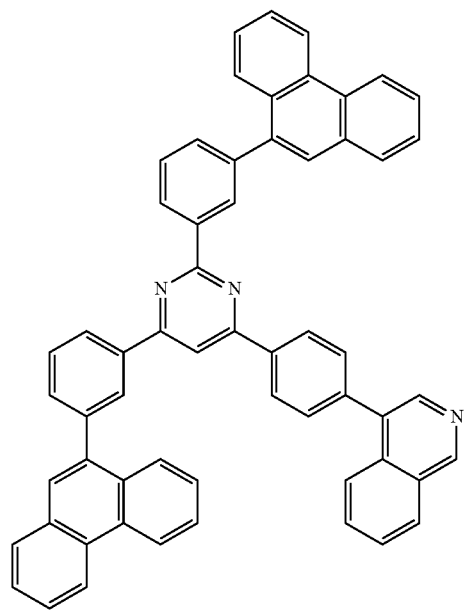
[Chemical Formula 490]
(4-190)
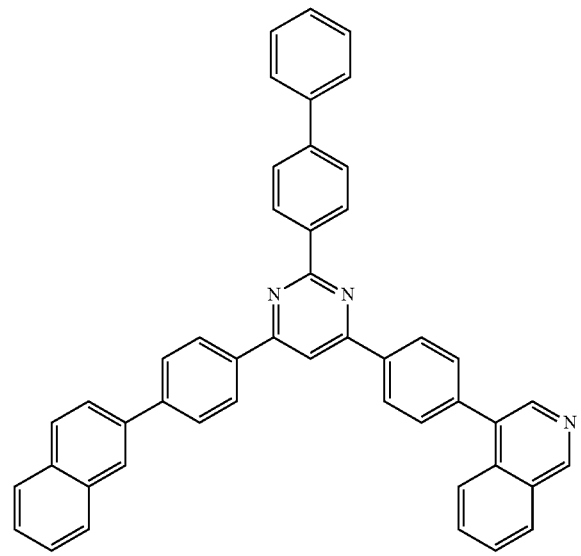
[Chemical Formula 491]
(4-191)
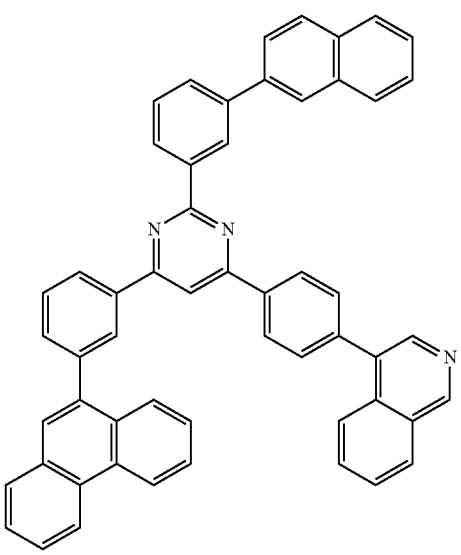
[Chemical Formula 492]
(4-192)
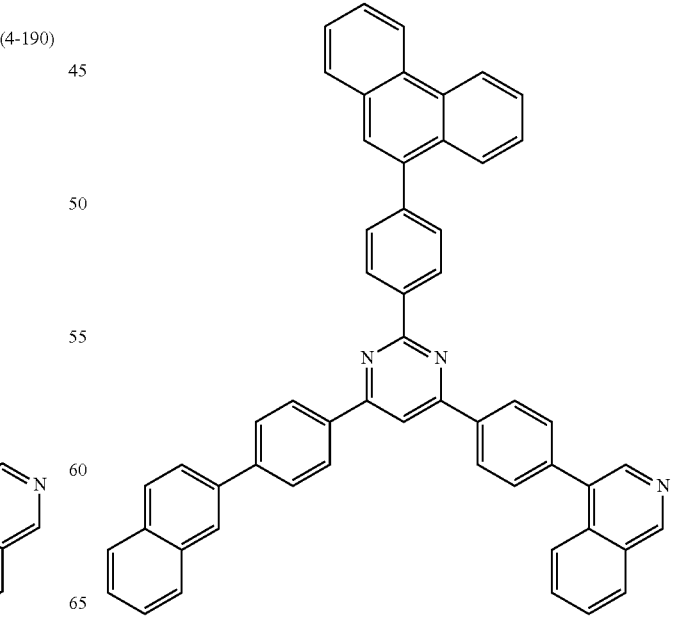

[Chemical Formula 493]
(4-193)
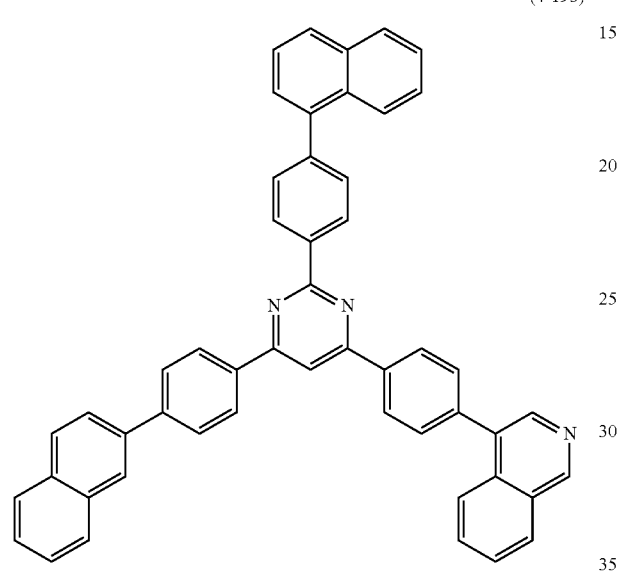
[Chemical Formula 494]
(4-194)
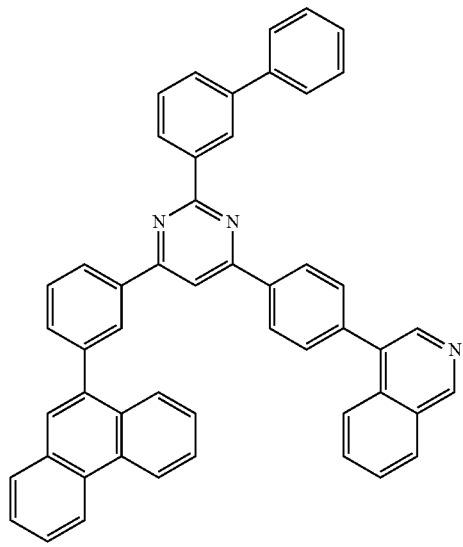
[Chemical Formula 495]
(4-195)
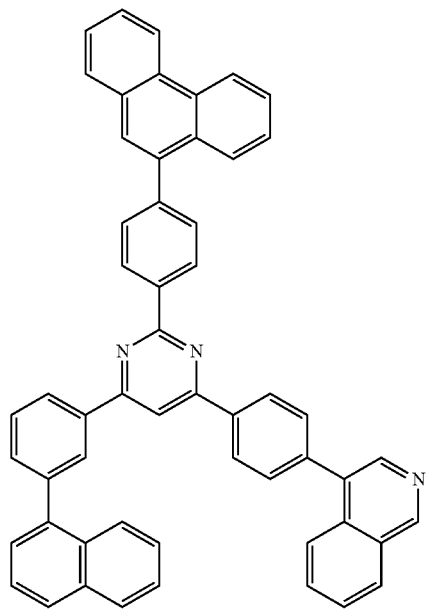
[Chemical Formula 496]
(4-196)
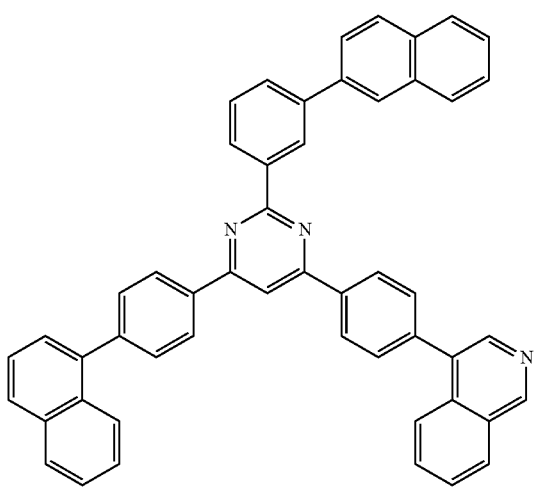

[Chemical Formula 497]
(4-197)
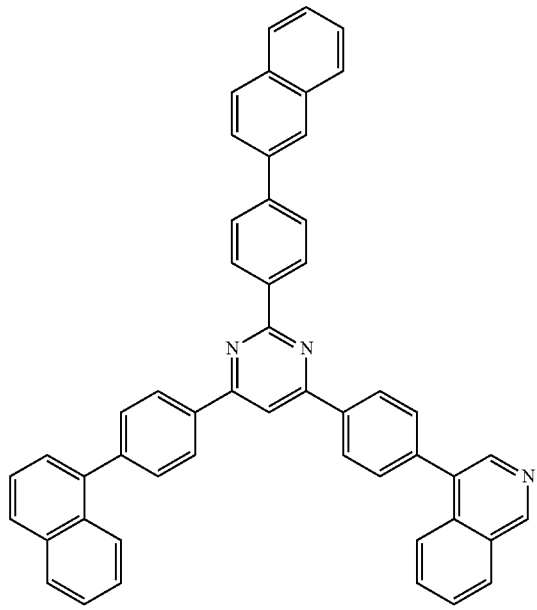
[Chemical Formula 498]
(4-198)
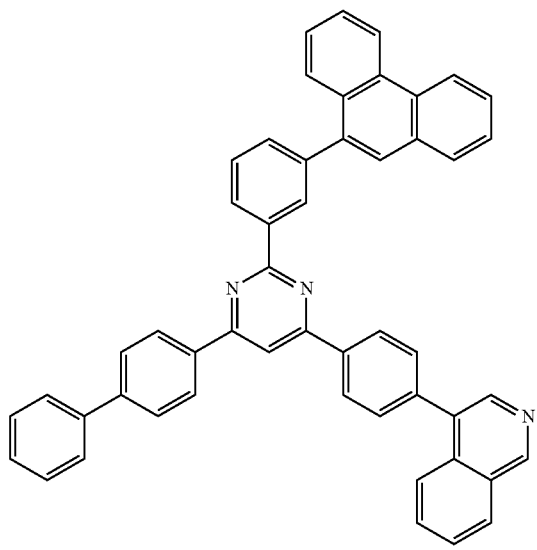
[Chemical Formula 499]
(4-199)
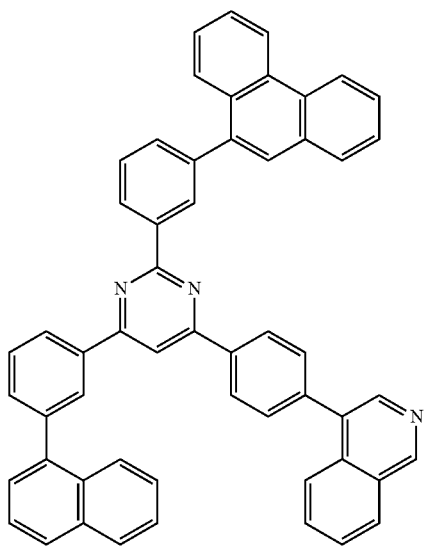
[Chemical Formula 500]
(4-200)
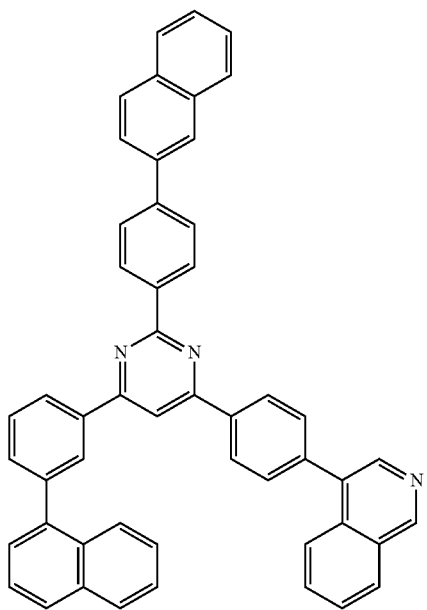

[Chemical Formula 501]
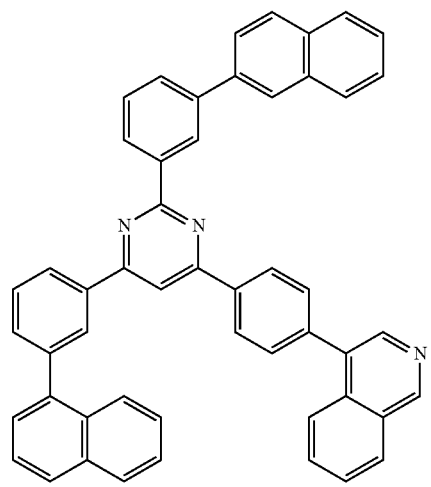
(4-201)
[Chemical Formula 502]
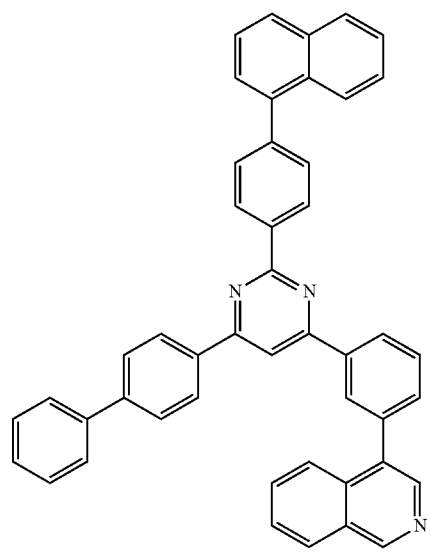
(4-202)
[Chemical Formula 503]
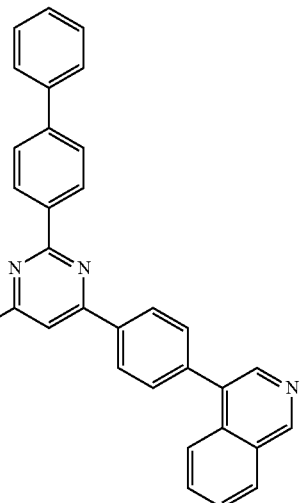
(4-203)
[Chemical Formula 504]
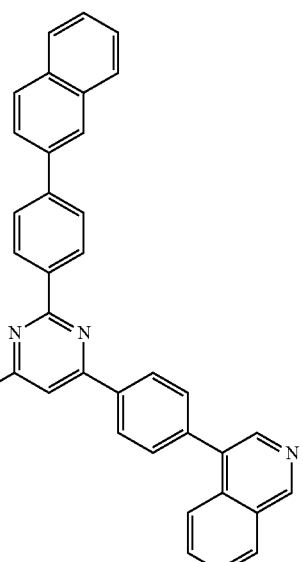
(4-204)

[Chemical Formula 505]
(4-205)
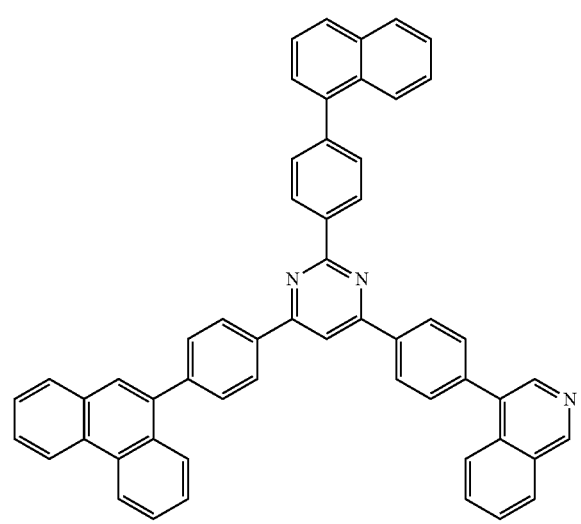
[Chemical Formula 506]
(4-206)
[Chemical Formula 507]
(4-207)
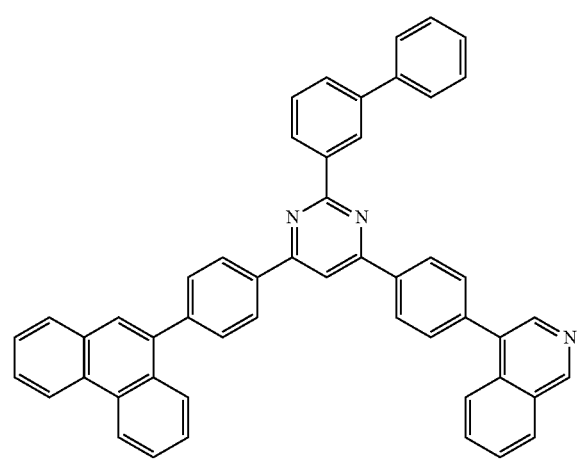
[Chemical Formula 508]
(4-208)
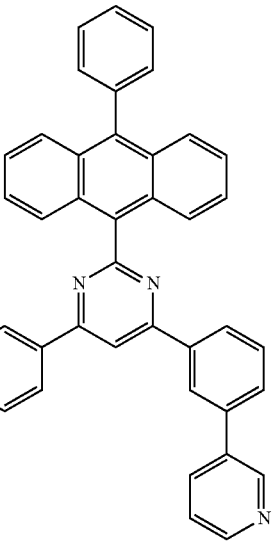
[Chemical Formula 509]
(4-209)
[Chemical Formula 510]
(4-210)
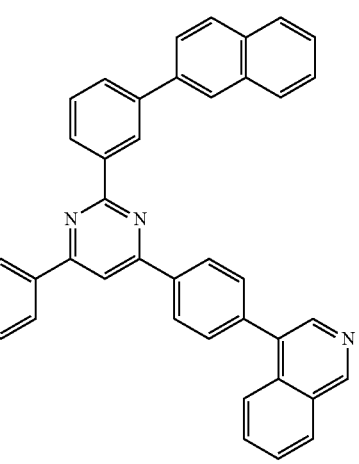
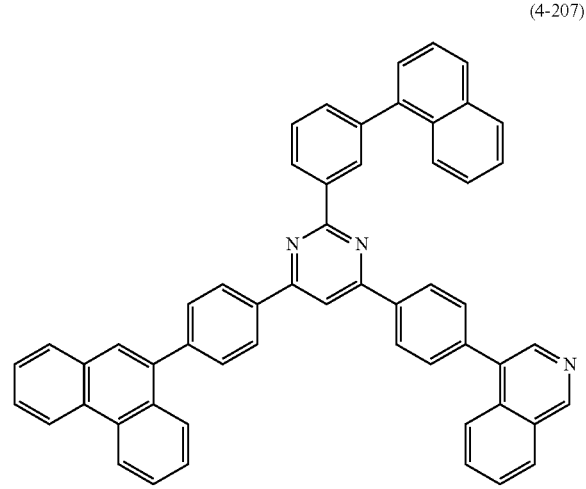

[Chemical Formula 511]
(4-211)
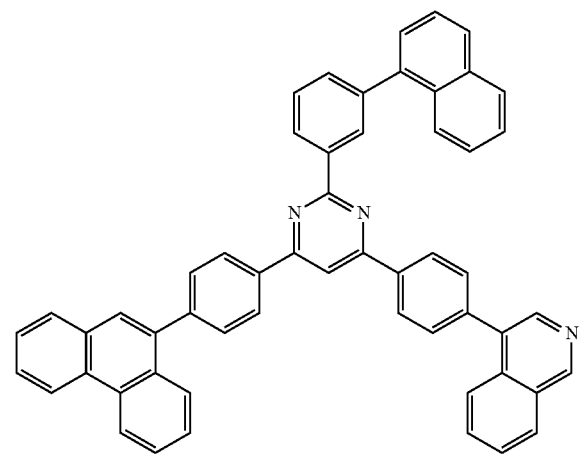
[Chemical Formula 512]
(4-212)
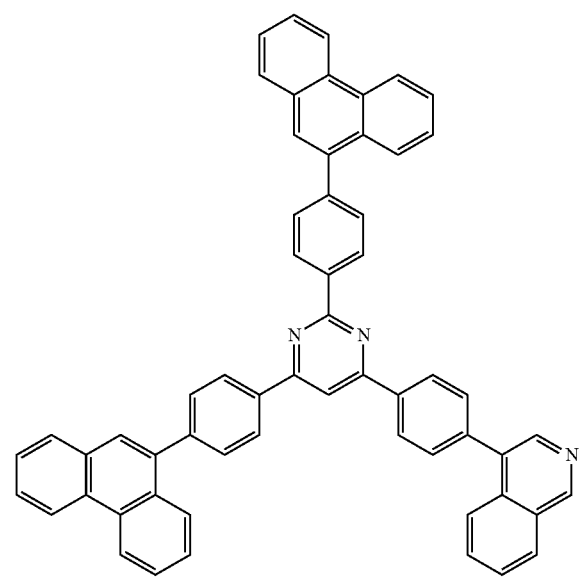
[Chemical Formula 513]
(4-213)
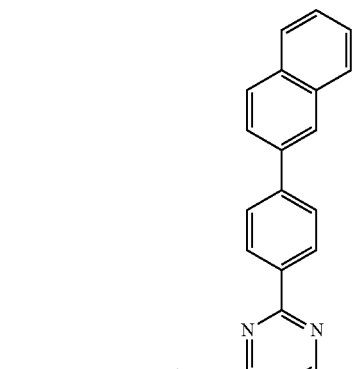
[Chemical Formula 514]
(4-214)
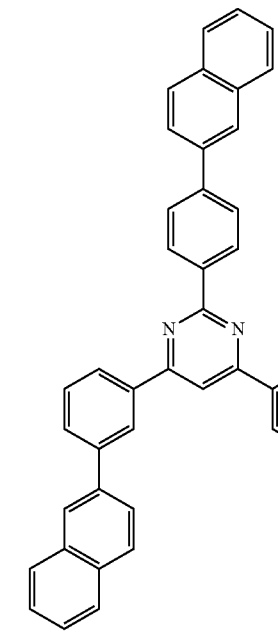

[Chemical Formula 515]
(4-215)
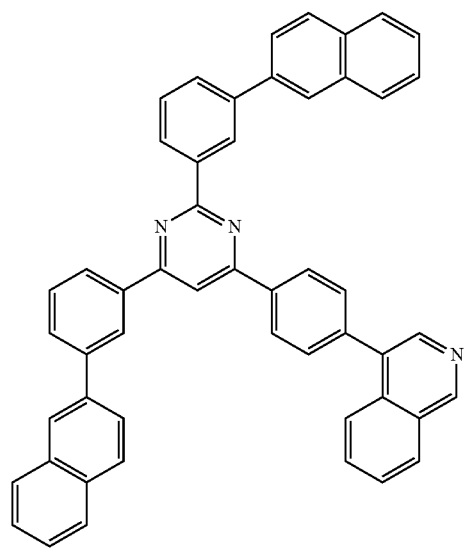
[Chemical Formula 516]
(4-216)
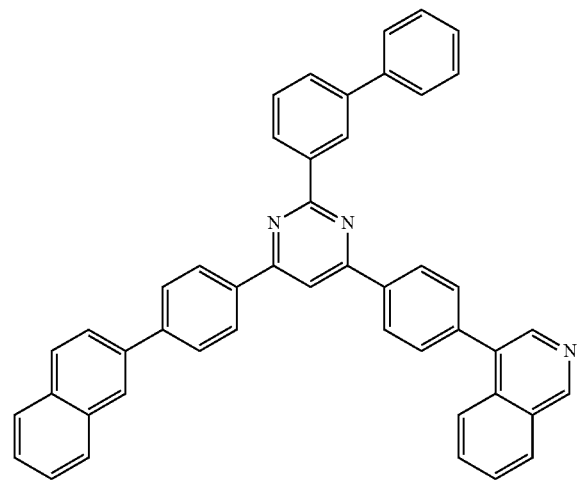
[Chemical Formula 517]
(4-217)
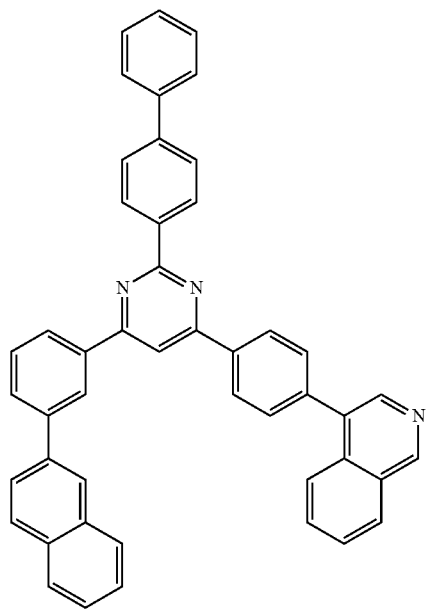
[Chemical Formula 518]
(4-218)
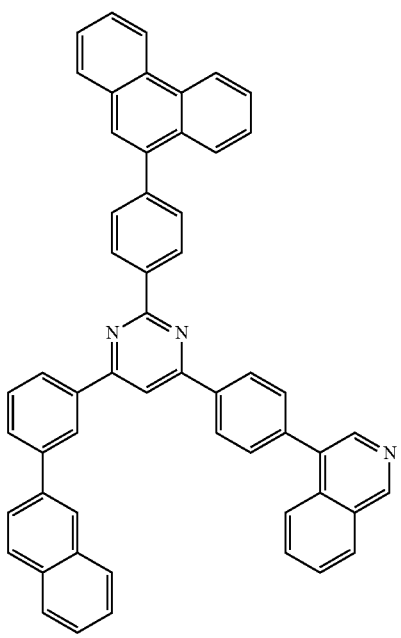

[Chemical Formula 519]
(4-219)
[Chemical Formula 520]
(4-220)
[Chemical Formula 521]
(4-221)
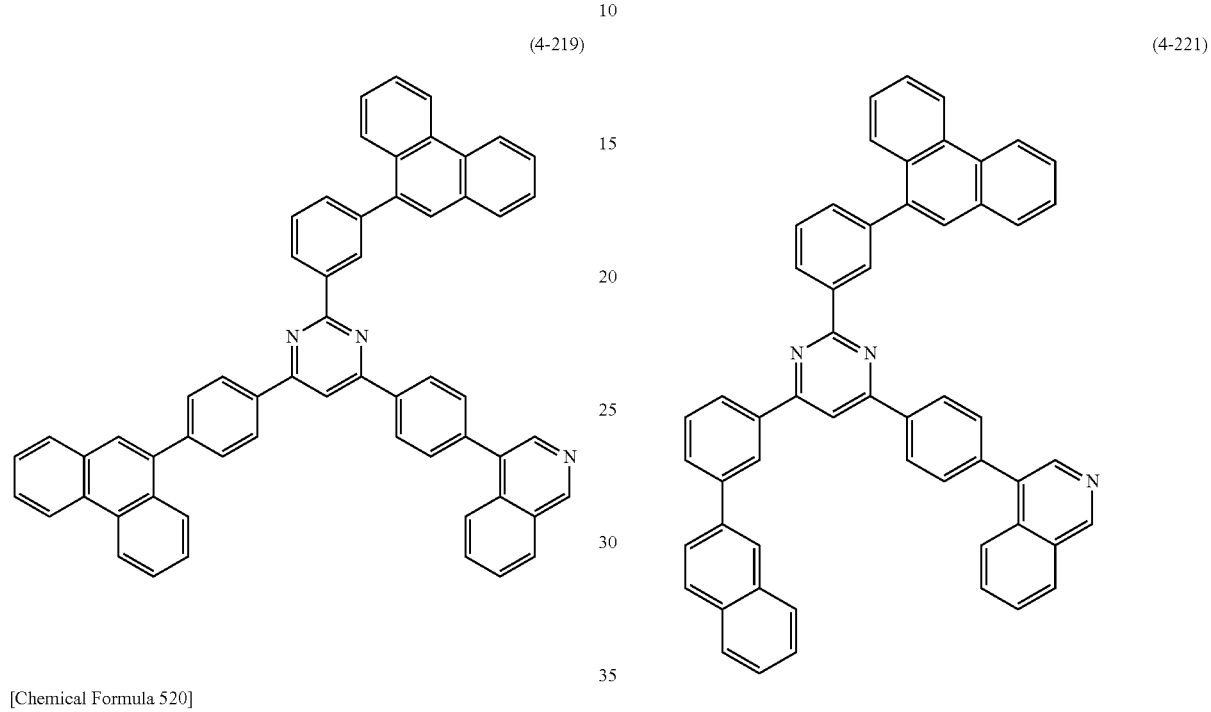
[Chemical Formula 522]
(4-222)
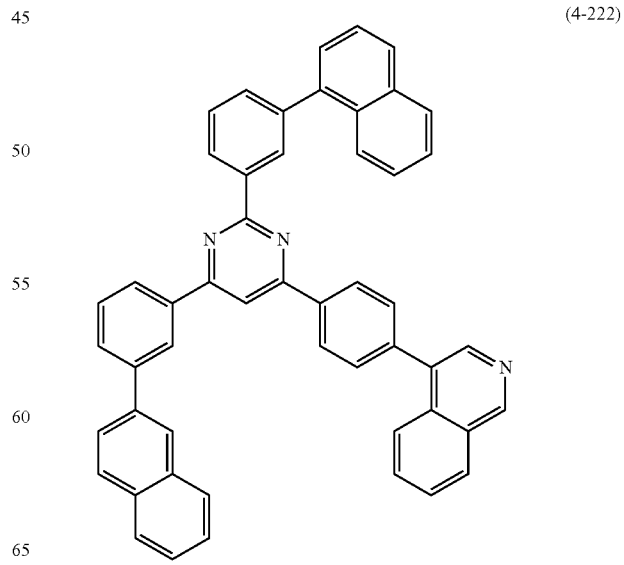

[Chemical Formula 523]
(4-223)
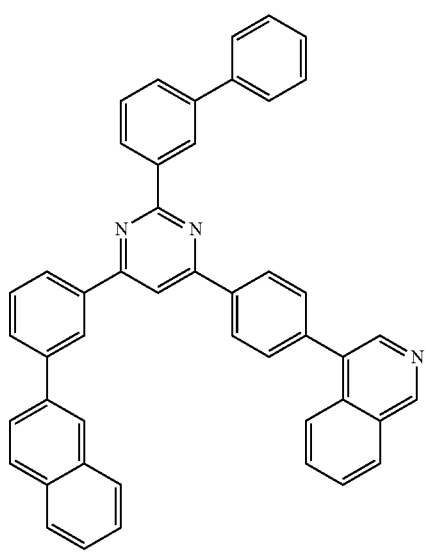
[Chemical Formula 524]
(4-224)
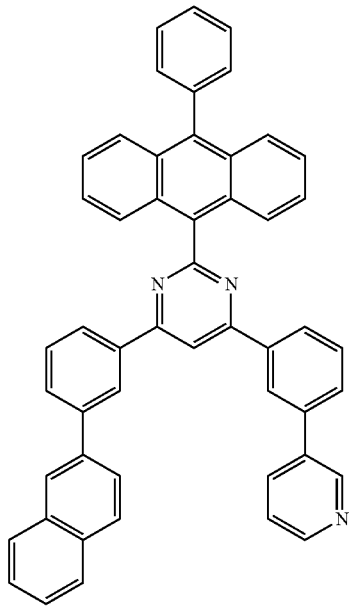
[Chemical Formula 525]
(4-225)
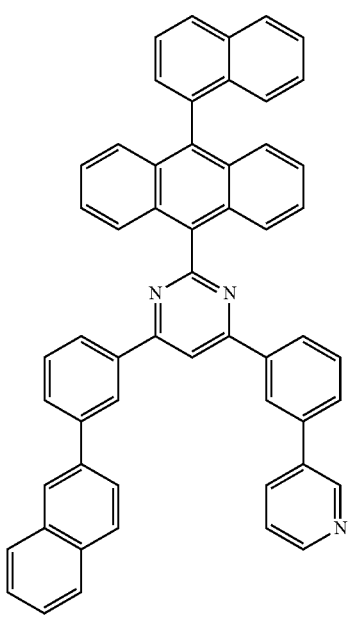
[Chemical Formula 526]
(4-226)
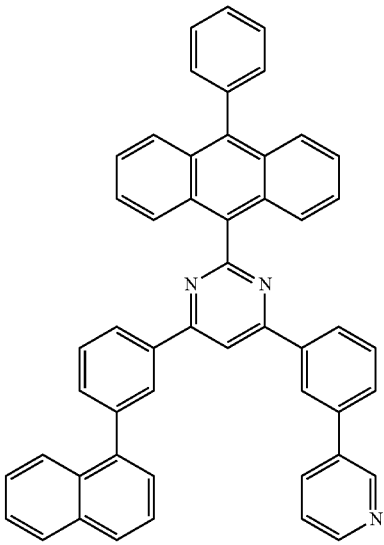

[Chemical Formula 527]
(4-227)
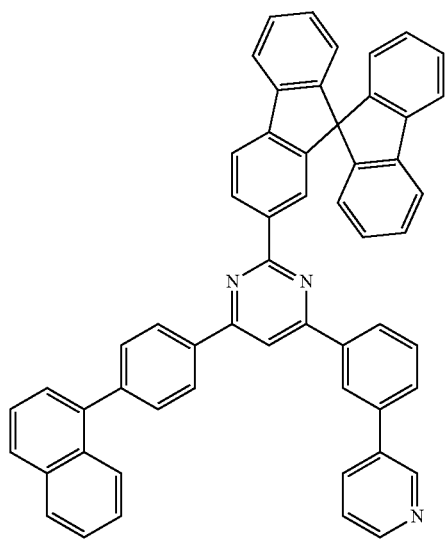
[Chemical Formula 528]
(4-228)
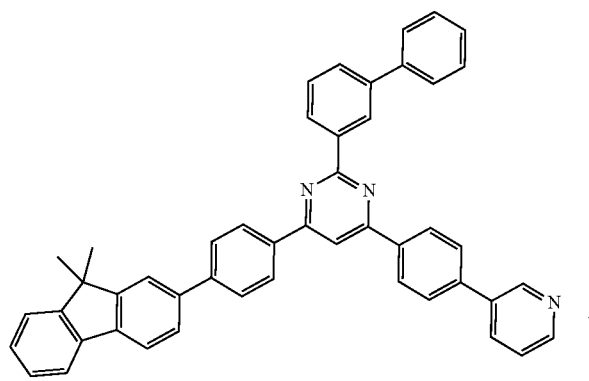
[Chemical Formula 529]
(4-229)
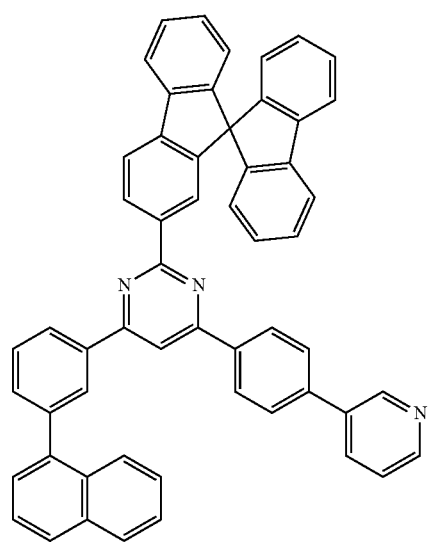
[Chemical Formula 530]
(4-230)
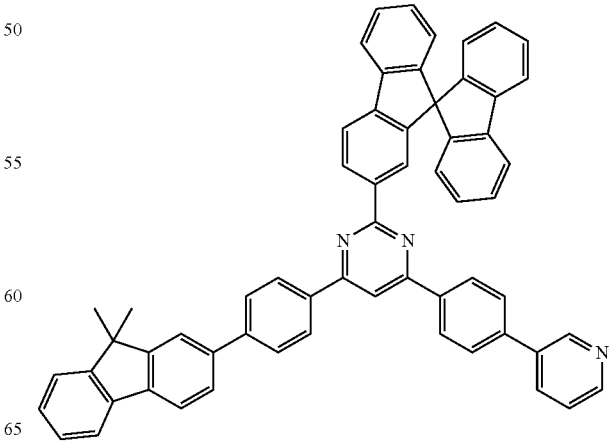
[Chemical Formula 531]
(4-231)
[Chemical Formula 532]
(4-232)

[Chemical Formula 533]
(4-233)
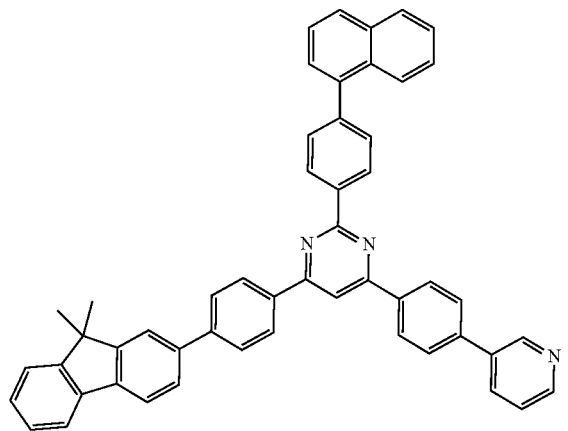
[Chemical Formula 534]
(4-234)
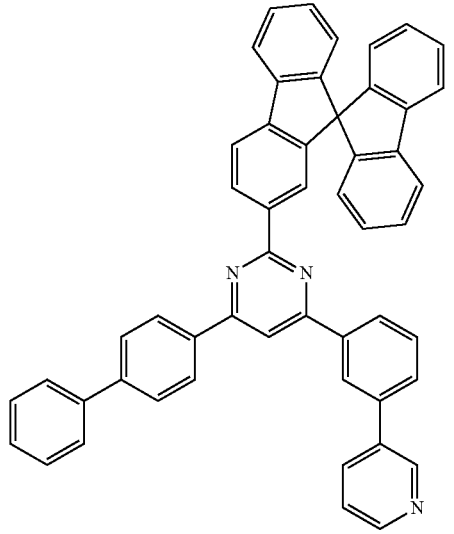
[Chemical Formula 535]
(4-235)
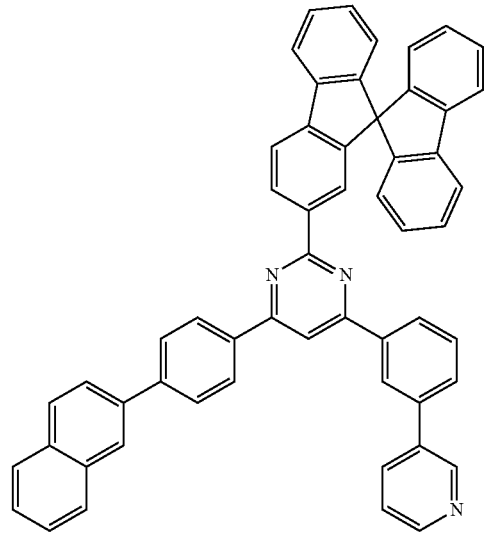
[Chemical Formula 536]
(4-236)
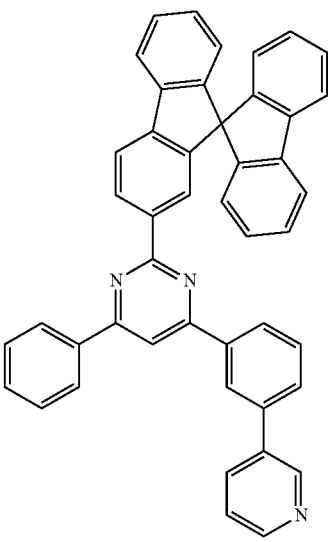
[Chemical Formula 537]
(4-237)
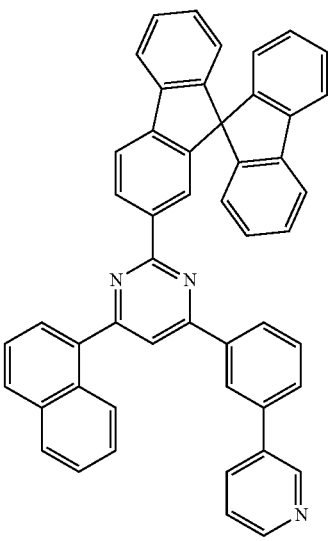

[Chemical Formula 538]
(4-238)
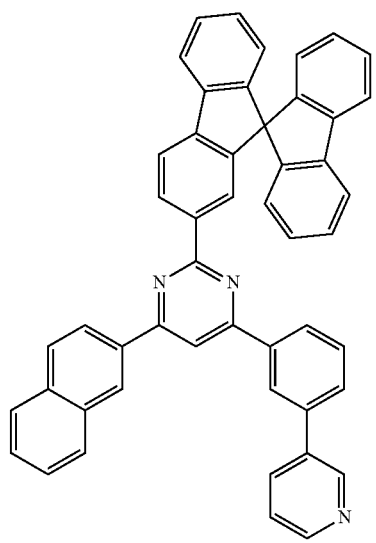
[Chemical Formula 539]
(4-239)
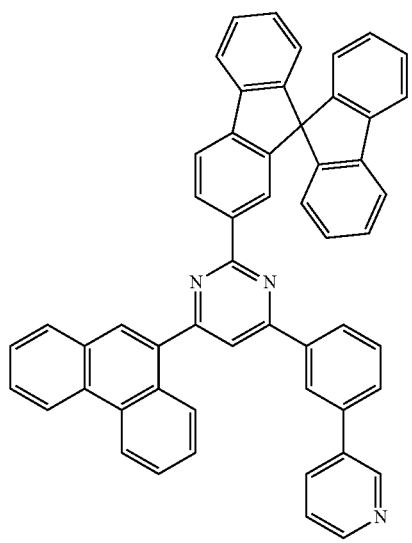
[Chemical Formula 540]
(4-240)
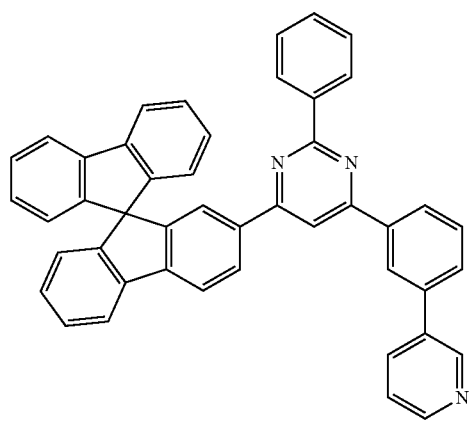
[Chemical Formula 541]
(4-241)
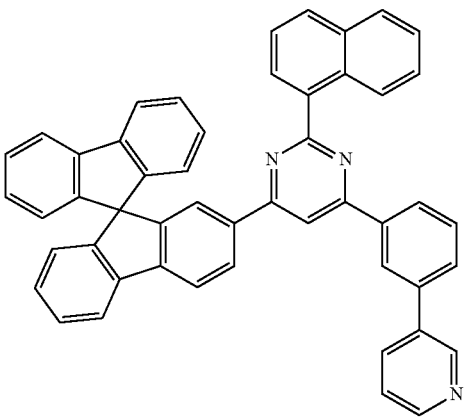
[Chemical Formula 542]
(4-242)
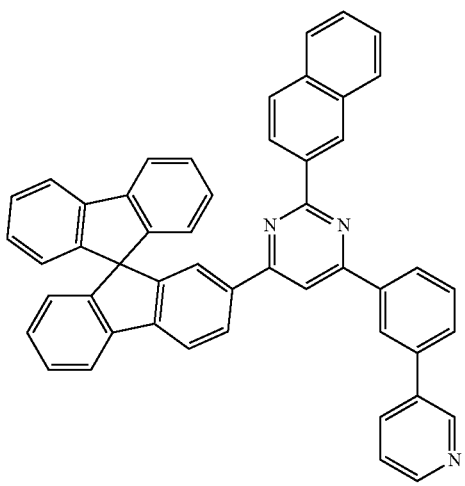
[Chemical Formula 543]
(4-243)
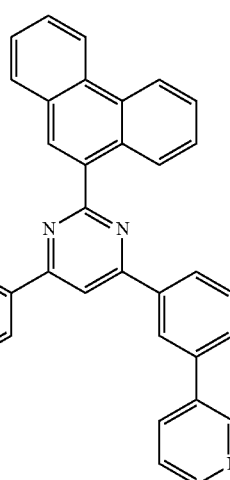

[Chemical Formula 544]
(4-244)
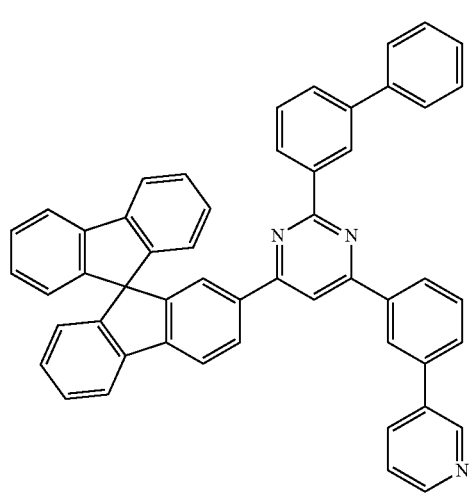
[Chemical Formula 545]
(4-245)
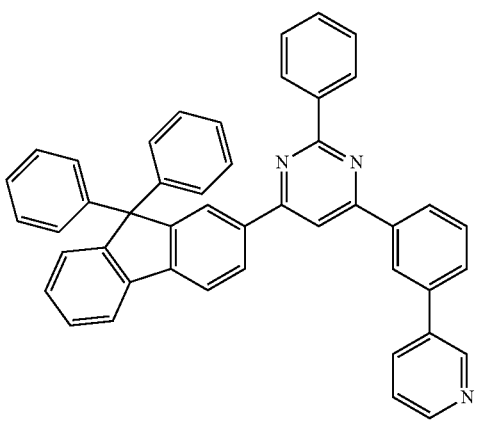
[Chemical Formula 546]
(4-246)
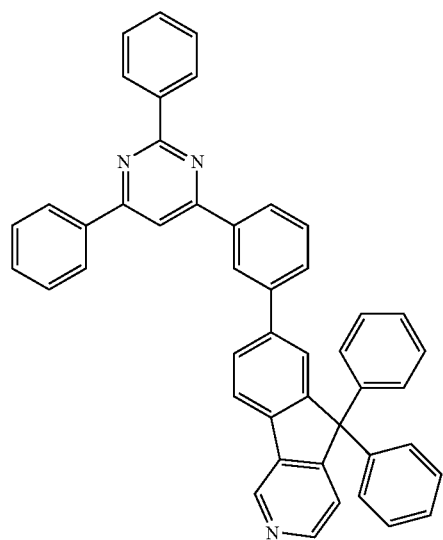
[Chemical Formula 547]
(4-247)
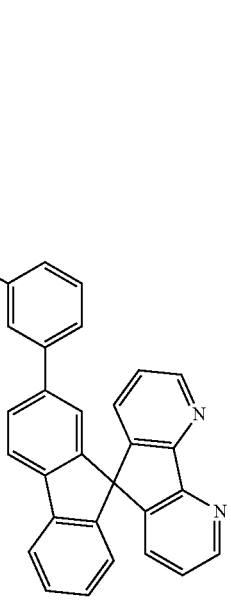
[Chemical Formula 548]
(4-248)
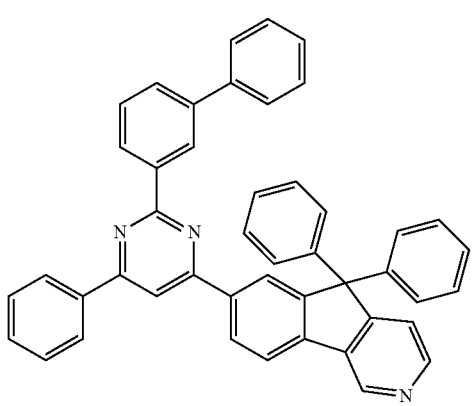
[Chemical Formula 549]
(4-249)

[Chemical Formula 550]
(4-250)
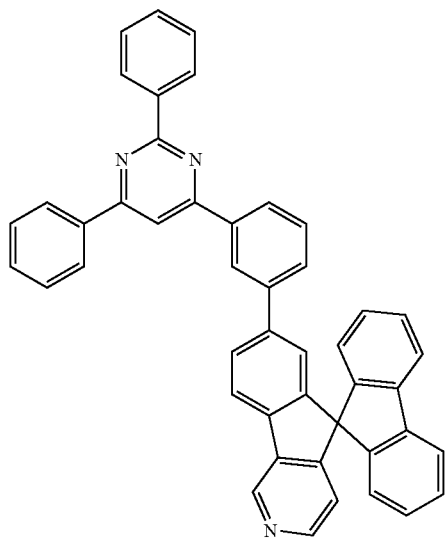
[Chemical Formula 551]
(4-251)
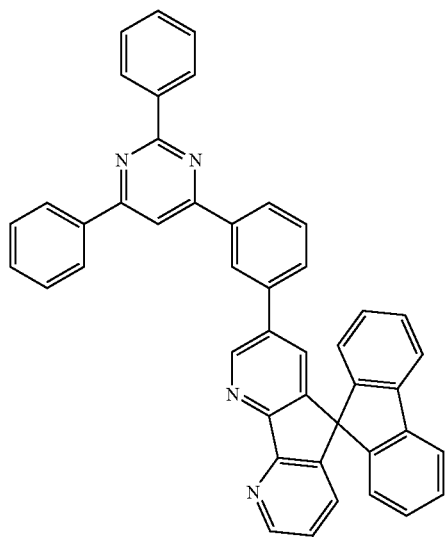
[Chemical Formula 552]
(4-252)
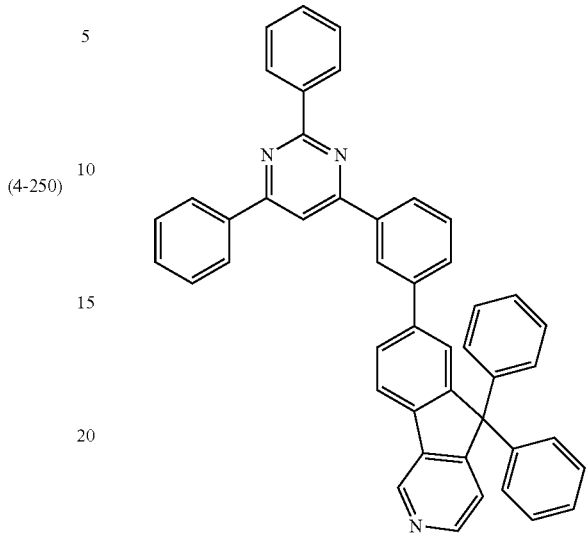
[Chemical Formula 553]
(4-253)
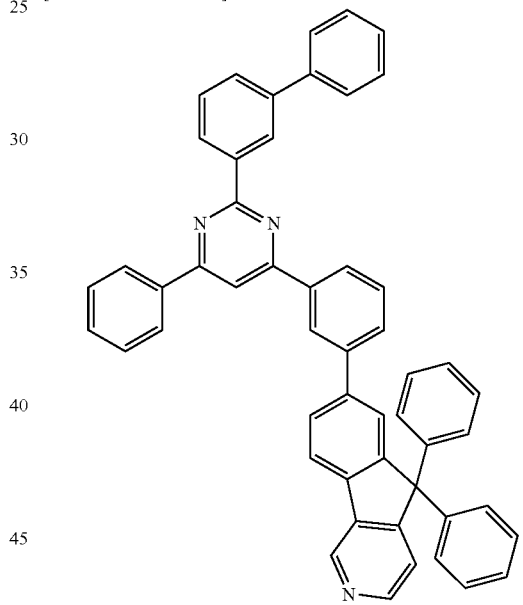
[Chemical Formula 554]
(4-254)
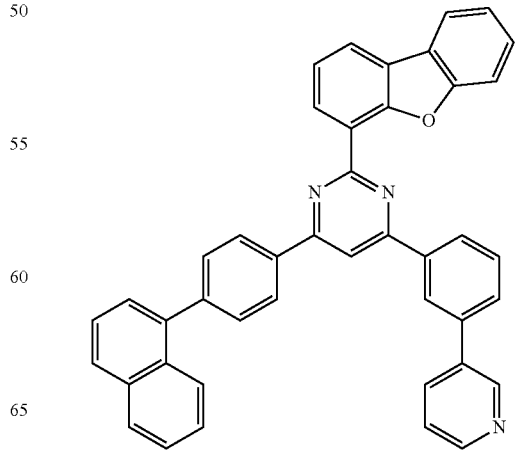

[Chemical Formula 555]
(4-255)
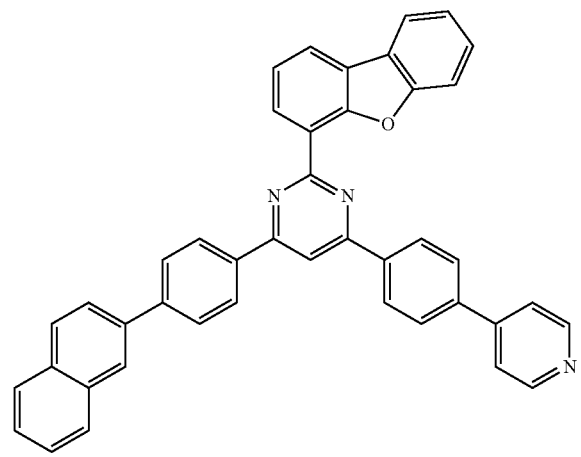
[Chemical Formula 556]
(4-256)
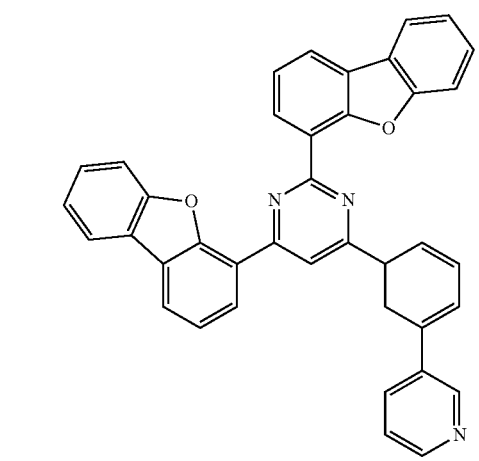
[Chemical Formula 557]
(4-257)
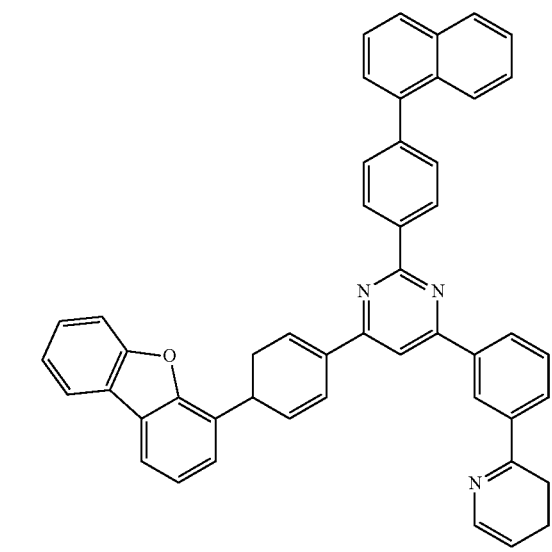
[Chemical Formula 558]
(4-258)
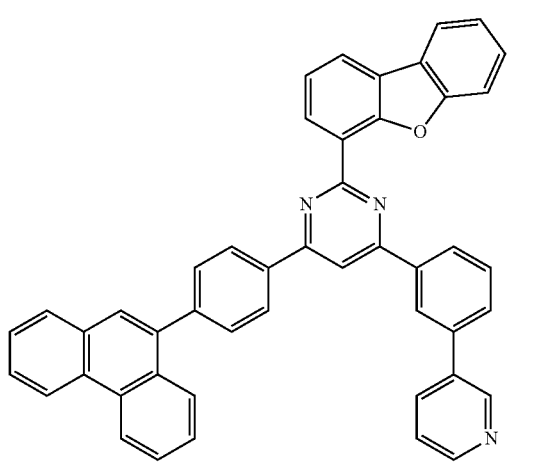
[Chemical Formula 559]
(4-259)
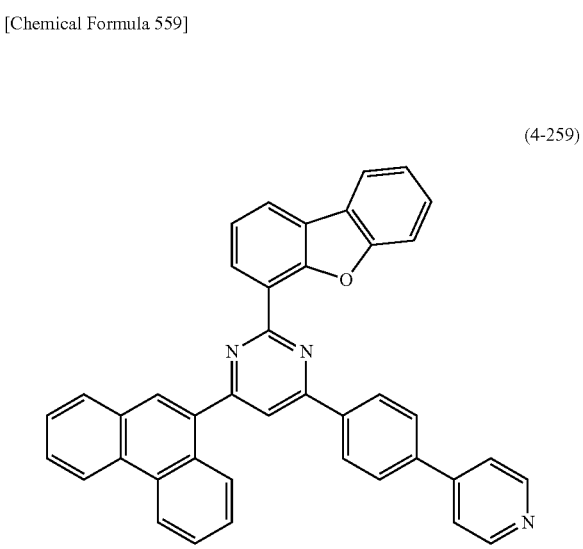
[Chemical Formula 560]
(4-260)
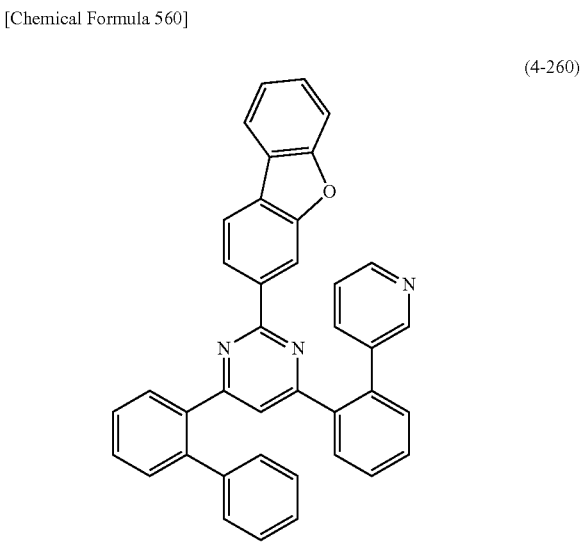

-continued

[Chemical Formula 561]

(4-261)

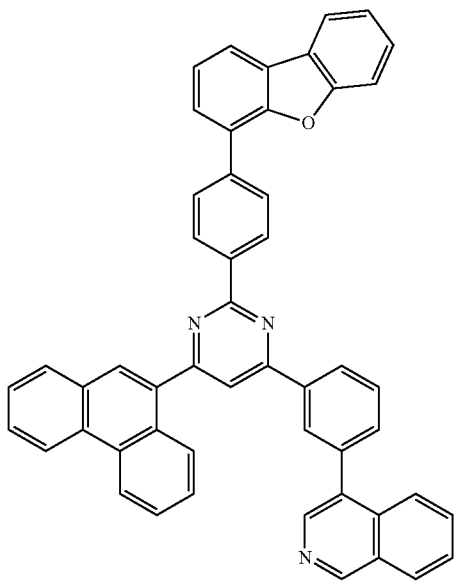

[Chemical Formula 562]

(4-262)

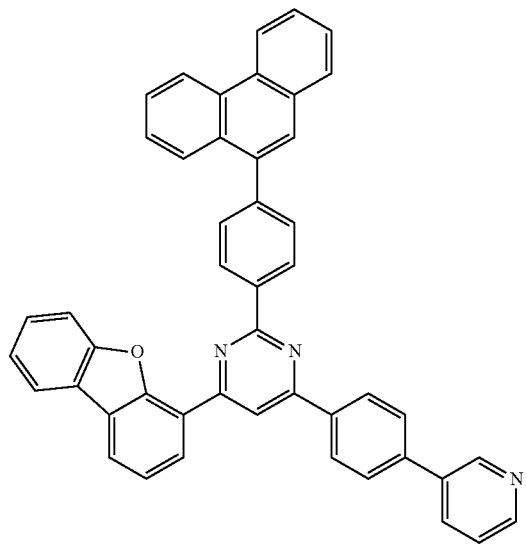

-continued

[Chemical Formula 563]

(4-263)

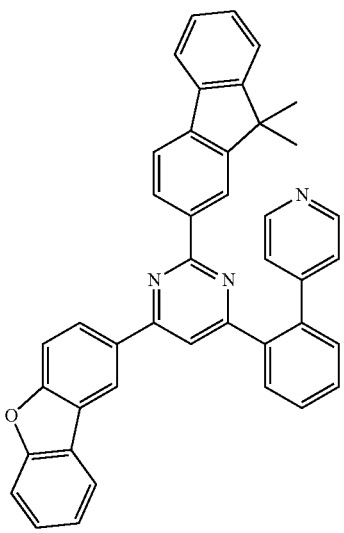

[Chemical Formula 564]

(4-264)

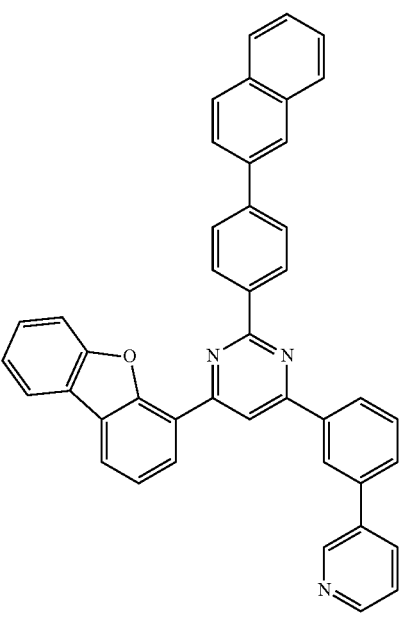

The compounds having a pyrimidine ring structure described above can be synthesized by a known method (refer to Patent Documents 8 and 9, for example).

The following presents specific examples of preferred compounds among the compounds of the general formula (6) preferably used in the organic EL device of the present invention and having a benzotriazole ring structure. The present invention, however, is not restricted to these compounds.

[Chemical Formula 565]
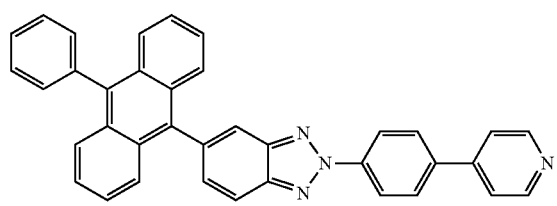
(6-1)
[Chemical Formula 566]
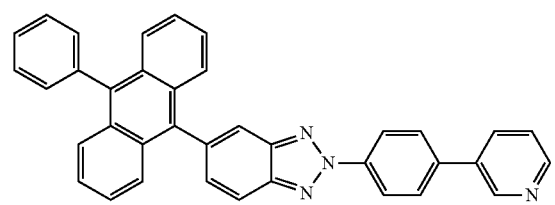
(6-2)
[Chemical Formula 567]
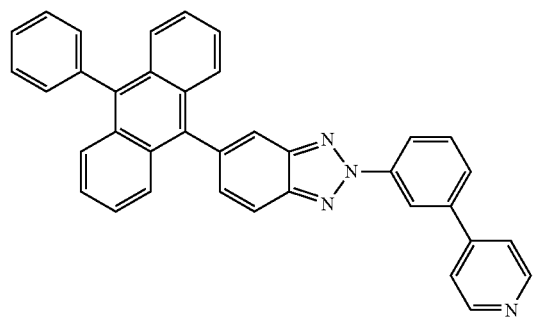
(6-3)
[Chemical Formula 568]
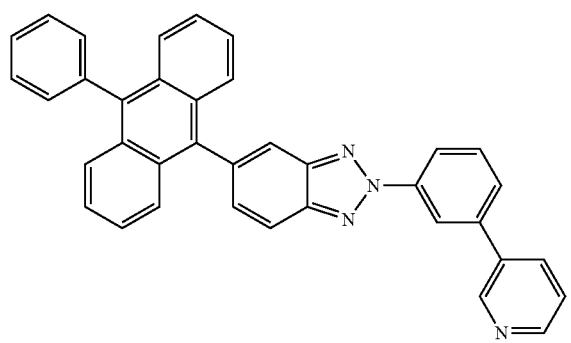
(6-4)
-continued
[Chemical Formula 569]
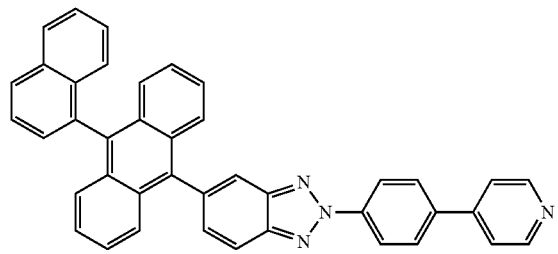
(6-5)
[Chemical Formula 570]
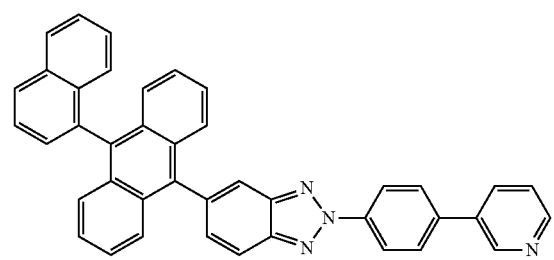
(6-6)
[Chemical Formula 571]
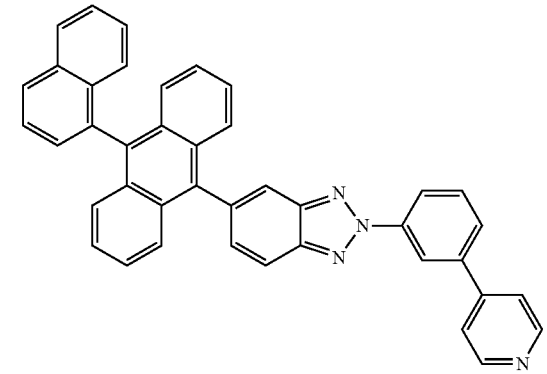
(6-7)
[Chemical Formula 572]
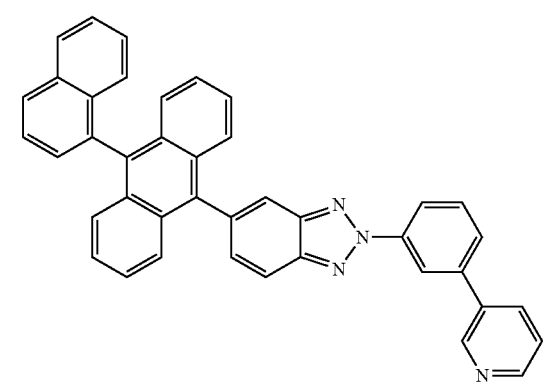
(6-8)

[Chemical Formula 573]
(6-9)
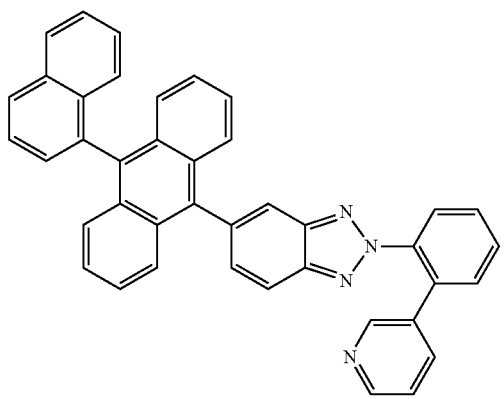
[Chemical Formula 574]
(6-10)
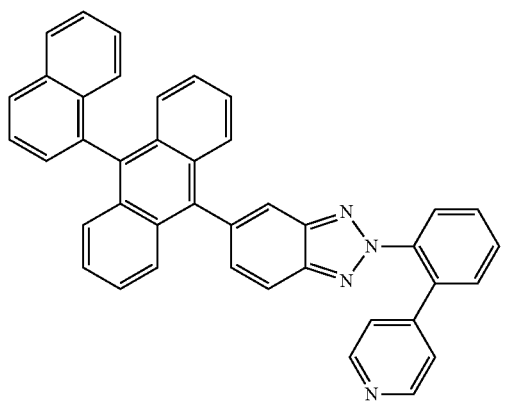
[Chemical Formula 575]
(6-11)
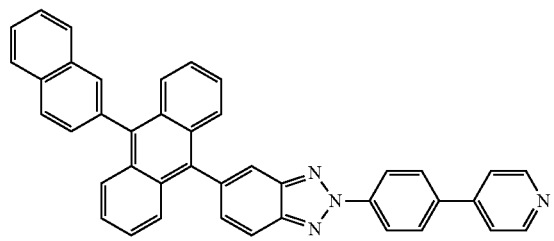
[Chemical Formula 576]
(6-12)
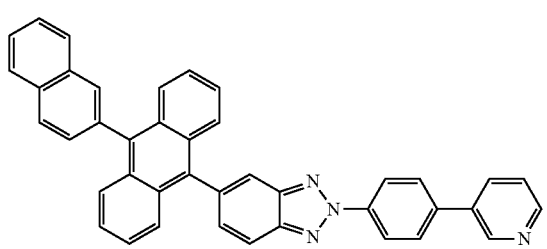
[Chemical Formula 577]
(6-13)
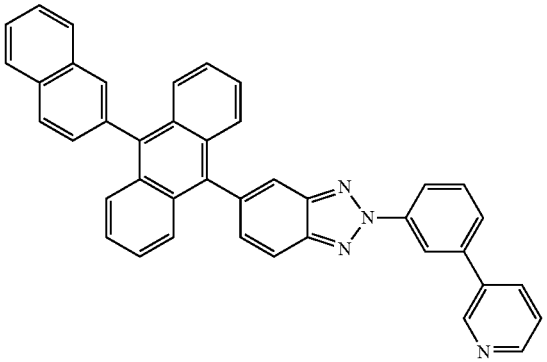
[Chemical Formula 578]
(6-14)
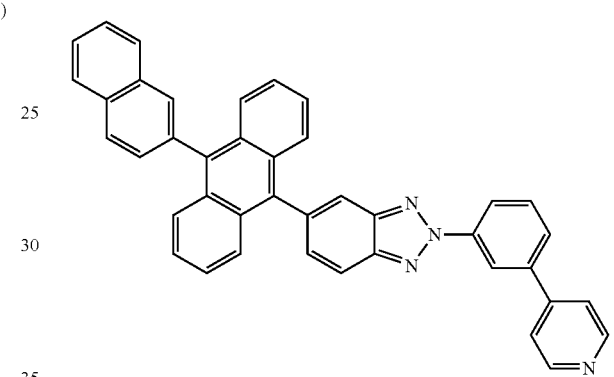
[Chemical Formula 579]
(6-15)
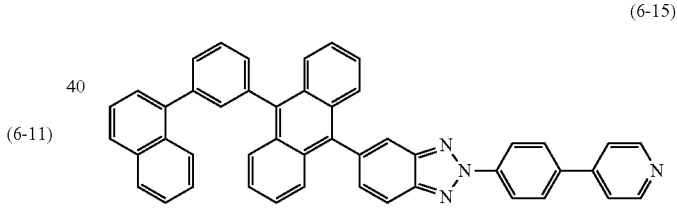
[Chemical Formula 580]
(6-16)
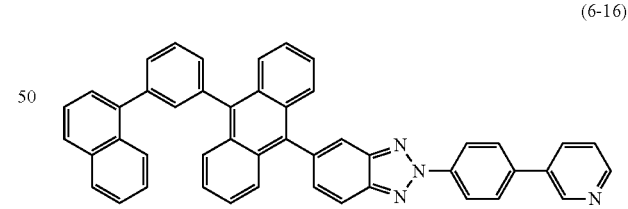
[Chemical Formula 581]
(6-17)
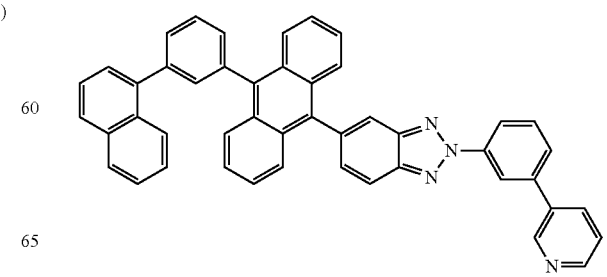

[Chemical Formula 582]
(6-18)
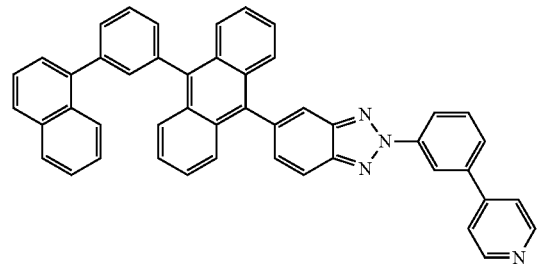
[Chemical Formula 583]
(6-19)
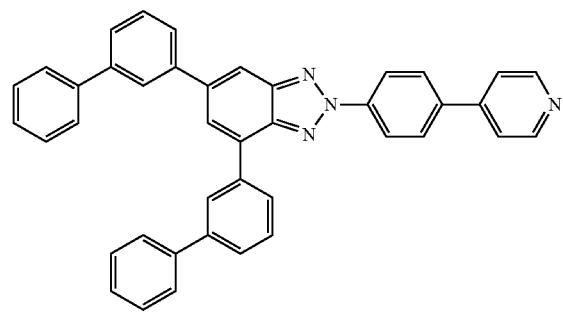
[Chemical Formula 584]
(6-20)
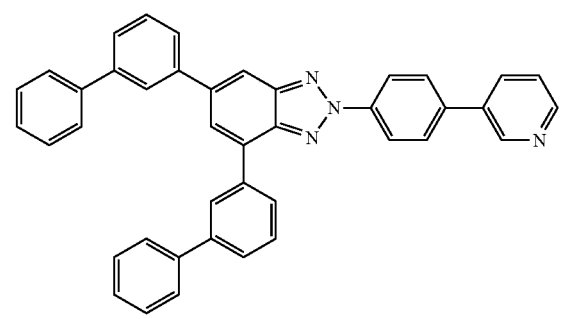
[Chemical Formula 585]
(6-21)
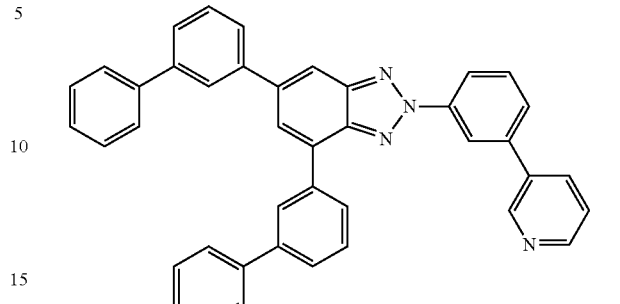
[Chemical Formula 586]
(6-22)
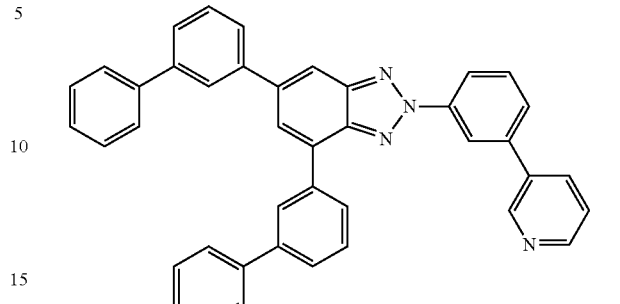
[Chemical Formula 587]
(6-23)
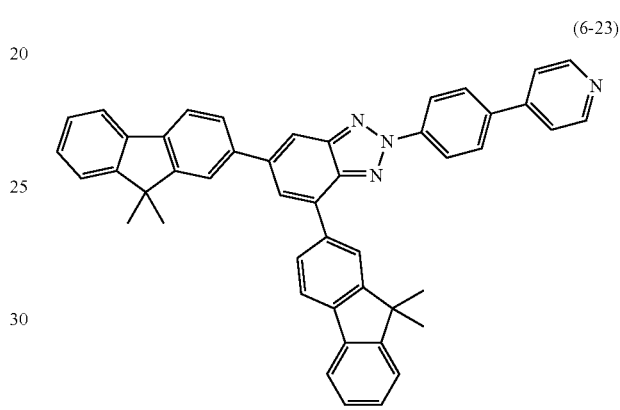
[Chemical Formula 588]
(6-24)
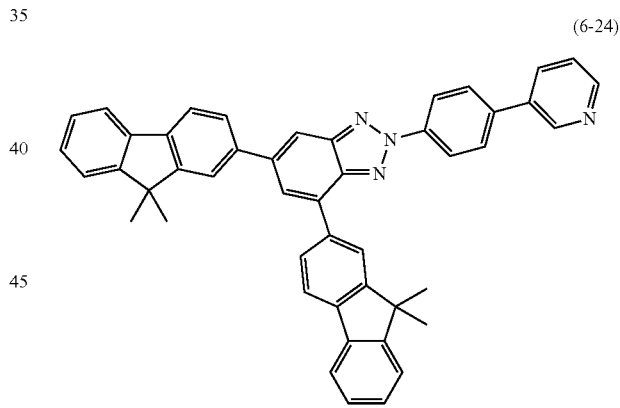
[Chemical Formula 589]
(6-25)
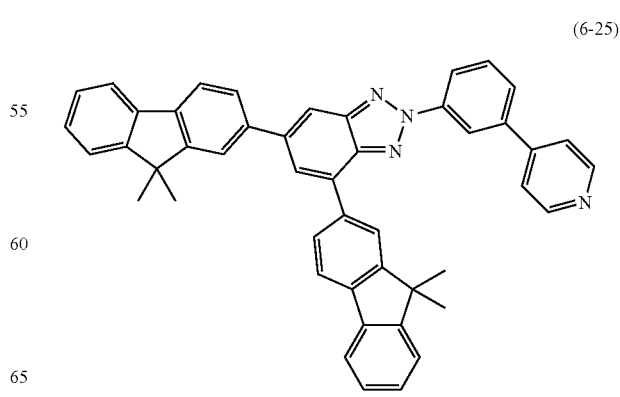

[Chemical Formula 590]
(6-26)
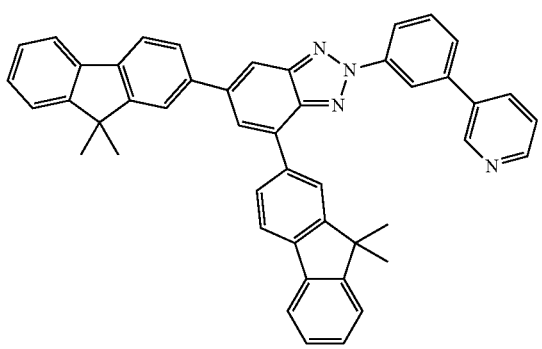
[Chemical Formula 591]
(6-27)
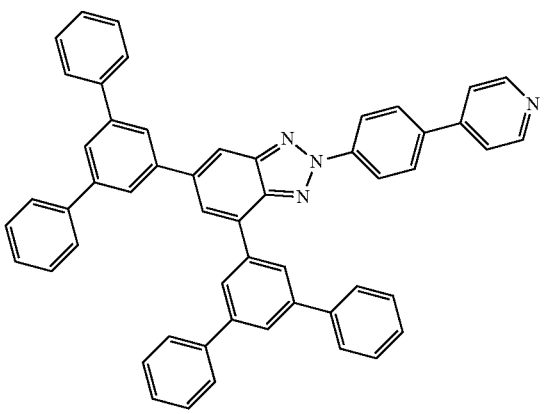
[Chemical Formula 592]
(6-28)
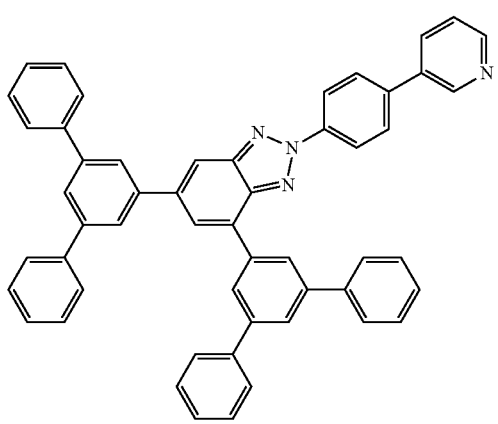
[Chemical Formula 593]
(6-29)
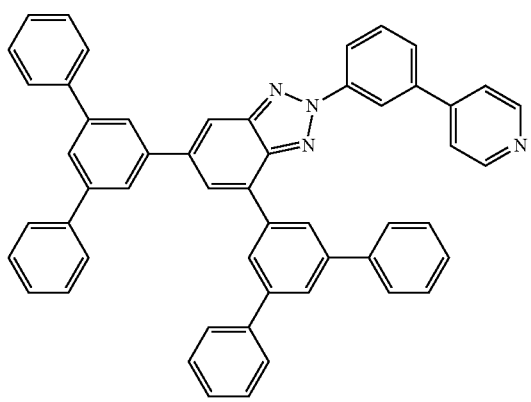
[Chemical Formula 594]
(6-30)
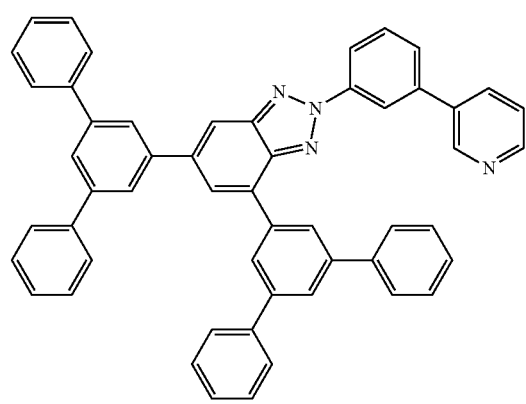
[Chemical Formula 595]
(6-31)
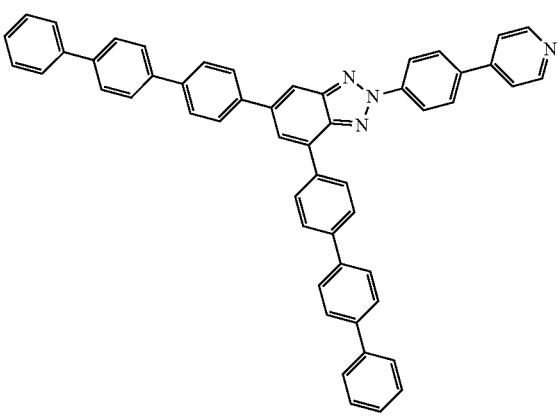

[Chemical Formula 596]
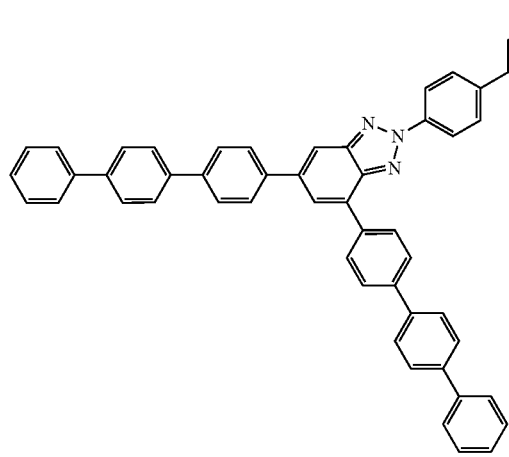
(6-32)
[Chemical Formula 597]
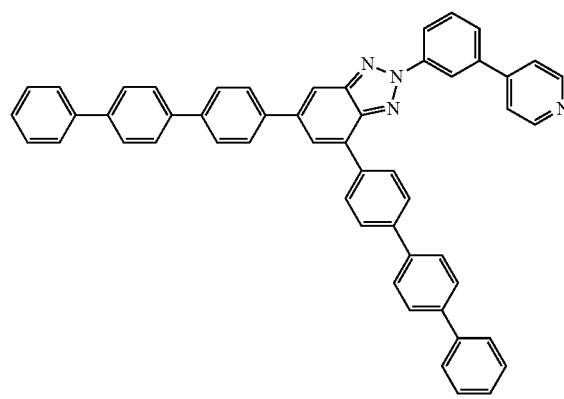
(6-33)
[Chemical Formula 598]
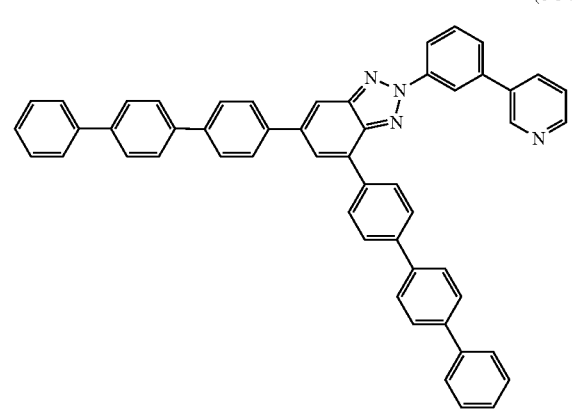
(6-34)
[Chemical Formula 599]
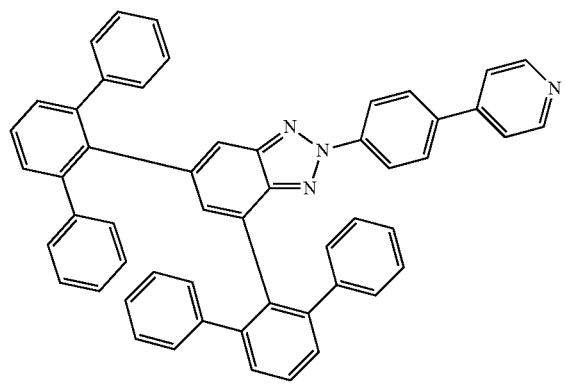
(6-35)
[Chemical Formula 600]
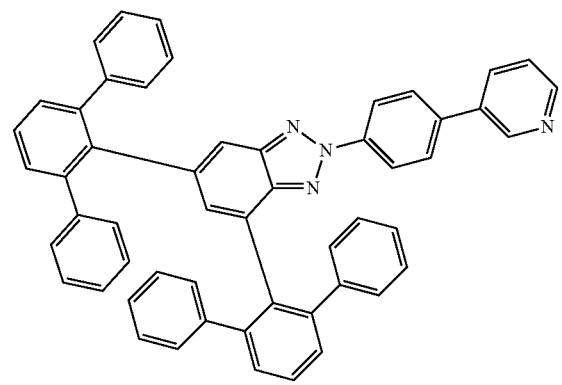
(6-36)
[Chemical Formula 601]
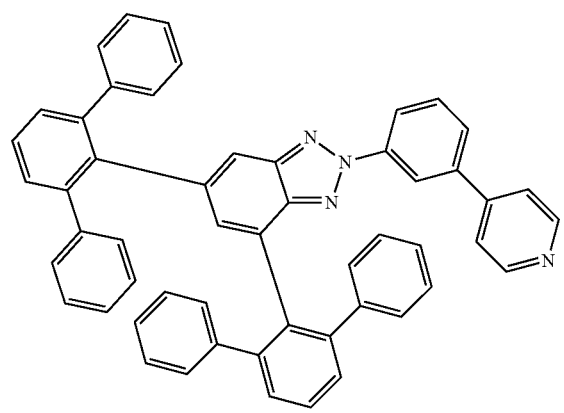
(6-37)

[Chemical Formula 602]
(6-38)
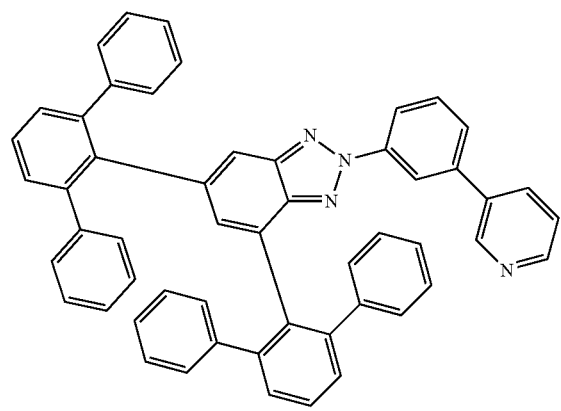
[Chemical Formula 603]
(6-39)
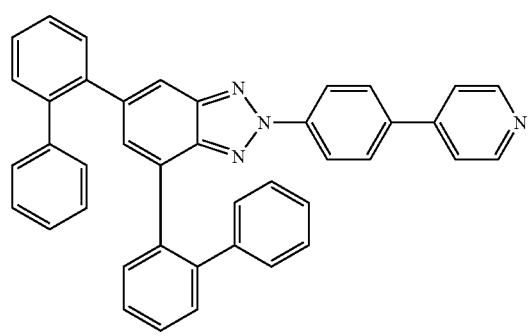
[Chemical Formula 604]
(6-40)
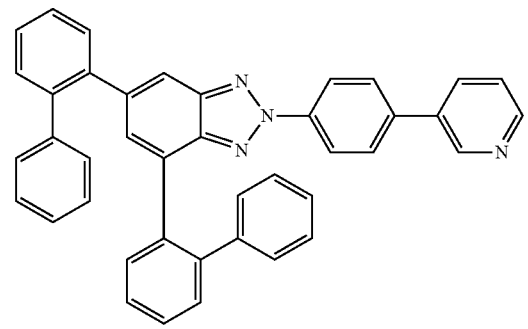
[Chemical Formula 605]
(6-41)
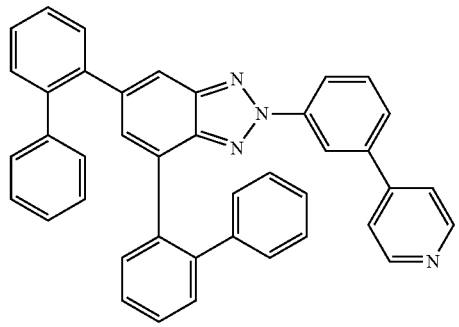
[Chemical Formula 606]
(6-42)
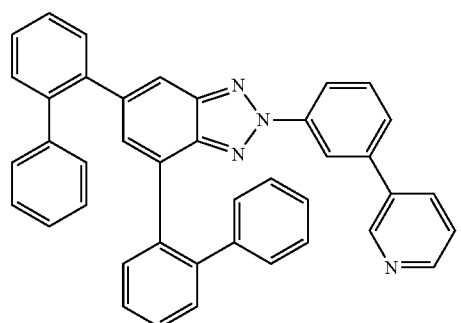
[Chemical Formula 607]
(6-43)
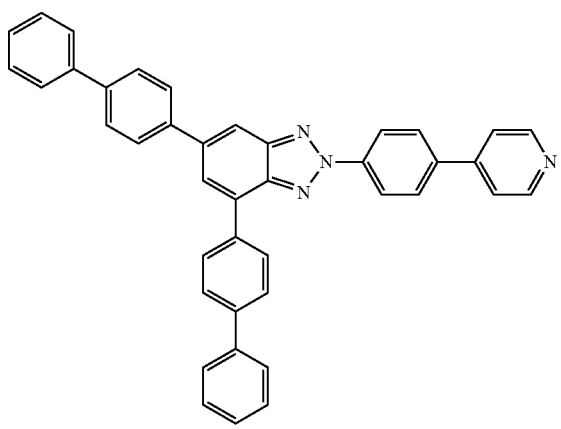
[Chemical Formula 608]
(6-44)
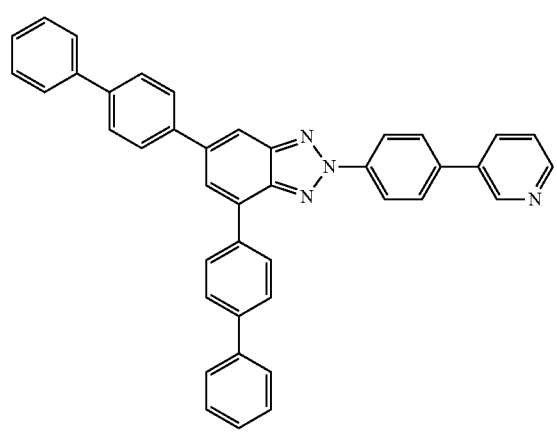

[Chemical Formula 609]
(6-45)
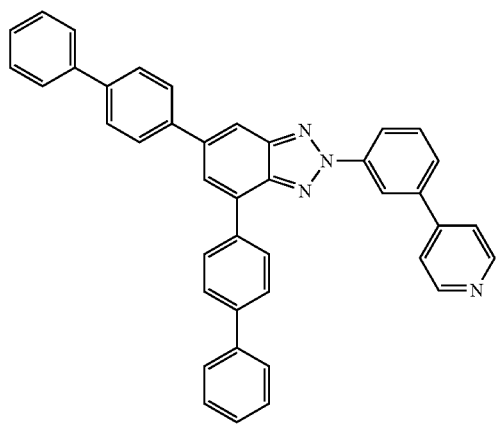
[Chemical Formula 610]
(6-46)
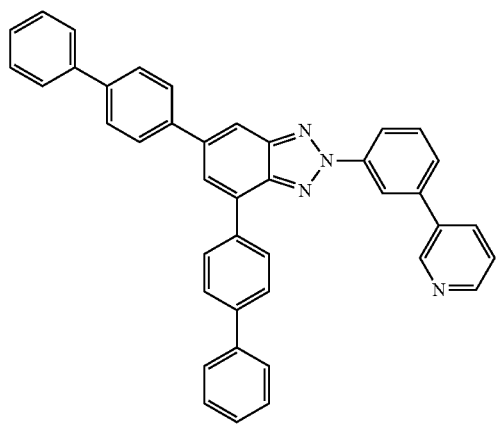
[Chemical Formula 611]
(6-47)
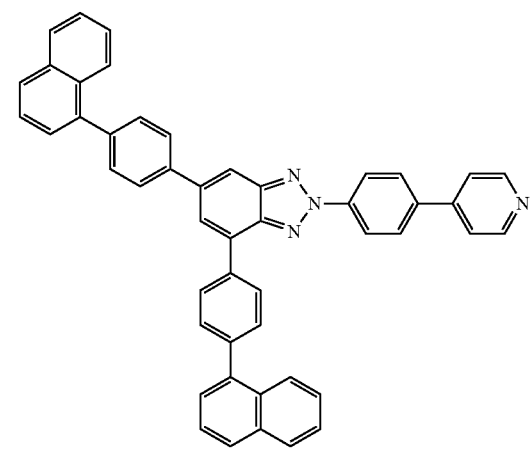
[Chemical Formula 612]
(6-48)
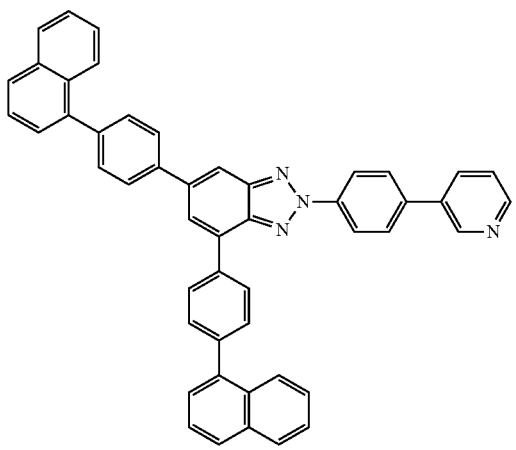
[Chemical Formula 613]
(6-49)
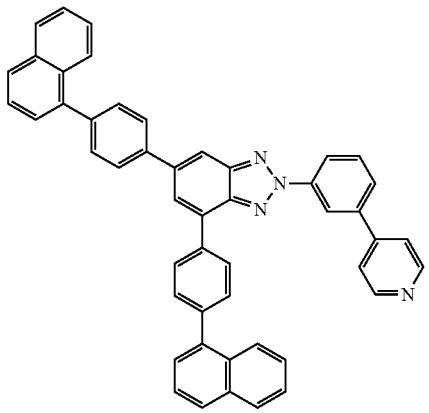
[Chemical Formula 614]
(6-50)
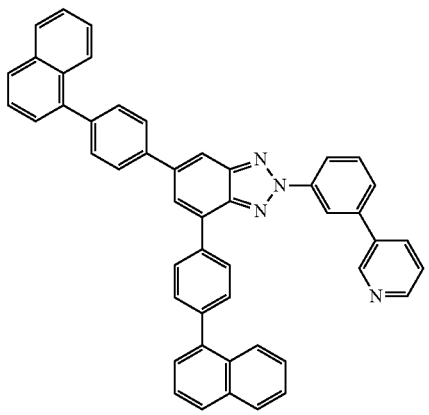

[Chemical Formula 615]
(6-51)
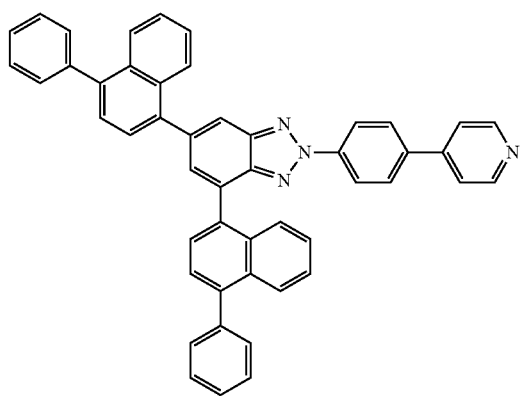
[Chemical Formula 616]
(6-52)
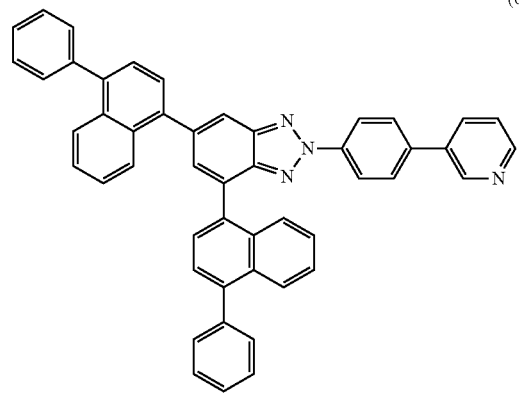
[Chemical Formula 617]
(6-53)
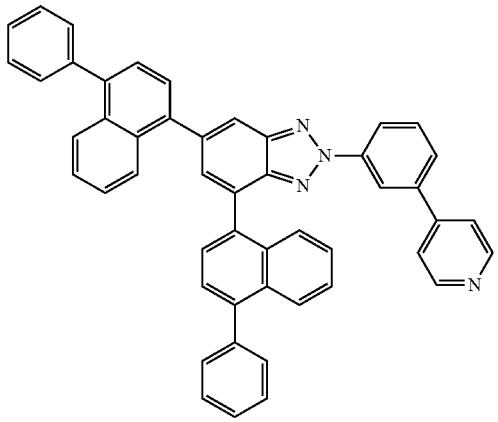
[Chemical Formula 618]
(6-54)
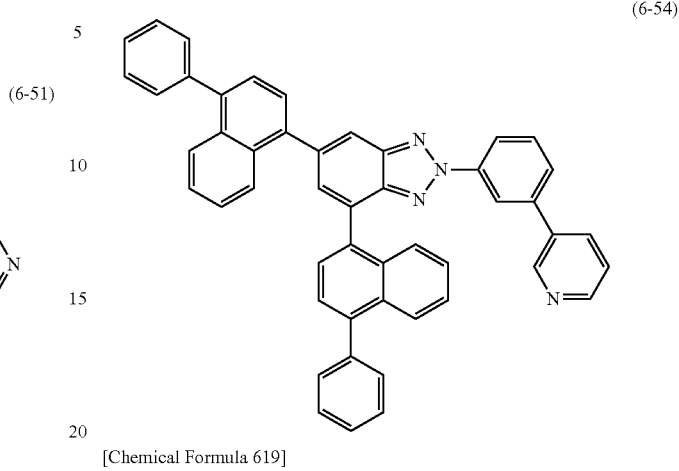
[Chemical Formula 619]
(6-55)
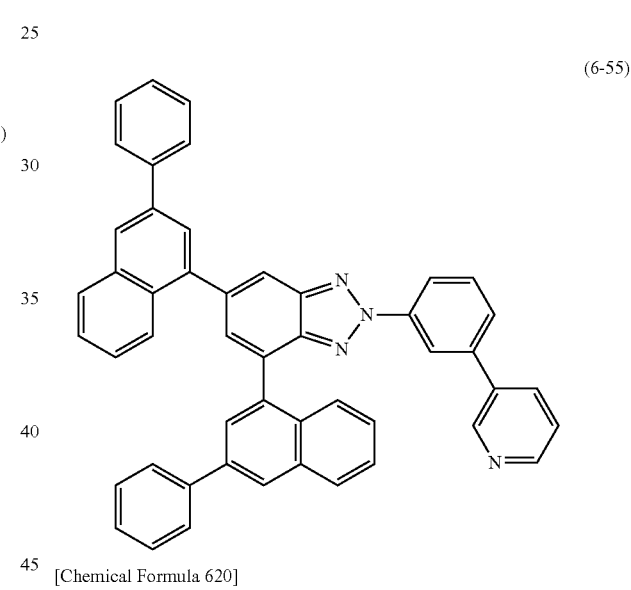
[Chemical Formula 620]
(6-56)
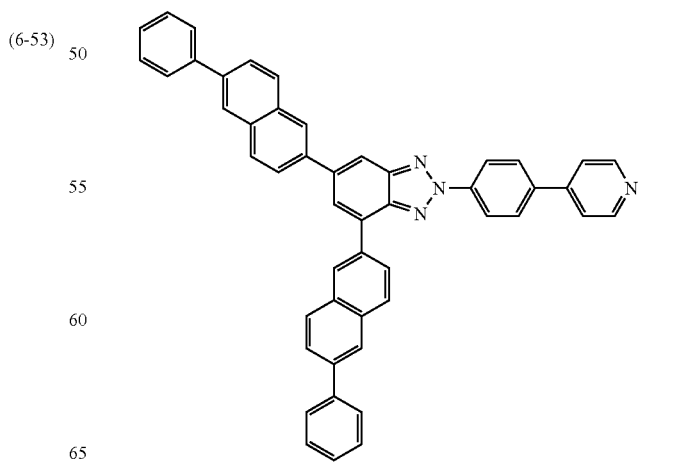

[Chemical Formula 621]
(6-57)
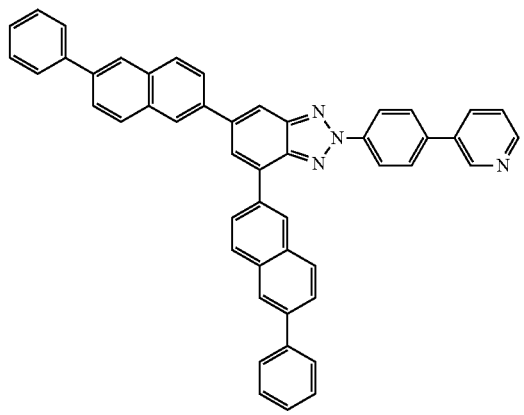
[Chemical Formula 622]
(6-58)
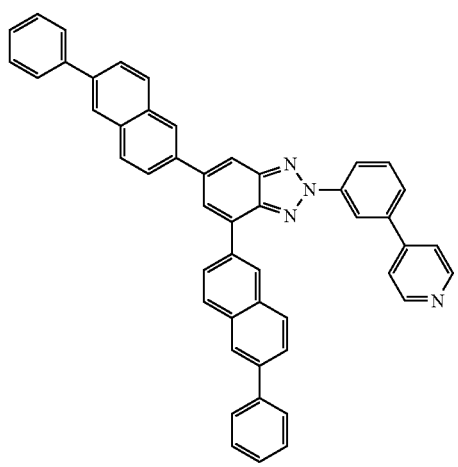
[Chemical Formula 623]
(6-59)
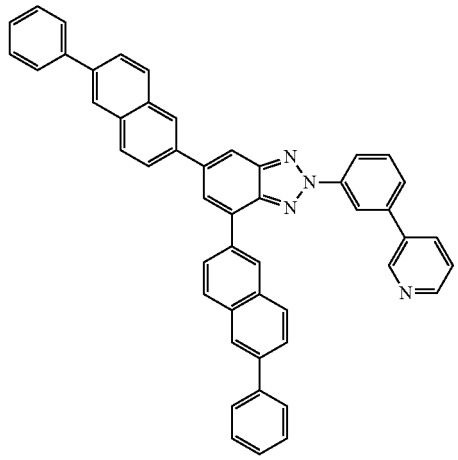
[Chemical Formula 624]
(6-60)
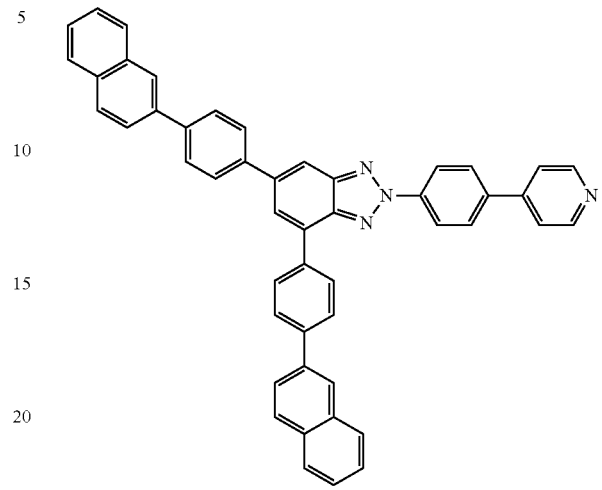
[Chemical Formula 625]
(6-61)
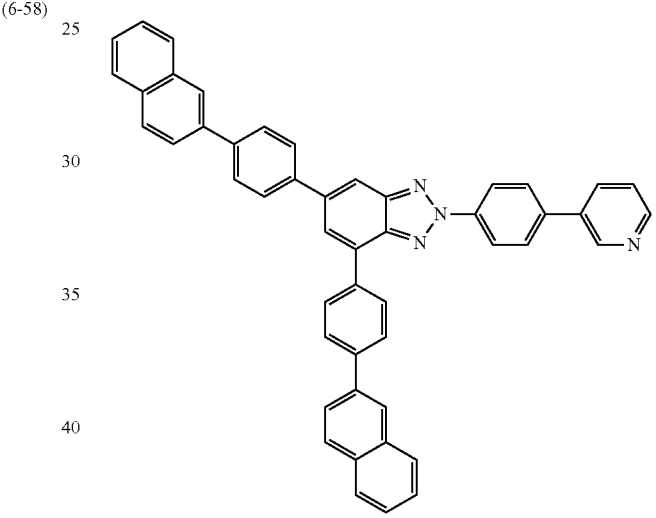
[Chemical Formula 626]
(6-62)
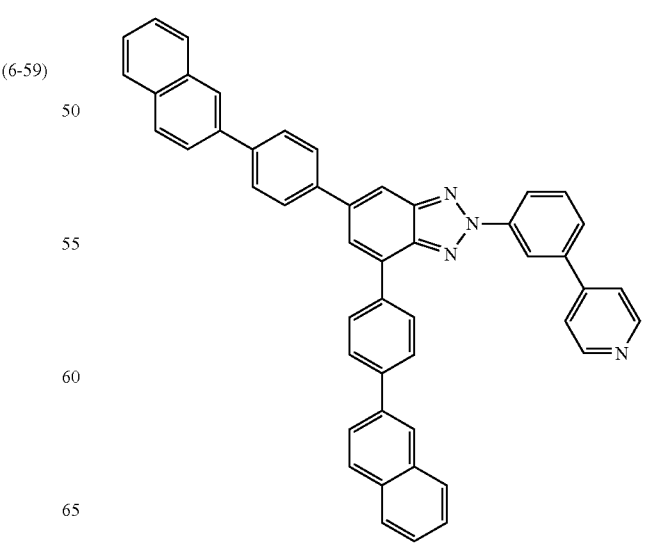

[Chemical Formula 627]
(6-63)
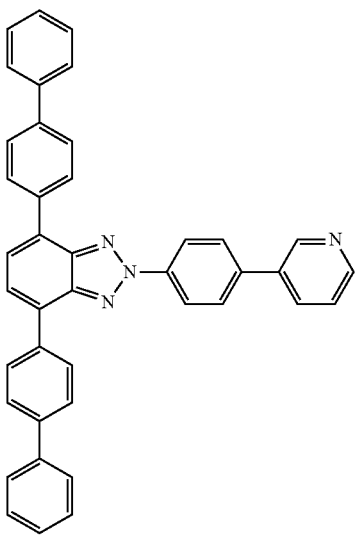
[Chemical Formula 628]
(6-64)
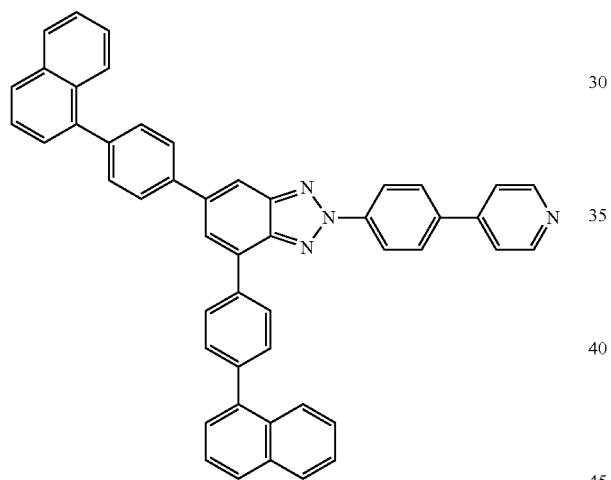
[Chemical Formula 629]
(6-65)
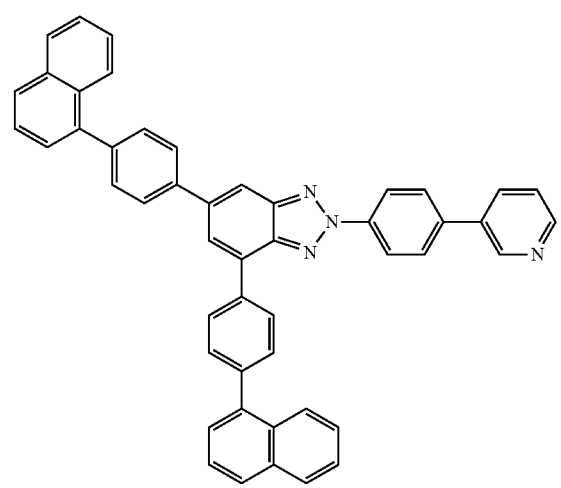
[Chemical Formula 630]
(6-66)
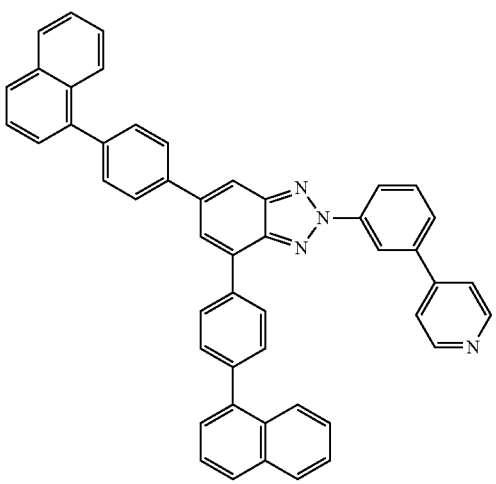
[Chemical Formula 631]
(6-67)
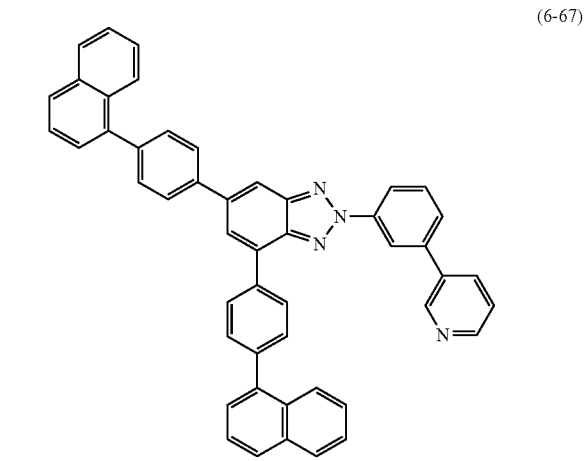
[Chemical Formula 632]
(6-68)
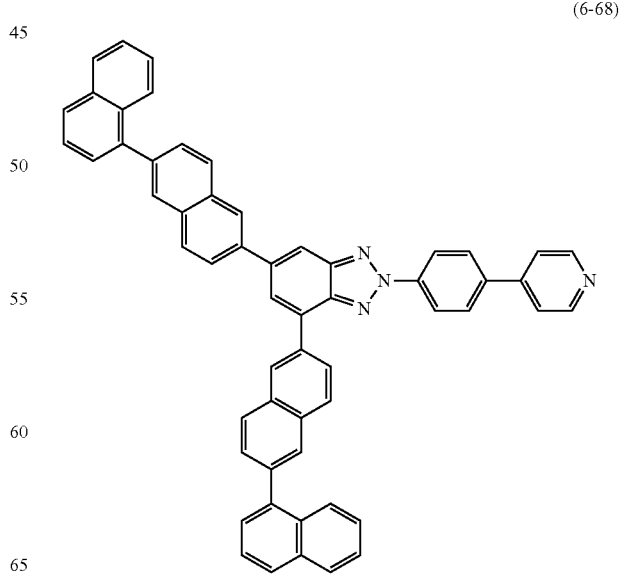

[Chemical Formula 633] (6-69)
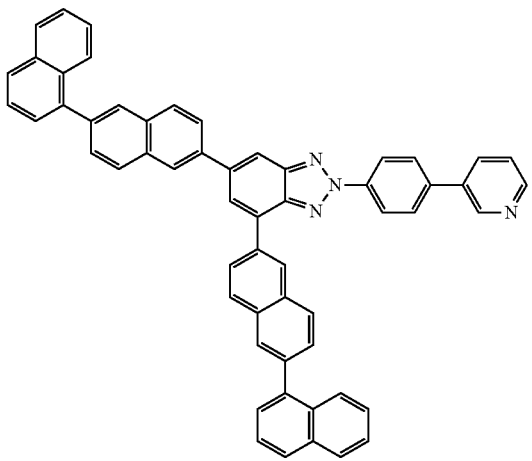
[Chemical Formula 634] (6-70)
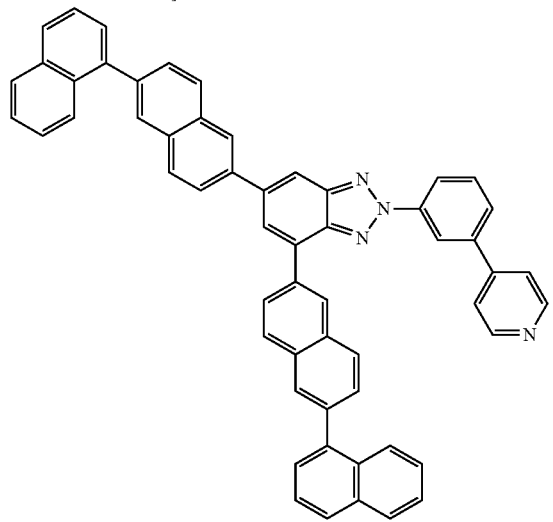
[Chemical Formula 635] (6-71)
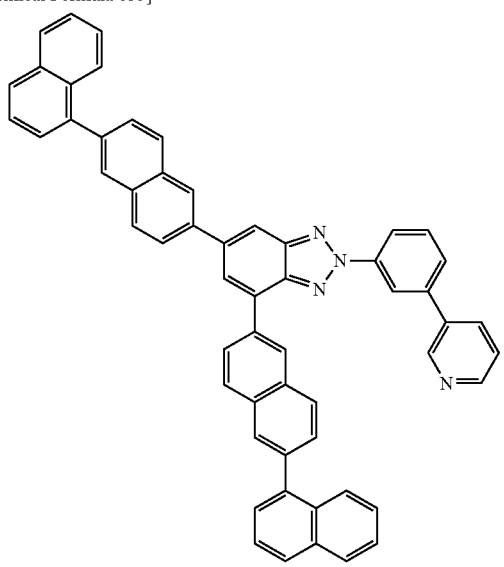
[Chemical Formula 636] (6-72)
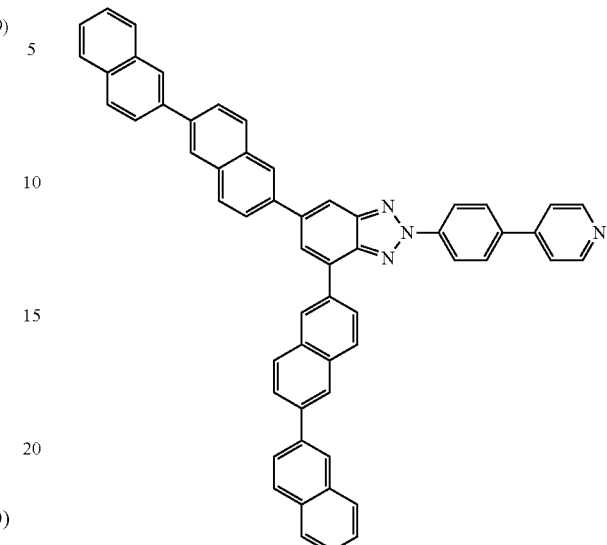
[Chemical Formula 637] (6-73)
[Chemical Formula 638] (6-74)
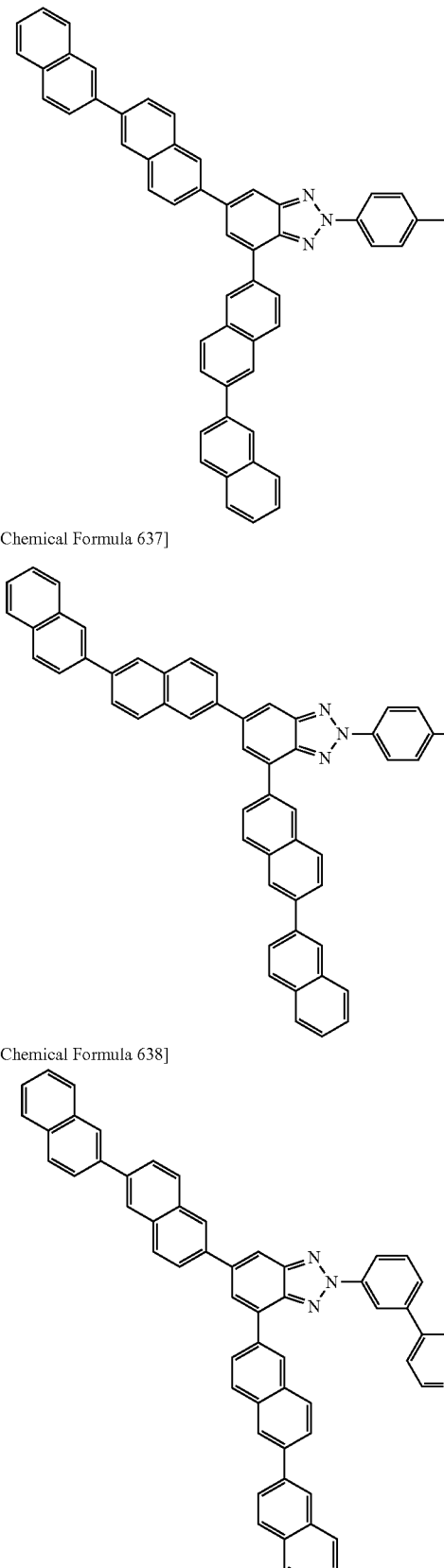

[Chemical Formula 639]
(6-75)
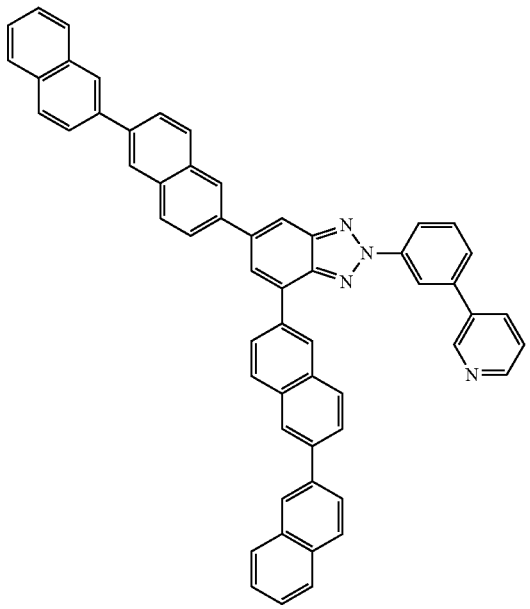
[Chemical Formula 640]
(6-76)
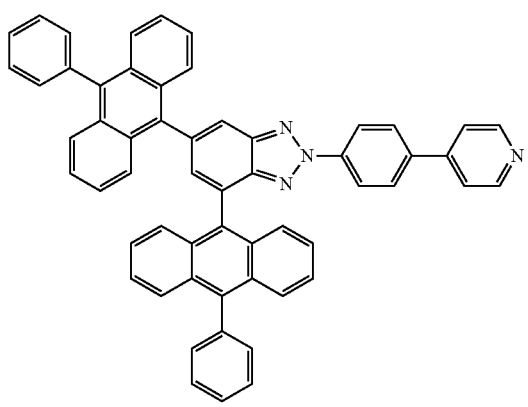
[Chemical Formula 641]
(6-77)
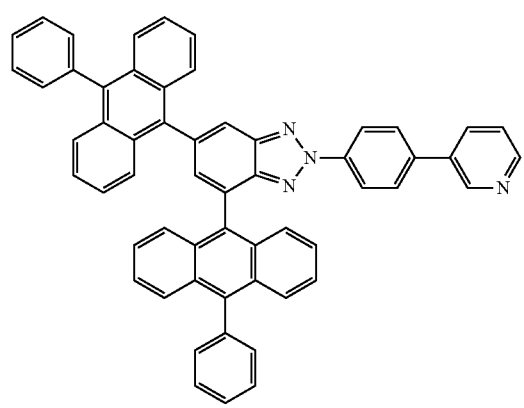
[Chemical Formula 642]
(6-78)
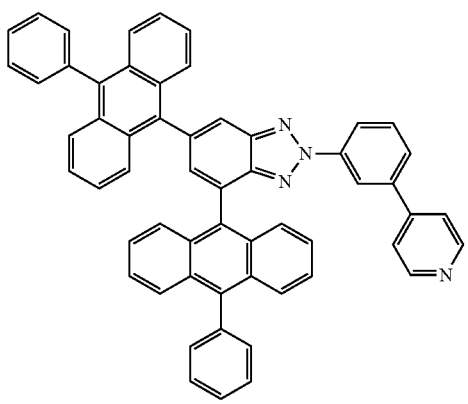
[Chemical Formula 643]
(6-79)
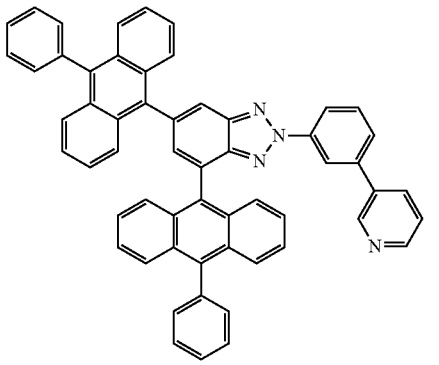
[Chemical Formula 644]
(6-80)
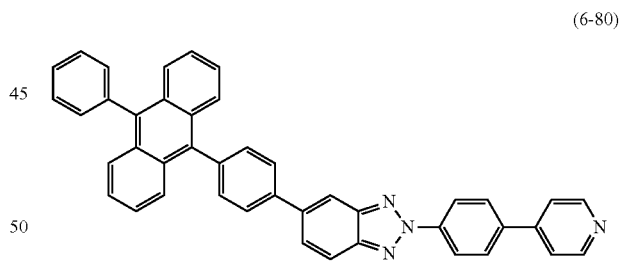
[Chemical Formula 645]
(6-81)
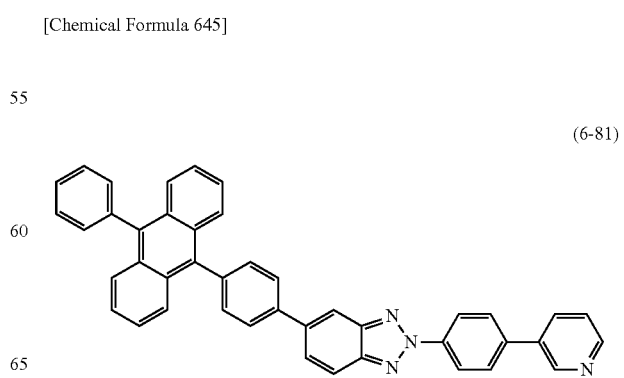

[Chemical Formula 646]
(6-82)
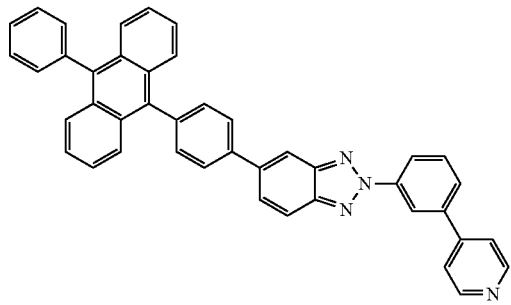
[Chemical Formula 647]
(6-83)
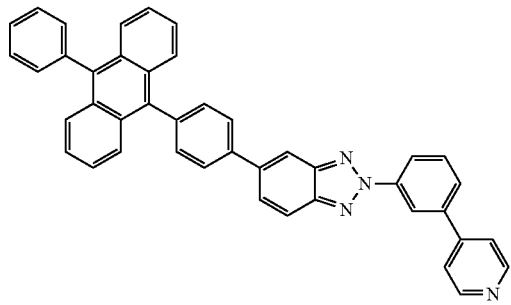
[Chemical Formula 648]
(6-84)
[Chemical Formula 649]
(6-85)
[Chemical Formula 650]
(6-86)
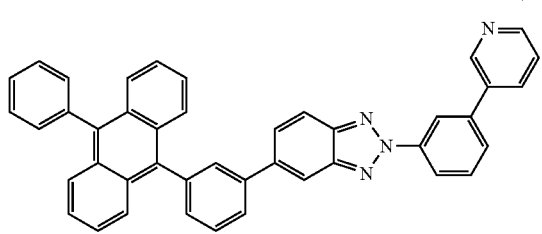
[Chemical Formula 651]
(6-87)
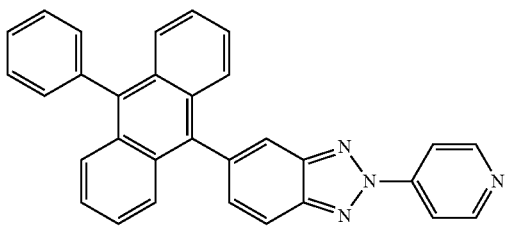
[Chemical Formula 652]
(6-88)
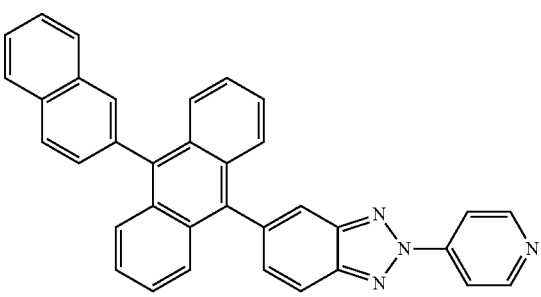
[Chemical Formula 653]
(6-89)
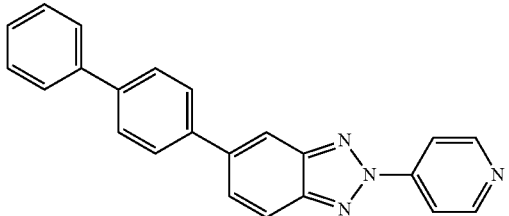

[Chemical Formula 654]
(6-90)
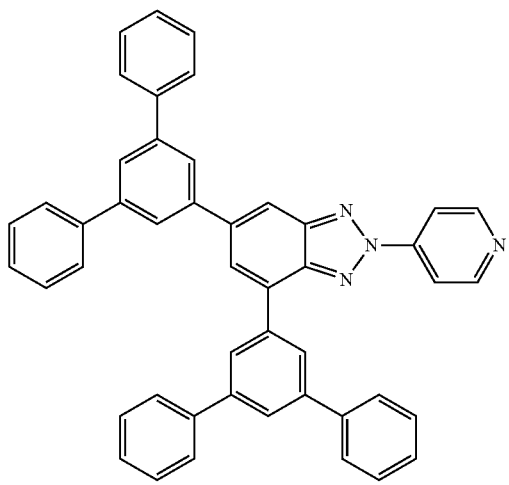
[Chemical Formula 655]
(6-91)
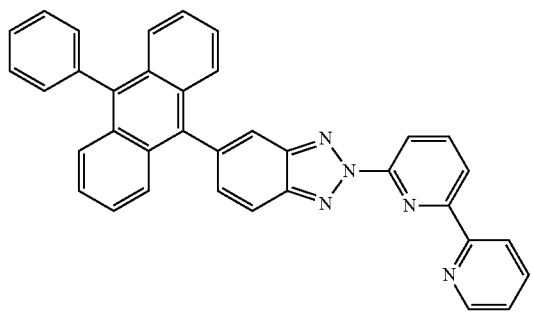
[Chemical Formula 656]
(6-92)
[Chemical Formula 657]
(6-93)
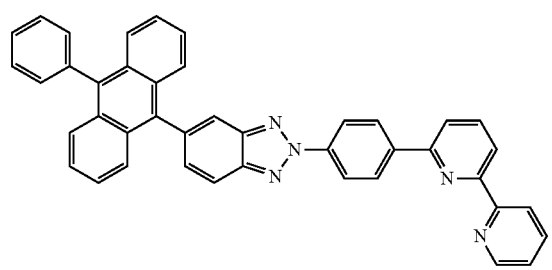
[Chemical Formula 658]
(6-94)
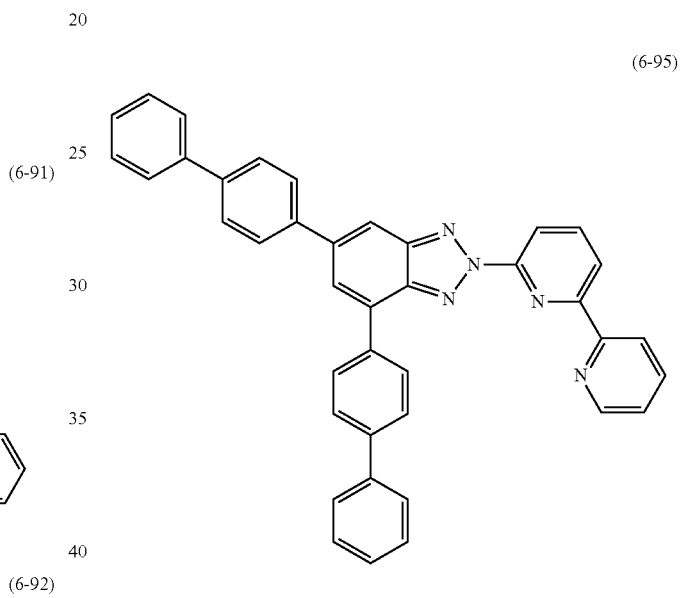
[Chemical Formula 659]
(6-95)
[Chemical Formula 660]
(6-96)
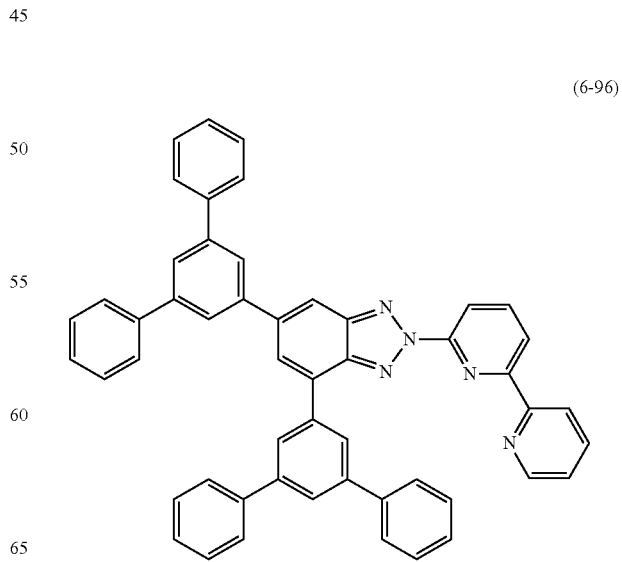

[Chemical Formula 661]
(6-97)
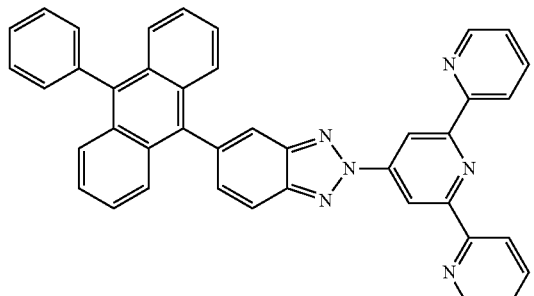
[Chemical Formula 662]
(6-98)
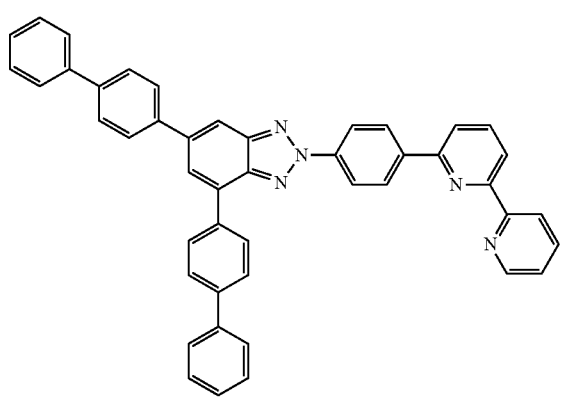
[Chemical Formula 663]
(6-99)
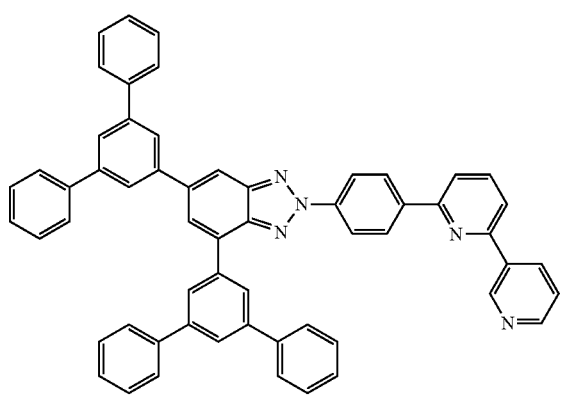
[Chemical Formula 664]
(6-100)
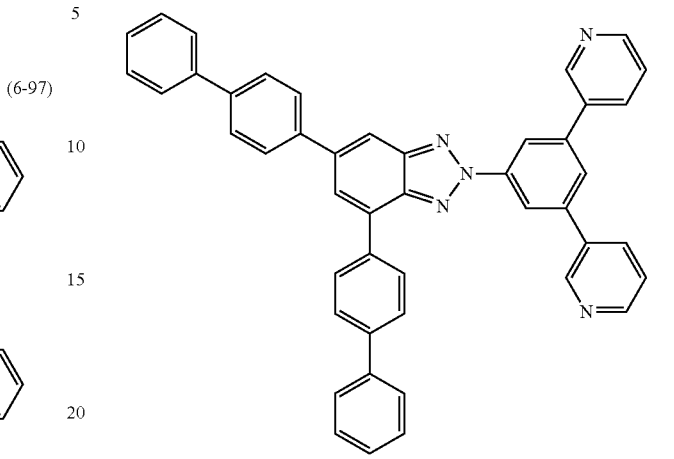
[Chemical Formula 665]
(6-101)
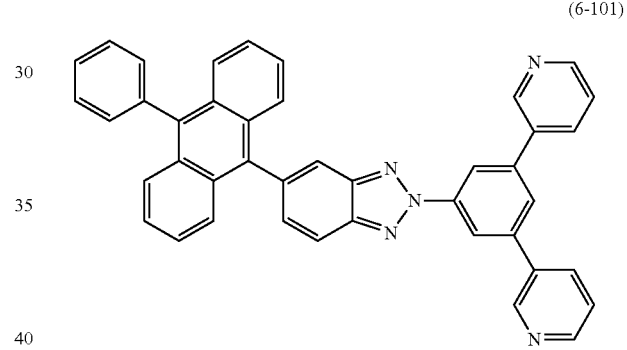
[Chemical Formula 666]
(6-102)
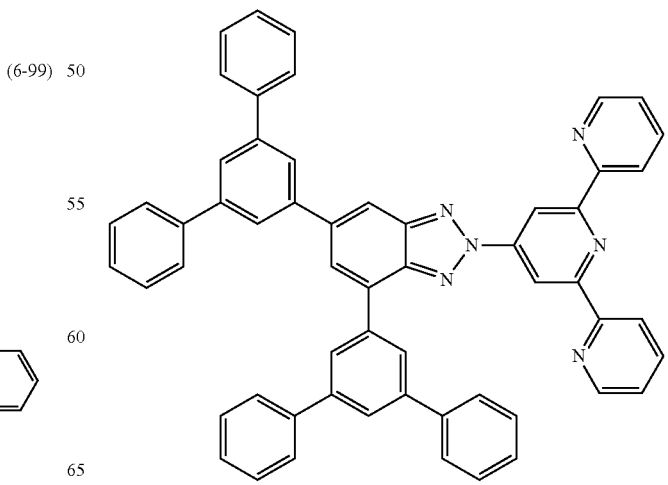

[Chemical Formula 667]
(6-103)
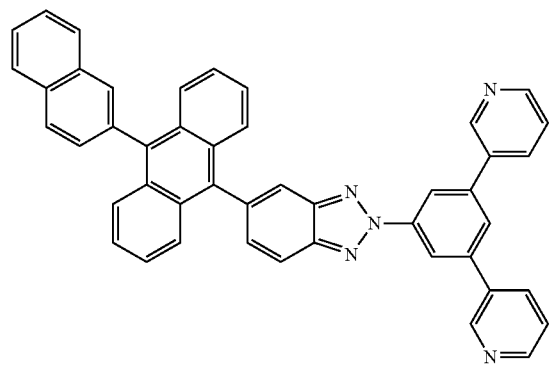
[Chemical Formula 668]
(6-104)
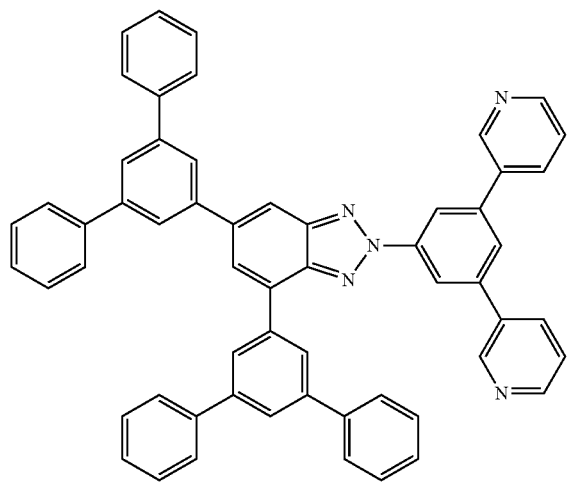
[Chemical Formula 669]
(6-105)
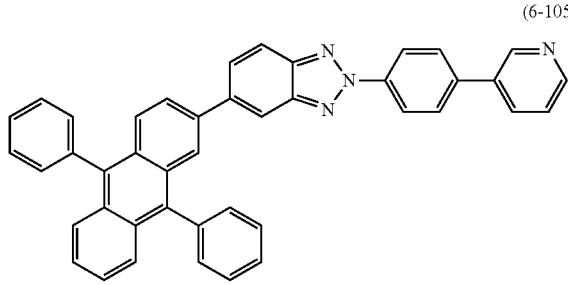
[Chemical Formula 670]
(6-106)
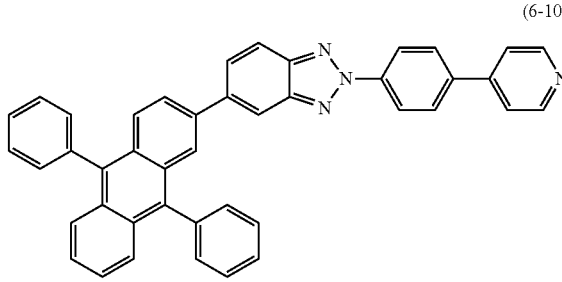
[Chemical Formula 671]
(6-107)
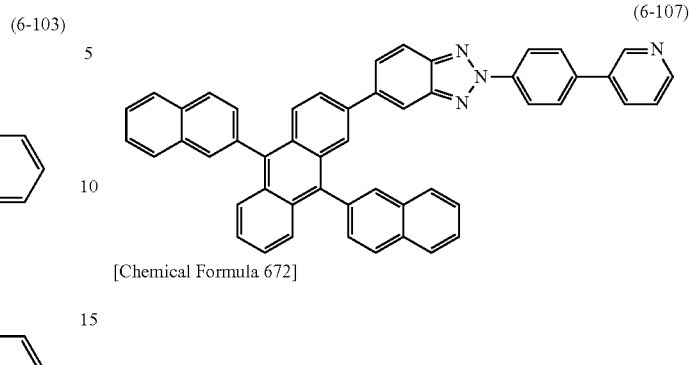
[Chemical Formula 672]
(6-108)
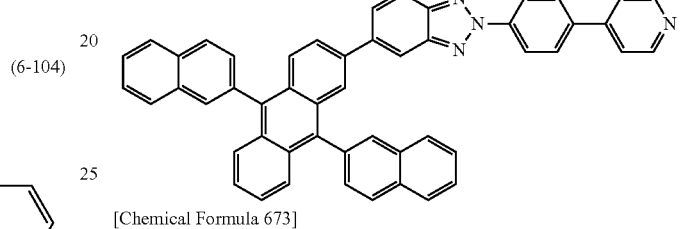
[Chemical Formula 673]
(6-109)
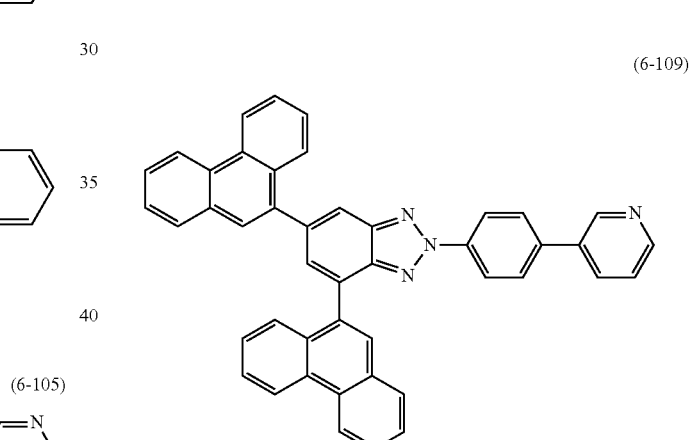
[Chemical Formula 674]
(6-110)
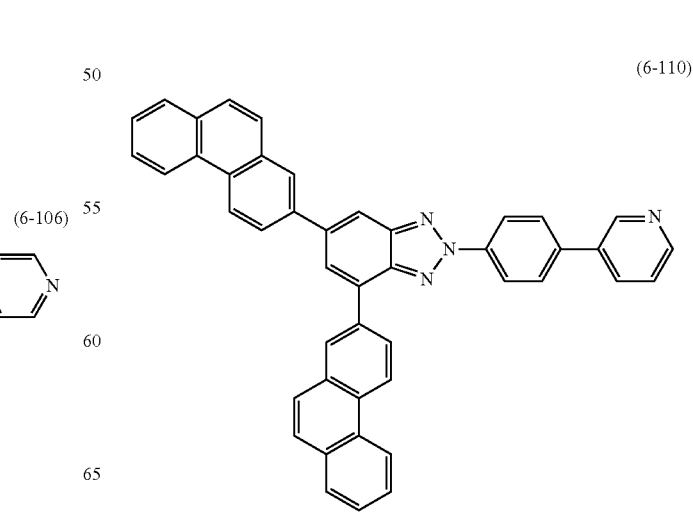

[Chemical Formula 675]
(6-111)
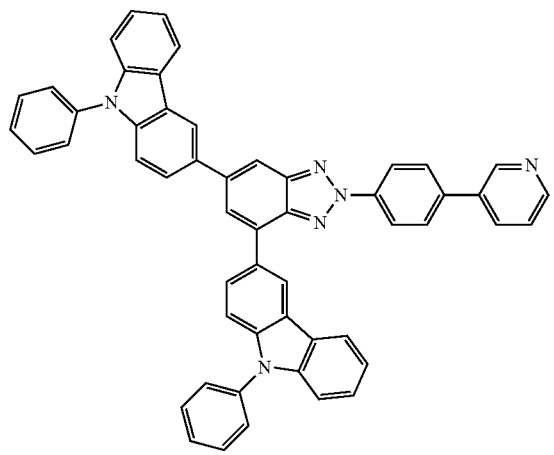
[Chemical Formula 676]
(6-112)
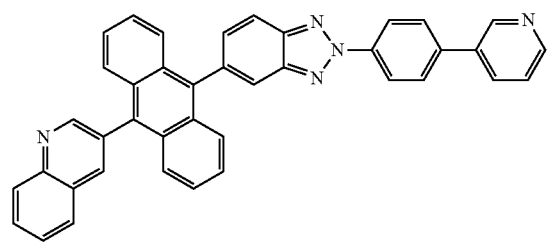
[Chemical Formula 677]
(6-113)
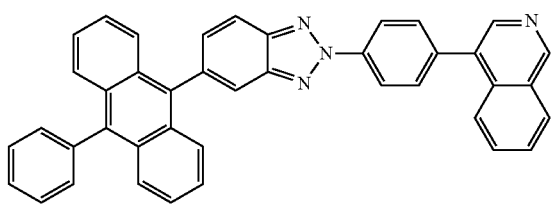
[Chemical Formula 678]
(6-114)
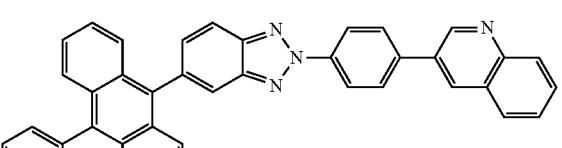
[Chemical Formula 679]
(6-115)
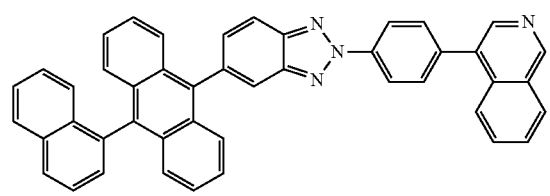
[Chemical Formula 680]
(6-116)
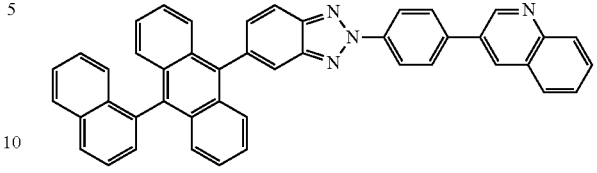
[Chemical Formula 681]
(6-117)
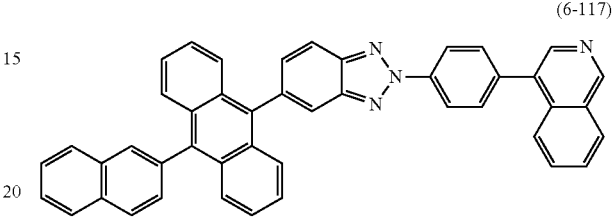
[Chemical Formula 682]
(6-118)
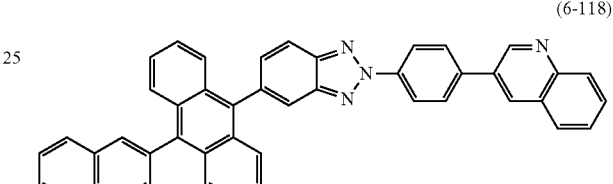
[Chemical Formula 683]
(6-119)
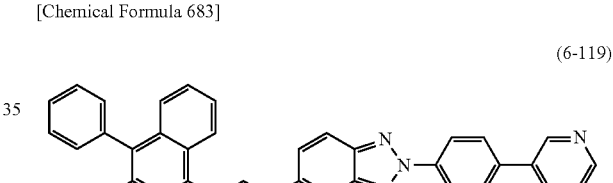
[Chemical Formula 684]
(6-120)
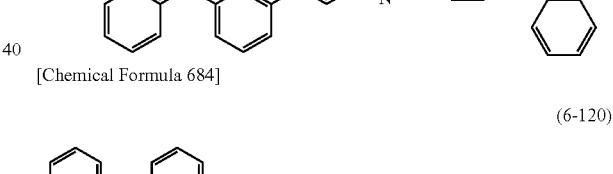
[Chemical Formula 685]
(6-121)
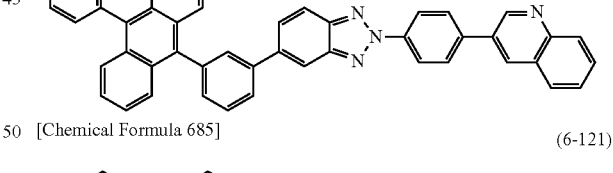
[Chemical Formula 686]
(6-122)
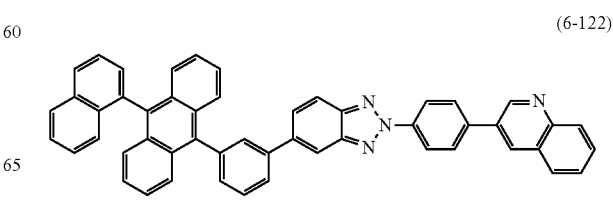

-continued
[Chemical Formula 687]
(6-123)
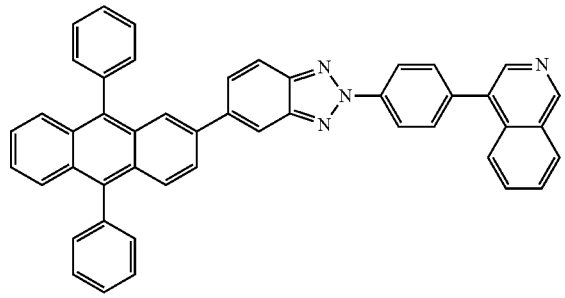
[Chemical Formula 688]
(6-124)
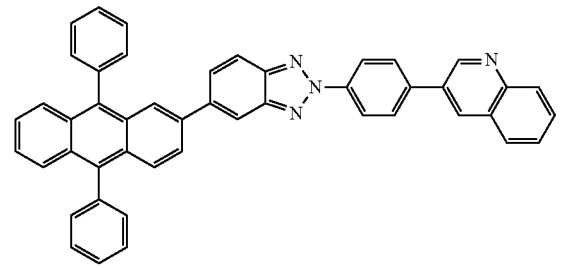
[Chemical Formula 689]
(6-125)
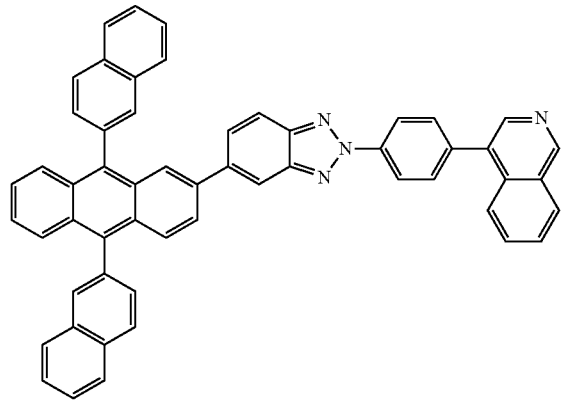
[Chemical Formula 690]
(6-126)
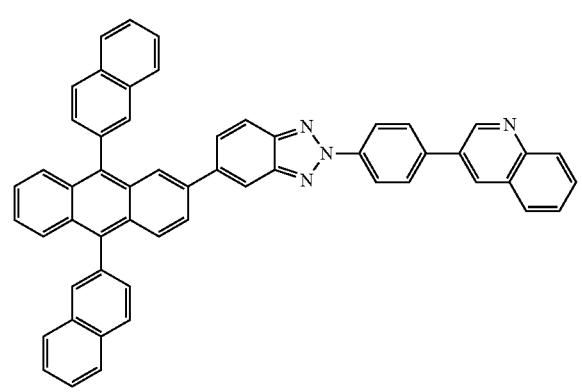
-continued
[Chemical Formula 691]
(6-127)
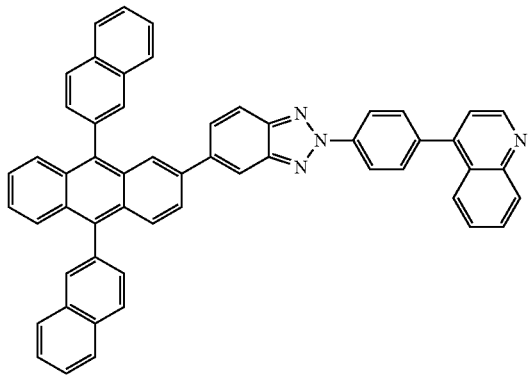
[Chemical Formula 692]
(6-128)
[Chemical Formula 693]
(6-129)
[Chemical Formula 694]
(6-130)
[Chemical Formula 695]
(6-131)

[Chemical Formula 696]
(6-132)
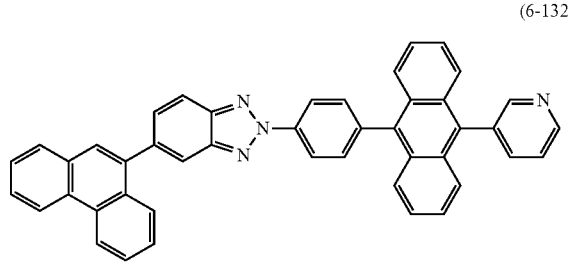
[Chemical Formula 697]
(6-133)
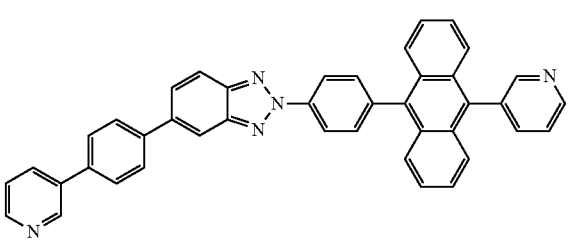
[Chemical Formula 698]
(6-134)
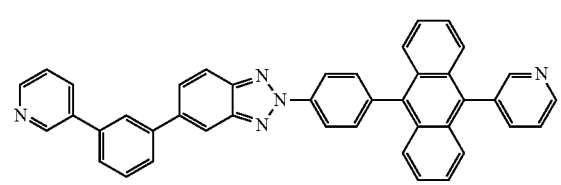
[Chemical Formula 699]
(6-135)
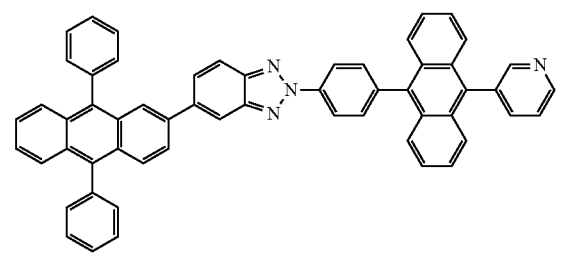
[Chemical Formula 700]
(6-136)
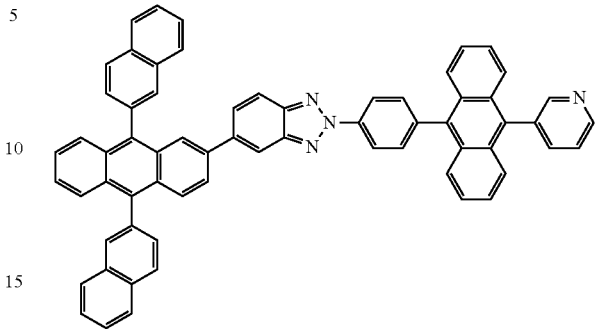
[Chemical Formula 701]
(6-137)
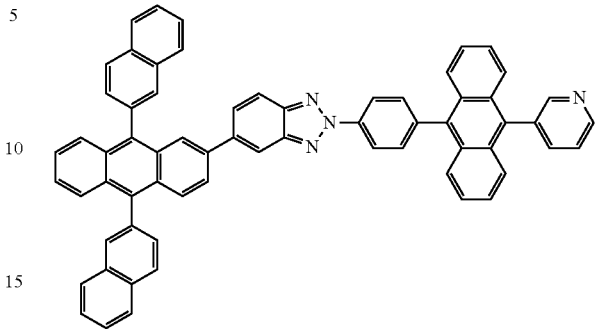
[Chemical Formula 702]
(6-138)
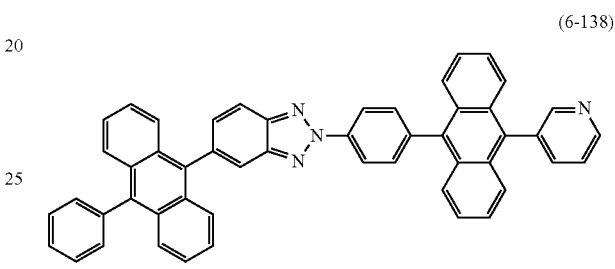
[Chemical Formula 703]
(6-139)
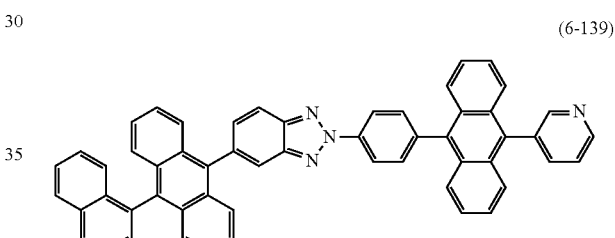
[Chemical Formula 704]
(6-140)
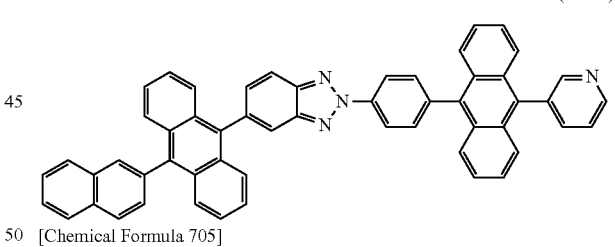
[Chemical Formula 705]
(6-141)
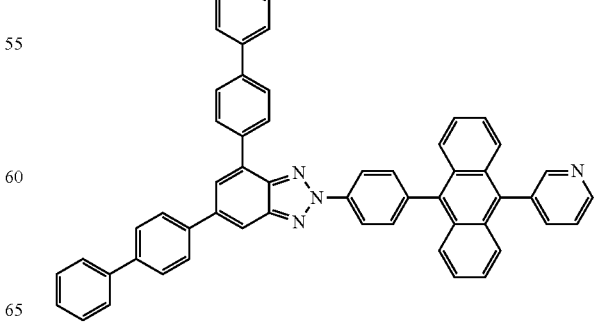

[Chemical Formula 706]
(6-142)
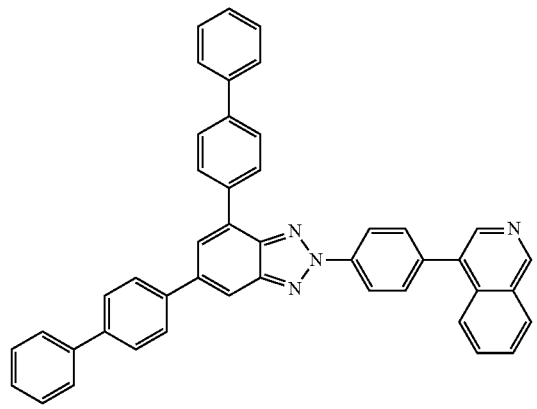
[Chemical Formula 707]
(6-143)
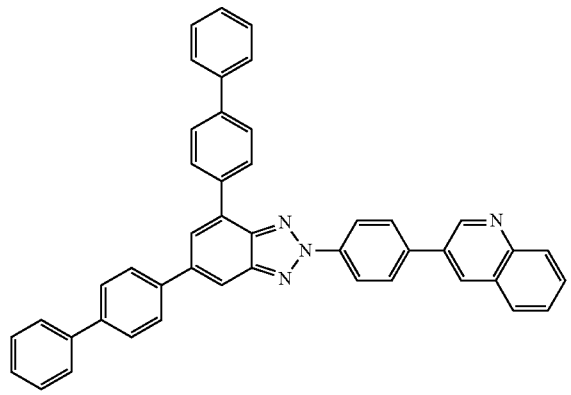
[Chemical Formula 708]
(6-144)
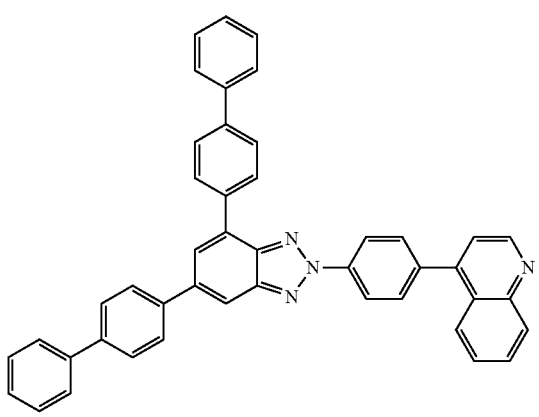
[Chemical Formula 709]
(6-145)
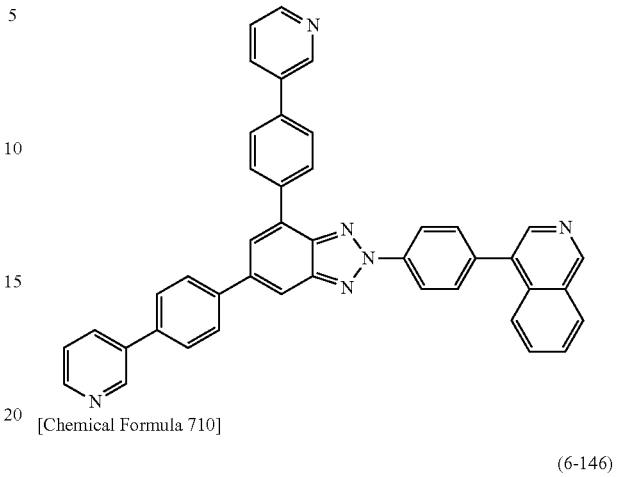
[Chemical Formula 710]
(6-146)
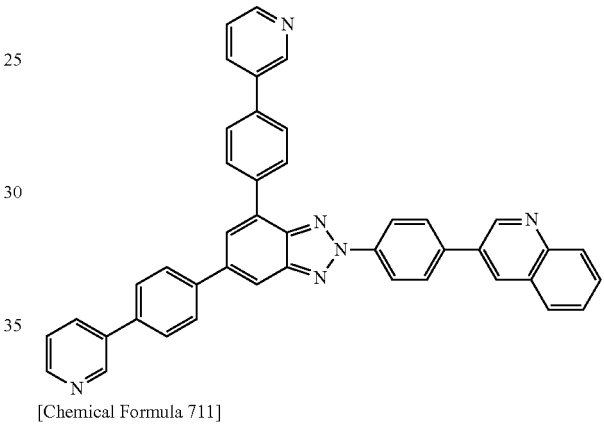
[Chemical Formula 711]
(6-147)
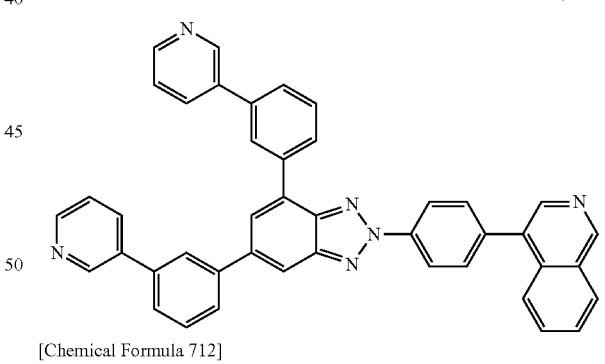
[Chemical Formula 712]
(6-148)
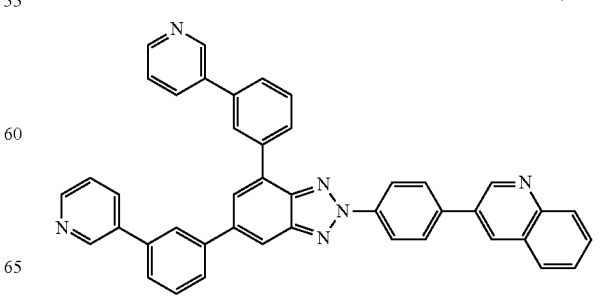

[Chemical Formula 713]
(6-149)
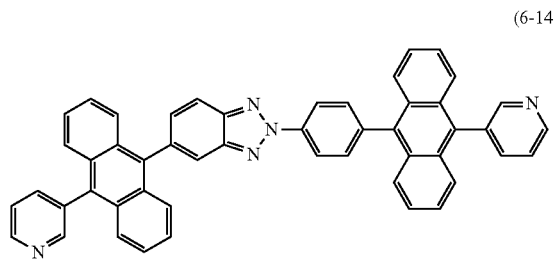
[Chemical Formula 714]
(6-150)
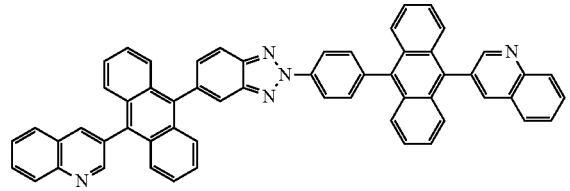
[Chemical Formula 715]
(6-151)
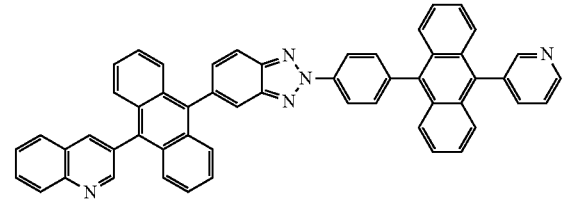
[Chemical Formula 716]
(6-152)
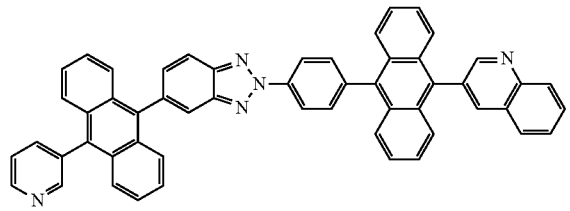
[Chemical Formula 717]
(6-153)
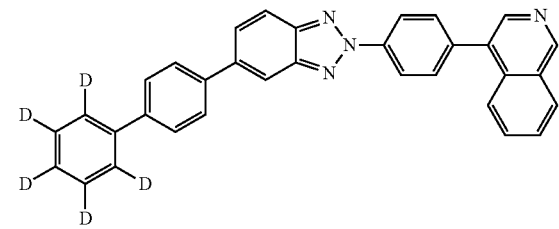
[Chemical Formula 718]
(6-154)
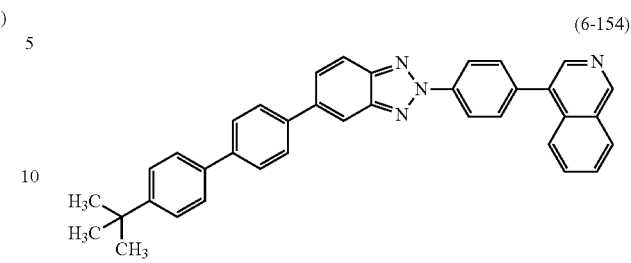
[Chemical Formula 719]
(6-155)
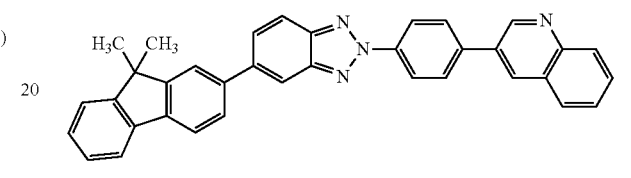
[Chemical Formula 720]
(6-156)
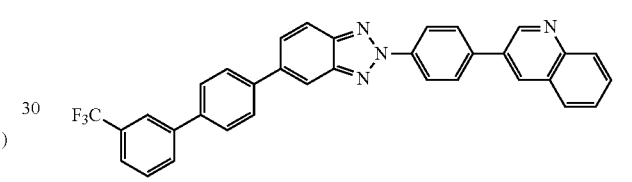
[Chemical Formula 721]
(6-157)
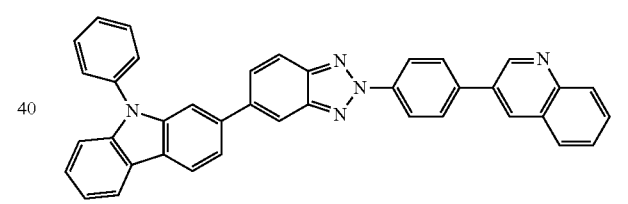
[Chemical Formula 722]
(6-158)
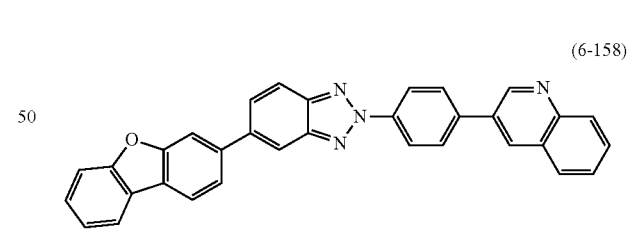
[Chemical Formula 723]
(6-159)
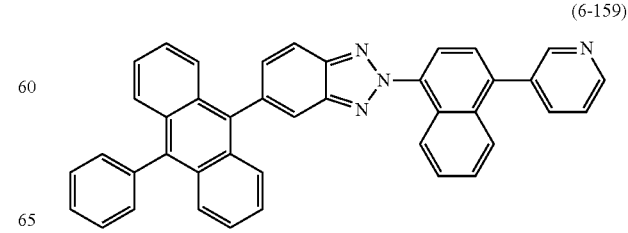

[Chemical Formula 724]
(6-160)
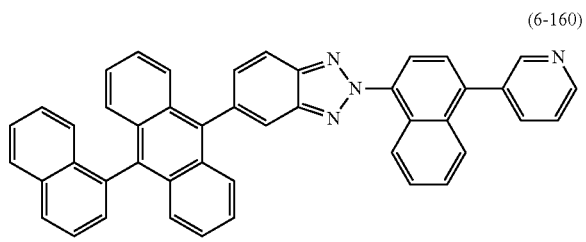
[Chemical Formula 725]
(6-161)
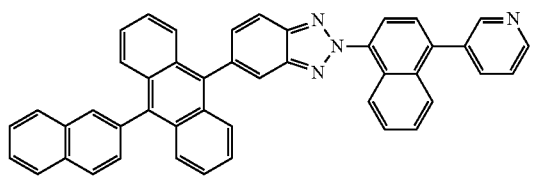
[Chemical Formula 726]
(6-162)
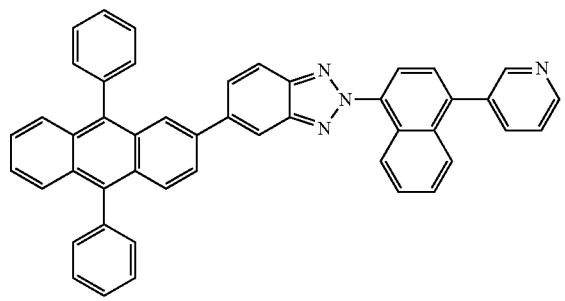
[Chemical Formula 727]
(6-163)
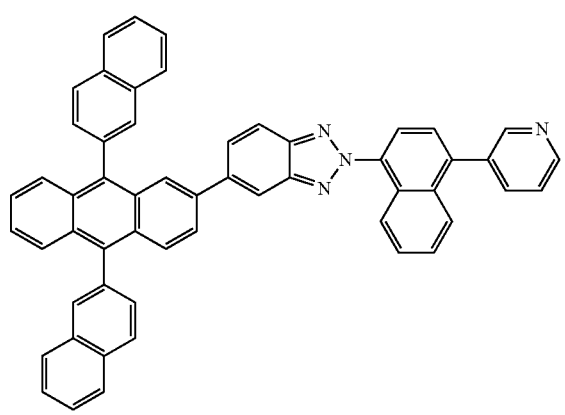
[Chemical Formula 728]
(6-164)
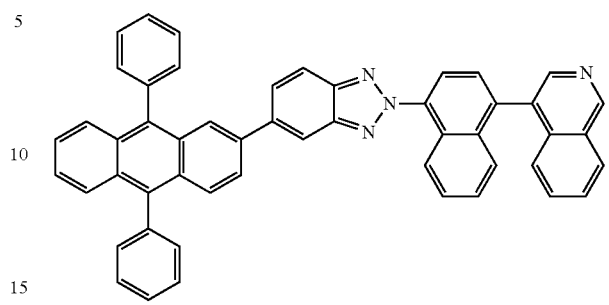
[Chemical Formula 729]
(6-165)
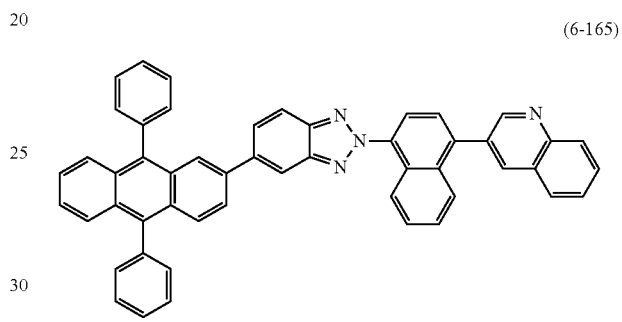
[Chemical Formula 730]
(6-166)
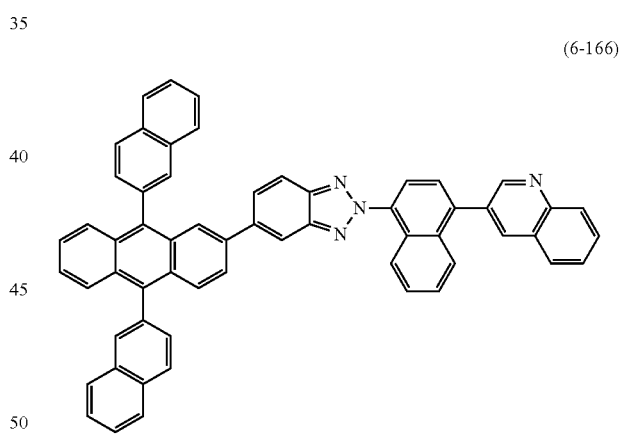
[Chemical Formula 731]
(6-167)
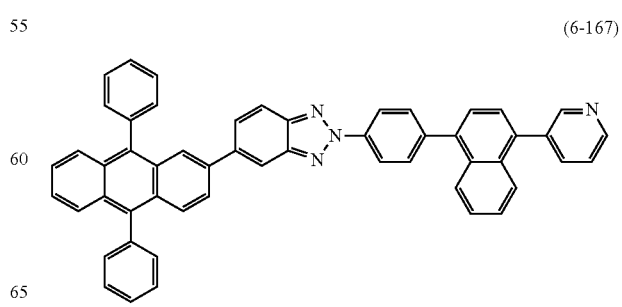

[Chemical Formula 732]

(6-168)

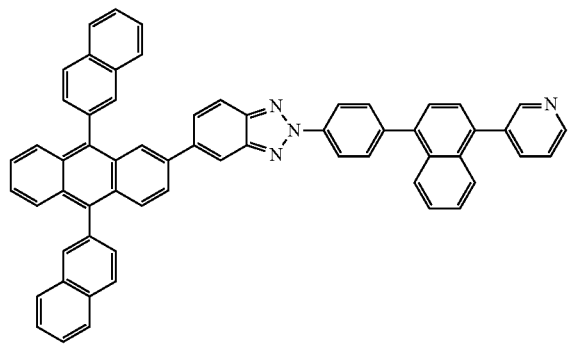

[Chemical Formula 733]

(6-169)

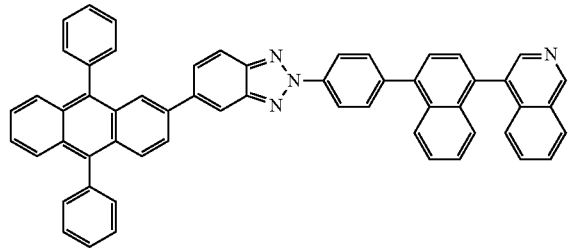

[Chemical Formula 734]

(6-170)

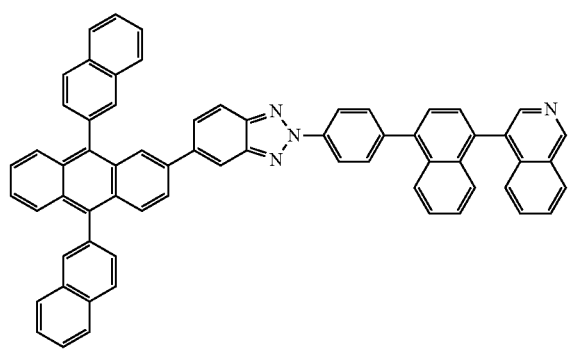

[Chemical Formula 735]

(6-171)

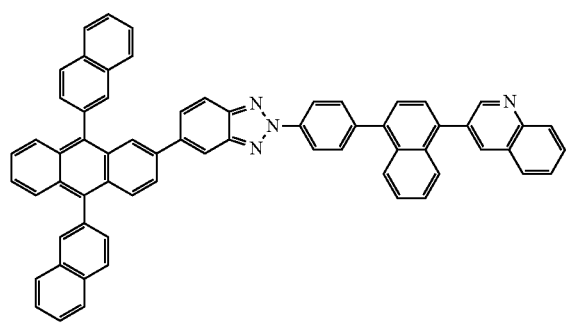

[Chemical Formula 736]

(6-172)

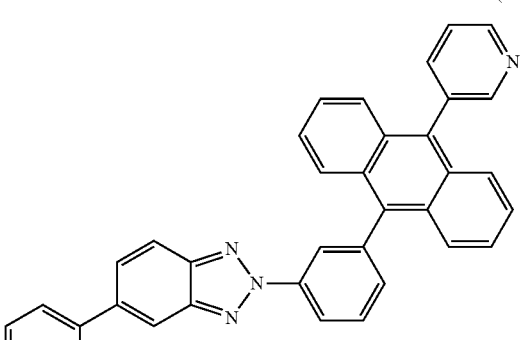

[Chemical Formula 737]

(6-173)

The compounds having a benzotriazole ring structure described above can be synthesized by a known method (refer to Patent Document 11, for example).

The following presents specific examples of preferred compounds among the amine derivatives of the general formula (7) preferably used in the organic EL device of the present invention and having a condensed ring structure. The present invention, however, is not restricted to these compounds.

[Chemical Formula 738]

(7-1)

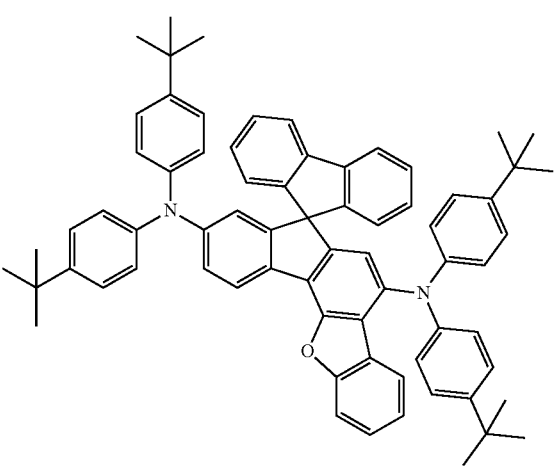

[Chemical Formula 739]
(7-2)
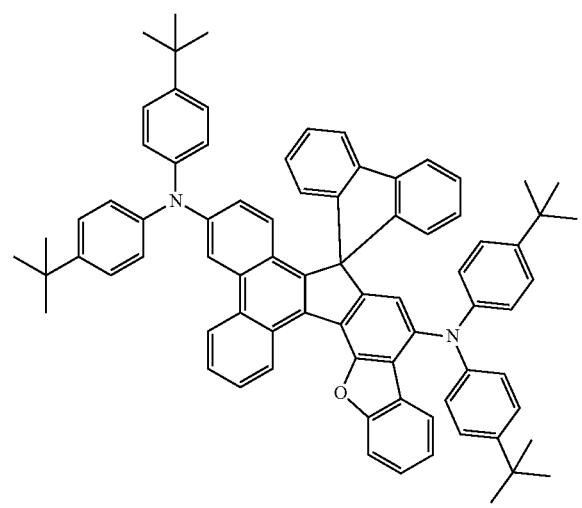
[Chemical Formula 740]
(7-3)
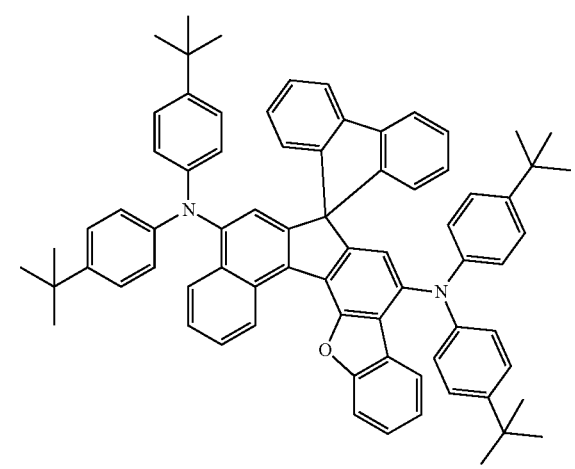
[Chemical Formula 741]
(7-4)
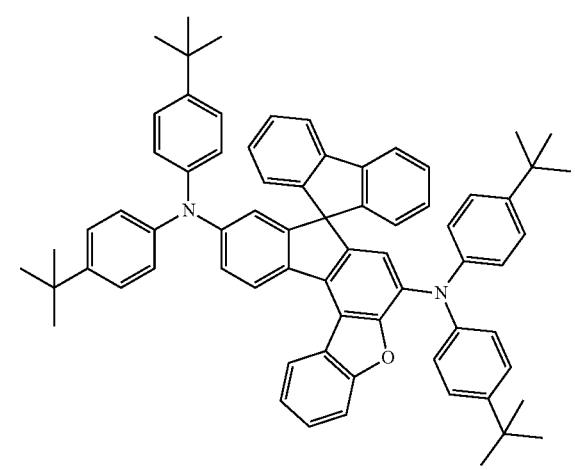
[Chemical Formula 742]
(7-5)
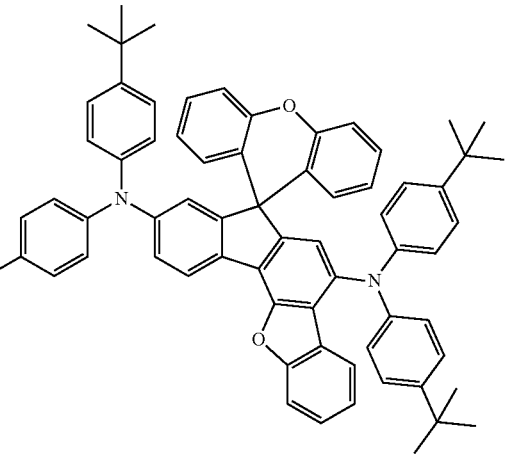
[Chemical Formula 743]
(7-6)
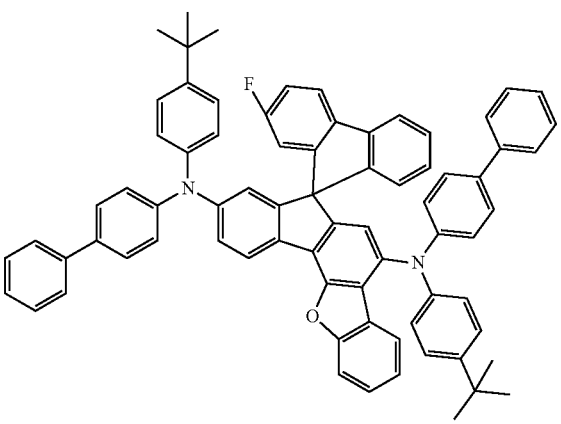
[Chemical Formula 744]
(7-7)
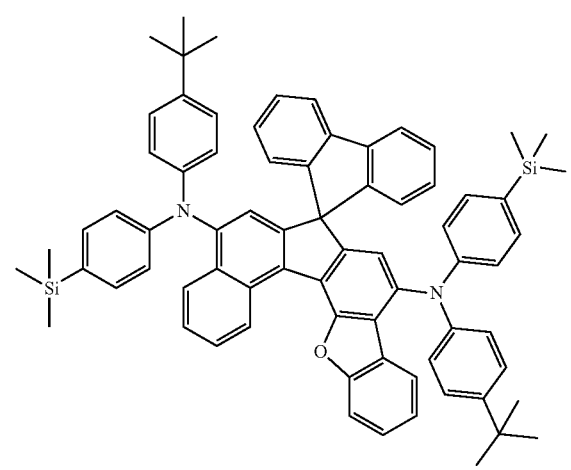

[Chemical Formula 745]
(7-8)
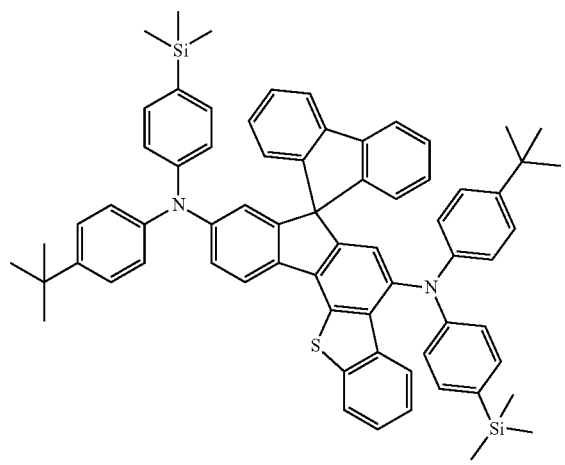
[Chemical Formula 746]
(7-9)
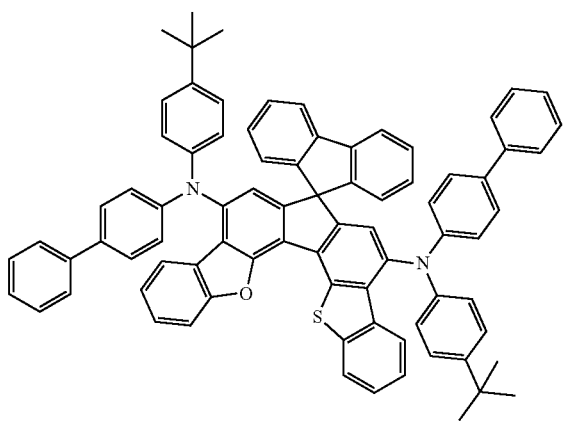
[Chemical Formula 747]
(7-10)
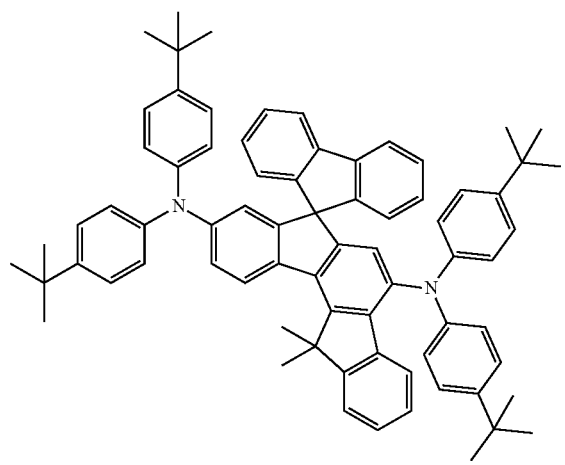
[Chemical Formula 748]
(7-11)
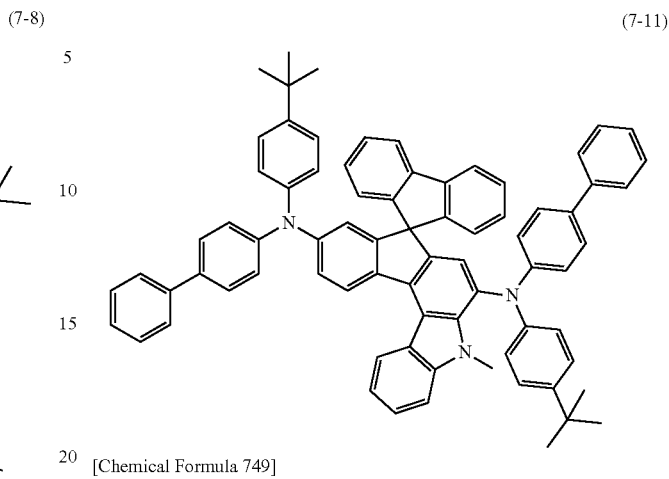
[Chemical Formula 749]
(7-12)
[Chemical Formula 750]
(7-13)
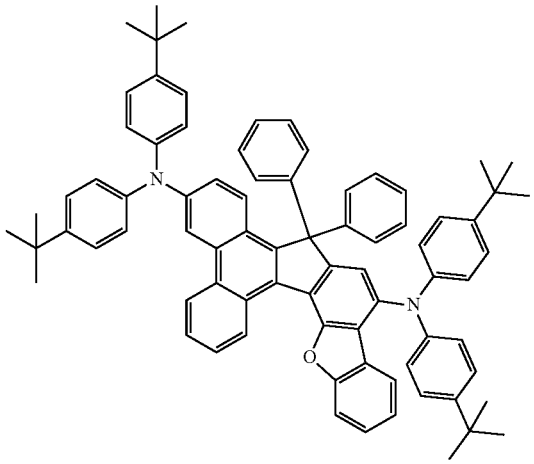

303
-continued
[Chemical Formula 751]
(7-14)
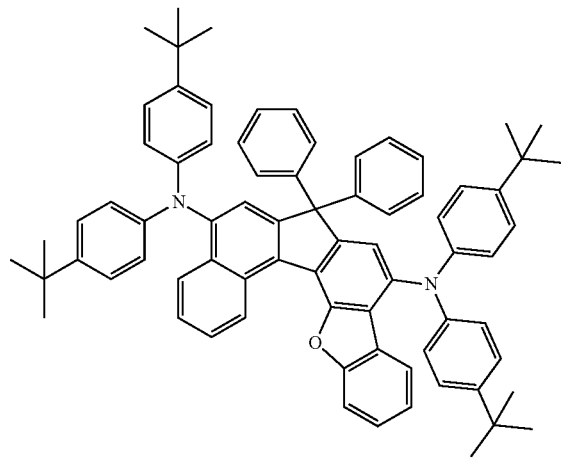
[Chemical Formula 752]
(7-15)
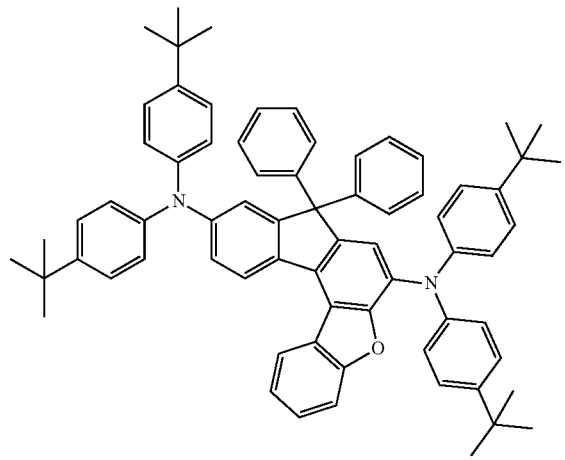
[Chemical Formula 753]
(7-16)
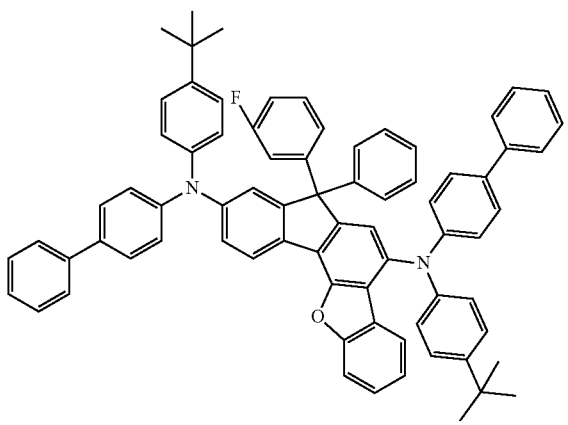
304
-continued
[Chemical Formula 754]
(7-17)
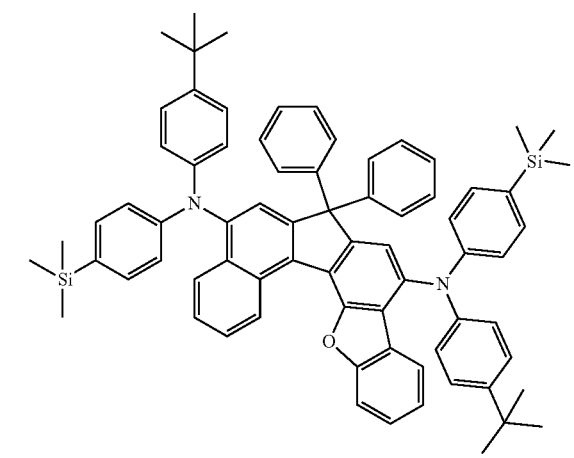
[Chemical Formula 755]
(7-18)
[Chemical Formula 756]
(7-19)
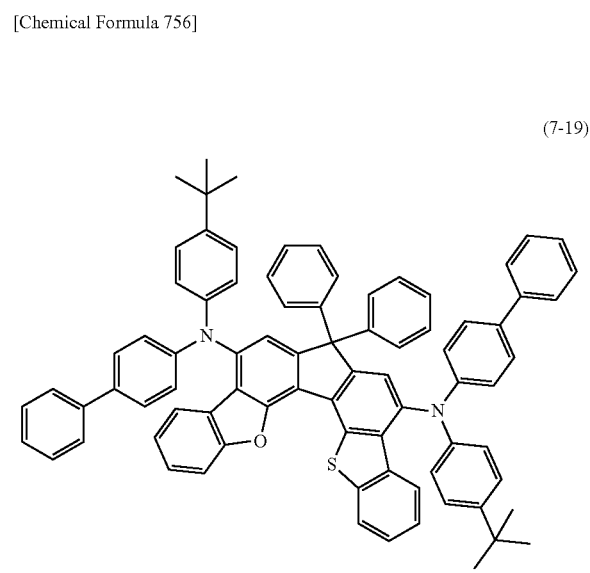

[Chemical Formula 757]
(7-20)
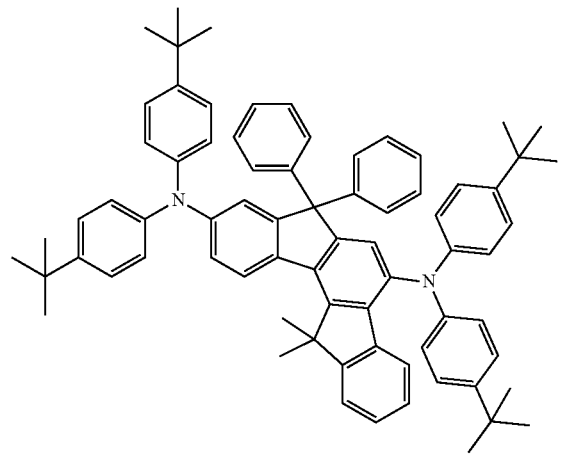
[Chemical Formula 758]
(7-21)
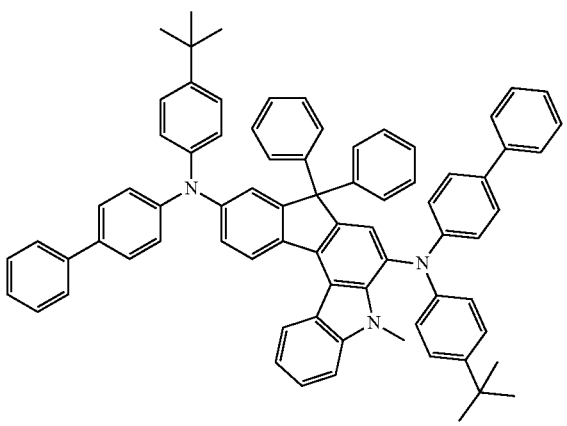
[Chemical Formula 759]
(7-22)
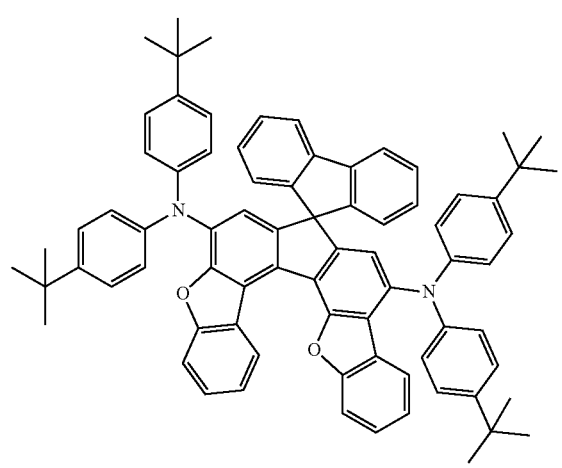
[Chemical Formula 760]
(7-23)
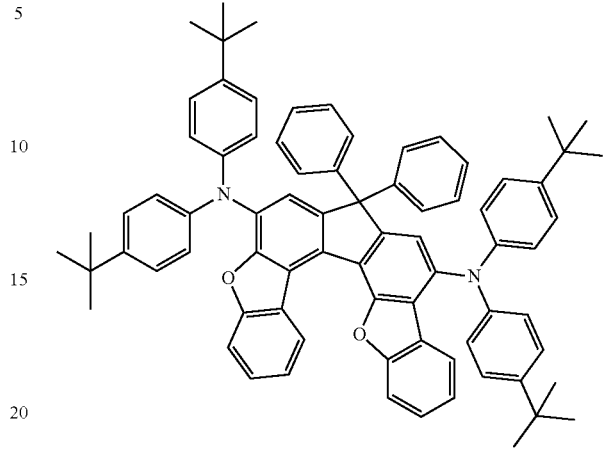
[Chemical Formula 761]
(7-24)
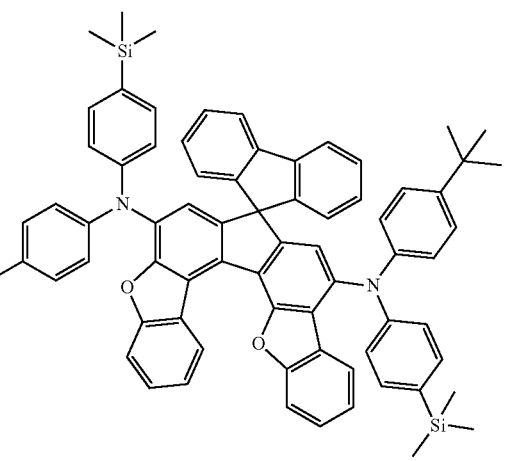
[Chemical Formula 762]
(7-25)
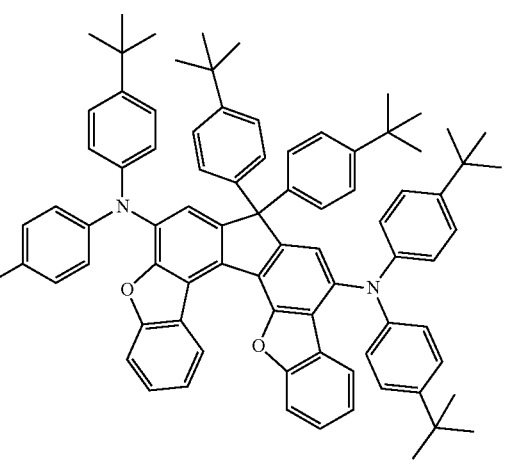
The arylamine compounds of the general formula (1) were purified by methods such as column chromatography, adsorption using, for example, a silica gel, activated carbon, or activated clay, recrystallization or crystallization using a solvent, and a sublimation purification method. The compounds were identified by an NMR analysis. A melting point, a glass transition point (Tg), and a work function were measured as material property values. The melting point can be used as an index of vapor deposition, the glass transition point (Tg) as an index of stability in a thin-film state, and the work function as an index of hole transportability and hole blocking performance.

Other compounds used for the organic EL device of the present invention were purified by methods such as column chromatography, adsorption using, for example, a silica gel, activated carbon, or activated clay, and recrystallization or crystallization using a solvent, and finally purified by sublimation.

The melting point and the glass transition point (Tg) were measured by a high-sensitive differential scanning calorimeter (DSC3100SA produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a hole transport layer, a light emitting layer, an electron transport layer, an electron injection layer, and a cathode successively formed on a substrate, optionally with an electron blocking layer between the hole transport layer and the light emitting layer, and a hole blocking layer between the light emitting layer and the electron transport layer. Some of the organic layers in the multilayer structure may be omitted, or may serve more than one function. For example, a single organic layer may serve as the electron injection layer and the electron transport layer. Further, the organic layers having a same function may have a laminate structure of two or more layers, for example, the hole transport layers may have a laminate structure of two or more layers, the light emitting layers may have a laminate structure of two or more layers, or the electron transport layers may have a laminate structure of two or more layers.

Electrode materials with high work functions such as ITO and gold are used as the anode of the organic EL device of the present invention.

As the hole injection layer of the organic EL device of the present invention, a material obtained by p-doping an arylamine compound represented by the above general formula (1) with an electron acceptor is preferably used.

As hole-injecting and transporting materials which can be mixed with or used simultaneously with the arylamine compound represented by the above general formula (1), materials such as starburst-type triphenylamine derivatives and various triphenylamine tetramers; porphyrin compounds as represented by copper phthalocyanine; accepting heterocyclic compounds such as hexacyano azatriphenylene and coating-type polymer materials; and the like can be used. These materials may be formed into a thin film by a vapor deposition method or other known methods such as a spin coating method and an inkjet method.

As the hole transport layer of the organic EL device of the present invention, in addition to the arylamine compounds represented by the above general formula (1), benzidine derivatives such as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine, arylamine compounds having a structure in which two triphenylamine structures are joined within a molecule via a single bond or a divalent group that does not contain a heteroatom, such as 1,1-bis[4-(di-4-tolylamino)phenyl]cyclohexane (TAPC), arylamine compounds having a structure in which four triphenylamine structures are joined within a molecule via a single bond or a divalent group that does not contain a heteroatom, various triphenylamine trimers, and the like can be used. Further, as the hole injection and transport layers, coating-type polymer materials such as poly(3,4-ethylenedioxythiophene) (PEDOT)/poly(styrene sulfonate) (PSS) can be used.

As the hole transport layer of the organic EL device of the present invention, hole-transporting arylamine compounds are preferably used, and particularly, the arylamine compounds represented by the above general formula (1) are preferably used. Then, the compounds which are not p-doped are preferably used.

These may be individually deposited for film forming, but may be used as a single layer deposited mixed with other materials, or may be formed as a laminate of individually deposited layers, a laminate of mixedly deposited layers, or a laminate of an individually deposited layer and a mixedly deposited layer. These materials may be formed into a thin film by a vapor deposition method or other known methods such as a spin coating method and an inkjet method.

As the electron blocking layer of the organic EL device of the present invention, the arylamine compounds represented by the above general formula (1) are preferably used, however, in addition thereto, arylamine compounds having a structure in which four triphenylamine structures are joined within a molecule via a single bond or a divalent group that does not contain a heteroatom, arylamine compounds having a structure in which two triphenylamine structures are joined within a molecule via a single bond or a divalent group that does not contain a heteroatom, compounds having an electron blocking effect, including, for example, carbazole derivatives such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz), and compounds having a triphenylsilyl group and a triarylamine structure, as represented by 9-[4-(carbazol-9-yl)phenyl]-9-[4-(triphenylsilyl)phenyl]-9H-fluorene can be used. These may be individually deposited for film forming, but may be used as a single layer deposited mixed with other materials, or may be formed as a laminate of individually deposited layers, a laminate of mixedly deposited layers, or a laminate of an individually deposited layer and a mixedly deposited layer. These materials may be formed into a thin film by using a vapor deposition method or other known methods such as a spin coating method and an inkjet method.

In the organic EL device of the present invention, it is preferable that layers (for example, the hole transport layer, the electron blocking layer, etc.) adjacent to the light emitting layer are not p-doped with an electron acceptor.

In these layers, arylamine compounds having high electron blocking performance are preferably used, and the arylamine compounds represented by the above general formula (1) and the like are preferably used.

Further, the film thickness of these layers is not particularly limited as long as it is a commonly used film thickness, however, as the hole transport layer, a layer having a film thickness of 20 to 100 nm is used, and as the electron blocking layer, a layer having a film thickness of 5 to 30 nm is used.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as Alq$_3$. Further, the light emitting layer may be made of a host material and a dopant material. Examples of the host material can be preferably anthracene derivatives. Other examples of the host material can be thiazole derivatives, benzimidazole derivatives, and polydialkyl fluorene derivatives, in addition to the above light-emitting materials. Examples of the dopant material can be preferably pyrene derivatives, amine derivatives of the general formula (7) having a condensed ring. Other examples of the dopant material can be quinacridone, coumarin, rubrene, perylene, derivatives thereof, benzopyran derivatives, indenophenanthrene derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes of metals such as iridium and platinum may be used. Examples of the phosphorescent materials include green phosphorescent materials such as Ir(ppy)$_3$, blue phosphorescent materials such as FIrpic and FIr6, and red phosphorescent materials such as Btp$_2$Ir(acac). Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2) and 2,2',2''-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, examples of the light-emitting material may be delayed fluorescent-emitting material such as a CDCB derivative of PIC-TRZ, CC2TA, PXZ-TRZ, 4CzIPN or the like (refer to Non-Patent Document 3, for example).

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to phenanthroline derivatives such as bathocuproine (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Material used for the electron transport layer of the organic EL device of the present invention can be preferably the compounds of the general formula (3) having an anthracene ring structure, and the compounds of the general formula (4) having a pyrimidine ring structure. Other examples of material can be metal complexes of quinolinol derivatives such as Alq$_3$ and BAlq, various metal complexes, triazole derivatives, triazine derivatives, oxadiazole derivatives, thiadiazole derivatives, carbodiimide derivatives, quinoxaline derivatives, phenanthroline derivatives, and silole derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of N,N-bis(biphenyl-4-yl)-N-(6-phenylbiphenyl-3-yl)amine (Compound 1-2)

N,N-bis(biphenyl-4-yl)-N-(6-bromobiphenyl-3-yl)amine (11.8 g), toluene (94 mL), phenylboronic acid (2.7 g), and an aqueous solution obtained by previously dissolving potassium carbonate (5.9 g) in water (36 mL) were added into a nitrogen-substituted reaction vessel and aerated with nitrogen gas under ultrasonic irradiation for 30 minutes. Tetrakistriphenylphosphine palladium (0.74 g) was added thereto, and the resulting mixture was heated and stirred at 72° C. for 18 hours. After the mixture was cooled to a room temperature, an organic layer was collected by liquid separation. The organic layer was washed with water, and washed with a saturated salt solution sequentially, and then dried over anhydrous magnesium sulfate and concentrated to obtain a crude product. Subsequently, the crude product was purified using column chromatography, whereby a white powder of N,N-bis(biphenyl-4-yl)-N-(6-phenylbiphenyl-3-yl)amine (Compound 1-2, 8.4 g, yield: 72%) was obtained.

The structure of the obtained white powder was identified by NMR.

$^1$H-NMR (CDCl$_3$) detected 31 hydrogen signals, as follows.

δ (ppm)=7.56-7.68 (7H), 7.45-7.52 (4H) 7.14-7.41 (20H)

[Chemical Formula 763]

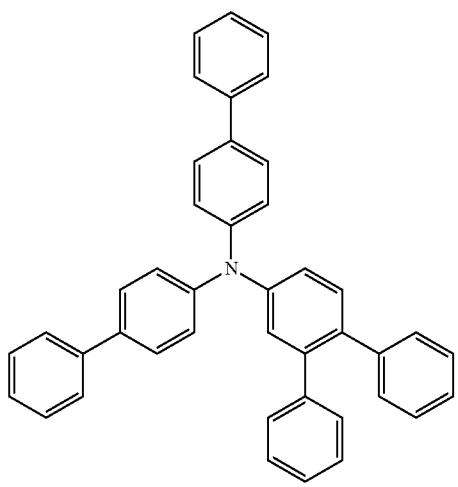

(1-2)

Example 2

Synthesis of N,N-bis(biphenyl-4-yl)-N-{6-(naphthyl-1-yl)biphenyl-3-yl}amine (Compound 1-3)

The reaction was carried out under the same conditions as those of Example 1, except that phenylboronic acid was replaced with 1-naphthylboronic acid, whereby a white powder of N,N-bis(biphenyl-4-yl)-N-{6-(naphthyl-1-yl)biphenyl-3-yl}amine (Compound 1-3, 9.2 g, yield: 61%) was obtained.

The structure of the obtained white powder was identified by NMR.

$^1$H-NMR (CDCl$_3$) detected 33 hydrogen signals, as follows.

δ (ppm)=7.84-7.87 (3H), 7.67-83 (6H), 7.26-7.64 (18H) 7.02-7.04 (6H)

[Chemical Formula 764]

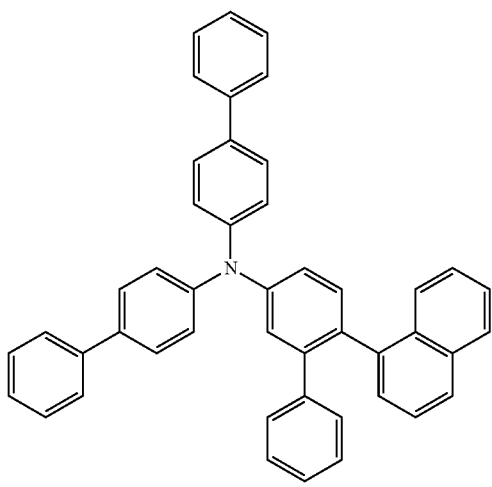

(1-3)

Example 3

Synthesis of N,N-bis(biphenyl-4-yl)-N-{6-(9,9-dimethylfluoren-2-yl)biphenyl-3-yl}amine (Compound 1-1)

The reaction was carried out under the same conditions as those of Example 1, except that phenylboronic acid was replaced with (9,9-dimethylfluoren-2-yl)boronic acid, whereby a white powder of N,N-bis(biphenyl-4-yl)-N-{6-(9,9-dimethylfluoren-2-yl)biphenyl-3-yl}amine (Compound 1-1, 9.0 g, yield: 57%) was obtained.

The structure of the obtained white powder was identified by NMR.

$^1$H-NMR (CDCl$_3$) detected 39 hydrogen signals, as follows.

δ (ppm)=7.56-7.64 (10H), 7.26-50 (18H), 7.02-7.16 (5H), 1.26 (6H)

[Chemical Formula 765]

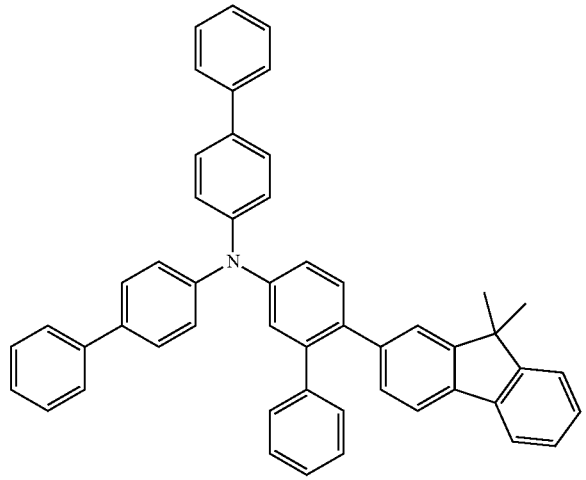

(1-1)

Example 4

Synthesis of N,N-bis(biphenyl-4-yl)-N-{6-(biphenyl-4-yl)biphenyl-3-yl}amine (Compound 1-4)

The reaction was carried out under the same conditions as those of Example 1, except that phenylboronic acid was replaced with 4-biphenylboronic acid, whereby a white powder of N,N-bis(biphenyl-4-yl)-N-{6-(biphenyl-4-yl)biphenyl-3-yl}amine (Compound 1-4, 8.6 g, yield: 64%) was obtained.

The structure of the obtained white powder was identified by NMR.

$^1$H-NMR (CDCl$_3$) detected 35 hydrogen signals, as follows.

δ (ppm)=7.66-7.53 (8H), 7.51-7.15 (27H)

[Chemical Formula 766]

(1-4)

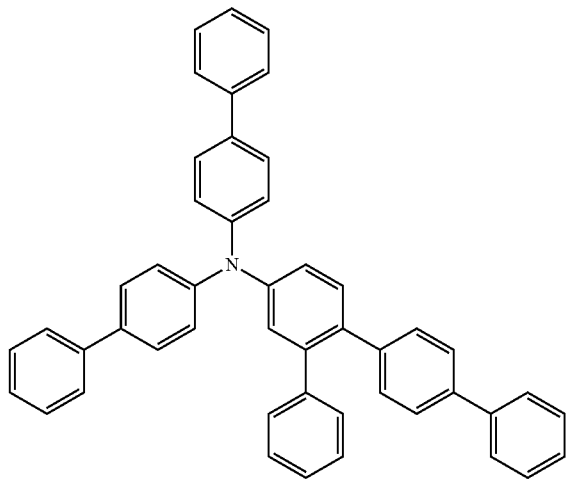

Example 5

Synthesis of N,N-bis(biphenyl-4-yl)-N-{6-(1,1'; 4',1''-terphenyl-4-yl)biphenyl-3-yl}amine (Compound 1-9)

The reaction was carried out under the same conditions as those of Example 1, except that phenylboronic acid was replaced with 4-bromo-1,1'; 4',1''-terphenyl, and N,N-bis(biphenyl-4-yl)-N-(6-bromobiphenyl-3-yl)amine was replaced with N,N-bis(biphenyl-4-yl)-N-{3-phenyl-4-(4,4,5,5-tetramethyl-1,3,2-dioxaborolan-2-yl)phenyl}amine, whereby a white powder of N,N-bis(biphenyl-4-yl)-N-{6-(1,1'; 4',1''-terphenyl-4-yl)biphenyl-3-yl}amine (Compound 1-9, 4.5 g, yield: 40%) was obtained.

The structure of the obtained white powder was identified by NMR.

$^1$H-NMR (THF-d$_8$) detected 39 hydrogen signals, as follows.

δ (ppm)=7.73-7.58 (15H), 7.46-7.12 (24H)

[Chemical Formula 767]

(1-9)

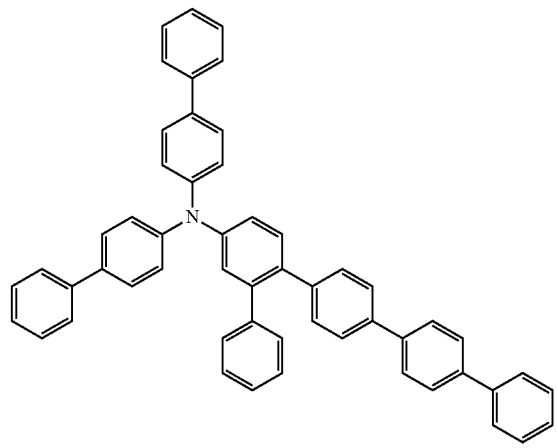

Example 6

Synthesis of N,N-bis(biphenyl-4-yl)-N-[6-{4-(naphthalen-1-yl)phenyl)}biphenyl-3-yl]amine (Compound 1-16)

The reaction was carried out under the same conditions as those of Example 1, except that phenylboronic acid was replaced with 4-(naphthalen-1-yl)phenylboronic acid, whereby a white powder of N,N-bis(biphenyl-4-yl)-N-[6-{4-(naphthalen-1-yl)phenyl)}biphenyl-3-yl]amine (Compound 1-16, 11.6 g, yield: 77%) was obtained.

The structure of the obtained white powder was identified by NMR.

$^1$H-NMR (CDCl$_3$) detected 37 hydrogen signals, as follows.

δ (ppm)=7.95-7.84 (3H), 7.67-7.18 (34H)

[Chemical Formula 768]

(1-16)

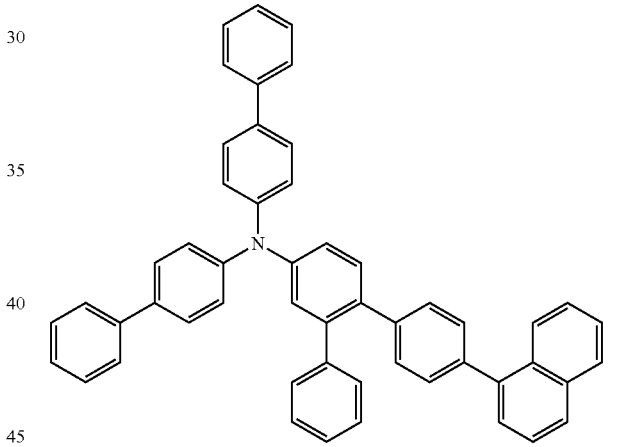

Example 7

Synthesis of N,N-bis(biphenyl-4-yl)-N-[6-(9,9-dimethylfluoren-2-yl)phenyl)}biphenyl-3-yl]amine (Compound 1-20)

The reaction was carried out under the same conditions as those of Example 1, except that phenylboronic acid was replaced with 4-(9,9-dimethylfluoren-2-yl)phenylboronic acid, whereby a white powder of N,N-bis(biphenyl-4-yl)-N-[6-(9,9-dimethylfluoren-2-yl)phenyl)}biphenyl-3-yl]amine (Compound 1-20, 13.1 g, yield: 81%) was obtained.

The structure of the obtained white powder was identified by NMR.

$^1$H-NMR (CDCl$_3$) detected 43 hydrogen signals, as follows.

δ (ppm)=7.78 (2H), 7.68-7.15 (35H), 1.55 (6H)

[Chemical Formula 769]

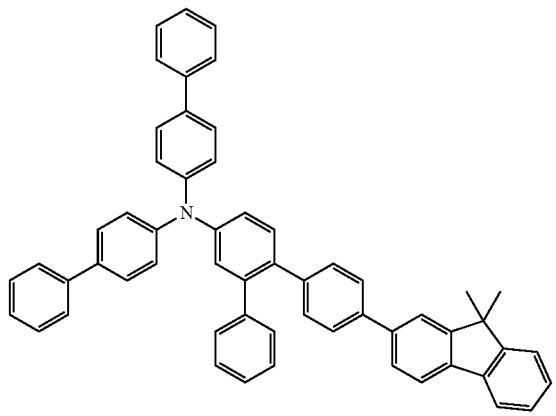

(1-20)

Example 8

Synthesis of N-(biphenyl-4-yl)-N-{6-(biphenyl-4-yl)biphenyl-3-yl}-N-(9,9-dimethylfluoren-2-yl)amine (Compound 1-56)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N-(biphenyl-4-yl)-N-(9,9-dimethylfluoren-2-yl)-N-(6-bromobiphenyl-3-yl)amine, whereby a white powder of N-(biphenyl-4-yl)-N-{6-(biphenyl-4-yl)biphenyl-3-yl}-N-(9,9-dimethylfluoren-2-yl)amine (Compound 1-56, 17.8 g, yield: 89%) was obtained.

The structure of the obtained white powder was identified by NMR.

$^1$H-NMR (CDCl$_3$) detected 39 hydrogen signals, as follows.

δ (ppm)=7.72-7.57 (7H), 7.52-7.33 (9H), 7.32-7.19 (17H), 1.45 (6H)

[Chemical Formula 770]

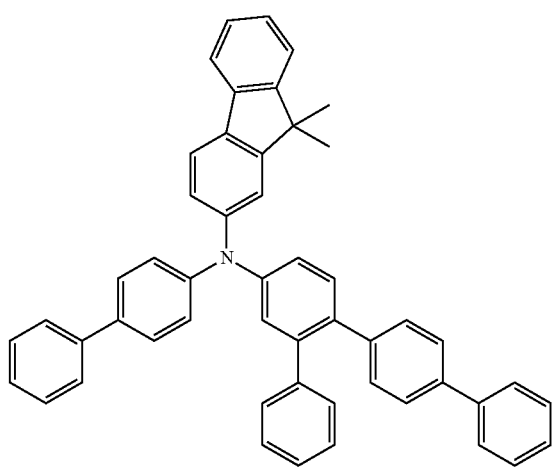

(1-56)

Example 9

Synthesis of N,N-bis(9,9-dimethylfluoren-2-yl)-N-(6-phenylbiphenyl-3-yl)-amine (Compound 1-62)

The reaction was carried out under the same conditions as those of Example 1, except that N,N-bis(biphenyl-4-yl)-N-(6-bromobiphenyl-3-yl)amine was replaced with N,N-bis(9,9-dimethylfluoren-2-yl)-N-(6-bromobiphenyl-3-yl)amine, whereby a white powder of N,N-bis(9,9-dimethylfluoren-2-yl)-N-(6-phenylbiphenyl-3-yl)amine (Compound 1-62, 11.5 g, yield: 57%) was obtained.

The structure of the obtained white powder was identified by NMR.

$^1$H-NMR (THF-d$_8$) detected 39 hydrogen signals, as follows.

δ (ppm)=7.70-7.63 (3H), 7.44-7.02 (24H), 1.46 (12H)

[Chemical Formula 771]

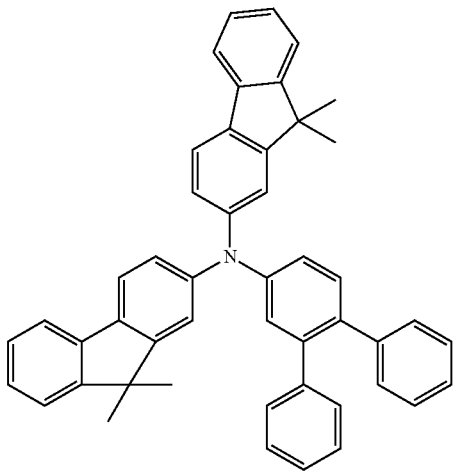

(1-62)

Example 10

Synthesis of N,N-bis(6-phenylbiphenyl-3-yl)-N-(biphenyl-4-yl)amine (Compound 1-108)

The reaction was carried out under the same conditions as those of Example 1, except that N,N-bis(biphenyl-4-yl)-N-(6-bromobiphenyl-3-yl)amine was replaced with N,N-bis(6-bromobiphenyl-3-yl)-N-(biphenyl-4-yl)amine, whereby a white powder of N,N-bis(6-phenylbiphenyl-3-yl)-N-(biphenyl-4-yl)amine (Compound 1-108, 10.2 g, yield: 73%) was obtained.

The structure of the obtained white powder was identified by NMR.

$^1$H-NMR (CDCl$_3$) detected 35 hydrogen signals, as follows.

δ (ppm)=7.57-7.66 (4H), 7.10-7.49 (31H)

[Chemical Formula 772]

(1-108)

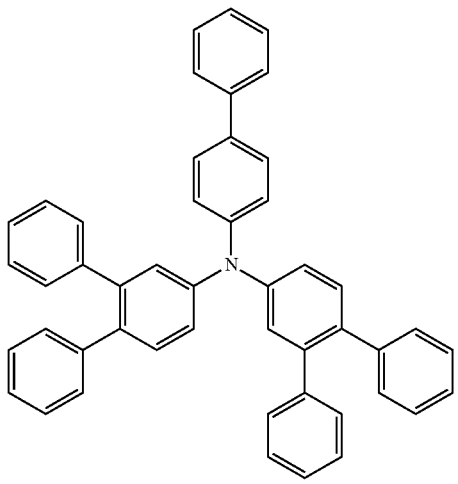

Example 11

Synthesis of N,N,N-tris(6-phenylbiphenyl-3-yl)amine (Compound 1-143)

The reaction was carried out under the same conditions as those of Example 1, except that N,N-bis(biphenyl-4-yl)-N-(6-bromobiphenyl-3-yl)amine was replaced with N,N,N-tris(6-bromobiphenyl-3-yl)amine, whereby a white powder of N,N,N-tris(6-phenylbiphenyl-3-yl)amine (Compound 1-143, 11.1 g, yield: 75%) was obtained.

The structure of the obtained white powder was identified by NMR.

$^1$H-NMR (CDCl$_3$) detected 39 hydrogen signals, as follows.

δ (ppm)=7.35-7.42 (6H), 7.15-7.35 (33H)

[Chemical Formula 773]

(1-143)

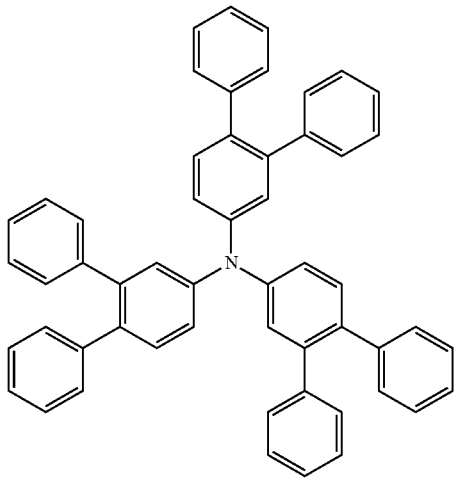

Example 12

Synthesis of N-(biphenyl-4-yl)-N-(6-phenylbiphenyl-3-yl)-N-(9,9-dimethylfluoren-2-yl)amine (Compound 1-50)

The reaction was carried out under the same conditions as those of Example 1, except that N,N-bis(biphenyl-4-yl)-N-(6-bromobiphenyl-3-yl)amine was replaced with N-(biphenyl-4-yl)-N-(9,9-dimethylfluoren-2-yl)-N-(6-bromobiphenyl-3-yl)amine, whereby a white powder of N-(biphenyl-4-yl)-N-(6-phenylbiphenyl-3-yl)-N-(9,9-dimethylfluoren-2-yl)amine (Compound 1-50, 13.6 g, yield: 76%) was obtained.

The structure of the obtained white powder was identified by NMR.

$^1$H-NMR (CDCl$_3$) detected 35 hydrogen signals, as follows.

δ (ppm)=7.72-7.61 (4H), 7.58 (2H), 7.50-7.09 (29H)

[Chemical Formula 774]

(1-50)

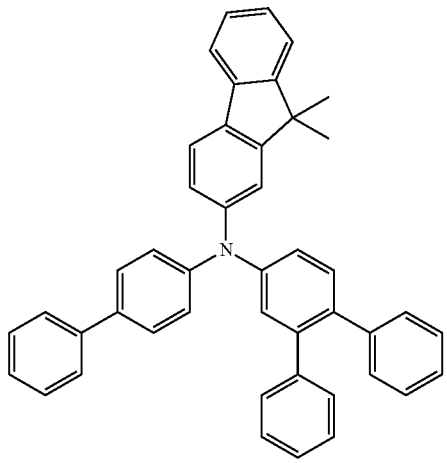

Example 13

Synthesis of N-(9,9-dimethylfluoren-2-yl)-N-{4-(naphthalen-1-yl)phenyl}-N-(6-phenylbiphenyl-3-yl)amine (Compound 1-63)

The reaction was carried out under the same conditions as those of Example 1, except that N,N-bis(biphenyl-4-yl)-N-(6-bromobiphenyl-3-yl)amine was replaced with N-(6-bromobiphenyl-3-yl)-N-(9,9-dimethylfluoren-2-yl)-N-{4-(naphthalen-1-yl)phenyl}amine, whereby a light yellowish white powder of N-(9,9-dimethylfluoren-2-yl)-N-{4-(naphthalen-1-yl)phenyl}-N-(6-phenylbiphenyl-3-yl)amine (Compound 1-63, 12.2, g, yield: 56%) was obtained.

The structure of the obtained light yellowish white powder was identified by NMR.

$^1$H-NMR (CDCl$_3$) detected 37 hydrogen signals, as follows.

δ (ppm)=8.10 (1H), 7.95 (1H), 7.88 (1H), 7.72-7.65 (2H), 7.60-7.10 (26H), 1.50 (6H)

[Chemical Formula 775]

(1-63)

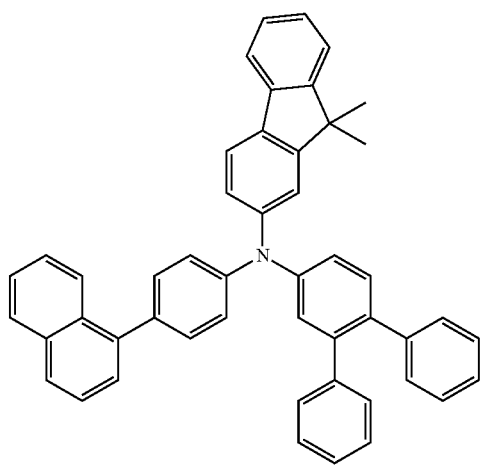

Example 14

Synthesis of N-(9,9-dimethylfluoren-2-yl)-N-{4-(naphthalen-2-yl)phenyl}-N-{6-phenylbiphenyl-3-yl}amine (Compound 1-64)

The reaction was carried out under the same conditions as those of Example 1, except that N,N-bis(biphenyl-4-yl)-N-(6-bromobiphenyl-3-yl)amine was replaced with N-(6-bromobiphenyl-3-yl)-N-(9,9-dimethylfluoren-2-yl)-N-{4-(naphthalen-2-yl)phenyl}amine, whereby a light yellowish white powder of N-(9,9-dimethylfluoren-2-yl)-N-{4-(naphthalen-2-yl)phenyl}-N-(6-phenylbiphenyl-3-yl)amine (Compound 1-64, 8.8 g, yield: 63%) was obtained.

The structure of the obtained light yellowish white powder was identified by NMR.

¹H-NMR (CDCl₃) detected 37 hydrogen signals, as follows.

δ (ppm)=8.08 (1H), 7.76-7.94 (4H), 7.60-7.71 (4H), 7.13-7.54 (22H), 1.52 (6H)

[Chemical Formula 776]

(1-64)

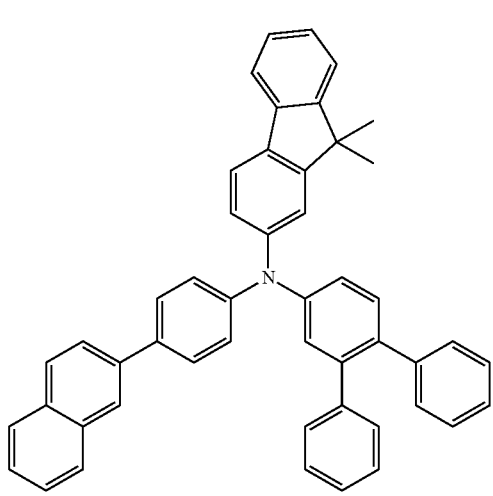

Example 15

Synthesis of N-(biphenyl-4-yl)-N-(9,9-dimethylfluoren-2-yl)-N-{6-(4-naphthalen-1-yl-phenyl)biphenyl-3-yl}amine (Compound 1-65)

The reaction was carried out under the same conditions as those of Example 1, except that phenylboronic acid was replaced with 4-(naphthalen-1-yl)phenylboronic acid, and N,N-bis(biphenyl-4-yl)-N-(6-bromobiphenyl-3-yl)amine was replaced with N-(biphenyl-4-yl)-N-(9,9-dimethylfluoren-2-yl)-N-(6-bromobiphenyl-3-yl)amine, whereby a white powder of N-(biphenyl-4-yl)-N-(9,9-dimethylfluoren-2-yl)-N-{6-(4-naphthalen-1-yl-phenyl)biphenyl-3-yl}amine (Compound 1-143, 49.8 g, yield: 84%) was obtained.

The structure of the obtained white powder was identified by NMR.

¹H-NMR (CDCl₃) detected 41 hydrogen signals, as follows.

δ (ppm)=7.92 (2H), 7.88 (1H), 7.72-7.18 (38H)

[Chemical Formula 777]

(1-65)

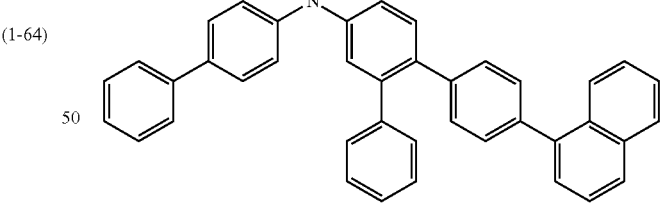

Example 16

Synthesis of N-(biphenyl-4-yl)-N-{4-(naphthalen-1-yl)phenyl}-N-{6-(biphenyl-4-yl)biphenyl-3-yl)}amine (Compound 1-147)

The reaction was carried out under the same conditions as those of Example 1, except that phenylboronic acid was replaced with 4-biphenylboronic acid, and N,N-bis(biphe nyl-4-yl)-N-(6-bromobiphenyl-3-yl)amine was replaced with N-(biphenyl-4-yl)-N-(6-bromobiphenyl-3-yl)-N-{4-(naphthalen-1-yl)phenyl}amine, whereby a white powder of N-(biphenyl-4-yl)-N-{4-(naphthalen-1-yl)phenyl}-N-{6-(biphenyl-4-yl)biphenyl-3-yl)}amine (Compound 1-147, 7.5 g, yield: 48%) was obtained.

The structure of the obtained white powder was identified by NMR.

$^1$H-NMR (CDCl$_3$) detected 37 hydrogen signals, as follows.

δ (ppm)=8.08 (1H), 7.95 (1H), 7.88 (1H), 7.68-7.18 (34H)

[Chemical Formula 778]

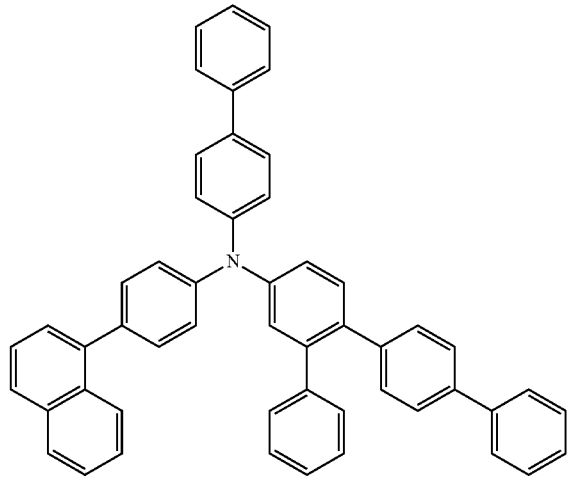

(1-147)

Example 17

Synthesis of N-(biphenyl-4-yl)-N-{4-(naphthalen-1-yl)phenyl}-N-[6-{4-(naphthalen-1-yl)phenyl}biphenyl-3-yl]amine (Compound 1-148)

The reaction was carried out under the same conditions as those of Example 1, except that phenylboronic acid was replaced with 4-(naphthalen-1-yl)phenylboronic acid, and N,N-bis(biphenyl-4-yl)-N-(6-bromobiphenyl-3-yl)amine was replaced with N-(biphenyl-4-yl)-N-{4-(naphthalen-1-yl)phenyl}-N-(6-bromobiphenyl-3-yl)amine, whereby a light yellowish white powder of N-(biphenyl-4-yl)-N-{4-(naphthalen-1-yl)phenyl}-N-[6-{4-(naphthalen-1-yl)phenyl}biphenyl-3-yl]amine (Compound 1-148, 8.4 g, yield: 60%) was obtained.

The structure of the obtained light yellowish white powder was identified by NMR.

$^1$H-NMR (CDCl$_3$) detected 39 hydrogen signals, as follows.

δ (ppm)=8.09 (1H), 7.98-7.84 (5H), 7.69-7.20 (33H)

[Chemical Formula 779]

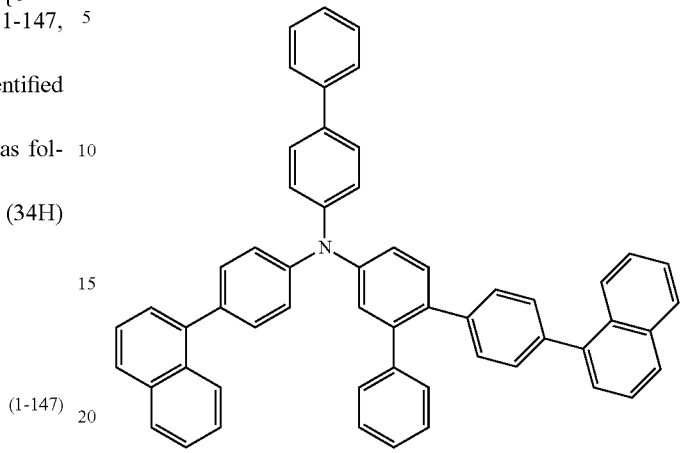

(1-148)

Example 18

Synthesis of N-(biphenyl-4-yl)-N-{4-(naphthalen-1-yl)phenyl}-N-{6-(p-terphenyl-4-yl)biphenyl-3-yl}amine (Compound 1-150)

The reaction was carried out under the same conditions as those of Example 1, except that phenylboronic acid was replaced with 4-(p-terphenyl)boronic acid, and N,N-bis(biphenyl-4-yl)-N-(6-bromobiphenyl-3-yl)amine was replaced with N-(biphenyl-4-yl)-N-{4-(naphthalen-1-yl)phenyl}-N-(6-bromobiphenyl-3-yl)amine, whereby a light yellowish white powder of N-(biphenyl-4-yl)-N-{4-(naphthalen-1-yl)phenyl}-N-{6-(p-terphenyl-4-yl)biphenyl-3-yl}amine (Compound 1-150, 6.3 g, yield: 47%) was obtained.

The structure of the obtained light yellowish white powder was identified by NMR.

$^1$H-NMR (CDCl$_3$) detected 41 hydrogen signals, as follows.

δ (ppm)=8.12 (1H), 7.98-7.83 (2H), 7.72-7.15 (38H)

[Chemical Formula 780]

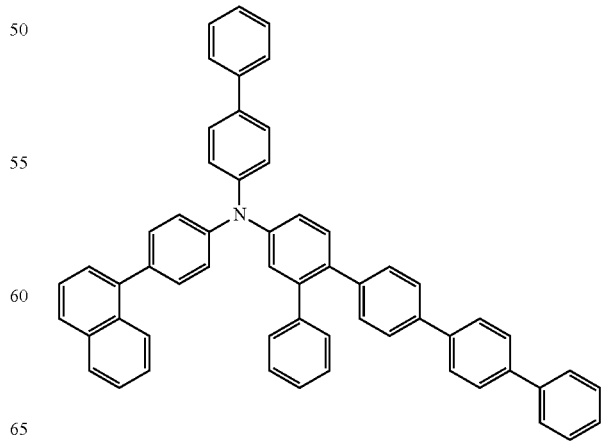

(1-150)

Example 19

Synthesis of N,N-bis(biphenyl-4-yl)-N-[4-phenyl-3-{4-(naphthalen-1-yl)phenyl}phenyl]amine (Compound 1-152)

4-Bromobiphenyl (13.5 g), 2-{4-(naphthalen-1-yl)phenyl)}-4-aminobiphenyl (9.0 g), palladium acetate (0.11 g), a toluene solution (50%) containing tri-tert-butylphosphine (0.15 g), and toluene (90 mL) were added into a nitrogen-substituted reaction vessel, and the mixture was heated and stirred at 100° C. for 24 hours. After insoluble matter was removed by filtration, concentration was carried out to obtain a crude product. Subsequently, the crude product was purified using column chromatography, whereby a yellowish white powder of N,N-bis(biphenyl-4-yl)-N-[4-phenyl-3-{4-(naphthalen-1-yl)phenyl}phenyl]amine (Compound 1-152, 5.4 g, yield: 33%) was obtained.

The structure of the obtained yellowish white powder was identified by NMR.

$^1$H-NMR (CDCl$_3$) detected 37 hydrogen signals, as follows.

δ (ppm)=7.94-7.76 (3H), 7.68-7.15 (34H)

[Chemical Formula 781]

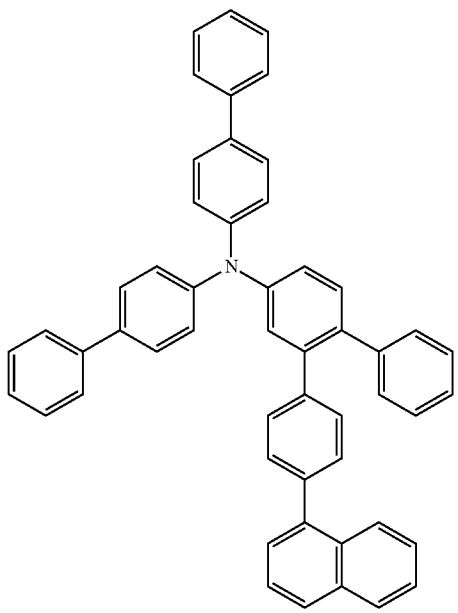

(1-152)

Example 20

Synthesis of N,N-bis(9,9-dimethylfluoren-2-yl)-N-{6-(biphenyl-4-yl)biphenyl-3-yl}amine (Compound 1-153)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N,N-bis(9,9-dimethylfluoren-2-yl)-N-(6-bromobiphenyl-3-yl)amine, whereby a light yellowish white powder of N,N-bis(9,9-dimethylfluoren-2-yl)-N-{6-(biphenyl-4-yl)biphenyl-3-yl}amine (Compound 1-153, 16.7 g, yield: 92%) was obtained.

The structure of the obtained light yellowish white powder was identified by NMR.

$^1$H-NMR (CDCl$_3$) detected 43 hydrogen signals, as follows.

δ (ppm)=7.80-7.59 (6H), 7.51-7.12 (25H), 1.51 (12H)

[Chemical Formula 782]

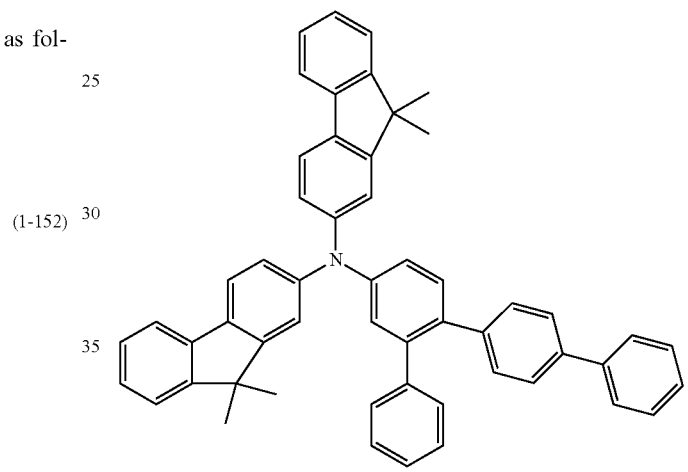

(1-153)

Example 21

Synthesis of N,N-bis{4-(naphthalen-1-yl)phenyl}-N-{6-(biphenyl-4-yl)biphenyl-3-yl}amine (Compound 1-155)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N,N-bis{4-(naphthalen-1-yl)phenyl}-N-(6-bromobiphenyl-3-yl)amine, whereby a light yellowish white powder of N,N-bis{4-(naphthalen-1-yl)phenyl}-N-{6-(biphenyl-4-yl)biphenyl-3-yl}amine (Compound 1-155, 10.6 g, yield: 79%) was obtained.

The structure of the obtained light yellowish white powder was identified by NMR.

$^1$H-NMR (CDCl$_3$) detected 39 hydrogen signals, as follows.

δ (ppm)=8.08-8.14 (2H), 7.88-7.96 (4H), 7.24-7.64 (33H)

[Chemical Formula 783]

(1-155)

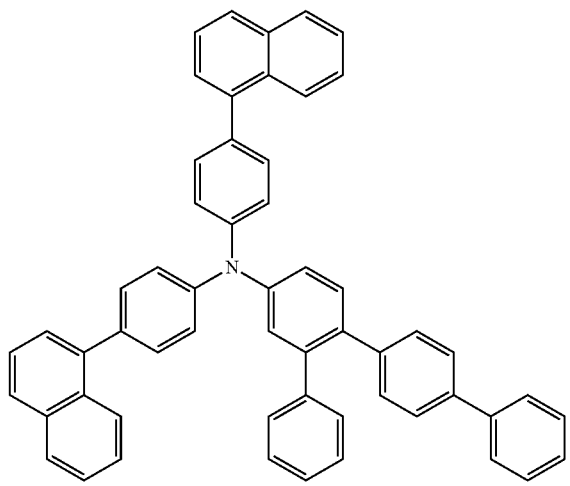

Example 22

Synthesis of N,N-bis{4-(naphthalen-1-yl)phenyl}-N-[6-{4-(naphthalen-1-yl)phenyl}biphenyl-3-yl]amine (Compound 1-156)

The reaction was carried out under the same conditions as those of Example 1, except that phenylboronic acid was replaced with 4-(naphthalen-1-yl)phenylboronic acid, and N,N-bis(biphenyl-4-yl)-N-(6-bromobiphenyl-3-yl)amine was replaced with N,N-bis{4-(naphthalen-1-yl)phenyl}-N-(6-bromobiphenyl-3-yl)amine, whereby a light yellowish white powder of N,N-bis{4-(naphthalen-1-yl)phenyl}-N-[6-{4-(naphthalen-1-yl)phenyl}biphenyl-3-yl]amine (Compound 1-156, 10.6 g, yield: 79%) was obtained.

The structure of the obtained light yellowish white powder was identified by NMR.

$^1$H-NMR (CDCl$_3$) detected 41 hydrogen signals, as follows.

δ (ppm)=8.14 (2H), 7.99-7.72 (6H), 7.61-7.10 (33H)

[Chemical Formula 784]

(1-156)

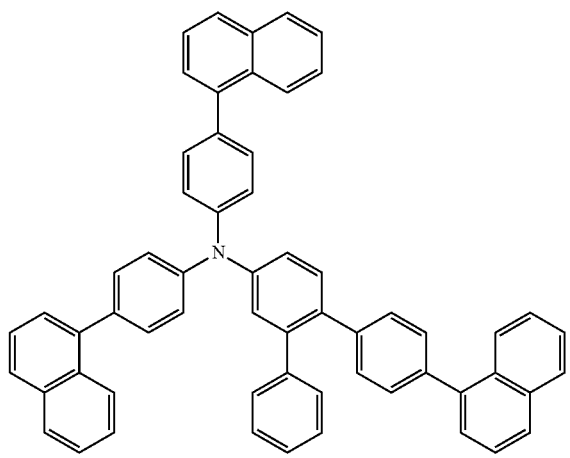

Example 23

Synthesis of N,N-bis{4-(naphthalen-1-yl)phenyl}-N-[6-{4-(naphthalen-2-yl)phenyl}biphenyl-3-yl]amine (Compound 1-157)

The reaction was carried out under the same conditions as those of Example 1, except that phenylboronic acid was replaced with 4-(naphthalen-2-yl)phenylboronic acid, and N,N-bis(biphenyl-4-yl)-N-(6-bromobiphenyl-3-yl)amine was replaced with N,N-bis{4-(naphthalen-1-yl)phenyl}-N-(6-bromobiphenyl-3-yl)amine, whereby a light yellowish white powder of N,N-bis{4-(naphthalen-1-yl)phenyl}-N-[6-{4-(naphthalen-2-yl)phenyl}biphenyl-3-yl]amine (Compound 1-157, 9.7 g, yield: 74%) was obtained.

The structure of the obtained light yellowish white powder was identified by NMR.

$^1$H-NMR (CDCl$_3$) detected 41 hydrogen signals, as follows.

δ (ppm)=8.08-8.14 (3H), 7.66-7.97 (8H), 7.28-7.66 (30H)

[Chemical Formula 785]

(1-157)

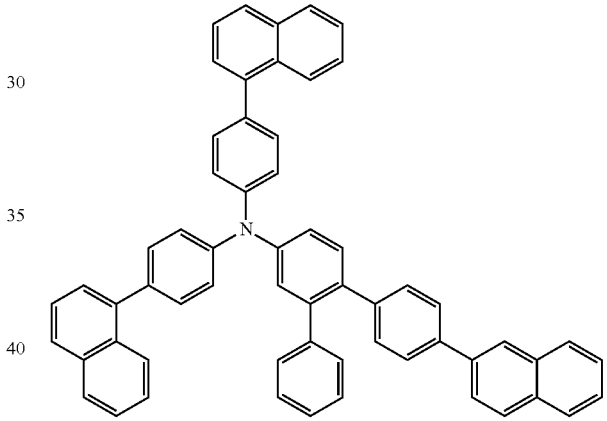

Example 24

Synthesis of N,N-bis{4-(naphthalen-1-yl)phenyl}-N-{6-(p-terphenyl-4-yl)biphenyl-3-yl}amine (Compound 1-158)

The reaction was carried out under the same conditions as those of Example 1, except that phenylboronic acid was replaced with 4-(p-terphenyl)boronic acid pinacol ester, and N,N-bis(biphenyl-4-yl)-N-(6-bromobiphenyl-3-yl)amine was replaced with N,N-bis{4-(naphthalen-1-yl)phenyl}-N-(6-bromobiphenyl-3-yl)amine, whereby a light yellowish white powder of N,N-bis{4-(naphthalen-1-yl)phenyl}-N-{6-(p-terphenyl-4-yl)biphenyl-3-yl}amine (Compound 1-158, 6.2 g, yield: 63%) was obtained.

The structure of the obtained light yellowish white powder was identified by NMR.

$^1$H-NMR (CDCl$_3$) detected 43 hydrogen signals, as follows.

δ (ppm)=8.08-8.14 (3H), 7.89-7.95 (4H), 7.25-7.71 (36H)

[Chemical Formula 786]

(1-158)

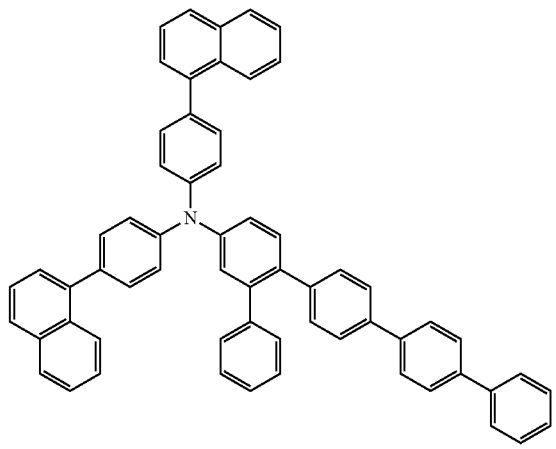

Example 25

Synthesis of N,N-bis{4-(naphthalen-1-yl)phenyl}-N-{6-(biphenyl-2-yl)biphenyl-3-yl}amine (Compound 1-159)

The reaction was carried out under the same conditions as those of Example 1, except that phenylboronic acid was replaced with 2-biphenylboronic acid, and N,N-bis(biphenyl-4-yl)-N-(6-bromobiphenyl-3-yl)amine was replaced with bis{4-(naphthalen-1-yl)phenyl}-N-(6-bromobiphenyl-3-yl)amine, whereby a light yellowish white powder of N,N-bis{4-(naphthalen-1-yl)phenyl}-N-{6-(biphenyl-2-yl)biphenyl-3-yl}amine (Compound 1-159, 4.9 g, yield: 48%) was obtained.

The structure of the obtained light yellowish white powder was identified by NMR.

$^1$H-NMR (CDCl$_3$) detected 39 hydrogen signals, as follows.

δ (ppm)=8.08-8.12 (2H), 7.86-7.94 (4H), 7.00-7.57 (29H), 6.63-6.75 (4H)

[Chemical Formula 787]

(1-159)

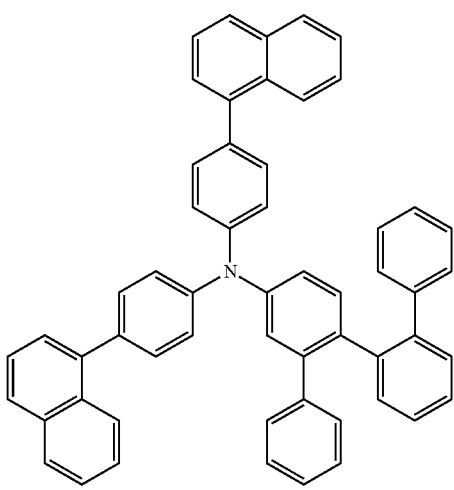

Example 26

Synthesis of N-(biphenyl-4-yl)-N-{4-(9,9-dimethylfluoren-2-yl)phenyl}-N-(6-phenylbiphenyl-3-yl) amine (Compound 1-160)

The reaction was carried out under the same conditions as those of Example 1, except that N,N-bis(biphenyl-4-yl)-N-(6-bromobiphenyl-3-yl)amine was replaced with N-(biphenyl-4-yl)-N-{4-(9,9-dimethylfluoren-2-yl)phenyl}-N-(6-bromobiphenyl-3-yl)amine, whereby a white powder of N-(biphenyl-4-yl)-N-{4-(9,9-dimethylfluoren-2-yl)phenyl}-N-(6-phenylbiphenyl-3-yl)amine (Compound 1-160, 8.3 g, yield: 48%) was obtained.

The structure of the obtained white powder was identified by NMR.

$^1$H-NMR (CDCl$_3$) detected 39 hydrogen signals, as follows.

δ (ppm)=7.79 (2H), 7.69-7.52 (7H), 7.50-7.41 (3H), 7.40-7.10 (21H), 1.57 (6H)

[Chemical Formula 788]

(1-160)

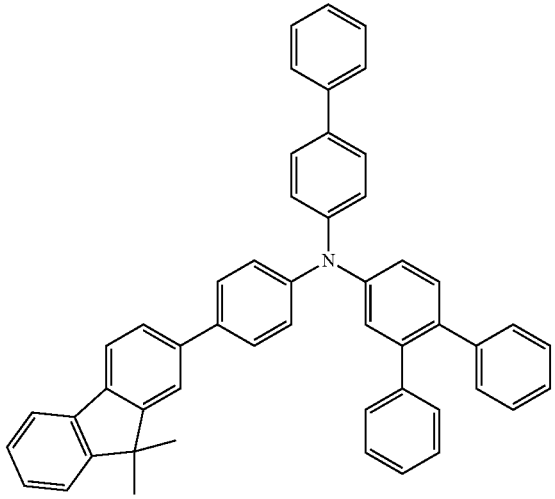

Example 27

Synthesis of N-(biphenyl-4-yl)-N-{4-(9,9-dimethylfluoren-2-yl)phenyl}-N-{6-(biphenyl-3-yl)biphenyl-3-yl}amine (Compound 1-162)

The reaction was carried out under the same conditions as those of Example 1, except that phenylboronic acid was replaced with 3-biphenylboronic acid, and N,N-bis(biphenyl-4-yl)-N-(6-bromobiphenyl-3-yl)amine was replaced with N-(biphenyl-4-yl)-N-{4-(9,9-dimethylfluoren-2-yl) phenyl}-N-(6-bromobiphenyl-3-yl)amine, whereby a white powder of N-(biphenyl-4-yl)-N-{4-(9,9-dimethylfluoren-2-yl)phenyl}-N-{6-(biphenyl-3-yl)biphenyl-3-yl}amine (Compound 1-162, 8.7 g, yield: 49%) was obtained.

The structure of the obtained white powder was identified by NMR.

$^1$H-NMR (CDCl$_3$) detected 43 hydrogen signals, as follows

δ (ppm)=7.78 (2H), 7.65-7.46 (6H), 7.45-7.05 (29H), 1.54 (6H) .

[Chemical Formula 789]

(1-162)

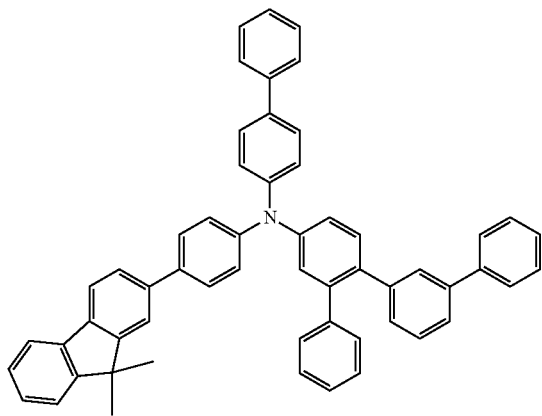

Example 28

Synthesis of N-(biphenyl-4-yl)-N-{4-(naphthalen-2-yl)phenyl}-N-{6-(biphenyl-4-yl)biphenyl-3-yl}amine (Compound 1-163)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N-(biphenyl-4-yl)-N-{4-(naphthalen-2-yl)phenyl}-N-(6-bromobiphenyl-3-yl)amine, whereby a white powder of N-(biphenyl-4-yl)-N-{4-(naphthalen-2-yl)phenyl}-N-{6-(biphenyl-4-yl)biphenyl-3-yl}amine (Compound 1-163, 4.9 g, yield: 44%) was obtained.

The structure of the obtained white powder was identified by NMR.

$^1$H-NMR (CDCl$_3$) detected 37 hydrogen signals, as follows.

δ (ppm)=7.73 (1H), 7.61-7.70 (3H), 7.54-7.58 (1H), 7.19-7.52 (32H)

[Chemical Formula 790]

(1-163)

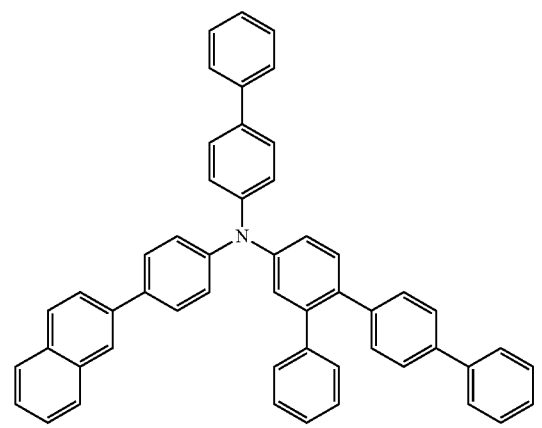

Example 29

Synthesis of N-(biphenyl-4-yl)-N-{4-(naphthalen-2-yl)phenyl}-N-[6-{4-(naphthalen-1-yl)phenyl}biphenyl-3-yl]amine (Compound 1-164)

The reaction was carried out under the same conditions as those of Example 1, except that phenylboronic acid was replaced with 4-(naphthalen-1-yl)phenylboronic acid, and N,N-bis(biphenyl-4-yl)-N-(6-bromobiphenyl-3-yl)amine was replaced with N-(biphenyl-4-yl)-N-{4-(naphthalen-2-yl)phenyl}-N-(6-bromobiphenyl-3-yl)amine, whereby a white powder of N-(biphenyl-4-yl)-N-{4-(naphthalen-2-yl)phenyl}-N-[6-{4-(naphthalen-1-yl)phenyl}biphenyl-3-yl]amine (Compound 1-164, 9.2 g, yield: 74%) was obtained.

The structure of the obtained white powder was identified by NMR.

$^1$H-NMR (CDCl$_3$) detected 39 hydrogen signals, as follows.

δ (ppm)=8.10 (1H), 7.89-7.10 (38H)

[Chemical Formula 791]

(1-164)

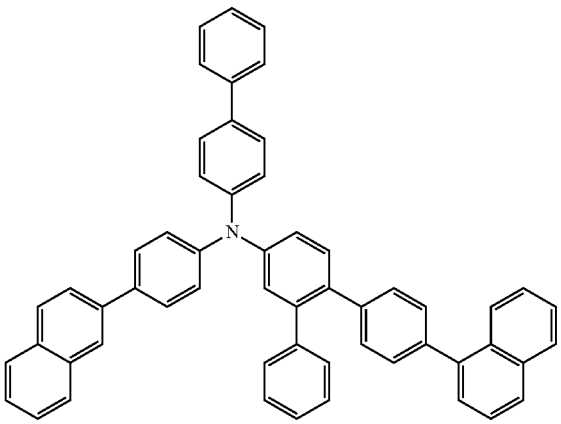

Example 30

Synthesis of N-(biphenyl-4-yl)-N-{4-(naphthalen-2-yl)phenyl}-N-[6-{4-(naphthalen-2-yl)phenyl}biphenyl-3-yl]amine (Compound 1-165)

The reaction was carried out under the same conditions as those of Example 1, except that phenylboronic acid was replaced with 4-naphthalen-2-ylphenylboronic acid, and N,N-bis(biphenyl-4-yl)-N-(6-bromobiphenyl-3-yl)amine was replaced with N-(biphenyl-4-yl)-N-{4-(naphthalen-2-yl)phenyl}-N-(6-bromobiphenyl-3-yl)amine, whereby a white powder of N-(biphenyl-4-yl)-N-{4-(naphthalen-2-yl)phenyl}-N-[6-{4-(naphthalen-2-yl)phenyl}biphenyl-3-yl]amine (Compound 1-165, 9.8 g, yield: 70%) was obtained.

The structure of the obtained white powder was identified by NMR.

$^1$H-NMR (CDCl$_3$) detected 39 hydrogen signals, as follows.

δ (ppm)=8.07 (2H), 7.99-7.85 (6H), 7.84-7.40 (15H), 7.39-7.12 (16H)

[Chemical Formula 792]

(1-165)

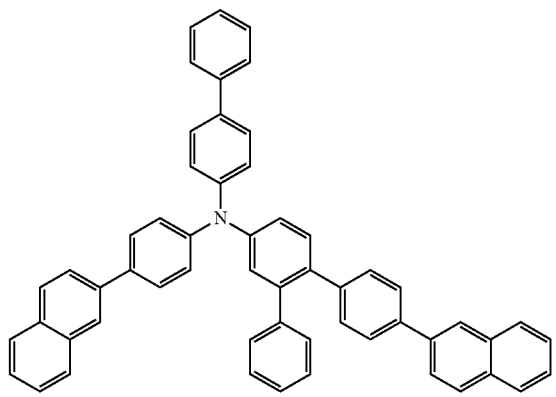

Example 31

Synthesis of N-(biphenyl-4-yl)-N-(9,9-diphenylfluoren-2-yl)-N-(6-phenylbiphenyl-3-yl)amine (Compound 1-166)

The reaction was carried out under the same conditions as those of Example 1, except that N,N-bis(biphenyl-4-yl)-N-(6-bromobiphenyl-3-yl)amine was replaced with N-(biphenyl-4-yl)-N-(9,9-diphenylfluoren-2-yl)-N-(6-bromobiphenyl-3-yl)amine, whereby a white powder of N-(biphenyl-4-yl)-N-(9,9-diphenylfluoren-2-yl)-N-(6-phenylbiphenyl-3-yl)amine (Compound 1-166, 11.0 g, yield: 61%) was obtained.

The structure of the obtained white powder was identified by NMR.

$^1$H-NMR (CDCl$_3$) detected 39 hydrogen signals, as follows.

δ (ppm)=7.60-7.74 (4H), 7.14-7.52 (33H), 7.00-7.03 (2H)

[Chemical Formula 793]

(1-166)

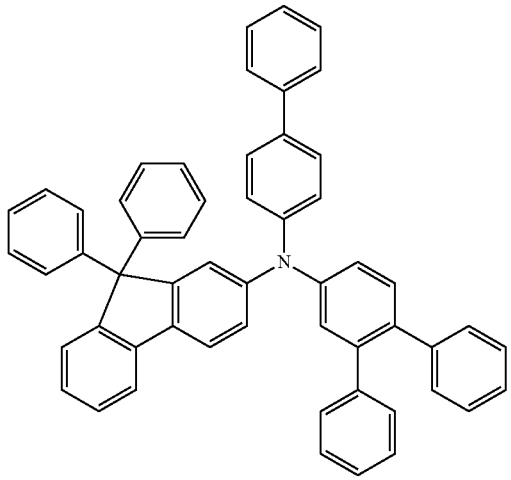

Example 32

Synthesis of N-(p-terphenyl-4-yl)-N-(9,9-dimethylfluoren-2-yl)-N-(6-phenylbiphenyl-3-yl)amine (Compound 1-167)

The reaction was carried out under the same conditions as those of Example 1, except that N,N-bis(biphenyl-4-yl)-N-(6-bromobiphenyl-3-yl)amine was replaced with N-(p-terphenyl-4-yl)-N-(9,9-dimethylfluoren-2-yl)-N-(6-bromobiphenyl-3-yl)amine, whereby a white powder of N-(p-terphenyl-4-yl)-N-(9,9-dimethylfluoren-2-yl)-N-(6-phenylbiphenyl-3-yl)amine (Compound 1-167, 18.3 g, yield: 74%) was obtained.

The structure of the obtained white powder was identified by NMR.

$^1$H-NMR (CDCl$_3$) detected 39 hydrogen signals, as follows.

δ (ppm)=7.72-7.57 (6H), 7.51-7.11 (27H), 1.53 (6H)

[Chemical Formula 794]

(1-167)

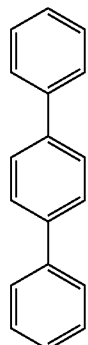
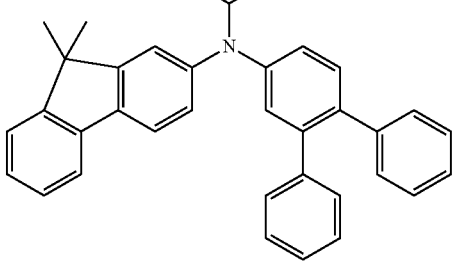

Example 33

Synthesis of N-(9,9-dimethylfluoren-2-yl)-N-{4-(naphthalen-2-yl)phenyl}-N-{6-(biphenyl-4-yl)biphenyl-3-yl}amine (Compound 1-169)

The reaction was carried out under the same conditions as those of Example 1, except that phenylboronic acid was replaced with 4-biphenylboronic acid, and N,N-bis(biphe nyl-4-yl)-N-(6-bromobiphenyl-3-yl)amine was replaced with N-(9,9-dimethylfluoren-2-yl)-N-{(4-naphthalen-2-yl)phenyl}-N-(6-bromobiphenyl-3-yl)amine, whereby a white powder of N-(9,9-dimethylfluoren-2-yl)-N-{4-(naphthalen-2-yl)phenyl}-N-{6-(biphenyl-4-yl)biphenyl-3-yl}amine (Compound 1-169, 10.4 g, yield: 67%) was obtained.

The structure of the obtained white powder was identified by NMR.

$^1$H-NMR (CDCl$_3$) detected 41 hydrogen signals, as follows.

δ (ppm)=8.12 (1H), 7.78-7.92 (4H), 7.60-7.71 (6H), 7.21-7.54 (24H), 1.53 (6H)

[Chemical Formula 795]

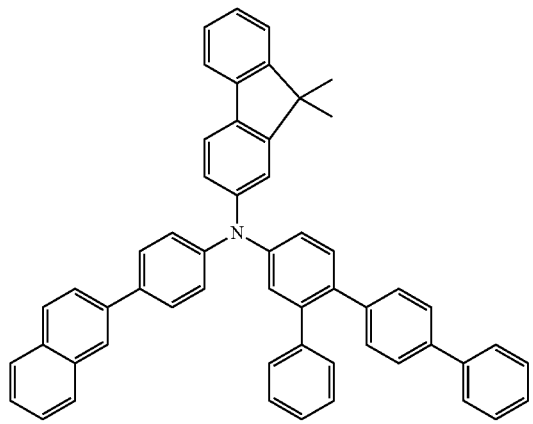

(1-169)

Example 34

Synthesis of N-(biphenyl-4-yl)-N-{4-(naphthalen-2-yl)phenyl}-N-{2-(biphenyl-4-yl)biphenyl-4-yl}amine (Compound 1-170)

The reaction was carried out under the same conditions as those of Example 1, except that N,N-bis(biphenyl-4-yl)-N-(6-bromobiphenyl-3-yl)amine was replaced with N-(biphenyl-4-yl)-N-{4-(naphthalen-2-yl)phenyl}-N-{2-(biphenyl-4-yl)-bromobenzene-4-yl}amine, whereby a white powder of N-(biphenyl-4-yl)-N-{4-(naphthalen-2-yl)phenyl}-N-{2-(biphenyl-4-yl)biphenyl-4-yl}amine (Compound 1-170, 10.4 g, yield: 67%) was obtained.

The structure of the obtained white powder was identified by NMR.

$^1$H-NMR (CDCl$_3$) detected 37 hydrogen signals, as follows.

δ (ppm)=8.08 (1H), 7.81-7.96 (3H), 7.79-7.81 (1H), 7.21-7.73 (32H)

[Chemical Formula 796]

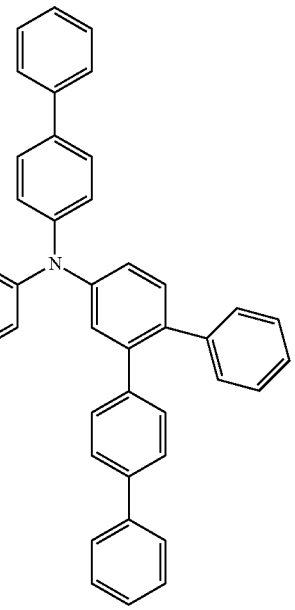

(1-170)

Example 35

Synthesis of N-(biphenyl-4-yl)-N-{4-(naphthalen-2-yl)phenyl}-N-[2-{4-(naphthalen-2-yl)phenyl}biphenyl-4-yl]amine (Compound 1-171)

The reaction was carried out under the same conditions as those of Example 1, except that N,N-bis(biphenyl-4-yl)-N-(6-bromobiphenyl-3-yl)amine was replaced with N-(biphenyl-4-yl)-N-{4-(naphthalen-2-yl)phenyl}-N-[2-{4-(naphthalen-2-yl)phenyl}-(bromobiphenyl-4-yl)]amine, whereby a white powder of N-(biphenyl-4-yl)-N-{4-(naphthalen-2-yl)phenyl}-N-[2-{4-(naphthalen-2-yl)phenyl}biphenyl-4-yl]amine (Compound 1-171, 10.0 g, yield: 81%) was obtained.

The structure of the obtained white powder was identified by NMR.

$^1$H-NMR (CDCl$_3$) detected 39 hydrogen signals, as follows.

δ (ppm)=8.04-8.10 (2H), 7.78-7.96 (8H), 7.24-7.65 (29H)

[Chemical Formula 797]

(1-171)

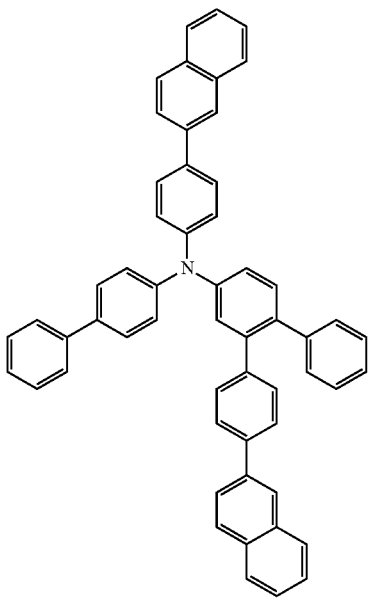

Example 36

Synthesis of N-(biphenyl-4-yl)-N-(9,9-diphenylfluoren-2-yl)-N-{6-(biphenyl-4-yl)biphenyl-3-yl}amine (Compound 1-174)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N-(biphenyl-4-yl)-N-(9,9-diphenylfluoren-2-yl)-N-(6-bromobiphenyl-3-yl)amine, whereby a white powder of N-(biphenyl-4-yl)-N-(9,9-diphenylfluoren-2-yl)-N-{6-(biphenyl-4-yl)biphenyl-3-yl}amine (Compound 1-174, 6.5 g, yield: 71%) was obtained.

The structure of the obtained white powder was identified by NMR.

$^1$H-NMR (CDCl$_3$) detected 43 hydrogen signals, as follows.

δ (ppm)=7.61-7.77 (6H), 7.20-7.51 (34H), 7.06-7.11 (3H)

[Chemical Formula 798]

(1-174)

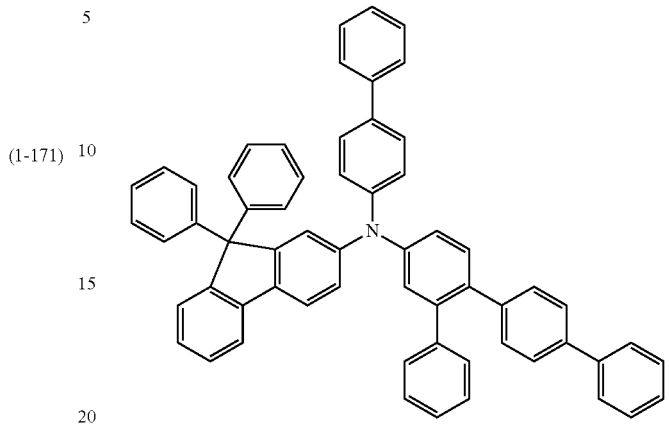

Example 37

Synthesis of N-(biphenyl-4-yl)-N-(9,9-diphenylfluoren-2-yl)-N-{6-(biphenyl-3-yl)biphenyl-3-yl}amine (Compound 1-175)

The reaction was carried out under the same conditions as those of Example 1, except that phenylboronic acid was replaced with 3-biphenylboronic acid, and N,N-bis(biphenyl-4-yl)-N-(6-bromobiphenyl-3-yl)amine was replaced with N-(biphenyl-4-yl)-N-(9,9-diphenylfluoren-2-yl)-(6-bromobiphenyl-3-yl)amine, whereby a white powder of N-(biphenyl-4-yl)-N-(9,9-diphenylfluoren-2-yl)-N-{6-(biphenyl-3-yl)biphenyl-3-yl}amine (Compound 1-175, 8.0 g, yield: 87%) was obtained.

The structure of the obtained white powder was identified by NMR.

$^1$H-NMR (CDCl$_3$) detected 43 hydrogen signals, as follows.

δ (ppm)=7.70-7.76 (2H), 7.63-7.65 (2H), 7.18-7.54 (36H), 7.08-7.12 (3H)

[Chemical Formula 799]

(1-175)

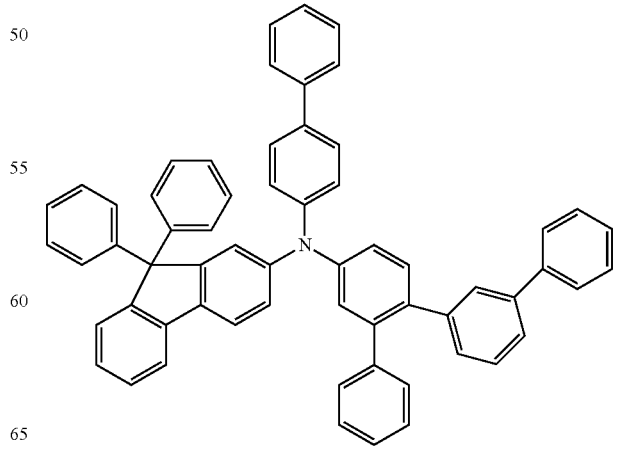

Example 38

Synthesis of N,N-bis(9,9-dimethylfluoren-2-yl)-N-{6-(biphenyl-3-yl)biphenyl-3-yl}amine (Compound 1-176)

The reaction was carried out under the same conditions as those of Example 1, except that phenylboronic acid was replaced with 3-biphenylboronic acid, and N,N-bis(biphenyl-4-yl)-N-(6-bromobiphenyl-3-yl)amine was replaced with N,N-bis(9,9-dimethylfluoren-2-yl)-N-(6-bromobiphenyl-3-yl)amine, whereby a white powder of N,N-bis(9,9-dimethylfluoren-2-yl)-N-{6-(biphenyl-3-yl)biphenyl-3-yl}amine (Compound 1-176, 17.0 g, yield: 85%) was obtained.

The structure of the obtained white powder was identified by NMR.

$^1$H-NMR (CDCl$_3$) detected 43 hydrogen signals, as follows.

δ (ppm)=7.30-7.62 (4H), 7.48-7.14 (27H), 1.50 (12H)

[Chemical Formula 800]

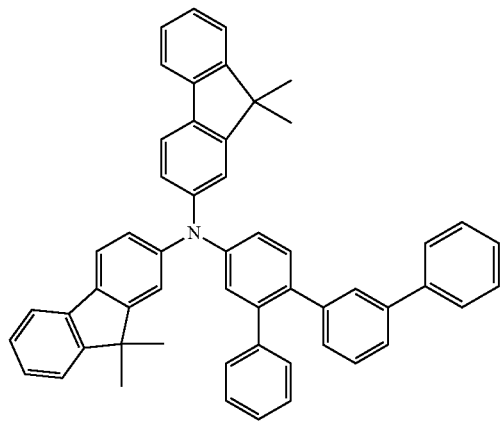

(1-176)

Example 39

Synthesis of N,N-bis(biphenyl-4-yl)-N-{6-(biphenyl-2-yl)-p-terphenyl-3-yl}amine (Compound 1-179)

The reaction was carried out under the same conditions as those of Example 1, except that phenylboronic acid was replaced with 2-biphenylboronic acid, and N,N-bis(biphenyl-4-yl)-N-(6-bromobiphenyl-3-yl)amine was replaced with N,N-bis(biphenyl-4-yl)-N-(6-bromo-p-terphenyl-3-yl)amine, whereby a white powder of N,N-bis(biphenyl-4-yl)-N-{6-(biphenyl-2-yl)-p-terphenyl-3-yl}amine (Compound 1-179, 9.6 g, yield: 86%) was obtained.

The structure of the obtained white powder was identified by NMR.

$^1$H-NMR (CDCl$_3$) detected 39 hydrogen signals, as follows.

δ (ppm)=7.54-7.66 (10H), 7.08-7.49 (25H), 6.63-6.74 (4H)

[Chemical Formula 801]

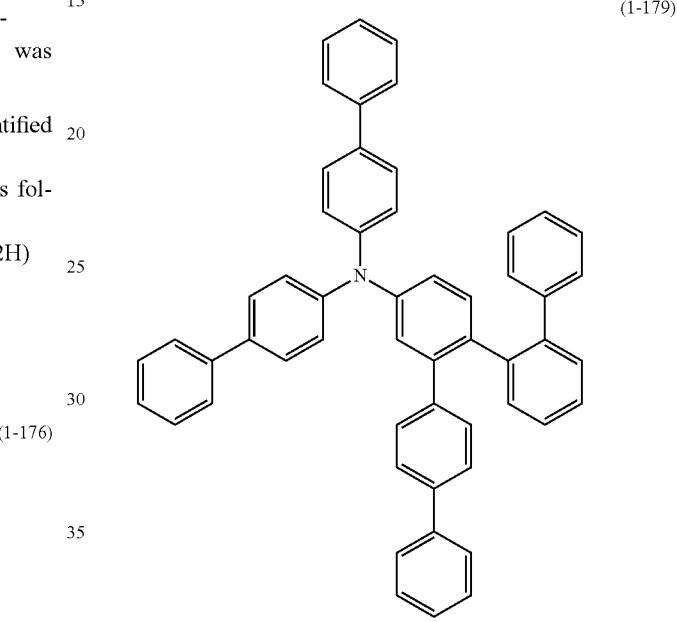

(1-179)

Example 40

Synthesis of N-(biphenyl-4-yl)-N-(9,9-diphenylfluoren-2-yl)-N-{6-(biphenyl-2-yl)biphenyl-3-yl}amine (Compound 1-180)

The reaction was carried out under the same conditions as those of Example 1, except that phenylboronic acid was replaced with 2-biphenylboronic acid, and N,N-bis(biphenyl-4-yl)-N-(6-bromobiphenyl-3-yl)amine was replaced with N-(biphenyl-4-yl)-N-(9,9-diphenylfluoren-2-yl)-N-(6-bromobiphenyl-3-yl)amine, whereby a white powder of N-(biphenyl-4-yl)-N-(9,9-diphenylfluoren-2-yl)-N-{6-(biphenyl-2-yl)biphenyl-3-yl}amine (Compound 1-180, 5.2 g, yield: 57%) was obtained.

The structure of the obtained white powder was identified by NMR.

$^1$H-NMR (CDCl$_3$) detected 43 hydrogen signals, as follows.

δ (ppm)=7.60-7.74 (4H), 6.95-7.49 (35H), 6.68-6.71 (2H), 6.54-6.57 (2H)

[Chemical Formula 802]

(1-180)

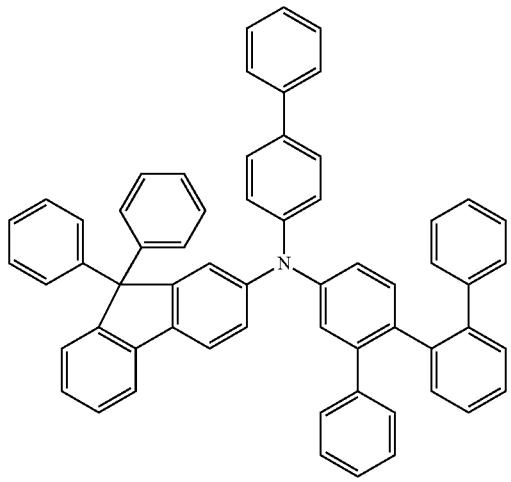

Example 41

Synthesis of N-(9,9-dimethylfluoren-2-yl)-N-{4-(naphthalen-1-yl)phenyl}-N-{6-(biphenyl-4-yl)biphenyl-3-yl}amine (Compound 1-183)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N-(9,9-dimethylfluoren-2-yl)-N-{4-(naphthalen-1-yl)phenyl}-N-(6-bromobiphenyl-3-yl)amine, whereby a white powder of N-(9,9-dimethylfluoren-2-yl)-N-{4-(naphthalen-1-yl)phenyl}-N-{6-(biphenyl-4-yl)biphenyl-3-yl}amine (Compound 1-183, 19.9 g, yield: 89%) was obtained.

The structure of the obtained white powder was identified by NMR.

$^1$H-NMR (CDCl$_3$) detected 41 hydrogen signals, as follows.

δ (ppm)=8.10 (1H), 7.93 (1H), 7.88 (1H), 7.71 (2H), 7.65-7.15 (30H), 1.53 (6H)

[Chemical Formula 803]

(1-183)

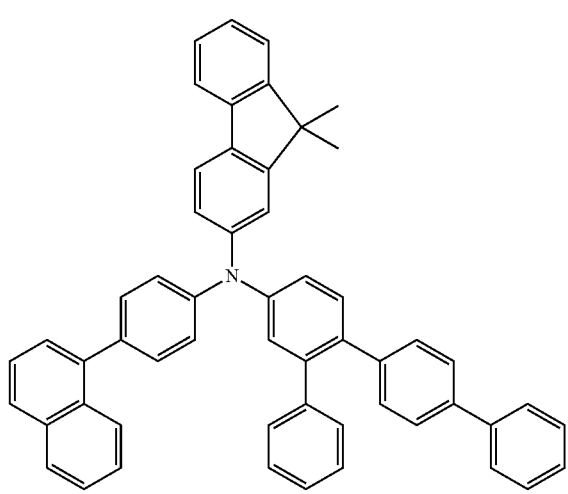

Example 42

Synthesis of N-(9,9-diphenylfluoren-2-yl)-N-{6-(biphenyl-4-yl)biphenyl-3-yl}aniline (Compound 1-217)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N-(9,9-diphenylfluoren-2-yl)-N-(6-bromobiphenyl-3-yl)aniline, whereby a white powder of N-(9,9-diphenylfluoren-2-yl)-N-{6-(biphenyl-4-yl)biphenyl-3-yl}aniline (Compound 1-217, 4.2 g, yield: 37%) was obtained.

The structure of the obtained white powder was identified by NMR.

$^1$H-NMR (CDCl$_3$) detected 39 hydrogen signals, as follows.

δ (ppm)=7.76-7.62 (4H), 7.44-7.03 (35H)

[Chemical Formula 804]

(1-217)

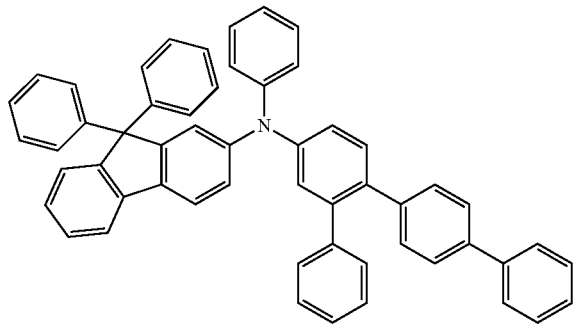

Example 43

Synthesis of N,N-bis{4-(naphthalen-2-yl)phenyl}-N-[6-{4-(naphthalen-1-yl)phenyl}biphenyl-3-yl]amine (Compound 1-185)

The reaction was carried out under the same conditions as those of Example 1, except that phenylboronic acid was replaced with 4-(naphthalen-1-yl)phenylboronic acid, and N,N-bis(biphenyl-4-yl)-N-(6-bromobiphenyl-3-yl)amine was replaced with N,N-bis{4-(naphthalen-2-yl)phenyl}-N-(6-bromobiphenyl-3-yl)amine, whereby a white powder of N,N-bis{4-(naphthalen-2-yl)phenyl}-N-[6-{4-(naphthalen-1-yl)phenyl}biphenyl-3-yl]amine (Compound 1-185, 6.5 g, yield: 73%) was obtained.

The structure of the obtained white powder was identified by NMR.

$^1$H-NMR (CDCl$_3$) detected 41 hydrogen signals, as follows.

δ (ppm)=8.11 (2H), 7.98-7.68 (18H), 7.59-7.23 (21H)

[Chemical Formula 805]

(1-185)

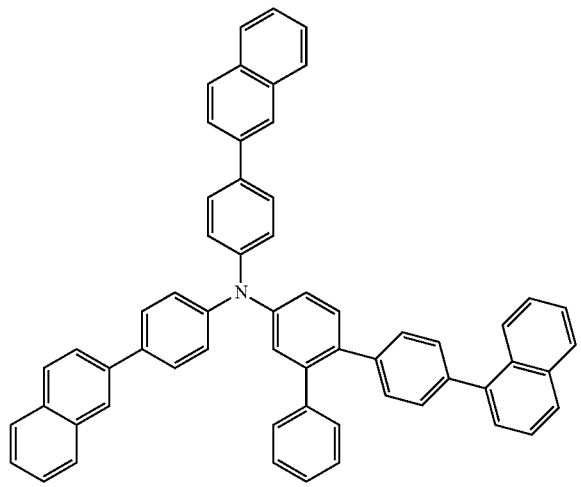

Example 44

Synthesis of N-(biphenyl-4-yl)-N-(phenanthren-9-yl)-N-(6-phenylbiphenyl-3-yl)amine (Compound 1-187)

The reaction was carried out under the same conditions as those of Example 1, except that N,N-bis(biphenyl-4-yl)-N-(6-bromobiphenyl-3-yl)amine was replaced with N-(biphenyl-4-yl)-N-(phenanthren-9-yl)-N-(6-bromobiphenyl-3-yl)amine, whereby a white powder of N-(biphenyl-4-yl)-N-(phenanthren-9-yl)-N-(6-phenylbiphenyl-3-yl)amine (Compound 1-187, 3.5 g, yield: 22%) was obtained.

The structure of the obtained white powder was identified by NMR.

$^1$H-NMR (CDCl$_3$) detected 31 hydrogen signals, as follows.

δ (ppm)=8.81-8.70 (2H), 8.17 (1H), 7.83 (1H), 7.78 (1H), 7.74-7.72 (26H)

[Chemical Formula 806]

(1-187)

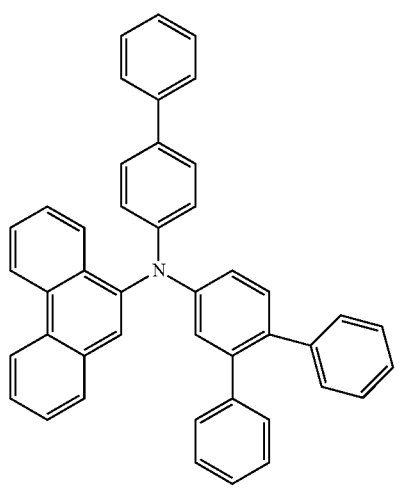

Example 45

Synthesis of N-(biphenyl-4-yl)-N-(phenanthren-9-yl)-N-{6-(biphenyl-4-yl)biphenyl-3-yl}amine (Compound 1-188)

The reaction was carried out under the same conditions as those of Example 1, except that phenylboronic acid was replaced with 4-biphenylboronic acid, and N,N-bis(biphenyl-4-yl)-N-(6-bromobiphenyl-3-yl)amine was replaced with N-(biphenyl-4-yl)-N-(phenanthren-9-yl)-N-(6-bromobiphenyl-3-yl)amine, whereby a white powder of N-(biphenyl-4-yl)-N-(phenanthren-9-yl)-N-{6-(biphenyl-4-yl)biphenyl-3-yl}amine (Compound 1-188, 13.0 g, yield: 77%) was obtained.

The structure of the obtained white powder was identified by NMR.

$^1$H-NMR (CDCl$_3$) detected 35 hydrogen signals, as follows.

δ (ppm)=8.82-8.73 (2H), 8.17 (1H), 7.85 (1H), 7.78 (1H), 7.75-7.09 (30H)

[Chemical Formula 807]

(1-188)

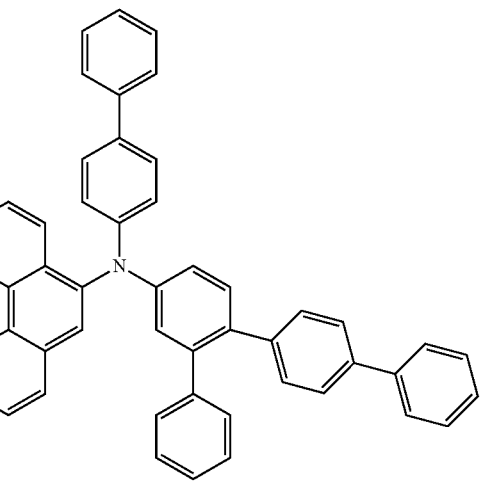

Example 46

Synthesis of N-(biphenyl-4-yl)-N-(9-phenylcarbazol-2-yl)-N-{6-(biphenyl-4-yl)biphenyl-3-yl}amine (Compound 1-189)

The reaction was carried out under the same conditions as those of Example 19, except that 4-bromobiphenyl was replaced with 2-bromo-9-phenylcarbazole, and 2-{4-(naphthalen-1-yl)phenyl)}-4-aminobiphenyl was replaced with N-(biphenyl-4-yl)-N-{6-(biphenyl-4-yl)biphenyl-3-yl}amine, whereby a white powder of N-(biphenyl-4-yl)-N-(9-phenylcarbazol-2-yl)-N-{6-(biphenyl-4-yl)biphenyl-3-yl}amine (Compound 1-189, 18.0 g, yield: 85%) was obtained.

The structure of the obtained white powder was identified by NMR.

$^1$H-NMR (CDCl$_3$) detected 38 hydrogen signals, as follows.

δ (ppm)=8.13-8.06 (2H), 7.65-7.59 (4H), 7.57-7.50 (6H), 7.49-7.10 (26H)

[Chemical Formula 808]

(1-189)

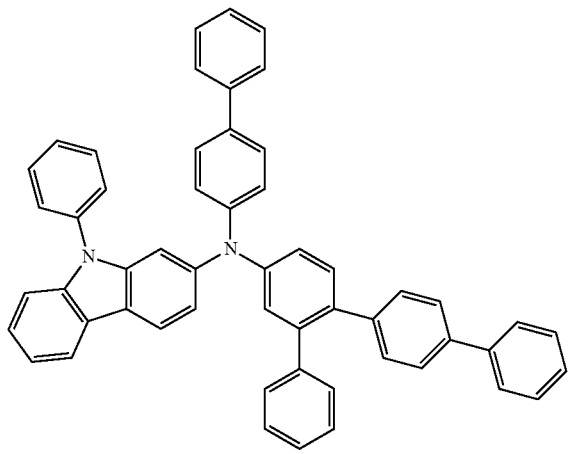

Example 47

Synthesis of N-(biphenyl-4-yl)-N-(9,9'-spirobi[9H-fluoren]-2-yl)-N-(6-phenylbiphenyl-3-yl)amine (Compound 1-190)

The reaction was carried out under the same conditions as those of Example 1, except that N,N-bis(biphenyl-4-yl)-N-(6-bromobiphenyl-3-yl)amine was replaced with N-(biphenyl-4-yl)-N-(9,9'-spirobi[9H-fluoren]-2-yl)-N-(6-bromobiphenyl-3-yl)amine, whereby a white powder of N-(biphenyl-4-yl)-N-(9,9'-spirobi[9H-fluoren]-2-yl)-N-(6-phenylbiphenyl-3-yl)amine (Compound 1-190, 6.0 g, yield: 52%) was obtained.

The structure of the obtained white powder was identified by NMR.

$^1$H-NMR (CDCl$_3$) detected 37 hydrogen signals, as follows.

δ (ppm)=7.85-7.72 (4H), 7.57 (2H), 7.49-7.29 (8H), 7.23-6.95 (17H), 6.88-6.82 (4H), 6.80-6.66 (2H)

[Chemical Formula 809]

(1-190)

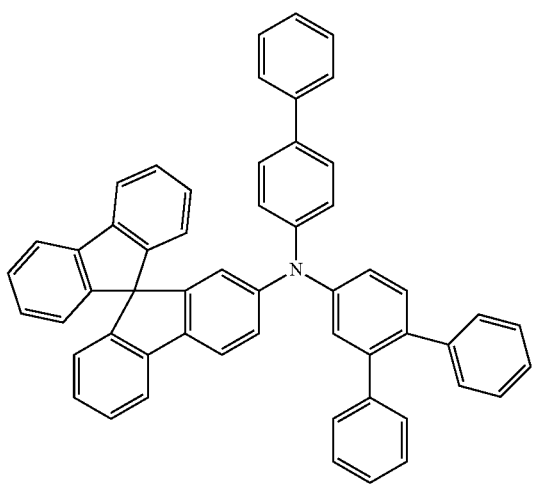

Example 48

The melting points and the glass transition points of the arylamine compounds of the general formula (1) were measured using a high-sensitive differential scanning calorimeter (DSC3100SA produced by Bruker AXS).

|  | Melting point | Glass transition point |
| --- | --- | --- |
| Compound of Example 2 | 242° C. | 103° C. |
| Compound of Example 3 | No melting point observed | 115° C. |
| Compound of Example 4 | No melting point observed | 104° C. |
| Compound of Example 5 | No melting point observed | 117° C. |
| Compound of Example 6 | No melting point observed | 107° C. |
| Compound of Example 7 | 240° C. | 127° C. |
| Compound of Example 8 | No melting point observed | 116° C. |
| Compound of Example 9 | No melting point observed | 119° C. |
| Compound of Example 10 | No melting point observed | 101° C. |
| Compound of Example 11 | No melting point observed | 112° C. |
| Compound of Example 12 | No melting point observed | 102° C. |
| Compound of Example 13 | No melting point observed | 109° C. |
| Compound of Example 14 | 237° C. | 108° C. |
| Compound of Example 15 | No melting point observed | 119° C. |
| Compound of Example 16 | No melting point observed | 109° C. |
| Compound of Example 17 | No melting point observed | 113° C. |
| Compound of Example 18 | No melting point observed | 121° C. |
| Compound of Example 19 | No melting point observed | 111° C. |
| Compound of Example 20 | 246° C. | 132° C. |
| Compound of Example 21 | No melting point observed | 117° C. |
| Compound of Example 22 | No melting point observed | 119° C. |
| Compound of Example 23 | 245° C. | 120° C. |
| Compound of Example 24 | 240° C. | 125° C. |
| Compound of Example 25 | No melting point observed | 107° C. |
| Compound of Example 26 | 244° C. | 113° C. |
| Compound of Example 27 | No melting point observed | 112° C. |
| Compound of Example 28 | No melting point observed | 110° C. |
| Compound of Example 29 | No melting point observed | 112° C. |
| Compound of Example 30 | No melting point observed | 115° C. |
| Compound of Example 31 | No melting point observed | 125° C. |
| Compound of Example 32 | No melting point observed | 114° C. |
| Compound of Example 33 | No melting point observed | 122° C. |
| Compound of Example 34 | No melting point observed | 111° C. |
| Compound of Example 35 | No melting point observed | 119° C. |
| Compound of Example 36 | No melting point observed | 137° C. |
| Compound of Example 37 | No melting point observed | 125° C. |
| Compound of Example 38 | 233° C. | 120° C. |
| Compound of Example 39 | 232° C. | 110° C. |
| Compound of Example 40 | No melting point observed | 126° C. |
| Compound of Example 41 | No melting point observed | 122° C. |
| Compound of Example 42 | No melting point observed | 125° C. |
| Compound of Example 43 | No melting point observed | 116° C. |
| Compound of Example 44 | No melting point observed | 115° C. |
| Compound of Example 45 | No melting point observed | 129° C. |
| Compound of Example 46 | No melting point observed | 121° C. |
| Compound of Example 47 | No melting point observed | 129° C. |

The arylamine compounds of the general formula (1) have glass transition points of 100° C. or higher, demonstrating that the compounds have a stable thin-film state.

Example 49

A 100 nm-thick vapor-deposited film was fabricated on an ITO substrate using the arylamine compounds of the general formula (1), and a work function was measured using an ionization potential measuring device (PYS-202 produced by Sumitomo Heavy Industries, Ltd.).

|  | Work function |
| --- | --- |
| Compound of Example 1 | 5.68 eV |
| Compound of Example 2 | 5.72 eV |
| Compound of Example 3 | 5.66 eV |

-continued

| | Work function |
|---|---|
| Compound of Example 4 | 5.67 eV |
| Compound of Example 5 | 5.70 eV |
| Compound of Example 6 | 5.71 eV |
| Compound of Example 7 | 5.66 eV |
| Compound of Example 8 | 5.62 eV |
| Compound of Example 9 | 5.55 eV |
| Compound of Example 10 | 5.72 eV |
| Compound of Example 11 | 5.75 eV |
| Compound of Example 12 | 5.62 eV |
| Compound of Example 13 | 5.62 eV |
| Compound of Example 14 | 5.62 eV |
| Compound of Example 15 | 5.63 eV |
| Compound of Example 16 | 5.73 eV |
| Compound of Example 17 | 5.69 eV |
| Compound of Example 18 | 5.71 eV |
| Compound of Example 19 | 5.72 eV |
| Compound of Example 20 | 5.55 eV |
| Compound of Example 21 | 5.72 eV |
| Compound of Example 22 | 5.73 eV |
| Compound of Example 23 | 5.72 eV |
| Compound of Example 24 | 5.73 eV |
| Compound of Example 25 | 5.73 eV |
| Compound of Example 26 | 5.63 eV |
| Compound of Example 27 | 5.64 eV |
| Compound of Example 28 | 5.69 eV |
| Compound of Example 29 | 5.69 eV |
| Compound of Example 30 | 5.67 eV |
| Compound of Example 31 | 5.66 eV |
| Compound of Example 32 | 5.61 eV |
| Compound of Example 33 | 5.62 eV |
| Compound of Example 34 | 5.70 eV |
| Compound of Example 35 | 5.71 eV |
| Compound of Example 36 | 5.67 eV |
| Compound of Example 37 | 5.68 eV |
| Compound of Example 38 | 5.58 eV |
| Compound of Example 39 | 5.72 eV |
| Compound of Example 40 | 5.64 eV |
| Compound of Example 41 | 5.63 eV |
| Compound of Example 42 | 5.71 eV |
| Compound of Example 43 | 5.68 eV |
| Compound of Example 44 | 5.76 eV |
| Compound of Example 45 | 5.74 eV |
| Compound of Example 46 | 5.60 eV |
| Compound of Example 47 | 5.64 eV |

As the results show, the arylamine compounds of the general formula (1) have desirable energy levels compared to the work function 5.4 eV of common hole transport materials such as NPD and TPD, and thus possess desirable hole transportability.

Example 50

Synthesis of N5',N5',N9',N9'-tetrakis{4-(tert-butyl)phenyl}spiro(fluorene-9,7'-fluoreno[4,3-b]benzofuran)-5',9'-diamine (Compound 7-1)

5',9'-dibromospiro(fluorene-9,7'-fluoreno[4,3-b]benzofuran) (5.0 g), bis{4-(tert-butyl)phenyl}amine (6.0 g), palladium acetate (0.08 g), sodium tert-butoxide (3.4 g), tri-tert-butylphosphine (0.07 g), and toluene (60 mL) were added into a nitrogen-substituted reaction vessel and the mixture was heated and stirred for 2 hours under reflux. The mixture was cooled to a room temperature, dichloromethane and water were added, and an organic layer was collected by liquid separation. After the organic layer was concentrated, purification by column chromatography was performed to obtain a powder of N5',N5',N9',N9'-tetrakis{4-(tert-butyl)phenyl}spiro(fluorene-9,7'-fluoreno[4,3-b]benzofuran)-5',9'-diamine (Compound 7-1; 3.1 g; yield 36%)

[Chemical Formula 810]

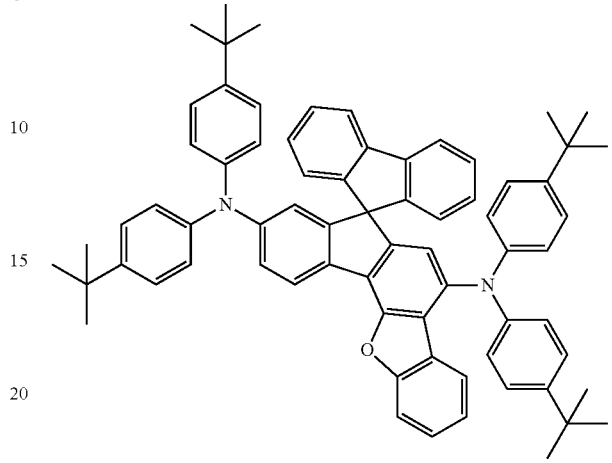

(7-1)

Example 51

Synthesis of N2,N2,N7,N7-tetrakis{4-(tert-butyl)phenyl}spiro(dibenzo[5,6:7,8]fluoreno[4,3-b]benzofuran-5,9'-fluorene)-2,7-diamine (Compound 7-2)

The reaction was carried out under the same conditions as those of Example 50, except that 5',9'-dibromospiro(fluorene-9,7'-fluoreno[4,3-b]benzofuran) was replaced with 2,7-dibromospiro(dibenzo[5,6:7,8]fluoreno[4,3-b]benzofuran-5,9'-fluorene). As a result, a powder of N2,N2,N7,N7-tetrakis{4-(tert-butyl)phenyl}spiro(dibenzo[5,6:7,8]fluoreno[4,3-b]benzofuran-5,9'-fluorene)-2,7-diamine (Compound 7-2; 2.5 g; yield 31%) was obtained.

[Chemical Formula 811]

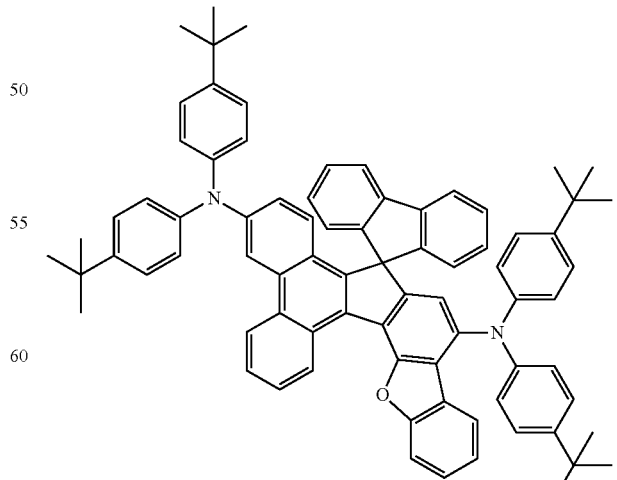

(7-2)

Example 52

Synthesis of N5,N5,N9,N9-tetrakis{4-(tert-butyl)phenyl}spiro(benzo[5,6]fluoreno[4,3-b]benzofuran-7,9'-fluorene)-5,9-diamine (Compound 7-3)

The reaction was carried out under the same conditions as those of Example 50, except that 5',9'-dibromospiro(fluorene-9,7'-fluoreno[4,3-b]benzofuran) was replaced with 5,9-dibromospiro(benzo[5,6]fluoreno[4,3-b]benzofuran-7,9'-fluorene). As a result, a powder of N5,N5,N9,N9-tetrakis{4-(tert-butyl)phenyl}spiro(benzo[5,6]fluoreno[4,3-b]benzofuran-7,9'-fluorene)-5,9-diamine (Compound 7-3; 3.0 g; yield 36%) was obtained.

[Chemical Formula 813]

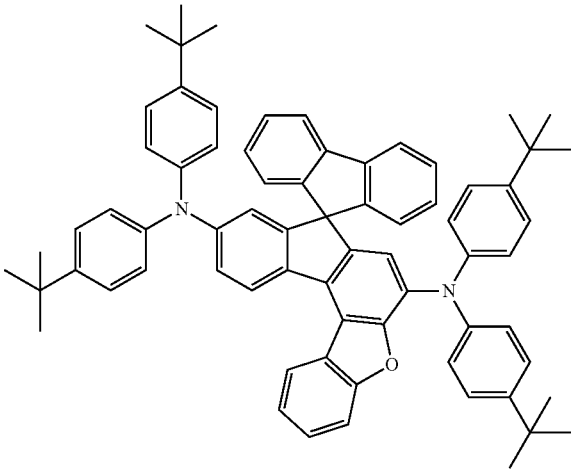

(7-4)

[Chemical Formula 812]

(7-3)

Example 54

Synthesis of N5,N5,N9,N9-tetrakis{4-(tert-butyl)phenyl}spiro(fluoreno[4,3-b]benzofuran-7,9'-xanthene)-5,9-diamine (Compound 7-5)

The reaction was carried out under the same conditions as those of Example 50, except that 5',9'-dibromospiro(fluorene-9,7'-fluoreno[4,3-b]benzofuran) was replaced with 5,9-dibromospiro(fluoreno[4,3-b]benzofuran-7,9'-xanthene). As a result, a powder of N5,N5,N9,N9-tetrakis{4-(tert-butyl)phenyl}spiro(fluoreno[4,3-b]benzofuran-7,9'-xanthene)-5,9-diamine (Compound 7-5; 2.4 g; yield 28%) was obtained.

[Chemical Formula 814]

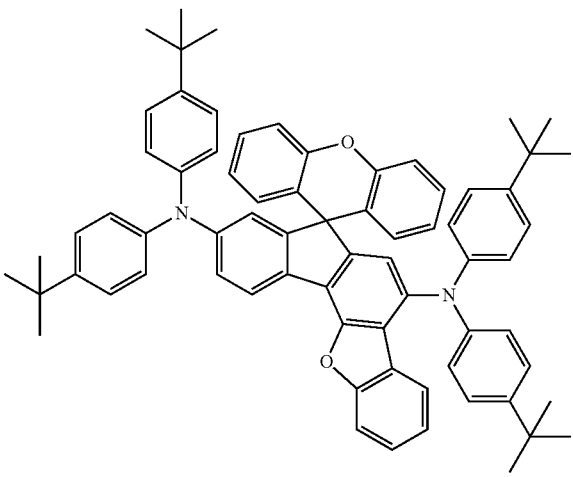

(7-5)

Example 53

Synthesis of N6',N6',N10',N10'-tetrakis{4-(tert-butyl)phenyl}spiro(fluorene-9,8'-fluoreno[3,4-b]benzofuran)-6',10'-diamine (Compound 7-4)

The reaction was carried out under the same conditions as those of Example 50, except that 5',9'-dibromospiro(fluorene-9,7'-fluoreno[4,3-b]benzofuran) was replaced with 6',10'-dibromospiro(fluorene-9,8'-fluoreno[3,4-b]benzofuran). As a result, a powder of N6',N6',N10',N10'-tetrakis{4-(tert-butyl)phenyl}spiro(fluorene-9,8'-fluoreno[3,4-b]benzofuran)-6',10'-diamine (Compound 7-4; 2.5 g; yield 34%) was obtained.

Example 55

Synthesis of N5',N9'-bis(biphenyl-4-yl)-N5',N9'-bis{4-(tert-butyl)phenyl}-2-fluorospiro(fluorene-9,7'-fluoreno[4,3-b]benzofuran)-5',9'-diamine (Compound 7-6)

The reaction was carried out under the same conditions as those of Example 50, except that 5',9'-dibromospiro(fluorene-9,7'-fluoreno[4,3-b]benzofuran) was replaced with 5',9'-dibromo-2-fluorospiro(fluorene-9,7'-fluoreno[4,3-b]benzofuran), and bis{4-(tert-butyl)phenyl}amine was replaced with (biphenyl-4-yl)-{4-(tert-butyl)phenyl}amine. As a result, a powder of N5',N9'-bis(biphenyl-4-yl)-N5',N9'-bis{4-(tert-butyl)phenyl}-2-fluorospiro(fluorene-9,7'-fluoreno[4,3-b]benzofuran)-5',9'-diamine (Compound 7-6; 2.4 g; yield 28%) was obtained.

[Chemical Formula 815]

(7-6)

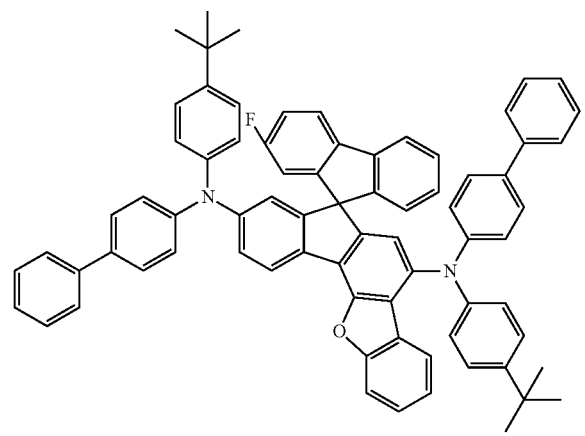

Example 56

Synthesis of N5,N9-bis{4-(tert-butyl)phenyl}-N5,N9-bis{4-(trimethylsilyl)phenyl}spiro(benzo[5,6]fluoreno[4,3-b]benzofuran-7,9'-fluorene)-5,9-diamine (Compound 7-7)

The reaction was carried out under the same conditions as those of Example 50, except that 5',9'-dibromospiro(fluorene-9,7'-fluoreno[4,3-b]benzofuran) was replaced with 5,9-dibromospiro(benzo[5,6]fluoreno[4,3-b]benzofuran-7,9'-fluorene), and bis{4-(tert-butyl)phenyl}amine was replaced with {4-(tert-butyl)phenyl}-{4-(trimethylsilyl)phenyl}amine. As a result, a powder of N5,N9-bis{4-(tert-butyl)phenyl}-N5,N9-bis{4-(trimethylsilyl)phenyl}spiro(benzo[5,6]fluoreno[4,3-b]benzofuran-7,9'-fluorene)-5,9-diamine (Compound 7-7; 3.0 g; yield 35%) was obtained.

[Chemical Formula 816]

(7-7)

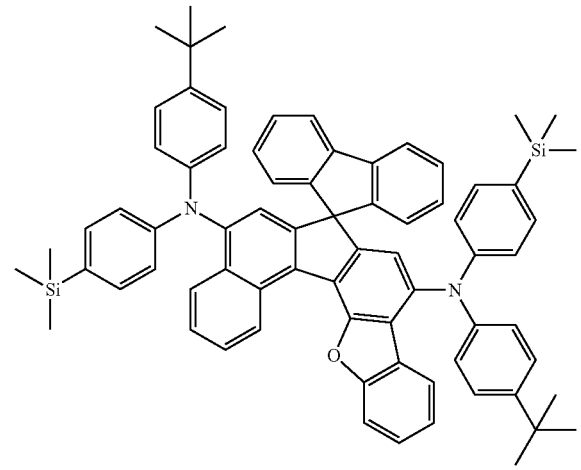

Example 57

Synthesis of N5',N9'-bis{4-(tert-butyl)phenyl}-N5',N9'-bis{4-(trimethylsilyl)phenyl}spiro(fluorene-9,7'-fluoreno[4,3-b]benzothiophene)-5',9'-diamine (Compound 7-8)

The reaction was carried out under the same conditions as those of Example 50, except that 5',9'-dibromospiro(fluorene-9,7'-fluoreno[4,3-b]benzofuran) was replaced with 5',9'-dibromospiro(fluorene-9,7'-fluoreno[4,3-b]benzothiophene), and bis{4-(tert-butyl)phenyl}amine was replaced with {4-(tert-butyl)phenyl}-{4-(trimethylsilyl)phenyl}amine. As a result, a powder of N5',N9'-bis{4-(tert-butyl)phenyl}-N5',N9'-bis{4-(trimethylsilyl)phenyl}spiro(fluorene-9,7'-fluoreno[4,3-b]benzothiophene)-5',9'-diamine (Compound 7-8; 3.2 g; yield 37%) was obtained.

[Chemical Formula 817]

(7-8)

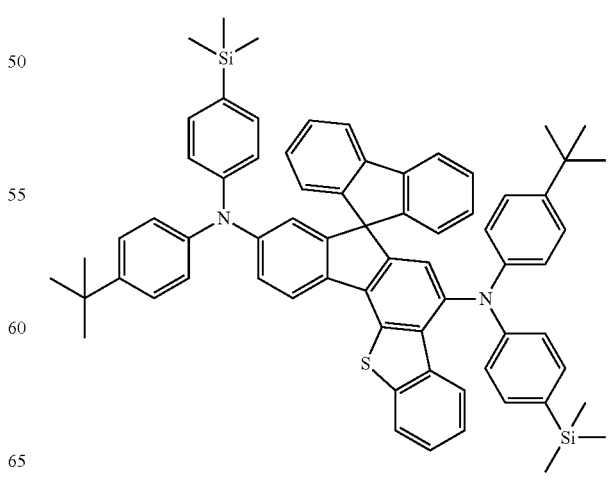

Example 58

Synthesis of N5,N9-bis(biphenyl-4-yl)-N5,N9-bis{4-(tert-butyl)phenyl}spiro(benzo[4',5']thieno[2',3':5,6]fluoreno[4,3-b]benzofuran-7,9'-fluorene)-5,9-diamine (Compound 7-9)

The reaction was carried out under the same conditions as those of Example 50, except that 5',9'-dibromospiro(fluorene-9,7'-fluoreno[4,3-b]benzofuran) was replaced with 5,9-dibromospiro(benzo[4',5']thieno[2',3':5,6]fluoreno[4,3-b]benzofuran-7,9'-fluorene), and bis{4-(tert-butyl)phenyl}amine was replaced with {4-(tert-butyl)phenyl}-(biphenyl-4-yl)amine. As a result, a powder of N5,N9-bis(biphenyl-4-yl)-N5,N9-bis{4-(tert-butyl)phenyl}spiro(benzo[4',5']thieno[2',3':5,6]fluoreno[4,3-b]benzofuran-7,9'-fluorene)-5,9-diamine (Compound 7-9; 2.8 g; yield 34%) was obtained.

[Chemical Formula 818]

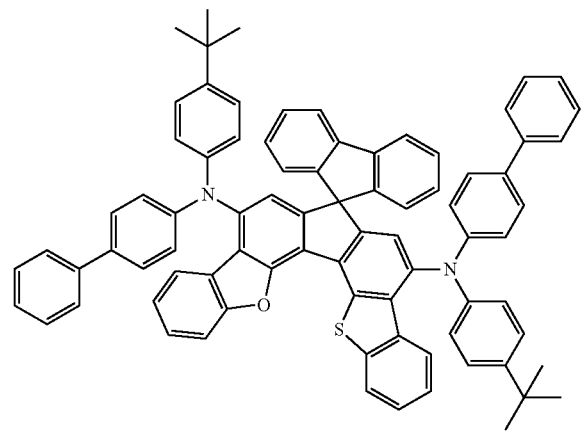

(7-9)

Example 59

Synthesis of N5',N5',N9',N9'-tetrakis{4-(tert-butyl)phenyl}-12',12'-dimethyl-12'H-spiro(fluorene-9,7'-indeno[1,2-a]fluorene)-5',9'-diamine (Compound 7-10)

The reaction was carried out under the same conditions as those of Example 50, except that 5',9'-dibromospiro(fluorene-9,7'-fluoreno[4,3-b]benzofuran) was replaced with 5',9'-dibromo-12',12'-dimethyl-12'H-spiro(fluorene-9,7'-indeno[1,2-a]fluorene). As a result, a powder of N5',N5',N9',N9'-tetrakis{4-(tert-butyl)phenyl}-12',12'-dimethyl-12'H-spiro(fluorene-9,7'-indeno[1,2-a]fluorene)-5',9'-diamine (Compound 7-10; 1.8 g; yield 49%) was obtained.

[Chemical Formula 819]

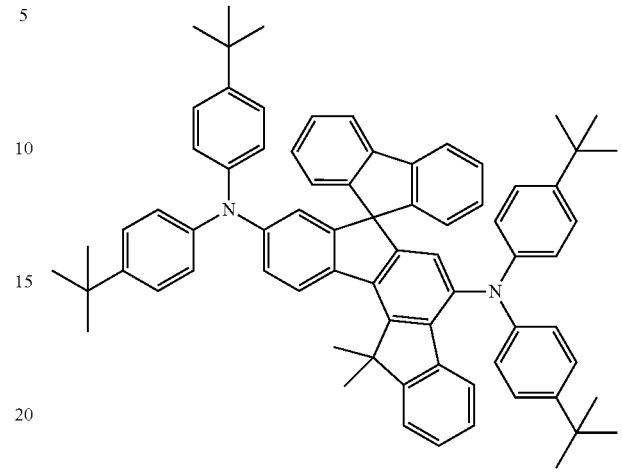

(7-10)

Example 60

Synthesis of N6',N10'-bis(biphenyl-4-yl)-N6',N10'-bis{4-(tert-butyl)phenyl}-5'-methyl-5'H-spiro(fluorene-9,8'-indeno[2,1-c]carbazole)-6',10'-diamine (Compound 7-11)

The reaction was carried out under the same conditions as those of Example 50, except that 5',9'-dibromospiro(fluorene-9,7'-fluoreno[4,3-b]benzofuran) was replaced with 6',10'-dibromo-5'-methyl-5'H-spiro(fluorene-9,8'-indeno[2,1-c]carbazole), and bis{4-(tert-butyl)phenyl}amine was replaced with {4-(tert-butyl)phenyl}-(biphenyl-4-yl)amine. As a result, a powder of N6',N10'-bis(biphenyl-4-yl)-N6',N10'-bis{4-(tert-butyl)phenyl}-5'-methyl-5'H-spiro(fluorene-9,8'-indeno[2,1-c]carbazole)-6',10'-diamine (Compound 7-11; 2.3 g; yield 41%) was obtained.

[Chemical Formula 820]

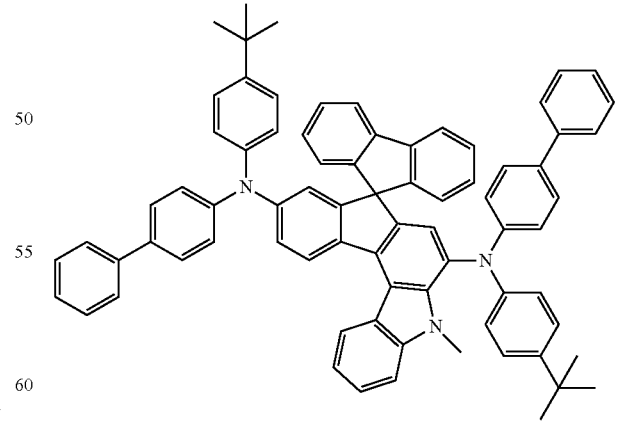

(7-11)

Example 61

The organic EL device, as shown in FIG. 1, was fabricated by vapor-depositing a hole injection layer 3, a hole transport layer 4, a light emitting layer 5, an electron transport layer 6, an electron injection layer 7, and a cathode (aluminum electrode) 8 in this order on a glass substrate 1 on which an ITO electrode was formed as a transparent anode 2 beforehand.

Specifically, the glass substrate 1 having ITO (film thickness of 150 nm) formed thereon was subjected to ultrasonic washing in isopropyl alcohol for 20 minutes and then dried for 10 minutes on a hot plate heated to 200° C. After UV ozone treatment for 15 minutes, the glass substrate with ITO was installed in a vacuum vapor deposition apparatus, and the pressure was reduced to 0.001 Pa or lower. The hole injection layer 3 was formed so as to cover the transparent anode 2 in a film thickness of 30 nm by dual vapor deposition of the electron acceptor (Acceptor-1) of the structural formula below and the compound (1-2) of Example 1 at a vapor deposition rate ratio of Acceptor-1:the compound (1-2)=3:97. The hole transport layer 4 was formed on the hole injection layer 3 by forming the compound (1-2) of Example 1 in a film thickness of 40 nm. The light emitting layer 5 was formed on the hole transport layer 4 in a film thickness of 20 nm by dual vapor deposition of Compound EMD-1 of the structural formula below and Compound EMH-1 of the structural formula below at a vapor deposition rate ratio of EMD-1:EMH-1=5:95. The electron transport layer 6 was formed on the light emitting layer 5 in a film thickness of 30 nm by dual vapor deposition of the compound (3b-1) of the structural formula below having an anthracene ring structure and Compound ETM-1 of the structural formula below at a vapor deposition rate ratio of the compound (3b-1):ETM-1=50:50. The electron injection layer 7 was formed on the electron transport layer 6 by forming lithium fluoride in a film thickness of 1 nm. Finally, the cathode 8 was formed by vapor-depositing aluminum in a thickness of 100 nm. The characteristics of the thus fabricated organic EL device were measured in the atmosphere at an ordinary temperature. Table 1 summarizes the results of emission characteristics measurements performed by applying a DC voltage to the fabricated organic EL device.

[Chemical Formula 821]

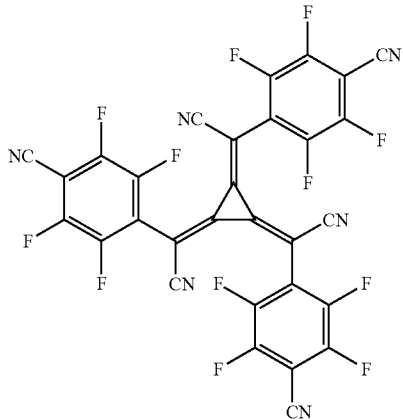

(Acceptor-1)

[Chemical Formula 822]

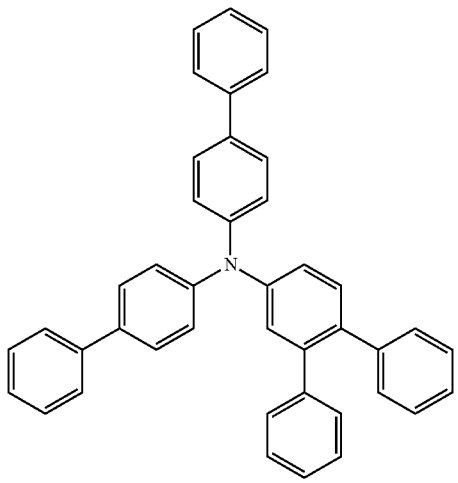

(1-2)

[Chemical Formula 823]

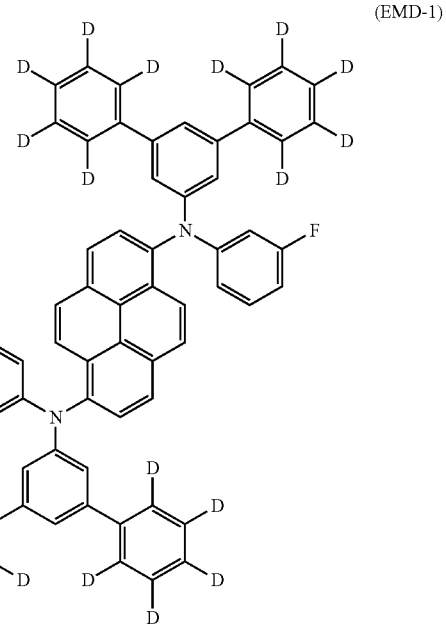

(EMD-1)

[Chemical Formula 824]

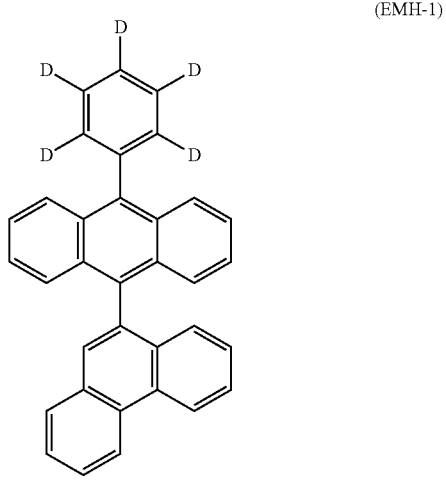

(EMH-1)

-continued

[Chemical Formula 825]

(3b-1)

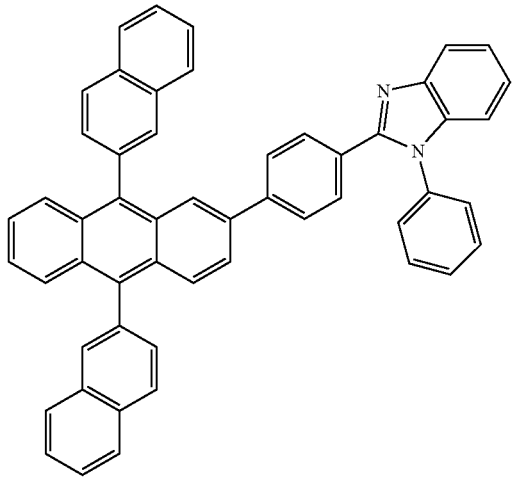

[Chemical Formula 826]

(ETM-1)

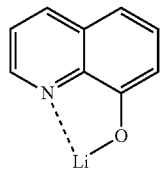

Example 62

An organic EL device was fabricated under the same conditions as those of Example 61, except that the compound (3b-1) having an anthracene ring structure was replaced with the compound (4-125) having a pyrimidine ring structure as the material of the electron transport layer 6, and the layer was formed in a film thickness of 30 nm by dual vapor deposition of the compound (4-125) and the compound ETM-1 of the above structural formula at a vapor deposition rate ratio of the compound (4-125):ETM-1=50:50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 827]

(4-125)

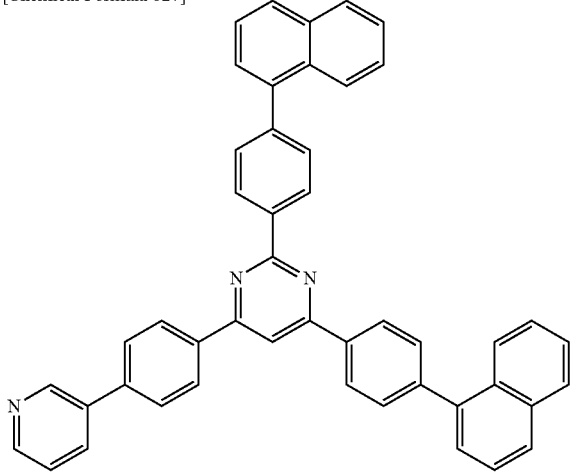

Example 63

An organic EL device was fabricated under the same conditions as those of Example 61, except that the compound (3b-1) having an anthracene ring structure was replaced with the compound (6-55) having a benzotriazole ring structure as the material of the electron transport layer 6, and the layer was formed in a film thickness of 30 nm by dual vapor deposition of the compound (6-55) and the compound ETM-1 of the above structural formula at a vapor deposition rate ratio of the compound (6-55):ETM-1=50:50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 828]

(6-55)

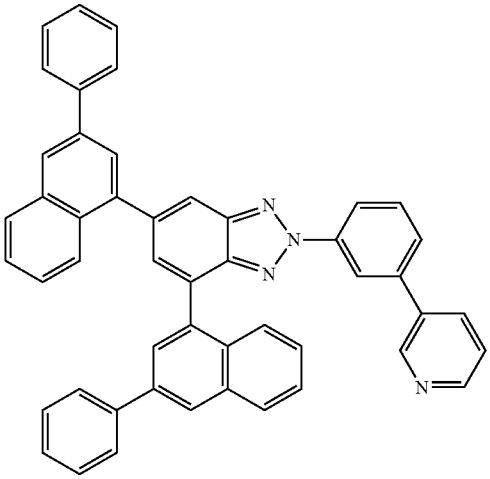

Example 64

An organic EL device was fabricated under the same conditions as those of Example 61, except that the compound EMD-1 of the above structural formula was replaced with an amine derivative (7-1) having a condensed ring structure as the material of the light emitting layer 5, and the layer was formed in a film thickness of 25 nm by dual vapor deposition of the amine derivative (7-1) having a condensed ring structure and the compound EMH-1 of the above structural formula at a vapor deposition rate ratio of the amine derivative (7-1):EMH-1=5:95. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 829]

(7-1)

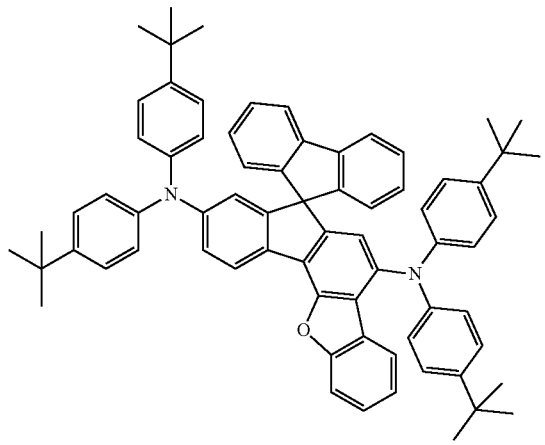

Example 65

An organic EL device was fabricated under the same conditions as those of Example 62, except that the compound EMD-1 of the above structural formula was replaced with an amine derivative (7-1) having a condensed ring structure as the material of the light emitting layer 5, and the layer was formed in a film thickness of 25 nm by dual vapor deposition of the amine derivative (7-1) having a condensed ring structure and the compound EMH-1 of the above structural formula at a vapor deposition rate ratio of the amine derivative (7-1):EMH-1=5:95. The characteristics of the organic EL device thus fabricated were measured in the atmosphere at an ordinary temperature. Table 1 summarizes the results of measurement of emission characteristics when applying a DC voltage to the fabricated organic EL device.

Example 66

An organic EL device was fabricated under the same conditions as those of Example 63, except that the compound EMD-1 of the above structural formula was replaced with the amine derivative (7-1) having a condensed ring structure as the material of the light emitting layer 5, and the layer was formed in a film thickness of 25 nm by dual vapor deposition of the amine derivative (7-1) having a condensed ring structure and the compound EMH-1 of the above structural formula at a vapor deposition rate ratio of the amine derivative (7-1):EMH-1=5:95. The characteristics of the organic EL device thus fabricated were measured in the atmosphere at an ordinary temperature. Table 1 summarizes the results of measurement of emission characteristics when applying a DC voltage to the fabricated organic EL device.

Example 67

An organic EL device was fabricated under the same conditions as those of Example 61, except that the compound (1-2) of Example 1 was replaced with the compound (1-4) of Example 4 as the material of the hole injection layer 3, and the layer was formed in a film thickness of 30 nm by dual vapor deposition of the electron acceptor (Acceptor-1) of the above structural formula and the compound (1-4) of Example 4 at a vapor deposition rate ratio of Acceptor-1:the compound (1-4)=3:97, and the compound (1-2) of Example 1 was replaced with the compound (1-4) of Example 4 as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 830]

(1-4)

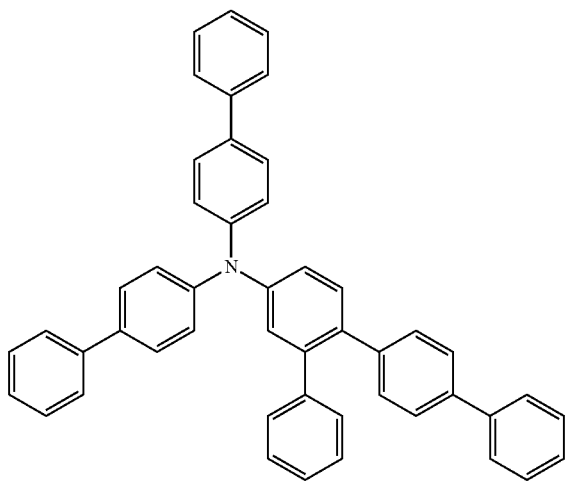

Example 68

An organic EL device was fabricated under the same conditions as those of Example 62, except that the compound (1-2) of Example 1 was replaced with the compound (1-4) of Example 4 as the material of the hole injection layer 3, and the layer was formed in a film thickness of 30 nm by dual vapor deposition of the electron acceptor (Acceptor-1) of the above structural formula and the compound (1-4) of Example 4 at a vapor deposition rate ratio of Acceptor-1:the compound (1-2)=3:97, and the compound (1-2) of Example 1 was replaced with the compound (1-4) of Example 4 as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Example 69

An organic EL device was fabricated under the same conditions as those of Example 63, except that the compound (1-2) of Example 1 was replaced with the compound (1-4) of Example 4 as the material of the hole injection layer 3, and the layer was formed in a film thickness of 30 nm by dual vapor deposition of the electron acceptor (Acceptor-1) of the above structural formula and the compound (1-4) of Example 4 at a vapor deposition rate ratio of Acceptor-1:the compound (1-2)=3:97, and the compound (1-2) of Example 1 was replaced with the compound (1-4) of Example 4 as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Example 70

An organic EL device was fabricated under the same conditions as those of Example 64, except that the compound (1-2) of Example 1 was replaced with the compound (1-4) of Example 4 as the material of the hole injection layer 3, and the layer was formed in a film thickness of 30 nm by dual vapor deposition of the electron acceptor (Acceptor-1) of the above structural formula and the compound (1-4) of Example 4 at a vapor deposition rate ratio of Acceptor-1:the compound (1-4)=3:97, and the compound (1-2) of Example 1 was replaced with the compound (1-4) of Example 4 as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Example 71

An organic EL device was fabricated under the same conditions as those of Example 65, except that the compound (1-2) of Example 1 was replaced with the compound (1-4) of Example 4 as the material of the hole injection layer 3, and the layer was formed in a film thickness of 30 nm by dual vapor deposition of the electron acceptor (Acceptor-1) of the above structural formula and the compound (1-4) of Example 4 at a vapor deposition rate ratio of Acceptor-1:the compound (1-4)=3:97, and the compound (1-2) of Example 1 was replaced with the compound (1-4) of Example 4 as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Example 72

An organic EL device was fabricated under the same conditions as those of Example 66, except that the compound (1-2) of Example 1 was replaced with the compound (1-4) of Example 4 as the material of the hole injection layer 3, and the layer was formed in a film thickness of 30 nm by dual vapor deposition of the electron acceptor (Acceptor-1) of the above structural formula and the compound (1-4) of Example 4 at a vapor deposition rate ratio of Acceptor-1:the compound (1-4)=3:97, and the compound (1-2) of Example 1 was replaced with the compound (1-4) of Example 4 as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 1

For comparison, an organic EL device was fabricated under the same conditions as those of Example 61, except that the compound (1-2) of Example 1 was replaced with a compound HTM-1 of the structural formula below as the material of the hole injection layer 3, and the layer was formed in a film thickness of 30 nm by dual vapor deposition of the electron acceptor (Acceptor-1) of the above structural formula and the compound HTM-1 of the structural formula below at a vapor deposition rate ratio of Acceptor-1:HTM-1=3:97, and the compound (1-2) of Example 1 was replaced with the compound HTM-1 of the structural formula below as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 831]

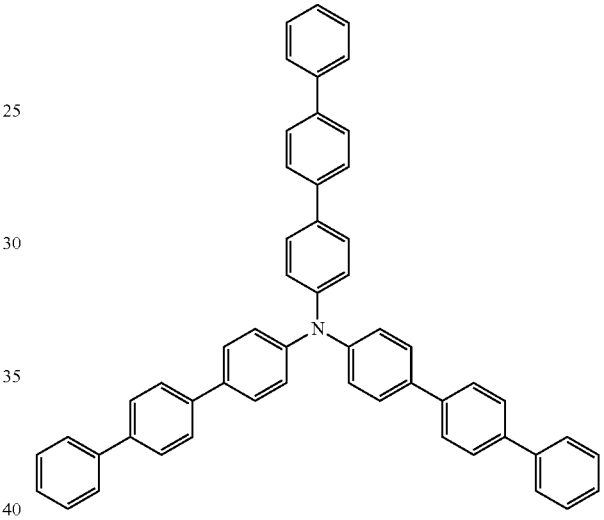

(HTM-1)

Comparative Example 2

For comparison, an organic EL device was fabricated under the same conditions as those of Example 62, except that the compound (1-2) of Example 1 was replaced with the compound HTM-1 of the structural formula below as the material of the hole injection layer 3, and the layer was formed in a film thickness of 30 nm by dual vapor deposition of the electron acceptor (Acceptor-1) of the above structural formula and the compound HTM-1 of the above structural formula at a vapor deposition rate ratio of Acceptor-1:HTM-1=3:97, and the compound (1-2) of Example 1 was replaced with the compound HTM-1 of the above structural formula as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 3

For comparison, an organic EL device was fabricated under the same conditions as those of Example 63, except that the compound (1-2) of Example 1 was replaced with the compound HTM-1 of the structural formula below as the material of the hole injection layer 3, and the layer was formed in a film thickness of 30 nm by dual vapor deposition of the electron acceptor (Acceptor-1) of the above structural formula and the compound HTM-1 of the above structural formula at a vapor deposition rate ratio of Acceptor-1:HTM-1=3:97, and the compound (1-2) of Example 1 was replaced with the compound HTM-1 of the above structural formula as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 4

For comparison, an organic EL device was fabricated under the same conditions as those of Example 64, except that the compound (1-2) of Example 1 was replaced with the compound HTM-1 of the structural formula below as the material of the hole injection layer 3, and the layer was formed in a film thickness of 30 nm by dual vapor deposition of the electron acceptor (Acceptor-1) of the above structural formula and the compound HTM-1 of the above structural formula at a vapor deposition rate ratio of Acceptor-1:HTM-1=3:97, and the compound (1-2) of Example 1 was replaced with the compound HTM-1 of the above structural formula as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 5

For comparison, an organic EL device was fabricated under the same conditions as those of Example 65, except that the compound (1-2) of Example 1 was replaced with the compound HTM-1 of the structural formula below as the material of the hole injection layer 3, and the layer was formed in a film thickness of 30 nm by dual vapor deposition of the electron acceptor (Acceptor-1) of the above structural formula and the compound HTM-1 of the above structural formula at a vapor deposition rate ratio of Acceptor-1:HTM-1=3:97, and the compound (1-2) of Example 1 was replaced with the compound HTM-1 of the above structural formula as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 6

For comparison, an organic EL device was fabricated under the same conditions as those of Example 66, except that the compound (1-2) of Example 1 was replaced with the compound HTM-1 of the structural formula below as the material of the hole injection layer 3, and the layer was formed in a film thickness of 30 nm by dual vapor deposition of the electron acceptor (Acceptor-1) of the above structural formula and the compound HTM-1 of the above structural formula at a vapor deposition rate ratio of Acceptor-1:HTM-1=3:97, and the compound (1-2) of Example 1 was replaced with the compound HTM-1 of the above structural formula as the material of the hole transport layer 4, and the layer was formed in a film thickness of 40 nm. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 7

For comparison, an organic EL device was fabricated under the same conditions as those of Example 62, except that the compound (1-2) of Example 1 was replaced with the electron acceptor (Acceptor-1) of the above structural formula and the compound (1-2) of Example 1 as the material of the hole transport layer 4, and the layer was formed in a film thickness of 40 nm by dual vapor deposition of the electron acceptor (Acceptor-1) of the above structural formula and the compound (1-2) of Example 1 at a vapor deposition rate ratio of Acceptor-1:the compound (1-2)=3:97. The characteristics of the organic EL device thus fabricated were measured in the atmosphere at an ordinary temperature. Table 1 summarizes the results of measurement of emission characteristics when applying a DC voltage to the fabricated organic EL device.

Comparative Example 8

For comparison, an organic EL device was fabricated under the same conditions as those of Example 68, except that the compound (1-4) of Example 4 was replaced with the electron acceptor (Acceptor-1) of the above structural formula and the compound (1-4) of Example 4 as the material of the hole transport layer 4, and the layer was formed in a film thickness of 40 nm by dual vapor deposition of the electron acceptor (Acceptor-1) of the above structural formula and the compound (1-1) of Example 1 at a vapor deposition rate ratio of Acceptor-1:the compound (1-4)=3:97. The characteristics of the organic EL device thus fabricated were measured in the atmosphere at an ordinary temperature. Table 1 summarizes the results of measurement of emission characteristics when applying a DC voltage to the fabricated organic EL device.

Table 1 summarizes the results of measurement of a device lifetime using the organic EL devices fabricated in Examples 61 to 72 and Comparative Examples 1 to 8. The device lifetime was measured as a time elapsed until the emission luminance of 2,000 cd/m$^2$ (initial luminance) at the start of emission was attenuated to 1,900 cd/m$^2$ (corresponding to 95% when taking the initial luminance as 100%: Attenuation to 95%) when carrying out constant current driving.

TABLE 1

| | Hole injection layer | Hole transport layer | Light emitting layer | Electron transport layer | Voltage [V] (@10 mA/cm²) | Luminance [cd/m²] (@10 mA/cm²) | Current efficiency [cd/A] (@10 mA/cm²) | Power efficiency [lm/W] (@10 mA/cm²) | Device lifetime (Attenuation to 95%) |
|---|---|---|---|---|---|---|---|---|---|
| Ex. 61 | Compound 1-2/ Acceptor-1 | Compound 1-2 | EMD-1/ EMH-1 | Compound 3b-1/ ETM-1 | 4.01 | 725 | 7.25 | 5.68 | 235 h |
| Ex. 62 | Compound 1-2/ Acceptor-1 | Compound 1-2 | EMD-1/ EMH-1 | Compound 4-125/ ETM-1 | 4.00 | 791 | 7.91 | 6.21 | 204 h |
| Ex. 63 | Compound 1-2/ Acceptor-1 | Compound 1-2 | EMD-1/ EMH-1 | Compound 6-55/ ETM-1 | 4.13 | 753 | 7.53 | 5.69 | 211 h |
| Ex. 64 | Compound 1-2/ Acceptor-1 | Compound 1-2 | Compound 7-1/ EMH-1 | Compound 3b-1/ ETM-1 | 4.05 | 774 | 7.74 | 6.13 | 322 h |
| Ex. 65 | Compound 1-2/ Acceptor-1 | Compound 1-2 | Compound 7-1/EMH-1 | Compound 4-125/ ETM-1 | 4.05 | 826 | 8.26 | 6.42 | 314 h |
| Ex. 66 | Compound 1-2/ Acceptor-1 | Compound 1-2 | Compound 7-1/ EMH-1 | Compound 6-55/ ETM-1 | 4.07 | 822 | 8.22 | 6.34 | 280 h |
| Ex. 67 | Compound 1-4/ Acceptor-1 | Compound 1-4 | EMD-1/ EMH-1 | Compound 3b-1/ ETM-1 | 4.05 | 740 | 7.39 | 5.75 | 239 h |
| Ex. 68 | Compound 1-4/ Acceptor-1 | Compound 1-4 | EMD-1/ EMH-1 | Compound 4-125/ ETM-1 | 3.95 | 778 | 7.77 | 6.18 | 246 h |
| Ex. 69 | Compound 1-4/ Acceptor-1 | Compound 1-4 | EMD-1/ EMH-1 | Compound 6-55/ ETM-1 | 4.10 | 806 | 8.06 | 6.11 | 203 h |
| Ex. 70 | Compound 1-4/ Acceptor-1 | Compound 1-4 | Compound 7-1/ EMH-1 | Compound 3b-1/ ETM-1 | 4.04 | 756 | 7.56 | 5.92 | 311 h |
| Ex. 71 | Compound 1-4/ Acceptor-1 | Compound 1-4 | Compound 7-1/ EMH-1 | Compound 4-125/ ETM-1 | 4.00 | 795 | 7.95 | 6.19 | 306 h |
| Ex. 72 | Compound 1-4/ Acceptor-1 | Compound 1-4 | Compound 7-1/ EMH-1 | Compound 6-55/ ETM-1 | 4.10 | 826 | 8.26 | 6.38 | 275 h |
| Com. Ex. 1 | HTM-1/ Acceptor-1 | HTM-1 | EMD-1/ EMH-1 | Compound 3b-1/ ETM-1 | 4.00 | 671 | 6.71 | 5.28 | 72 h |
| Com. Ex. 2 | HTM-1/ Acceptor-1 | HTM-1 | EMD-1/ EMH-1 | Compound 4-125/ ETM-1 | 3.95 | 700 | 7.00 | 5.58 | 62 h |
| Com. Ex. 3 | HTM-1/ Acceptor-1 | HTM-1 | EMD-1/ EMH-1 | Compound 6-55/ ETM-1 | 4.03 | 708 | 7.08 | 5.42 | 48 h |
| Com. Ex. 4 | HTM-1/ Acceptor-1 | HTM-1 | Compound 7-1/ EMH-1 | Compound 3b-1/ ETM-1 | 3.99 | 705 | 7.05 | 5.36 | 85 h |
| Com. Ex. 5 | HTM-1/ Acceptor-1 | HTM-1 | Compound 7-1/ EMH-1 | Compound 4-125/ ETM-1 | 3.96 | 703 | 7.03 | 5.55 | 78 h |
| Com. Ex. 6 | HTM-1/ Acceptor-1 | HTM-1 | Compound 7-1/ EMH-1 | Compound 6-55/ ETM-1 | 3.99 | 711 | 7.11 | 5.42 | 75 h |
| Com. Ex. 7 | Compound 1-2/ Acceptor-1 | Compound 1-2/ Acceptor-1 | EMD-1/ EMH-1 | Compound 4-125/ ETM-1 | 4.00 | 60 | 0.60 | 0.50 | 1 h |
| Com. Ex. 8 | Compound 1-4/ Acceptor-1 | Compound 1-4/ Acceptor-1 | EMD-1/ EMH-1 | Compound 4-125/ ETM-1 | 3.95 | 65 | 0.65 | 0.62 | 1 h |

As shown in Table 1, the luminous efficiency when passing a current with a current density of 10 mA/cm² was 6.71 to 7.11 cd/A for the organic EL devices of Comparative Examples 1 to 6 including the hole transport layer undoped with an electron acceptor, which was higher than 0.60 to 0.65 cd/A for the organic EL devices of Comparative Examples 7 to 8 including the hole transport layer also doped with an electron acceptor. Then, the luminous efficiency was 7.25 to 8.26 cd/A, which was further higher, for the organic EL devices of Examples 61 to 72 using the arylamine compounds represented by the general formula (1) in the hole injection layer. Further, also the power efficiency was 5.28 to 5.58 lm/W for the organic EL devices of Comparative Examples 1 to 6 including the hole transport layer undoped with an electron acceptor, which was higher than 0.50 to 0.62 lm/W for the organic EL devices of Comparative Examples 7 to 8 including the hole transport layer also doped with an electron acceptor. Then, the power efficiency was 5.68 to 6.42 lm/W, which was further higher, for the organic EL devices of Examples 61 to 72 using the arylamine compounds represented by the general formula (1) in the hole injection layer. On the other hand, the device lifetime (attenuation to 95%) was 45 to 85 hours for the organic EL devices of Comparative Examples 1 to 6 including the hole transport layer undoped with an electron acceptor, which was longer than 1 hour for the organic EL devices of Comparative Examples 7 to 8 including the hole transport layer also doped with an electron acceptor. Then, it is found that the device lifetime was 203 to 322 hours, which was further greatly increased, for the organic EL devices of Examples 61 to 72 using the arylamine compounds represented by the general formula (1) in the hole injection layer.

It was found that the organic EL device of the present invention can achieve an organic EL device having higher luminous efficiency and a longer lifetime compared to the conventional organic EL devices by selecting a specific arylamine compound (having a specific structure) as a material of a hole injection layer and p-doping the compound with an electron acceptor so that holes can be efficiently injected and transported into a hole transport layer from an electrode, and by further selecting a specific arylamine compound (having a specific structure) without p-doping as a material of the hole transport layer so as to improve the carrier balance inside the organic EL device.

INDUSTRIAL APPLICABILITY

The organic EL device of the present invention in which a specific arylamine compound (having a specific structure) and an electron acceptor are combined so as to be able to refine the carrier balance inside the organic EL device can enhance luminous efficiency and also can improve durability of the organic EL device, and therefore can be applied to, for example, home electric appliances and illuminations.

DESCRIPTION OF REFERENCE NUMERAL

1 Glass substrate
2 Transparent anode
3 Hole injection layer
4 Hole transport layer
5 Light emitting layer
6 Electron transport layer
7 Electron injection layer
8 Cathode

The invention claimed is:
1. An organic electroluminescent device comprising at least an anode, a hole injection layer, a hole transport layer, a light emitting layer, an electron transport layer, and a cathode in this order, wherein the hole injection layer comprises an arylamine compound represented by the following general formula (1) and an electron acceptor:

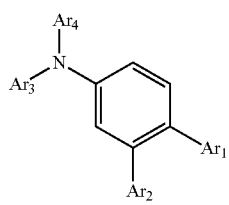

(1)

wherein $Ar_1$ and $Ar_2$ may be the same or different, and represent a substituted or unsubstituted aromatic hydrocarbon group, a substituted or unsubstituted aromatic heterocyclic group, or a substituted or unsubstituted condensed polycyclic aromatic group;

and wherein $Ar_3$ and $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group, wherein the aromatic hydrocarbon group, the aromatic heterocyclic group, or the condensed polycyclic aromatic group in the substituted or unsubstituted aromatic hydrocarbon group, the substituted or unsubstituted aromatic heterocyclic group, or the substituted or unsubstituted condensed polycyclic aromatic group is a phenyl group, a biphenylyl group, a terphenylyl group, a naphthyl group, an anthracenyl group, a phenanthrenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, or a carbolinyl group.

2. The organic electroluminescent device according to claim 1, wherein a layer adjacent to the light emitting layer does not contain an electron acceptor.

3. The organic electroluminescent device according to claim 2, wherein the electron acceptor is an electron acceptor selected from trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative.

4. The organic electroluminescent device according to claim 2, wherein the electron acceptor is a radialene derivative represented by the following general formula (2):

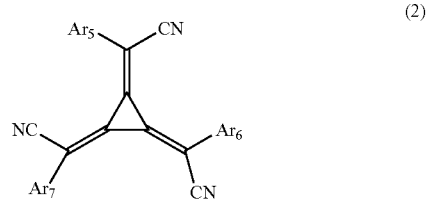

(2)

wherein $Ar_5$ to $Ar_7$ may be the same or different, and represent an aromatic hydrocarbon group, an aromatic heterocyclic group, or a condensed polycyclic aromatic group, having an electron acceptor group as a substituent.

5. The organic electroluminescent device according to claim 2, wherein the hole transport layer comprises only a hole transporting arylamine compound.

6. The organic electroluminescent device according to claim 2, wherein the electron transport layer comprises a compound having an anthracene ring structure represented by the following general formula (3):

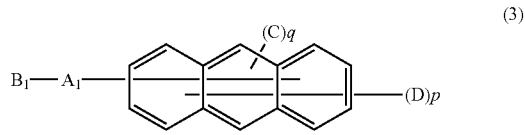

(3)

wherein $A_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $B_1$ represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group; and while p and q maintain a relationship that the sum of p and q is 9, p represents 7 or 8, and q represents 1 or 2.

7. The organic electroluminescent device according to claim 2, wherein the electron transport layer comprises a compound having a pyrimidine ring structure represented by the following general formula (4):

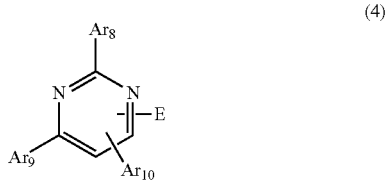

(4)

wherein $Ar_8$ represents a substituted or unsubstituted aromatic hydrocarbon group or a substituted or unsubstituted condensed polycyclic aromatic group; $Ar_9$ and $Ar_{10}$ may be the same or different, and represent a hydrogen atom, a substituted or unsubstituted aromatic hydrocarbon group, or a substituted or unsubstituted condensed polycyclic aromatic group; and E represents a monovalent group represented by the following structural formula (5), provided that $Ar_9$ and $Ar_{10}$ are not simultaneously a hydrogen atom:

(5)

wherein $Ar_{11}$ represents a substituted or unsubstituted aromatic heterocyclic group; $R_1$ to $R_4$ may be the same or different, and represent a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group.

8. The organic electroluminescent device according to claim 2, wherein the electron transport layer comprises a compound having a benzotriazole ring structure represented by the following general formula (6):

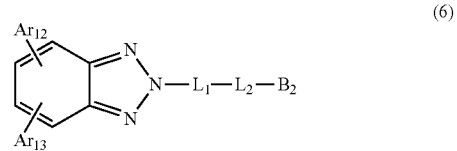

(6)

wherein $Ar_{12}$ represents a substituted or unsubstituted aromatic hydrocarbon group, a substituted or unsubstituted aromatic heterocyclic group, or a substituted or unsubstituted condensed polycyclic aromatic group; $Ar_{13}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group; $L_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $L_2$ represents a divalent group of a substituted or unsubstituted condensed polycyclic aromatic or a single bond; and $B_2$ represents a substituted or unsubstituted aromatic heterocyclic group.

9. The organic electroluminescent device according to claim 1, wherein the electron acceptor is an electron acceptor selected from trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative.

10. The organic electroluminescent device according to claim 1, wherein the electron acceptor is a radialene derivative represented by the following general formula (2):

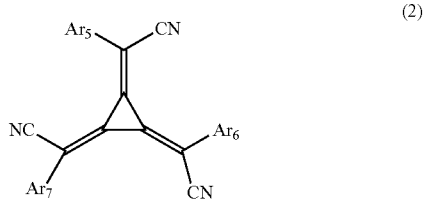

(2)

wherein $Ar_5$ to $Ar_7$ may be the same or different, and represent an aromatic hydrocarbon group, an aromatic heterocyclic group, or a condensed polycyclic aromatic group, having an electron acceptor group as a substituent.

11. The organic electroluminescent device according to claim 1, wherein the hole transport layer comprises only a hole transporting arylamine compound.

12. The organic electroluminescent device according to claim 11, wherein the hole transport layer comprises an arylamine compound represented by the general formula (1).

13. The organic electroluminescent device according to claim 1, wherein the electron transport layer comprises a compound having an anthracene ring structure represented by the following general formula (3):

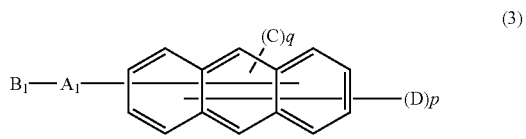

(3)

wherein $A_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $B_1$ represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group; and while p and q maintain a relationship that the sum of p and q is 9, p represents 7 or 8, and q represents 1 or 2.

14. The organic electroluminescent device according to claim 1, wherein the electron transport layer comprises a compound having a pyrimidine ring structure represented by the following general formula (4):

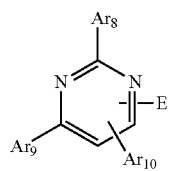

(4)

wherein $Ar_8$ represents a substituted or unsubstituted aromatic hydrocarbon group or a substituted or unsubstituted condensed polycyclic aromatic group; $Ar_9$ and $Ar_{10}$ may be the same or different, and represent a hydrogen atom, a substituted or unsubstituted aromatic hydrocarbon group, or a substituted or unsubstituted condensed polycyclic aromatic group; and E represents a monovalent group represented by the following structural formula (5), provided that $Ar_9$ and $Ar_{10}$ are not simultaneously a hydrogen atom:

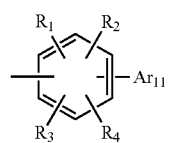

(5)

wherein $Ar_{11}$ represents a substituted or unsubstituted aromatic heterocyclic group; $R_1$ to $R_4$ may be the same or different, and represent a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group.

15. The organic electroluminescent device according to claim 1, wherein the electron transport layer comprises a compound having a benzotriazole ring structure represented by the following general formula (6):

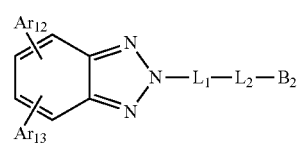

(6)

wherein $Ar_{12}$ represents a substituted or unsubstituted aromatic hydrocarbon group, a substituted or unsubstituted aromatic heterocyclic group, or a substituted or unsubstituted condensed polycyclic aromatic group; $Ar_{13}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group; $L_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $L_2$ represents a divalent group of a substituted or unsubstituted condensed polycyclic aromatic or a single bond; and $B_2$ represents a substituted or unsubstituted aromatic heterocyclic group.

16. The organic electroluminescent device according to claim 1, wherein the light emitting layer comprises a blue light emitting dopant.

17. The organic electroluminescent device according to claim 16, wherein the light emitting layer comprises a blue light emitting dopant which is a pyrene derivative.

18. The organic electroluminescent device according to claim 16, wherein the blue light emitting dopant comprises a light emitting dopant which is an amine derivative having a condensed ring structure represented by the following general formula (7):

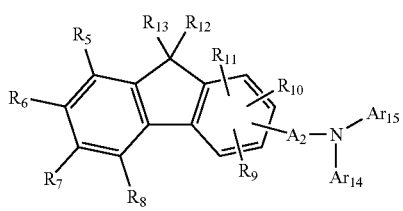

(7)

wherein $A_2$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $Ar_{14}$ and $Ar_{15}$ may be the same or different, and represent a substituted or unsubstituted aromatic hydrocarbon group, a substituted or unsubstituted aromatic heterocyclic group, or a substituted or unsubstituted condensed polycyclic aromatic group, and may bind to each other via a single bond, a substituted or unsubstituted methylene group, an oxygen atom, or a sulfur atom to form a ring; $R_5$ to $R_8$ may be the same or different, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with a group selected from an aromatic hydrocarbon group, an aromatic heterocyclic group, or a condensed polycyclic aromatic group, where the respective groups may bind to each other via a single bond, a substituted or unsubstituted methylene group, an oxygen atom, or a sulfur atom to form a ring, or may bind to the benzene ring to which $R_5$ to $R_8$ bind via a substituted or unsubstituted methylene group, an oxygen atom, a sulfur atom, or a monosubstituted amino group to form a ring; $R_9$ to $R_{11}$ may be the same or different, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, where the respective groups may bind to each other via a single bond, a substituted or unsubstituted methylene group, an oxygen atom, or a sulfur atom to form a ring, or may bind to the benzene ring to which $R_9$ to $R_{11}$ bind via a substituted or unsubstituted methylene group, an oxygen atom, a sulfur atom, or a monosubstituted amino group to form a ring; and $R_{12}$ and $R_{13}$ may be the same or different, and represent a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, where the respective groups may bind to each other via a single bond, a substituted or unsubstituted methylene group, an oxygen atom, a sulfur atom, or a monosubstituted amino group to form a ring.

19. The organic electroluminescent device according to claim 1, wherein the light emitting layer comprises an anthracene derivative.

20. The organic electroluminescent device according to claim 19, wherein the light emitting layer comprises a host material which is an anthracene derivative.

* * * * *